(12) United States Patent
Pernerstorfer et al.

(10) Patent No.: US 9,018,383 B2
(45) Date of Patent: Apr. 28, 2015

(54) ACYLAMINO-SUBSTITUTED CYCLIC CARBOXYLIC ACID DERIVATIVES AND THEIR USE AS PHARMACEUTICALS

(71) Applicant: Sanofi, Paris (FR)

(72) Inventors: Josef Pernerstorfer, Hofheim Langenhein (DE); Heinz-Werner Kleemann, Bischofsheim (DE); Matthias Schaefer, Ehringshausen (DE); Alena Safarova, Tucson, AZ (US); Marcel Patek, Tucson, AZ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/091,511

(22) Filed: Nov. 27, 2013

(65) Prior Publication Data
US 2014/0088158 A1  Mar. 27, 2014

Related U.S. Application Data

(63) Continuation of application No. 13/461,264, filed on May 1, 2012, now Pat. No. 8,618,304, which is a continuation of application No. PCT/US2010/055035, filed on Nov. 2, 2010.

(60) Provisional application No. 61/319,619, filed on Mar. 31, 2010.

(30) Foreign Application Priority Data

Nov. 2, 2009  (EP) ..................................... 09290831

(51) Int. Cl.
| C07D 401/00 | (2006.01) |
|---|---|
| A61K 31/44 | (2006.01) |
| C07C 235/54 | (2006.01) |
| C07C 235/42 | (2006.01) |
| C07C 235/84 | (2006.01) |
| C07C 255/50 | (2006.01) |
| C07C 255/54 | (2006.01) |
| C07C 255/57 | (2006.01) |

(Continued)

(52) U.S. Cl.
CPC ............. *C07C 235/54* (2013.01); *C07C 235/42* (2013.01); *C07C 235/84* (2013.01); *C07C 255/50* (2013.01); *C07C 255/54* (2013.01); *C07C 255/57* (2013.01); *C07C 307/10* (2013.01); *C07C 317/46* (2013.01); *C07D 213/16* (2013.01); *C07D 213/69* (2013.01); *C07D 213/81* (2013.01); *C07D 213/82* (2013.01); *C07D 231/12* (2013.01); *C07D 305/04* (2013.01); *C07D 305/06* (2013.01); *C07D 309/04* (2013.01); *C07D 309/08* (2013.01); *C07D 313/04* (2013.01); *C07D 317/06* (2013.01); *C07D 317/68* (2013.01); *C07D 317/72* (2013.01); *C07D 333/16* (2013.01); *C07D 335/14* (2013.01); *C07D 335/18* (2013.01); *C07D 493/10* (2013.01); *C07C 231/00* (2013.01); *C07C 231/02* (2013.01); *C07D 213/64* (2013.01); *C07D 231/18* (2013.01); *C07D 305/08* (2013.01); *C07D 309/14* (2013.01); *C07D 333/32* (2013.01); *C07D 335/02* (2013.01); *C07C 2101/02* (2013.01); *C07C 2101/04* (2013.01); *C07C 2101/08* (2013.01); *C07C 2101/14* (2013.01); *C07C 2101/18* (2013.01); *C07C 2102/22* (2013.01); *C07C 2102/50* (2013.01)

(58) Field of Classification Search
None
See application file for complete search history.

(56) References Cited

U.S. PATENT DOCUMENTS

| 4,871,387 A | 10/1989 | Sasse et al. |
|---|---|---|
| 6,358,960 B1 | 3/2002 | Senokuchi et al. |

(Continued)

FOREIGN PATENT DOCUMENTS

| EP | 1258484 A1 | 11/2002 |
|---|---|---|
| EP | 1533294 A1 | 5/2005 |

(Continued)

OTHER PUBLICATIONS

Sedlak, M. et al., J. Heterocyclic Chem. (1997), 34(4), 1227-1232.*
Zwaagstra, M., E., et al., Synthesis and Structure-Activity Relationships of Carboxylated Chalcones: A Novel Series of CysLT1 (LTD4) Receptor Antagonists, J. Med. Chem., (1997), vol. 40, pp. 1075-1089.
Benati, L., et al., Radical Chain Reactions of a-Azido-B-Keto Esters with Tributyltin Hydride. A Novel Entry to Amides and Lactams Through Regiospecific Nitrogen Insertion, J. Org. Chem., (1999), vol. 64, pp. 7836-7841.

(Continued)

*Primary Examiner* — Heidi Reese
(74) *Attorney, Agent, or Firm* — Jiang Lin

(57) ABSTRACT

The present invention relates to compounds of the formula I,

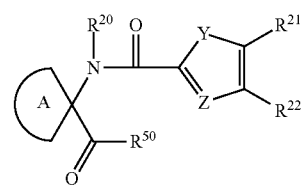

I wherein A, Y, Z, $R^{20}$ to $R^{22}$ and $R^{50}$ have the meanings indicated in the claims, which are valuable pharmaceutical active compounds. Specifically, they are inhibitors of the endothelial differentiation gene receptor 2 (Edg-2, EDG2), which is activated by lysophosphatidic acid (LPA) and is also termed as $LPA_1$ receptor, and are useful for the treatment of diseases such as atherosclerosis, myocardial infarction and heart failure, for example. The invention furthermore relates to processes for the preparation of the compounds of the formula I, their use and pharmaceutical compositions comprising them.

9 Claims, No Drawings

(51) Int. Cl.

| | | |
|---|---|---|
| C07C 307/10 | (2006.01) | |
| C07C 317/46 | (2006.01) | |
| C07D 213/16 | (2006.01) | |
| C07D 213/69 | (2006.01) | |
| C07D 213/81 | (2006.01) | |
| C07D 213/82 | (2006.01) | |
| C07D 231/12 | (2006.01) | |
| C07D 305/04 | (2006.01) | |
| C07D 305/06 | (2006.01) | |
| C07D 309/04 | (2006.01) | |
| C07D 309/08 | (2006.01) | |
| C07D 313/04 | (2006.01) | |
| C07D 317/06 | (2006.01) | |
| C07D 317/68 | (2006.01) | |
| C07D 317/72 | (2006.01) | |
| C07D 333/16 | (2006.01) | |
| C07D 335/14 | (2006.01) | |
| C07D 335/18 | (2006.01) | |
| C07D 493/10 | (2006.01) | |
| C07C 231/00 | (2006.01) | |
| C07C 231/02 | (2006.01) | |
| C07D 213/64 | (2006.01) | |
| C07D 231/18 | (2006.01) | |
| C07D 305/08 | (2006.01) | |
| C07D 309/14 | (2006.01) | |
| C07D 333/32 | (2006.01) | |
| C07D 335/02 | (2006.01) | |

(56) References Cited

U.S. PATENT DOCUMENTS

| | | |
|---|---|---|
| 6,455,502 B1 | 9/2002 | Bryant et al. |
| 6,472,412 B1 | 10/2002 | Fenton et al. |
| 7,045,660 B2 | 5/2006 | Fenton et al. |
| 7,342,027 B2 * | 3/2008 | Lee et al. ............ 514/326 |
| 7,378,252 B2 | 5/2008 | Kostenis |
| 7,652,144 B2 | 1/2010 | Fenton et al. |
| 7,683,097 B2 * | 3/2010 | Murphy et al. ........ 514/615 |
| 8,129,537 B2 | 3/2012 | Fenton et al. |
| 2002/0127601 A1 | 9/2002 | Kostenis |
| 2003/0013713 A1 | 1/2003 | Fenton et al. |
| 2004/0002109 A9 | 1/2004 | Kostenis |
| 2004/0171618 A1 | 9/2004 | Fenton et al. |
| 2005/0255531 A1 | 11/2005 | Kostenis |
| 2006/0084809 A1 | 4/2006 | Fenton et al. |
| 2007/0249670 A1 | 10/2007 | Evans et al. |
| 2008/0132706 A1 | 6/2008 | Fenton et al. |
| 2009/0227625 A1 | 9/2009 | Hachtel et al. |
| 2010/0130737 A1 | 5/2010 | Itoh et al. |
| 2010/0240677 A1 | 9/2010 | Fenton et al. |
| 2011/0152290 A1 | 6/2011 | Schaefer et al. |

FOREIGN PATENT DOCUMENTS

| | | |
|---|---|---|
| EP | 1695955 A1 | 8/2006 |
| EP | 1849465 A1 | 10/2007 |
| EP | 1972615 A1 | 9/2008 |
| WO | WO 95/04045 A1 | 7/1995 |
| WO | WO 99/49856 A2 | 10/1999 |
| WO | WO 02/04665 A2 | 1/2002 |
| WO | WO 02/06232 A1 | 1/2002 |
| WO | WO 02/29001 A2 | 4/2002 |
| WO | WO 03/062392 A2 | 7/2003 |
| WO | WO 2004/011457 A1 | 2/2004 |
| WO | WO 2004/052921 A1 | 6/2004 |
| WO | WO 2004/108681 A1 | 12/2004 |
| WO | WO 2005/009389 A2 | 2/2005 |
| WO | WO 2005/021544 | 3/2005 |
| WO | WO 2005/115150 A2 | 12/2005 |
| WO | WO 2005/115510 A1 | 12/2005 |
| WO | WO 2006/044775 A2 | 4/2006 |
| WO | WO 2006/044975 A2 | 4/2006 |
| WO | WO 2006/088246 A1 | 8/2006 |
| WO | WO 2006/122788 A1 | 11/2006 |
| WO | WO 2006/128184 A2 | 11/2006 |
| WO | WO 2008/000409 A1 | 1/2008 |

OTHER PUBLICATIONS

Borchardt, R. T., et al., Catechol O-Methyltransferase. 11. Inactivation by 5-Hydroxy-3-Mercapto-4-Methoxybenzoic Acid, J. Med. Chem., (1982), vol. 25, pp. 321-323.

Boucharaba, A., et al., The Type 1 Lysophosphatidic Acid Receptor is a Target for Therapy in Bone Metastases, PNAS, (2006), vol. 103, No. 25, pp. 9643-9648.

Brault, S., et al., Lysophosphatidic Acid Induces Endothelial Cell Death by Modulating the Redox Environment, Am. J. Physiol. Regul. Integr Comp. Physiol., vol. 292, pp. R1174-R1183, (2007).

Canonne, P., et al., Reactions Selectives Des Organomagnesiens Avec Les Lactols et Les Lactones. Synthese Des Diols Primaires-Secondaires, Tetrahedron, vol. 44, No. 10, pp. 2903-2912, (1988).

Chattaway, F. D., et al., The Condensation of Chloral With Anisic Acid with p-Nitroanisole, and with 2:6-Dichloroquinol, J. Chemical Soc., (1928), pp. 2913-2918.

Chen, J., et al., Specific LPA Receptor Subtype Mediation of LPA-induced Hypertrophy of Cardiac Myocytes and Involvement of Akt and NFkB Signal Pathways, Journal of Cellular Biochemistry, vol. 103, pp. 1718-1731, (2008).

Chen, J., et al., Specific Receptor Subtype Mediation of LPA-Induced Dual Effects in Cardiac Fibroblasts, FEBS Letters, vol. 580, (2006), pp. 4737-4745.

Chen, X., et. al., Serum Lysophosphatidic Acid Concentrations Measured by Dot Immunogold Filtration Assay in Patients with Acure Myocardial Infarction, Scand. J. Clin. Lab. Invest., vol. 63, pp. 497-504, (2003).

Chinchilla, R., et al., The Sonogashira Reaction: A Booming Methodology in Synthetic Organic Chemistry, Chem. Rev., vol. 107, pp. 874-922, (2007).

Cremers, B., et al., Modulation of Myocardial Contractility by Lysophosphatidic Acid (LPA), Journal of Molecular and Cellular Cardiology, vol. 35, (2003), pp. 71-80.

Guo, R., et al., Expression and Function of Lysophosphatidic Acid LPA1 Receptor in Prostate Cancer Cells, Endocrinology, vol. 147, No. 10, pp. 4883-4892, (2006).

Hilal-Dandan, R., et al., Lysophosphatidic Acid Induces Hypertrophy of Neonatal Cardiac Myocytes Via Activation of G1 and Rho, Journal of Molecular and Cellular Cardiology, vol. 36, (2004), pp. 481-493.

Hollingworth, G. J., et al., A Convenient Method for the Preparation of Aryl Cyclopropyl Ethers from Phenols, Tetrahedron Letters, vol. 40, (1999), pp. 2633-2636.

Inoue, M., et al., Initiation of Neuropathic Pain Requires Lysophosphatidic Acid Receptor Signaling, Nature Medicine, vol. 10, No. 7, pp. 712-718, (2004).

Ishii, I., et al., Lysophospholipid Receptors: Signaling and Biology, Annu. Rev. Biochem., vol. 73, pp. 321-354, (2004).

Jorgensen, M., et al., Efficient Synthesis of a-Aryl Esters by Room-Temperature Palladium-Catalyzed Coupling of Aryl Halides With Ester Enolates, J. Am. Chem. Soc., vol. 124, (2002), pp. 12557-12565.

Kaneyuki, U., et al., Pitavastatin Inhibits Lysophosphatidic Acid-Induced Proliferation and Monocyte Chemoattractant Protein-1 Expression in Aortic Smooth Muscle Cells by Suppressing Rac-1-Mediated Reactive Oxygen Species Generation, Vasular Pharmacology, vol. 46, (2007), pp. 286-292.

Kanoh, S., et al., Unusual Cyclodimerization of Small Cyclic Ethers Via Neighboring Carbonyl-Group Participation and Cation Transfer, Tetrahedron, vol. 58, pp. 7065-7074, (2002).

Kerdesky, F. A. J., et al., 4-Hydroxythiazole Inhibitors of 5-Lipoxygenase, J. Med. Chem., (1991), vol. 34, pp. 2158-2165.

Kotha, S., et al., Synthesis of Indan-Based Unusual a-Amino Acid Derivatives Under Phase-Transfer Catalysis Conditions, J. Org. Chem., (2000), vol. 65. pp. 1359-1365.

(56) References Cited

OTHER PUBLICATIONS

Lee, H., et al., Lysophospholipids Increase ICAM-1 Expression in HUVEC Through a Gi- and NF-kB-Dependent Mechanism, Am. J. Physiol. Cell Physiol., vol. 287, C1657-C1666, (2004).

Linz, W., et al., Vasopeptidase Inhibition Prevents Target Organ Damage and Improves Survival in Spontaneously Hypertensive Rats, JRAAS, vol. 7, No. 3, pp. 155-161, (2006).

Lohmar, R., et al., Synthese Symmetrischer Ketone Unter Verwendung Von 2-Phenyl-2-Oxazolin-5-on, Chemische Berichte, (1980), vol. 113, No. 12, pp. 3706-3715.

Mitsunobu, O., et al., The Use of Diethyl Azodicarboxylate and Triphenylphosphine in Synthesis and Transformation of Natural Products, Synthesis, (1981), pp. 1-28.

Miyaura, et al, Palladium-Catalyzed Cross-Coupling Reactions of Organoboron Compounds, Chem Rev., 1995 (95) 7 pp. 2457-2483.

Nagano, T., et al., Preparation of 3',4'-Dihydroxy-6-Carboxyflavonol, J. Am. Chem. Soc., vol. 75, (1953), pp. 6237-6238.

Okusa, M. D., et al., Selective Blockade of Lysophosphatidic Acid LPA3 Receptors Reduces Murine Renal Ischemia-Reperfusion Injury, Am. J. Phsiol Renal Physiol, vol. 285, pp. F565-F574, (2003).

Palmetshofer, A., et al., Lysophosphatidic Acid Activates Nuclear Factor Kapppa B and Induces Proinflammatory Gene Expression in Endothelial Cells, Thromb. Haemost., vol. 82, pp. 1532-1537, (1999).

Pradere, J.-P., et al., LPA1 Receptor Activation Promotes Renal Interstitial Fibrosis, J. Am. Soc. Nephrol., vol. 18, pp. 3110-3118, (2007).

Rother, E., et al., Subtype-Selective Antagonists of Lysophosphatidic Acid Receptors Inhibit Platelet Activation Triggered by the Lipid Core of Atherosclerotic Plaques, Circulation, vol. 108, pp. 741-747, (2003).

Sano, T., et al., Multiple Mechanisms Linked to Platelet Activation Result in Lysophosphatidic Acid and Sphingosine 1-Phosphate Generation in Blood, The Journal of Biological Chemistry, vol. 277, No. 24, pp. 21197-21206, (2002).

Seewald, S., et al., Lysophosphatidic Acid and Intracellular Signalling in Vascular Smooth Muscle Cells, Atherosclerosis, vol. 130, (1997), pp. 121-131.

Shida, D., et al., Lysophosphatidic Acid (LPA) Enhances the Metastatic Potential of Human Colon Carcinoma DLD1 Cells Through LPA11, Cancer Research, vol. 63, pp. 1706-1711, (2003).

Siess, W., et al., Lysophosphatidic Acid Mediates the Rapid Activation of Platelets and Endothelial Cells by Mildly Oxidized Low Density Lipoprotein and Accumulates in Human Atherosclerotic Lesions, Proc. Natl. Acad. Sci. USA, vol. 96, pp. 6931-6936, (1999).

Tager, A. M., et al., The Lysophosphatidic Acid Receptor LPA1 Links Pulmonary Fibrosis to Lung Injury by Mediating Fibroblast Recruitment and Vascular Leak, Nat. Med., vol. 14, (2008), pp. 45-54.

Thompson, W. J., et al., A General Synthesis of 5-Arylnicotinates, J. Org. Chem., vol. 49, pp. 5237-5243, (1984).

Tiemann, F., et al., Abkommlinge der Dimethylprotocatechusaure und der Vanillinsaure (Monomethylprotocatechusaure), Ber. dt. Chem. Ges., vol. 9, pp. 937-945, (1876).

Xing, Y., et al., Cell Density-Dependent Expression of EDG Family Receptors and Mesangial Cell Proliferation: Role in Lysophosphatidic Acid-Mediated Cell Growth, Am. J. Physiol Renal Physiol., vol. 287, pp. F1250-F1257, (2004).

Xu, Y.-J., et al., Stimulation of 90- and 70-kDa Ribosomal Protein S6 Kinases by Arginine Vasopressin and Lysophosphatidic Acid in Rat Cardiomyocytes, Biochemical Pharmacology, vol. 59, pp. 1163-1171, (2000).

Yoshida, K., et al., Vascular Remodeling Induced by Naturally Occurring Unsaturated Lysophosphatidic Acid in Vivo, Circulation, vol. 108, (2003), pp. 1746-1752.

Yoshiizumi, K., et al., Synthesis and Structure-Activity Relationships of 5,6,7,8-Tetrahydropyrido[3,4-b] Pyrazine-Based Hydroxamic Acids as HB-EGF Shedding Inhibitors, Bioorganic & Medicinal Chemistry, vol. 11, pp. 433-450, (2003).

Lohmar, R., et al., a-Amino Acids as Nucleophilic Acyl Equivalents. IV. Synthesis of Symmetrical Ketones by Means of 2-Phenyl-2-Oxazolin-5-One, Database Accession No. 1981:156251, CAPLUS (abstract), (1981).

Warm, et al., 74. Syntheses of (+)- and (−)-Methyl 8-Epinonactate and (+)- and (−)-Methyl Nonactate1), Helvetica Chimica Acta, vol. 70, (1987), pp. 690-700.

Wheeler, et al., A Convenient and Efficient Synthesis of 1-Aminocyclopropanecarboxylic Acid (ACC), Synthetic Communications, vol. 18, No. 2, pp. 141-149. (1988).

Gorecka, et al., Deprotonation-Triggered Heavy-Halogen Migrations as a Key to the Structural Elaboration of 2,2-Difluoro-1,3-Benzodioxole, European Journal of Organic Chemistry, vol. 1, pp. 64-68, (2004).

Peptide Reagents, Alfa Aesar.

International Search Report for WO2011/053498 dated May 5, 2011.

Palmer, et al., Design and Synthesis of Tri-Ring P3 Benzamide-Containing Aminonitriles as Potent, Selective, Orally Effective Inhibitors of Cathepsin K, J. Med. Chem., (2005), vol. 48, pp. 7520-7534.

Alonso, et al., Synthesis of 3- and 4-Substituted Cyclic a-Amino Acids Structurally Related to ACPD, Tetrahedron, vol. 51, No. 37, pp. 10259-10280, (1995).

Fohlisch, et al., Erzeugung und [4+3]-Cycloaddition von Cyclopentenylium-2-Olat aus 2-Chlorcyclopentanon unter Alkoholyse-Bedingungen, Chem. Ber., vol. 120, (1987), pp. 1951-1960.

Hammer, et al., Ruthenium(II) in Ring Closing Metathesis for the Stereoselective Preparation of Cyclic 1-Amino-1-Carboxylic Acids., Tetrahedron, vol. 53, No. 6, pp. 2309-2322, (1997).

Kline, et al., Potent, Novel in Vitro Inhibitors of the *Pseudomonas aeruginosa* Deacetylase LpxC, J. Med. Chem., vol. 45, pp. 3112-3129, (2002).

Munday, Amino-Acids of the Cyclohexane Series. Part I., J. Chem. Soc., (1961), pp. 4372-4379.

Oba, et al., Concise Synthetic Strategy Toward Cyclic a,a-Disubstituted a-Amino Acids Bearing a Beta-Nitrogen Atom: Chiral 1-Substituted 4-Aminopiperidine-4-Carboxylic Acids, Tetrahedron, vol. 61, (2005), pp. 593-598.

Pasto, et al., Reduction With Diimide, Organic Reactions, vol. 40. (1991), pp. 91-107, 151-155.

Prelog, et al., Geometrisch Enantiomorphe Cyclobutan-Derivate, Helvetica Chimica Acta, vol. 65, No. 8, (1982), pp. 2622-2644.

Smith, et al., Total Synthesis of (+)-Jatropholones A and B: Exploitation of the High-Pressure Technique, J. Am. Chem. Soc., (1986), vol. 108, pp. 3040-3048.

Tsang, et al., Peptide Sweeteners. 6. Structural Studies on the C-Terminal Amino Acid of L-Aspartyl Dipeptide Sweeteners, J. Med. Chem., (1984), vol. 27, pp. 1663-1668.

Silverman, The Organic Chemistry of Drug Design and Drug Action, (2004), pp. 29-32.

\* cited by examiner

ACYLAMINO-SUBSTITUTED CYCLIC CARBOXYLIC ACID DERIVATIVES AND THEIR USE AS PHARMACEUTICALS

The present invention relates to compounds of the formula I,

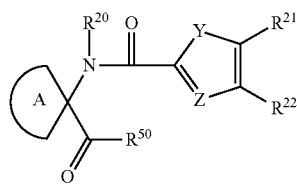

wherein A, Y, Z, $R^{20}$ to $R^{22}$ and $R^{50}$ have the meanings indicated below, which are valuable pharmaceutical active compounds. Specifically, they are inhibitors of the endothelial differentiation gene receptor 2 (Edg-2, EDG2), which is activated by lysophosphatidic acid (LPA) and is also termed as $LPA_1$ receptor, and are useful for the treatment of diseases such as atherosclerosis, myocardial infarction and heart failure, for example. The invention furthermore relates to processes for the preparation of the compounds of the formula I, their use and pharmaceutical compositions comprising them.

LPA is a group of endogenous lysophospholipid derivatives including 1-oleoyl-sn-glycerol 3-phosphate, for example. LPA activates G-protein-coupled receptors (GPCR's) from the endothelial differentiation gene receptor family which belong to the lysophospholipid receptors. LPA signaling exerts a variety of pleiotropic biological responses on many different cell types which interfere with processes such as cell proliferation, cell growth, cell hypertrophy, re-differentiation, cell retraction, cell contraction, cell migration, cell survival or inflammation. The Edg receptor family, originally identified as a family of orphan GPCR's, currently comprises eight different members which were recently termed according to their respective ligand as LPA receptors or S1P receptors (sphingosine-1-phosphate receptors). According to the nomenclature of the International Union of Basic and Clinical Pharmacology (IUPHAR), LPA receptors Edg-2, Edg-4 and Edg-7 are now also termed as $LPA_1$, $LPA_2$ and $LPA_3$ receptor (cf. I. Ishii et al., Annu. Rev. Biochem. 73 (2004), 321-354).

LPA is generated mainly in the extracellular compartment by different pathways predominantly by the cancer cell motility factor autotaxin which was recently found to be identical with lysophospholipase D. LPA can also be generated by alternative routes involving phospholipase hydrolysis ($PLA_1$ and $PLA_2$) or other mechanisms such as de novo phospholipid synthesis. Although LPA, in contrast to other phospholipids, is highly soluble in water, in plasma it is carried by different binding proteins such as albumin and gelsolin which display a high affinity to LPA and from which it can be released. Under pathophysiological conditions, levels of LPA can be elevated to an undesirable amount and thus increase LPA-mediated signaling and lead to detrimental processes such as abnormal cell proliferation, for example. Blocking LPA signaling, for example by Edg-2 inhibitors, allows to prevent such processes.

For example, increased liberation of LPA was observed during platelet activation and blood clotting and at sites of inflammation (T. Sano et. al., J. Biol. Chem. 277 (2002), 21197-21206). After acute myocardial infarction (AMI) in humans, LPA serum levels were significantly raised in humans to about 6-fold higher concentrations, and LPA was regarded to be involved in the pathophysiological processes in the cardiovascular system related to AMI (X. Chen et al., Scand. J. Clin. Lab. Invest. 63 (2003), 497-503). The importance of LPA and its receptor Edg-2 for the pathophysiological processes after myocardial infarction such as cardiac remodeling and for the prevention of cardiac hypertrophy and heart failure was confirmed in further investigations (J. Chen et al., J. Cell. Biochem. 103 (2008), 1718-1731). LPA was shown to be generated during mild oxidation of low density lipoprotein (LDL) particles and to be accumulated in the lipid core of human atherosclerotic plaques (W. Siess et al., Proc. Natl. Acad. Sci. 96 (1999), 6931-6936). Furthermore, LPA was identified as an important bioactive component of mox-LDL (mildly oxidized low density lipoprotein) leading to platelet activation, and it was shown that the effects of LPA, moxLDL or lipid core extracts from human atherosclerotic plaques on platelet activation could be abrogated by the Edg-2/Edg-7 receptor inhibitor dioctanoylglycerol pyrophosphate DGPP(8:0), implicating a causative role of LPA-mediated Edg receptor signaling in platelet aggregation and usefulness of such LPA receptor inhibitors in the treatment of cardiovascular diseases (E. Rother et al., Circulation 108 (2003), 741-747).

Further findings underline the detrimental role of LPA during initiation and progression of cardiovascular diseases such as atherosclerosis, left ventricular remodeling and heart failure. LPA leads to pertussis toxin-sensitive, NFκB (nuclear factor kappa B)-mediated pro-inflammatory responses of endothelial cells including upregulation of chemokines like monocyte chemoattractant protein-1 (MCP-1) and interleukin-8 (IL8) (A. Palmetshofer et al., Thromb. Haemost. 82 (1999), 1532-1537) and exposure of endothelial cell adhesion molecules like E-selectin or intercellular adhesion molecule-1 (ICAM-1) (H. Lee et al., Am. J. Physiol. 287 (2004), C1657-C1666). Direct evidence for the involvement of Edg-2 receptors arises from recent studies which demonstrate that LPA induces oxidative stress in vascular smooth muscle cells and endothelial cells which was attenuated by pharmacological inhibition by DGPP(8:0) or THG1603, a specific Edg-2 receptor antagonist (U. Kaneyuki et al., Vascular Pharmacology 46 (2007), 286-292; S. Brault et al., Am. J. Physiol. Regul. Integr. Comp. Physiol. 292 (2007), R1174-R1183). In vascular smooth muscle cells, LPA leads to pertussis toxin-sensitive $Ca^{2+}$ release from internal stores, to activation of 42 kDa mitogen-activated protein kinase (p42MAPK) and to cell proliferation (S. Seewald et al., Atherosclerosis 130 (1997), 121-131). Intravascular injection of LPA was shown to induce neointima formation in vivo (K. Yoshida et al., Circulation 108 (2003), 1746-1752). On isolated adult cardiac myocytes, LPA leads to cellular hypertrophy and to activation of different kinases known to be relevant for a hypertrophic response (Y.-J. Xu et al., Biochemical Pharmacology 59 (2000), 1163-1171). Studies on neonatal myocytes confirmed a role of LPA in the induction of hypertrophy and revealed the relevance of a rho kinase-dependent pathway (R. Hilal-Dandan et al., J. Mol. Cell. Cardiol. 36 (2004), 481-493). The relevance of rho kinase underlines the involvement of the Edg-2 receptors which, in contrast to Edg-7 receptors, are coupled to $G_{\alpha 12/13}$ proteins. LPA furthermore attenuates the force of contraction in human myocardial ventricular and atrial preparations and impairs isoprenaline-induced fractional shortening of isolated adult rat ventricular myocytes. The latter effects were reverted after pre-incubation with pertussis toxin indicating the relevance of a GPCR-mediated and $G_{\alpha i/o}$-mediated pathway (B. Cremers et al., J. Mol. Cell. Cardiol. 35 (2003), 71-80). LPA was also found to lead to enhanced matrix generation and proliferation of cardiac fibroblasts (J. Chen et al., FEBS Letters 580 (2006), 4737-4745).

The importance of influencing Edg-2 receptor signaling and LPA-mediated effects for many diseases was confirmed by pharmacological approaches using specific tool compounds or Edg-2 receptor knock-out mice or by experimental silencing of the Edg-2 receptors. For example, the relevance of LPA-activated Edg receptors for renal diseases was demonstrated by different kinds of Edg-2/Edg-7 receptor inhibitors. In one approach, it was shown that the LPA-induced proliferative response of mesangial cells could be inhibited by the compound DGPP(8:0) (Y. Xing et al., Am. J. Physiol. Cell Physiol. 287 (2004), F1250-F1257). In another approach using the Edg-2/Edg-7 receptor inhibitor VPC12249 it was demonstrated in an in vivo model of mouse renal ischemia reperfusion that LPA displays a dual role in renoprotection. While Edg-4 receptor signaling was shown to be beneficial, Edg-2 and Edg-7 receptor signaling aggravated renal injury, most probably due to enhanced infiltration of leukocytes into the renal tissue, and should therefore be blocked for treating or preventing ischemia/reperfusion-induced acute renal failure (M. D. Okusa et al., Am. J. Physiol. Renal Physiol. 285 (2003), F565-F574). The crucial role of Edg-2 receptors in the development of tubulointerstitial fibrosis was confirmed in a model of unilateral ureteral obstruction (J. P. Pradere et al., J. Am. Soc. Nephrol. 18 (2007), 3110-3118). In this model, renal injury was attenuated in Edg-2 receptor knock-out mice or by pharmacological treatment with the Edg-2/Edg-7 receptor inhibitor Ki16425. The impact of the LPA/Edg-2 receptor system in pulmonary fibrosis and vascular leakage was recently confirmed by the finding that the bioactive content of LPA was increased in bronchoalveolar fluid of humans suffering from idiopathic pulmonary fibrosis. Edg-2 receptor knock-out mice were protected from bleomycin-induced lung injury and vascular leakage, as compared to wild-type littermates (A. M. Tager et al., Nat. Med. 14 (2008), 45-54).

Direct involvement of Edg-2 receptors was recently demonstrated for the progression of bone metastasis in vivo. Progression was reduced under pharmacological treatment with the Edg-2/Edg-7 receptor inhibitor Ki16425 as well as after specific silencing of the Edg-2 receptors in the same order of magnitude (A. Boucharaba et al., Proc. Natl. Acad. Sci. 103 (2006), 9643-9648). The relevance of Edg-2 receptors was also shown in vitro with respect to prostate cancer cell proliferation and metastatic potential of human colon carcinoma cells (R. Guo et al., Endocrinology 147 (2006), 4883-4892; D. Shida et al., Cancer Res. 63 (2003), 1706-1711).

The relevance of LPA-mediated Edg-2 receptor signaling was also demonstrated in an in vivo model of neuropathic pain. Intrathecal injection of LPA mimicked behavioral, morphological and biochemical alterations similar to those observed after peripheral nerve injury. Non-redundant function of Edg-2 receptors was demonstrated in Edg-2 receptor deficient mice which did not develop signs of neuropathic pain after nerve injury. Therefore, Edg-2 receptor signaling is regarded as crucial in the initiation of neuropathic pain (M. Inoue et al., Nat. Med. 10 (2004), 712-718). Thus, it is evident that inhibition of the Edg-2 receptor and the effects of LPA by suitable inhibitors is an attractive approach for treating various diseases.

Certain compounds which exhibit Edg-2 inhibitory activity, have already been described. For example, as compounds which are structurally related to LPA, the above-mentioned compounds DGPP(8:0) or VPC12249 may be mentioned. In WO 02/29001 and WO 2005/115150 amino compounds comprising a phosphate group, phosphonate group or hydroxy group are described which have activity as agonists or antagonists of LPA receptors. LPA receptor antagonistic azole compounds which are characterized by a carbamate group in the 4-position of the azole ring, are described in EP 1258484. The use of azole compounds, further heterocycles and other compounds for modulating the Edg-2, Edg-3, Edg-4 and Edg-7 receptor is described in WO 03/062392. Compounds which have LPA receptor, especially Edg-2, antagonistic activity and which comprise a β-alanine moiety carrying a biphenyl-2-carbonyl group on the amino group, or an alcohol group and at least three cyclic groups, are described in EP 1533294 and EP 1695955, respectively. But there still is a need for further Edg-2 inhibitors which exhibit a favorable property profile and can be used in the treatment of diseases such as the above-mentioned ones and other diseases in which LPA signaling and Edg-2 receptors play a role. The present invention satisfies this need by providing the acylamino-substituted cyclic carboxylic acid derivatives of the formula I defined below.

Certain acylamino-substituted cyclic carboxylic acid derivatives have already been described. In WO 2004/011457, which relates to 1-phenylpiperidin-3-one derivatives carrying a 1-acylaminocyclohexylcarbonylamino substituent in the 4-position of the piperidine ring and exhibiting cysteine protease inhibitory activity, the compounds 1-[(biphenyl-4-carbonyl)-amino]-cyclohexanecarboxylic acid, 1-[4-(2-oxo-pyrrolidin-1-yl)-benzoylamino]-cyclohexanecarboxylic acid, 1-[4-(2-pyrrolidin-1-yl-ethoxy)-benzoylamino]-cyclohexanecarboxylic acid, 1-[4-(2-piperidin-1-yl-ethoxy)-benzoylamino]-cyclohexanecarboxylic acid and 1-{[4-(2-oxo-pyrrolidin-1-yl)-furan-2-carbonyl]-amino}-cyclohexanecarboxylic acid, i.e. the compounds of the formula I in which the ring A is an unsubstituted cyclohexane ring, $R^{20}$ is hydrogen, $R^{50}$ is hydroxy and the ring comprising Y and Z and carrying $R^{21}$ and $R^{22}$ is biphenyl-4-yl, 4-(2-oxo-pyrrolidin-1-yl)-phenyl, 4-(2-pyrrolidin-1-yl-ethoxy)-phenyl, 4-(2-piperidin-1-yl-ethoxy)-phenyl and 4-(2-oxo-pyrrolidin-1-yl)-furan-2-yl, are disclosed as intermediates in the synthesis of the pharmacological active compounds. In WO 2004/052921, which relates to acylamino-substituted carboxamides carrying a cyano group in the substituent on the carboxamide nitrogen atom and exhibiting likewise cysteine protease inhibitory activity, the compound I-(2',3-dichloro-biphen-4-ylcarbonylamino)-cycloheptanecarboxylic acid (=1-[(2',3-dichloro-biphenyl-4-carbonyl)-amino]-cycloheptanecarboxylic acid), i.e. the compound of the formula I in which the ring A is an unsubstituted cycloheptane ring, $R^{20}$ is hydrogen, $R^{50}$ is hydroxy and the ring comprising Y and Z and carrying $R^{21}$ and $R^{22}$ is 2',3-dichloro-biphen-4-yl (=2',3-dichloro-biphenyl-4-yl), is disclosed as an intermediate in the synthesis of the pharmacological active compounds. Elsewhere the said compound disclosed in WO 2004/052921 is identified as 1-[[(2,2'-dichloro[1,1']biphenyl)-4-yl)carbonyl)-amino]cycloheptanecarboxylic acid (=1-[(2,2'-dichloro-biphenyl-4-carbonyl)-amino]-cycloheptanecarboxylic acid), i.e. as the compound of the formula I in which the ring A is an unsubstituted cycloheptane ring, $R^{20}$ is hydrogen, $R^{50}$ is hydroxy and the ring comprising Y and Z and carrying $R^{21}$ and $R^{22}$ is 2,2'-dichloro-biphenyl-4-yl. In U.S. Pat. No. 4,871,387, which relates to pyri(mi)dyl-oxy- and -thio-benzoic acid derivatives exhibiting herbicidal and plant growth regulatory activity, the compound 1-[4-(4,6-dimethyl-pyrimidin-2-ylsulfanyl)-benzoylamino]-cyclopentanecarboxylic acid ethyl ester, i.e. the compound of the formula I in which the ring A is an unsubstituted cyclopentane ring, $R^{20}$ is hydrogen, $R^{50}$ is ethoxy and the ring comprising Y and Z and carrying $R^{21}$ and $R^{22}$ is 4-(4,6-dimethyl-pyrimidin-2- ylsulfanyl)-phenyl, is disclosed. In WO 02/06232, which relates to azacycloalkanes carrying a phenyl group on the ring nitrogen atom and a hydroxyalkyl-amino substituent on a ring carbon atom and exhibiting agonistic activity on $\beta_3$ adrenergic receptors, the compound 1-[4-(4-oxo-piperidin-1-yl)-benzoylamino]-cyclopropanecarboxylic acid methyl ester, i.e. the compound of the formula I in which the ring A is an unsubstituted cyclopropane ring, $R^{20}$ is hydrogen, $R^{50}$ is methoxy and the ring comprising Y and Z and carrying $R^{21}$ and $R^{22}$ is 4-(4-oxo-piperidin-1-yl)-phenyl, is disclosed as an intermediate in the synthesis of the pharmacological active compounds. In WO 99/49856, which relates to very broadly defined compounds which mediate immune or inflammatory response through the CD11/CD18 family of cellular adhesion molecules, the compound 1-[2-chloro-4-(3-hydroxy-benzyl-carbamoyl)-benzoylamino]-cyclopropanecarboxylic acid, i.e. the compound of the formula I in which the ring A is an unsubstituted cyclopropane ring, $R^{20}$ is hydrogen, $R^{50}$ is hydroxy and the ring comprising Y and Z and carrying $R^{21}$ and $R^{22}$ is 2-chloro-4-(3-hydroxy-benzylcarbamoyl)-phenyl, is disclosed.

A subject of the present invention is a compound of the formula I, in any of its stereoisomeric forms or a mixture of stereoisomeric forms in any ratio, or a physiologically acceptable salt thereof,

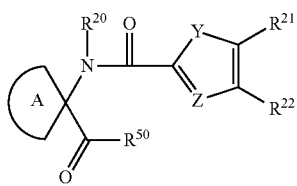

I wherein
ring A is a 3-membered to 12-membered monocyclic, bicyclic or spirocyclic ring which comprises 0, 1 or 2 identical or different hetero ring members chosen from the series consisting of N, N($R^0$), O, S, S(O) and S(O)$_2$, and which is saturated or comprises 1 double bond, provided that ring A is not a bicyclo[3.1.0]hexane or bicyclo[3.2.0]heptane ring carrying the groups N($R^{20}$) and C(O)—$R^{50}$ in its position 3, and not an octahydropentalene, octahydroindene or decahydroazulene ring carrying the groups N($R^{20}$) and C(O)—$R^{50}$ in its position 2, wherein ring A is optionally substituted on ring carbon atoms by one or more identical or different substituents chosen from the series consisting of halogen, $R^1$, $R^2$, ($C_2$-$C_6$)-alkenyl, HO—, $R^1$—O—, phenyl-($C_1$-$C_4$)-alkyl-O—, $R^1$—C(O)—O—, $R^1$—S(O)$_2$—O—, $R^1$—S(O)$_m$—, $H_2$N—, $R^1$—NH—, $R^1$—N($R^1$)—, $R^1$—C(O)—NH—, $R^1$—C(O)—N($R^1$)—, $R^1$—S(O)$_2$—NH—, $R^1$—S(O)$_2$—N($R^1$)—, $R^1$—C(O)—, HO—C(O)—, $R^1$—O—C(O)—, $H_2$N—C(O)—, $R^1$—NH—C(O)—, $R^1$—N($R^1$)—C(O)—, $H_2$N—S(O)$_2$—, $R^1$—NH—S(O)$_2$—, $R^1$—N($R^1$)—S(O)$_2$—, $F_5$S—, NC—, oxo and methylene;
Y is chosen from the series consisting of N($R^{10}$), S, O, C($R^{12}$)=C($R^{13}$), N=C($R^{14}$) and C($R^{15}$)=N;
Z is chosen from the series consisting of N and C($R^{16}$);
$R^0$ is chosen from the series consisting of hydrogen and $R^1$;
$R^1$ is chosen from the series consisting of ($C_1$-$C_6$)-alkyl, ($C_3$-$C_7$)-cycloalkyl and ($C_3$-$C_7$)-cycloalkyl-($C_1$-$C_4$)-alkyl-;
$R^2$ is ($C_1$-$C_4$)-alkyl which is substituted by one or more identical or different substituents chosen from the series consisting of HO— and ($C_1$-$C_4$)-alkyl-O—;
$R^{10}$ is chosen from the series consisting of hydrogen and $R^{11}$;

$R^{11}$, $R^{30}$, $R^{33}$, $R^{35}$, $R^{54}$, $R^{55}$, $R^{57}$ and $R^{58}$ are, independently of each other group $R^{11}$ $R^{30}$, $R^{33}$, $R^{35}$, $R^{54}$, $R^{55}$, $R^{57}$ and $R^{58}$, chosen from the series consisting of ($C_1$-$C_6$)-alkyl, ($C_2$-$C_6$)-alkenyl, ($C_2$-$C_6$)-alkynyl, ($C_3$-$C_7$)-cycloalkyl and ($C_3$-$C_7$)-cycloalkyl-($C_1$-$C_4$)-alkyl- which are all optionally substituted by one or more identical or different substituents $R^{70}$;
$R^{12}$, $R^{13}$, $R^{14}$, $R^{15}$ and $R^{16}$ are independently of each other chosen from the series consisting of hydrogen, halogen, ($C_1$-$C_4$)-alkyl, HO—($C_1$-$C_4$)-alkyl-, ($C_1$-$C_4$)-alkyl-O—, ($C_1$-$C_4$)-alkyl-S(O)$_m$—, $H_2$N—, ($C_1$-$C_4$)-alkyl-NH—, ($C_1$-$C_4$)-alkyl-N(($C_1$-$C_4$)-alkyl)-, ($C_1$-$C_4$)-alkyl-C(O)— and NC—, or $R^{13}$ or $R^{14}$, together with the one of the groups $R^{21}$ and $R^{22}$ which is not the group of the formula II, forms a chain consisting of 3 to 5 chain members of which 0, 1 or 2 chain members are identical or different hetero chain members chosen from the series consisting of N($R^{17}$), O and S, but two hetero chain members cannot be present in adjacent positions, and the other chain members are identical or different groups C($R^{18}$)($R^{18}$);
$R^{17}$ and $R^{25}$ are independently of each other chosen from the series consisting of hydrogen and ($C_1$-$C_4$)-alkyl;
$R^{18}$, independently of each other group $R^{18}$, is chosen from the series consisting of hydrogen, fluorine and ($C_1$-$C_4$)-alkyl, or two of the groups $R^{18}$ bonded to the same carbon atom, together with the carbon atom carrying them, form a 3-membered to 6-membered cycloalkane ring which is optionally substituted by one more identical or different substituents chosen from the series consisting of fluorine and ($C_1$-$C_4$)-alkyl;
$R^{20}$ is chosen from the series consisting of hydrogen and ($C_1$-$C_4$)-alkyl; one of the groups $R^{21}$ and $R^{22}$ is a group of the formula II $$R^{24}\text{—}R^{23}\text{—}$$

II and the other of the groups $R^{21}$ and $R^{22}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, $H_2$N—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, $H_2$N—C(O)—, $R^{30}$—NH—C(O)—, $R^{30}$—N($R^{30}$)—C(O)—, $H_2$N—S(O)$_2$—, $R^{30}$—NH—S(O)$_2$—, $R^{30}$—N($R^{30}$)—S(O)$_2$—, NC—, $O_2$N— and Het$^1$, or together with $R^{13}$ or $R^{14}$ forms a chain as specified in the definition of $R^{13}$ and $R^{14}$;
$R^{23}$ is a direct bond or a chain consisting of 1 to 5 chain members of which 0, 1 or 2 chain members are identical or different hetero chain members chosen from the series consisting of N($R^{25}$), O, S, S(O) and S(O)$_2$, but two hetero chain members can be present in adjacent positions only if one of them is chosen from the series consisting of S(O) and S(O)$_2$ and the other is chosen from the series consisting of N($R^{25}$), O and S, and the other chain members are identical or different groups C($R^{26}$)($R^{26}$);
$R^{24}$ is a 3-membered to 10-membered, monocyclic or bicyclic ring, which is saturated and contains 0 or 1 hetero ring members, or is unsaturated and contains 0, 1 or 2 identical or different hetero ring members, wherein the hetero ring members are chosen from the series consisting of N, N($R^{32}$), O, S, S(O) and S(O)$_2$, and wherein the ring is optionally substituted on ring carbon atoms by one or more identical or different substituents chosen from the series consisting of halogen, $R^{33}$, oxetanyl, HO—, $R^{33}$—O—, $R^{33}$—C(O)—O—, $R^{33}$—S(O)$_2$—O—, $R^{33}$—S(O)$_m$—, $H_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, $H_2$N—S(O)$_2$—NH—, $R^{33}$—NH—S(O)$_2$—NH—, $R^{33}$—N($R^{33}$)—S(O)$_2$ —NH—, $H_2N$—$S(O)_2$—$N(R^{71})$—, $R^{33}$—NH—$S(O)_2$—N$(R^{71})$—, $R^{33}$—$N(R^{33})$—$S(O)_2$—$N(R^{71})$—, $R^{33}$—C(O)—, HO—C(O)—, $R^{33}$—O—C(O)—, $H_2N$—C(O)—, $R^{33}$—NH—C(O)—, $R^{33}$—$N(R^{33})$—C(O)—, $H_2N$—$S(O)_2$—, $R^{33}$—NH—$S(O)_2$—, $R^{33}$—$N(R^{33})$—$S(O)_2$—, NC—, $O_2N$— and oxo;

$R^{26}$, independently of each other group $R^{26}$, is chosen from the series consisting of hydrogen, fluorine, $(C_1$-$C_4)$-alkyl and HO—, or two groups $R^{26}$ bonded to the same carbon atom together are oxo, or two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, $N(R^{34})$, O, S, S(O) and $S(O)_2$, which ring is optionally substituted on ring carbon atoms by one more identical or different substituents chosen from the series consisting of fluorine and $(C_1$-$C_4)$-alkyl;

$R^{32}$ and $R^{34}$ are independently of each other chosen from the series consisting of hydrogen, $R^{35}$, $R^{35}$—$S(O)_2$—, $R^{35}$—C(O)—, $R^{35}$—O—C(O)— and phenyl;

$R^{50}$ is chosen from the series consisting of $R^{51}$—O— and $R^{52}$—$N(R^{53})$—;

$R^{51}$ is chosen from the series consisting of hydrogen and $R^{54}$;

$R^{52}$ is chosen from the series consisting of hydrogen, $R^{55}$, NC— and $R^{56}$—$S(O)_2$—;

$R^{53}$ is chosen from the series consisting of hydrogen and $R^{57}$;

$R^{56}$ is chosen from the series consisting of $R^{58}$ and phenyl;

$R^{60}$, independently of each other group $R^{60}$, is chosen from the series consisting of hydrogen and $(C_1$-$C_4)$-alkyl;

$R^{70}$ is chosen from the series consisting of HO—, $R^{71}$—O—, $R^{71}$—C(O)—O—, $R^{71}$—$S(O)_m$—, $H_2N$—, $R^{71}$—NH—, $R^{71}$—$N(R^{71})$—, $R^{71}$—C(O)—NH—, $R^{71}$—C(O)—N$(R^{71})$—, $R^{71}$—$S(O)_2$—NH—, $R^{71}$—$S(O)_2$—$N(R^{71})$—, HO—C(O)—, $R^{71}$—O—C(O)—, $H_2N$—C(O)—, $R^{71}$—NH—C(O)—, $R^{71}$—$N(R^{71})$—C(O)—, $H_2N$—$S(O)_2$—, $R^{71}$—NH—$S(O)_2$—, $R^{71}$—$N(R^{71})$—$S(O)_2$— and oxo;

$R^{71}$, independently of each other group $R^{71}$, is chosen from $(C_1$-$C_4)$-alkyl, $(C_3$-$C_4)$-cycloalkyl and $(C_3$-$C_4)$-cycloalkyl-$(C_1$-$C_2)$-alkyl-;

Het$^1$ is a monocyclic 4-membered to 7-membered heterocyclic ring which comprises 1 or 2 identical or different hetero ring members chosen from the series consisting of N, $N(R^{60})$, O, S, S(O) and $S(O)_2$, which ring is saturated and is optionally substituted by one or more identical or different substituents chosen from the series consisting of fluorine and $(C_1$-$C_4)$-alkyl;

m, independently of each other number m, is an integer chosen from the series consisting of 0, 1 and 2;

phenyl, independently of each other group phenyl, is optionally substituted by one or more identical or different substituents chosen from the series consisting of halogen, $(C_1$-$C_4)$-alkyl, $(C_1$-$C_4)$-alkyl-O— and NC—, unless specified otherwise;

cycloalkyl, independently of each other group cycloalkyl, and independently of any other substituents on cycloalkyl, is optionally substituted by one or more identical or different substituents chosen from fluorine and $(C_1$-$C_4)$-alkyl;

alkyl, alkenyl and alkynyl, independently of each other group alkyl, alkenyl and alkynyl, and independently of any other substituents on alkyl, alkenyl and alkynyl, is optionally substituted by one or more fluorine substituents;

provided that the compound of the formula I is not 1-[(biphenyl-4-carbonyl)-amino]-cyclohexanecarboxylic acid, 1-[4-(2-pyrrolidin-1-yl-ethoxy)-benzoylamino]-cyclohexanecarboxylic acid, 1-[4-(2-piperidin-1-yl-ethoxy)-benzoylamino]-cyclohexanecarboxylic acid, 1-[4-(2-oxo-pyrrolidin-1-yl)-benzoylamino]-cyclohexanecarboxylic acid, 1-{[4-(2-oxo-pyrrolidin-1-yl)-furan-2-carbonyl]-amino}-cyclohexanecarboxylic acid, 1-[(2',3-dichloro-biphenyl-4-carbonyl)-amino]-cycloheptanecarboxylic acid, 1-[4-(4,6-dimethyl-pyrimidin-2-ylsulfanyl)-benzoylamino]-cyclopentanecarboxylic acid ethyl ester, 1-[4-(4-oxo-piperidin-1-yl)-benzoylamino]-cyclopropanecarboxylic acid methyl ester or 1-[2-chloro-4-(3-hydroxy-benzylcarbamoyl)-benzoylamino]-cyclopropanecarboxylic acid.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO-substituted alkyl group (hydroxyalkyl group). Depending on the respective definition, the number of carbon atoms in an alkyl group can be 1, 2, 3, 4, 5 or 6, or 1, 2, 3 or 4, or 1, 2 or 3, or 1 or 2, or 1. In one embodiment of the invention, a $(C_1$-$C_6)$-alkyl group present in any position of the compounds of the formula I is a $(C_1$-$C_4)$-alkyl group, in another embodiment a $(C_1$-$C_3)$-alkyl group, in another embodiment a $(C_1$-$C_2)$-alkyl group, in another embodiment a $(C_2$-$C_3)$-alkyl group, in another embodiment a methyl group, where any $(C_1$-$C_6)$-alkyl group present in the compounds of the formula I can independently of each other $(C_1$-$C_6)$-alkyl group be a group of any of these embodiments. In one embodiment of the invention, a $(C_1$-$C_4)$-alkyl group present in any position of the compounds of the formula I is a $(C_1$-$C_3)$-alkyl group, in another embodiment a $(C_1$-$C_2)$-alkyl group, in another embodiment a $(C_2$-$C_3)$-alkyl group, in another embodiment a methyl group, where any $(C_1$-$C_4)$-alkyl group present in the compounds of the formula I can independently of each other $(C_1$-$C_4)$-alkyl group be a group of any of these embodiments. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Examples of alkyl-O— groups are methoxy, ethoxy, n-propoxy, isopropoxy, n-butoxy, isobutoxy, tert-butoxy, n-pentoxy. Examples of alkyl-$S(O)_m$— are methylsulfanyl-($CH_3$—S—), methanesulfinyl-($CH_3$—S(O)—), methanesulfonyl ($CH_3$—$S(O)_2$—), ethylsulfanyl-($CH_3$—$CH_2$—S—), ethanesulfinyl-($CH_3$—$CH_2$—S(O)—), ethanesulfonyl ($CH_3$—$CH_2$—$S(O)_2$—), 1-methylethylsulfanyl-(($CH_3)_2$CH—S—), 1-methylethanesulfinyl-(($CH_3)_2$CH—S(O)—), 1-methylethanesulfonyl (($CH_3)_2$CH—$S(O)_2$—). In one embodiment of the invention the number m is chosen from 0 and 2, wherein all numbers m are independent of each other and can be identical or different. In another embodiment the number m in any of its occurrences is, independent of its meaning in other occurrences, 0. In another embodiment the number m in any of its occurrences is, independent of its meaning in other occurrences, 2.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I.

An alkyl group which is optionally substituted by one or more fluorine substituents can be unsubstituted, i.e. not carry fluorine substituents, or substituted, for example by 1, 2, 3, 4, 5, 6, 7, 8, 9, 10 or 11 fluorine substituents, or by 1, 2, 3, 4, 5, 6 or 7 fluorine substituents, or by 1, 2, 3, 4 or 5 fluorine substituents, or by 1, 2 or 3 fluorine substituents, which can be located in any positions. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-$S(O)_m$— groups are trifluoromethylsulfanyl-($CF_3$—S—), trifluoromethanesulfinyl-($CF_3$—S(O)—) and trifluoromethanesulfonyl ($CF_3$—$S(O)_2$—).

The above explanations with respect to alkyl groups apply correspondingly to unsaturated hydrocarbon residues, i.e. alkenyl groups, which in one embodiment of the invention contain one double bond, and alkynyl groups, which in one embodiment of the invention contain one triple bond. Thus, for example, alkenyl groups and alkynyl groups can likewise be linear or branched, and substituted alkenyl and alkynyl groups can be substituted in any positions, provided that the resulting compound is sufficiently stable and is suitable as a pharmaceutical active compound. Double bonds and triple bonds can be present in any positions. The number of carbon atoms in an alkenyl or alkynyl group can be 2, 3, 4, 5 or 6, for example 2, 3, 4 or 5, or 2, 3 or 4. Examples of alkenyl and alkynyl are ethenyl (vinyl), prop-1-enyl, prop-2-enyl(allyl), but-2-enyl, 2-methylprop-2-enyl, 3-methylbut-2-enyl, hex-3-enyl, hex-4-enyl, 4-methylhex-4-enyl, ethynyl, prop-1-ynyl, prop-2-ynyl(propargyl), but-2-ynyl, but-3-ynyl, 4-methylpent-2-ynyl, hex-4-ynyl and hex-5-ynyl. In one embodiment of the invention, an alkenyl or alkynyl group contains at least three carbon atoms and is bonded to the remainder of the molecule via a carbon atom which is not part of a double bond or triple bond.

The above explanations with respect to alkyl groups apply correspondingly to alkanediyl groups (divalent alkyl groups), including chains of one or more groups $C(R^{26})(R^{26})$ and chains of one or more groups $C(R^{18})(R^{18})$ which groups as such and chains of such groups are alkanediyl groups in case $R^{26}$ and $R^{18}$ is chosen from hydrogen and ($C_1$-$C_4$)-alkyl, or are substituted alkanediyl groups in case any of the groups $R^{26}$ and $R^{18}$ has a meaning different from hydrogen and ($C_1$-$C_4$)-alkyl. Likewise, the alkyl part of a substituted alkyl group can also be regarded as an alkanediyl group. Thus, alkanediyl groups can also be linear or branched, the bonds to the adjacent groups can be located in any positions and can start from the same carbon atom or from different carbon atoms, and they can be substituted by fluorine substituents. Examples of alkanediyl groups are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$—, —$CH_2$—$C(CH_3)_2$—. Examples of fluoro-substituted alkanediyl groups, which can contain 1, 2, 3, 4, 5 or 6 fluorine substituents, or 1, 2, 3 or 4 fluorine substituents, or 1 or 2 fluorine substituents for example, are —CHF—, —$CF_2$—, —$CF_2$—$CH_2$—, —$CH_2$—$CF_2$—, —$CF_2$—$CF_2$—, —CF($CH_3$)—, —$C(CF_3)_2$—, —$C(CH_3)_2$—$CF_2$—, —$CF_2$—$C(CH_3)_2$—.

The number of ring carbon atoms in a ($C_3$-$C_7$)-cycloalkyl group can be 3, 4, 5, 6 or 7. Examples of cycloalkyl are cyclopropyl, cyclobutyl, cyclopentyl, cyclohexyl and cycloheptyl. Cycloalkyl groups which are optionally substituted by one or more ($C_1$-$C_4$)-alkyl substituents, can be unsubstituted, i.e. not carry alkyl substituents, or substituted, for example by 1, 2, 3 or 4, or by 1 or 2, identical or different ($C_1$-$C_4$)-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl and 3,3,5,5-tetramethylcyclohexyl. Cycloalkyl groups which are optionally substituted by one or more fluorine substituents, can be unsubstituted, i.e. not carry fluorine substituents, or substituted, for example by 1, 2, 3, 4, 5, 6, 7, 8, 9, 10 or 11 fluorine substituents, or by 1, 2, 3, 4, 5 or 6 fluorine substituents, or by 1, 2, 3 or 4 fluorine substituents, or by 1 or 2 fluorine substituents. The fluorine substituents can be located in any positions of the cycloalkyl group and can also be located in an alkyl substituent on the cycloalkyl group. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl and 3,3,4,4,5,5-hexafluorocyclohexyl. Cycloalkyl groups can also be substituted simultaneously by fluorine and alkyl. Examples of the group ($C_3$-$C_7$)-cycloalkyl-($C_1$-$C_4$)-alkyl- are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. The explanations with respect cycloalkyl groups apply correspondingly to unsaturated cycloalkyl groups such as cycloalkenyl groups which can occur in the group $R^{24}$ and which in one embodiment of the invention contain one double bond which can be present in any positions, and to divalent cycloalkyl groups (cycloalkanediyl groups), which latter groups can occur in case two of the groups $R^{26}$ together with the comprised chain members form a ring or two of the groups $R^{18}$ together with the carbon atom carrying them form a ring. Likewise, the cycloalkyl part of a substituted cycloalkyl group can also be regarded as a cycloalkanediyl group. Thus, for example, the bonds through which a cycloalkanediyl group, such as a ring formed by two of the groups $R^{26}$ together with the comprised chain members, is connected to the adjacent groups, can be located in any positions and can start from the same ring carbon atom or from different ring carbon atoms, unless specified otherwise.

In substituted phenyl groups, including phenyl groups which represent the 3-membered to 10-membered, monocyclic or bicyclic ring representing $R^{24}$, the substituents can be located in any positions. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. If a phenyl group carries four substituents, some of which can be fluorine atoms, for example, the substituents can be located in 2,3,4,5-position, 2,3,4,6-position or 2,3,5,6-position. If a polysubstituted phenyl group or any other polysubstituted group such as a heteroaryl group carries different substituents, each substituent can be located in any suitable position, and the present invention comprises all positional isomers. The number of substituents in a substituted phenyl group can be 1, 2, 3, 4 or 5. In one embodiment of the invention, a substituted phenyl group, and likewise another substituted group such as a heteroaryl group, carries 1, 2 or 3, for example 1 or 2, identical or different substituents.

In heterocyclic groups, including the group $Het^1$ and heterocyclic rings which can be present in structural elements in the compounds of the formula I, such as the ring A, or the 3-membered to 10-membered ring representing $R^{24}$, or a ring formed by a group $R^{25}$ and a group $R^{26}$ together with the comprised chain members, or a ring formed by a group $R^{13}$ or $R^{14}$ with one of the groups $R^{21}$ and $R^{22}$ and the carbon atoms carrying these groups, for example, the hetero ring members specified in the respective definition can be present in any combination and located in any suitable ring positions, provided that the resulting group and the compound of the formula I are sufficiently stable and suitable as a pharmaceutical active compound. In one embodiment of the invention two oxygen atoms in any heterocyclic ring in the compounds of the formula I cannot be present in adjacent ring positions. In another embodiment of the invention two hetero ring members in any non-aromatic heterocyclic ring in the compounds of the formula I cannot be present in adjacent ring positions. In another embodiment two hetero ring members from the series consisting of O, S and N atoms carrying a hydrogen atom or a substituent, cannot be present in adjacent ring positions. Examples of such series are the hetero ring members O, S and $N(R^0)$, or O, S and $N(R^{32})$, or O, S and $N(R^{34})$, or O, S and $N(R^{60})$, or the hetero chain members O, S and $N(R^{17})$ which are part of a ring. In another embodiment of the invention two hetero ring members from the series consisting of $S(O)$ and $S(O)_2$ cannot be present in adjacent ring positions. In an aromatic heterocyclic ring the choice of hetero ring members and their positions is limited by the prerequisite that the ring is aromatic, i.e. it comprises a cyclic system of six delocalized pi electrons. The residue of a monocyclic, 5-membered or 6-membered, aromatic heterocyclic ring, which can occur as the 3-membered to 10 membered ring representing $R^{24}$, can also be designated as monocyclic, 5-membered or 6-membered heteroaryl group. The ring nitrogen atom in such a heteroaryl group which carries the group $R^{32}$, is the ring nitrogen atom in a 5-membered ring such as pyrrole, pyrazole or imidazole to which an exocyclic atom or group such as a hydrogen atom is bonded, and can be present once only in a 5-membered aromatic ring just as the hetero ring members O and S. Examples of rings from which such a heteroaryl group can be derived are pyrrole, furan, thiophene, imidazole, pyrazole, oxazole ([1,3]oxazole), isoxazole ([1,2]oxazole), thiazole ([1,3]thiazole), isothiazole ([1,2]thiazole), pyridine, pyridazine, pyrimidine, pyrazine. In one embodiment of the invention, a monocyclic, 5-membered or 6-membered heteroaryl group comprises one hetero ring member which is defined as indicated, and in another embodiment of the invention such a heteroaryl group is chosen from thiophenyl, thiazolyl and pyridinyl, in another embodiment from thiophenyl and pyrazolyl, in another embodiment from pyridinyl, thiophenyl and pyrazolyl, in another embodiment from thiophenyl and pyridinyl, and in another embodiment it is thiophenyl. A monocyclic, 5-membered or 6-membered heteroaryl group can be bonded via any ring carbon atom or, in the case of a 5-membered ring comprising a hetero ring member $N(R^{32})$, via a ring nitrogen atom, wherein in the latter case the bond via which the heteroaryl group is attached to the remainder of the molecule, replaces the group $R^{32}$. In one embodiment of the invention, a monocyclic, 5-membered or 6-membered heteroaryl group is bonded via a ring carbon atom. For example, a thiophenyl group (thienyl group) can be thiophen-2-yl (2-thienyl) or thiophen-3-yl (3-thienyl), furanyl can be furan-2-yl or furan-3-yl, pyridinyl(pyridyl) can be pyridin-2-yl, pyridin-3-yl or pyridin-4-yl, pyrazolyl can be 1H-pyrazol-3-yl, 1H-pyrazol-4-yl or 2H-pyrazol-3-yl, imidazolyl can be 1H-imidazol-1-yl, 1H-imidazol-2-yl, 1H-imidazol-4-yl or 3H-imidazolyl-4-yl, thiazolyl can be thiazol-2-yl, thiazol-4-yl or thiazol-5-yl.

In substituted monocyclic, 5-membered or 6-membered heteroaryl groups, the substituents can be located in any positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position. In one embodiment of the invention, a substituted monocyclic, 5-membered or 6-membered heteroaryl group is substituted by 1, 2 or 3, for example 1 or 2, identical or different substituents. Generally, besides optionally carrying the substituents indicated in the definition of the group, suitable ring nitrogen atoms in a monocyclic, 5-membered or 6-membered heteroaryl group representing $R^{24}$ or the aromatic ring comprising the groups Y and Z which are depicted in formula I, for example the nitrogen atom in a pyridinyl group, can also carry an oxido substituent $—O^-$ and be present as an N-oxide.

The above explanations with respect to monocyclic, 5-membered or 6-membered aromatic heterocyclic groups apply correspondingly to the bicyclic aromatic heterocyclic groups discussed below which can occur in the 3-membered to 10-membered ring representing $R^{24}$ and which can also be designated as a bicyclic heteroaryl group.

The rings of the groups $Het^1$ can be 4-membered, 5-membered, 6-membered or 7-membered, for example 4-membered, 5-membered or 6-membered, or 4-membered or 5-membered, or 5-membered or 6-membered. The group $Het^1$ can be bonded via any ring carbon atom or ring nitrogen atom. In one embodiment of the invention, $Het^1$ is bonded via a ring carbon atom. Examples of the group $Het^1$ from any one or more of which $Het^1$ can be chosen, are azetidinyl including azetidin-1-yl, oxetanyl including oxetan-3-yl, tetrahydrofuranyl including tetrahydrofuran-2-yl and tetrahydrofuran-3-yl, tetrahydrothiophenyl including tetrahydrothiophen-2-yl and tetrahydrothiophen-3-yl, 1-oxo-tetrahydrothiophenyl including 1-oxo-tetrahydrothiophen-2-yl and 1-oxo-tetrahydrothiophen-3-yl, 1,1-dioxo-tetrahydrothiophenyl including 1,1-dioxo-tetrahydrothiophen-2-yl and 1,1-dioxo-tetrahydrothiophen-3-yl, pyrrolidinyl including pyrrolidin-1-yl, pyrrolidin-2-yl and pyrrolidin-3-yl, tetrahydropyranyl including tetrahydropyran-2-yl, tetrahydropyran-3-yl and tetrahydropyran-4-yl, tetrahydrothiopyranyl including tetrahydrothiopyran-2-yl, tetrahydrothiopyran-3-yl and tetrahydrothiopyran-4-yl, piperidinyl including piperidin-1-yl, piperidin-2-yl, piperidin-3-yl and piperidin-4-yl, oxepanyl including oxepan-2-yl, oxepan-3-yl and oxepan-4-yl, azepanyl including azepan-1-yl, azepan-2-yl, azepan-3-yl and azepan-4-yl, 1,3-dioxolanyl including 1,3-dioxolan-2-yl and 1,3-dioxolan-4-yl, imidazolidinyl including imidazolidin-1-yl, imidazolidin-2-yl and imidazolidin-4-yl, [1,3]oxazolidinyl including [1,3]oxazolidin-2-yl, [1,3]oxazolidin-3-yl, [1,3]oxazolidin-4-yl and [1,3]oxazolidin-5-yl, [1,3]thiazolidinyl including [1,3]thiazolidin-2-yl, [1,3]thiazolidin-3-yl, [1,3]thiazolidin-4-yl and [1,3]thiazolidin-5-yl, [1,3]dioxanyl including [1,3]dioxan-2-yl, [1,3]dioxan-4-yl and [1,3]dioxan-5-yl, [1,4]dioxanyl including [1,4]dioxan-2-yl, piperazinyl including piperazin-1-yl and piperazin-2-yl, morpholinyl including morpholin-2-yl, morpholin-3-yl and morpholin-4-yl, thiomorpholinyl including thiomorpholin-2-yl, thiomorpholin-3-yl and thiomorpholin-4-yl, 1-oxo-thiomorpholinyl including 1-oxo-thiomorpholin-2-yl, 1-oxo-thiomorpholin-3-yl and 1-oxo-thiomorpholin-4-yl, 1,1-dioxo-thiomorpholinyl including 1,1-dioxo-thiomorpholin-2-yl, 1,1-dioxo-thiomorpholin-3-yl and 1,1-dioxo-thiomorpholin-4-yl, [1,3]diazepanyl, [1,4]diazepanyl, [1,4]oxazepanyl or [1,4]thiazepanyl. Besides by oxo groups in the ring members S(O) and S(O)$_2$ and alkyl groups representing $R^{60}$, the group Het$^1$ is optionally substituted on ring carbon atoms by one or more, for example 1, 2, 3, 4 or 5, or 1, 2, 3 or 4, or 1, 2 or 3, or 1 or 2, identical or different substituents as indicated, which can be located in any positions.

The 3-membered to 10-membered, monocyclic or bicyclic ring which is saturated or unsaturated and which contains 0, 1 or 2 identical or different hetero ring members chosen from the series consisting of N, N($R^{32}$), O, S, S(O) and S(O)$_2$, which ring represents $R^{24}$, can comprise 3, 4, 5, 6, 7, 8, 9 or 10 ring members. In one embodiment of the invention, a bicyclic ring representing $R^{24}$ is fused or bridged. An unsaturated ring can be partially unsaturated, i.e. non-aromatic, and contain, for example, one or two double bonds within the ring, or it can be aromatic and be a ring such as a benzene ring, for example, and altogether the number of double bonds within an unsaturated ring can be one, two, three, four or five. In a bicyclic ring, the two individual rings can independently of each other be saturated or partially unsaturated or aromatic. In one embodiment of the invention, a 3-membered or 4-membered ring representing $R^{24}$ is saturated. The 3-membered to 10-membered, monocyclic or bicyclic ring can be a carbocyclic ring, i.e. contain 0 (zero) hetero ring members, or a heterocyclic ring in which hetero ring members can be present as indicated above. In a bicyclic heterocyclic ring one or both individual rings can contain hetero ring members. In case nitrogen atoms are present as hetero ring members in a bicyclic ring, they can also be present at a fusion position or a bridgehead position. The free bond via which the ring is bonded to the group $R^{23}$, can be located at any suitable ring carbon atom or ring nitrogen atom. In one embodiment of the invention the free bond is located at a ring carbon atom. In general, besides by oxo groups in the ring members S(O) and S(O)$_2$ and substituents $R^{32}$ on ring nitrogen atoms, the 3-membered to 10 membered ring is optionally substituted on ring carbon atoms by one or more, for example 1, 2, 3, 4 or 5, or 1, 2, 3 or 4, or 1, 2 or 3, or 1 or 2, identical or different substituents as indicated, which can be located in any positions.

The 3-membered to 10-membered, monocyclic or bicyclic ring representing $R^{24}$ comprises (C$_3$-C$_7$)-cycloalkyl groups, phenyl groups, monocyclic, 5-membered or 6-membered aromatic heterocyclic groups and monocyclic 4-membered to 7-membered saturated groups as are comprised by the definitions of the group Het$^1$ referred to above. All these groups thus are examples of the said 3-membered to 10-membered ring, and all explanations given above with respect to these groups apply correspondingly to the said 3-membered to 10-membered ring unless specified otherwise in the definition of the said 3-membered to 10-membered ring. Thus, for example, the substituents in these groups when representing the said 3-membered 5 to 10-membered ring, such as in a phenyl group representing the said 3-membered 5 to 10-membered ring, can then be as is specified in the definition of $R^{24}$. As further examples of cyclic groups which are comprised by the said 3-membered to 10-membered ring, (C$_5$-C$_7$)-cycloalkenyl groups, naphthalenyl groups and hydrogenated naphthalenyl groups, indenyl groups and hydrogenated indenyl groups, bicyclic heterocyclic groups, and bicycloalkyl and bicycloalkenyl groups and hetero analogs thereof may be mentioned.

In a (C$_5$-C$_7$)-cycloalkenyl group representing $R^{24}$, the number of ring carbon atoms can be 5, 6 or 7. Examples of cycloalkenyl groups are cyclopentenyl including cyclopent-1-enyl, cyclopent-2-enyl and cyclopent-3-enyl, cyclohexyl including cyclohex-1-enyl, cyclohex-2-enyl and cyclohex-3-enyl, and cycloheptyl including cyclohept-1-enyl, cyclohept-2-enyl, cyclohept-3-enyl and cyclohept-4-enyl. Cycloalkenyl groups representing $R^{24}$ can be unsubstituted or substituted as indicated with respect to the 3-membered to 10-membered ring representing $R^{24}$, for example by one or more, or 1, 2, 3 or 4, or 1, 2 or 3, identical or different (C$_1$-C$_4$)-alkyl substituents, for example by methyl groups, which can be located in any positions. Examples of such alkyl-substituted cycloalkenyl groups are 1-methylcyclopent-2-enyl, 1-methylcyclopent-3-enyl, 2,3-dimethylcyclohex-2-enyl and 3,4-dimethylcyclohex-3-enyl. Cycloalkenyl groups also are optionally substituted by one or more fluorine substituents, i.e., they can be unsubstituted by fluorine and not carry any fluorine substituents, or substituted, for example by 1, 2, 3, 4, 5, 6 or 7, or by 1, 2, 3, 4 or 5, or by 1, 2, 3 or 4, fluorine substituents. Cycloalkenyl groups can also be substituted simultaneously by fluorine and alkyl. The fluorine atoms can be located in any positions of the cycloalkenyl group and can also be located in an alkyl substituent on the cycloalkenyl group. Examples of fluoro-substituted cycloalkyl groups are 1-fluorocyclohex-2-enyl, 1-fluorocyclohex-3-enyl and 4,4-difluorocyclohex-2-enyl.

Naphthalenyl groups (naphthyl groups) representing $R^{24}$ can be naphthalen-1-yl (1-naphthyl) and naphthalen-2-yl (2-naphthyl) groups, and are optionally substituted by one or more, for example by 1, 2, 3, 4 or 5, or by 1, 2 or 3, for example by 1 or 2, identical or different substituents as indicated above. The substituents in a substituted naphthalenyl group can be located in any positions, for example in the 2-position, 3-position, 4-position, 5-position, 6-position, 7-position or 8-position in the case of a monosubstituted naphthalen-1-yl group and in the 1-position, 3-position, 4-position, 5-position, 6-position, 7-position or 8-position in the case of a monosubstituted naphthalen-2-yl group. Likewise, in a naphthalenyl group which carries two or more substituents, the substituents can be located in the ring to which the remainder of the molecule is bonded, and/or in the other ring. Examples of hydrogenated naphthalenyl groups representing $R^{24}$ are dihydronaphthalenyl including 1,4-dihydronaphthalenyl, tetrahydronaphthalenyl including 1,2,3,4-tetrahydronaphthalenyl and 5,6,7,8-tetrahydronaphthalenyl, octahydronaphthalenyl including 1,2,3,4,5,6,7,8-octahydronaphthalenyl, and decahydronaphthalenyl. Hydrogenated naphthalenyl groups can be bonded to the remainder of the molecule via any ring carbon atom in a saturated or partially unsaturated or aromatic ring and are optionally substituted by one or more, for example by 1, 2, 3, 4 or 5, or by 1, 2 or 3, for example by 1 or 2, identical or different substituents as indicated above which can be located in any positions.

Indenyl groups representing $R^{24}$ can be 1H-inden-1-yl, 1H-inden-2-yl, 1H-inden-3-yl, 1H-inden-4-yl, 1H-inden-5-yl, 1H-inden-6-yl or 1H-inden-7-yl, for example, and are optionally substituted by one or more, for example by 1, 2, 3, 4 or 5, or by 1, 2 or 3, for example by 1 or 2, identical or different substituents as indicated above which can be located in any positions. Examples of hydrogenated indenyl groups representing $R^{24}$ are indanyl (2,3-dihydro-1H-indenyl) and octahydroindenyl (=octahydro-1H-indenyl), which can be bonded to the remainder of the molecule via any ring carbon atom in a saturated or partially unsaturated or aromatic ring, for example via the 1-position, 2-position, 4-position or 5-position in the case of an indanyl group, and are optionally substituted by one or more, for example by 1, 2, 3, 4 or 5, or by 1, 2 or 3, for example by 1 or 2, identical or different substituents as indicated above which can be located in any positions.

In one embodiment of the invention, bicyclic heterocyclic groups representing $R^{24}$ are fused bicyclic groups in which the two rings have a bond in common, and can be saturated, partially unsaturated or aromatic as indicated above with respect to the 3-membered to 10-membered ring representing $R^{24}$ in general. They can contain 1, 2, 3, 4 or 5 double bonds within the rings. Both of the rings can be saturated, or one of the rings can be saturated or partially unsaturated and the other ring partially unsaturated or aromatic, or both rings can be aromatic, i.e. comprise a cyclic system of six delocalized pi electrons. In one embodiment of the invention, both rings are aromatic or one of the rings is aromatic and the other ring is partially unsaturated and comprises at least one double bond due to the condensation to the aromatic ring. In one embodiment of the invention, a bicyclic heterocyclic group comprises 8, 9 or 10 ring members and two fused 5-membered rings or two fused 6-membered rings or a 6-membered ring fused to a 5-membered ring or a 7-membered ring fused to a 5-membered ring, in another embodiment 9 or 10 ring members and two fused 6-membered rings or a 6-membered ring fused to a 5-membered ring. Hetero ring members can be present in both rings of a bicyclic heterocyclic group or in one of the rings only and the other ring contain no hetero ring members. Ring nitrogen atoms can also be common to both rings. Besides being a hetero ring member in a 3-membered to 10-membered rings representing $R^{24}$ such as saturated rings, a ring nitrogen atom carrying a group $R^{32}$ can be the ring nitrogen atom in a fused 5-membered ring in an aromatic bicyclic heterocyclic group, such as in a fused pyrrole, pyrazole or imidazole, to which an exocyclic atom or group is bonded. Examples of rings from which a fused bicyclic heterocyclic group can be derived, are indole, isoindole, benzo[b]thiophene, benzofuran, benzo[1,3]dioxole ([1,3]benzodioxole, 1,2-methylenedioxybenzene), benzo[1,3]oxazole, benzo[1,3]thiazole, benzoimidazole, chromane, isochromane, benzo[1,4]dioxane ([1,4]benzodioxane, 1,2-ethylenedioxybenzene), quinoline, isoquinoline, cinnoline, quinazoline, quinoxaline, phthalazine, pyrroloazepines, imidazoazepines, thienothiophenes, thienopyrroles, thienopyridines, naphthyridines, and the respective rings in which one or some or all of the double bonds are hydrogenated, i.e. replaced with single bonds, such as 2,3-dihydro-1H-indole, 2,3-dihydro-1H-isoindole, 2,3-dihydrobenzofuran, 1,2,3,4-tetrahydroquinoline, 5,6,7,8-tetrahydroquinoline, decahydroquinoline, 1,2,3,4-tetrahydroisoquinoline, 5,6,7,8-tetrahydroisoquinoline, decahydroisoquinoline, for example. A bicyclic heterocyclic group can be bonded via any ring carbon atom or ring nitrogen atom. In one embodiment of the invention, a bicyclic heteroaromatic group is bonded via a ring carbon atom. For example, an indolyl group can be indol-1-yl, indol-2-yl, indol-3-yl, indol-4-yl, indol-5-yl, indol-6- or indol-7-yl, a benzoimidazolyl group can be 1H-benzoimidazol-1-yl, 1H-benzoimidazol-2-yl, 1H-benzoimidazol-4-yl, 1H-benzoimidazol-5-yl, 1H-benzoimidazol-6-yl or 1H-benzoimidazol-7-yl, a benzo[1,4]dioxanyl group can be benzo[1,4]dioxan-2-yl, benzo[1,4]dioxan-5-yl or benzo[1,4]dioxan-6-yl, a quinolinyl group (quinolyl group) can be quinolin-2-yl, quinolin-3-yl, quinolin-4-yl, quinolin-5-yl, quinolin-6-yl, quinolin-7-yl or quinolin-8-yl, an isoquinolinyl group can be isoquinolin-1-yl, isoquinolin-3-yl, isoquinolin-4-yl, isoquinolin-5-yl, isoquinolin-6-yl, isoquinolin-7-yl or isoquinolin-8-yl. In a substituted bicyclic heteroaromatic group, the substituents can be located in any desired positions such as, for example, in an indol-2-yl group in the 1-position and/or the 3-position and/or the 4-position and/or the 5-position and/or the 6-position and/or the 7-position, in an indol-5-yl group in the 1-position and/or the 2-position and/or the 3-position and/or the 4-position and/or the 6-position and/or the 7-position, in a 1H-benzoimidazol-2-yl group in the 1-position and/or the 4-position and/or the 5-position and/or the 6-position and/or the 7-position. Generally, besides the substituents indicated above, a bicyclic heterocyclic group can also carry on suitable ring nitrogen atoms in aromatic rings, for example the nitrogen atom in a quinolinyl group or isoquinolinyl group, an oxido substituent —O⁻ and be present as an N-oxide.

In one embodiment of the invention, bicycloalkyl and bicycloalkenyl groups representing $R^{24}$ are bridged 6-membered to 10-membered, in another embodiment 7-membered to 10-membered and bicyclic groups which can contain carbon atoms only as ring members, i.e. they can be derived from carbocyclic bicycloalkanes and bicycloalkenes, or which can also contain hetero ring members as indicated above, i.e. they can be derived from the respective heteroanalogous aza-, oxa- and thia-bicycloalkanes and -bicycloalkenes. If they contain hetero ring members, in one embodiment they contain one hetero ring member, for example one ring member chosen from the series consisting of N, N($R^{32}$) and O. The hetero ring members can be present in any desired positions in the bicyclic system including positions in the bridges and, in the case of nitrogen atoms, positions at the bridgeheads. Bicycloalkenyl and their hetero analogs can contain one or more double bonds within the rings. In one embodiment of the invention they contain one or two double bonds, in another embodiment one double bond, within the ring. Bicycloalkyl and bicycloalkenyl can be bonded to the remainder of the molecule via any ring carbon atom or ring nitrogen atom. The free bond can be located in any stereochemical position, for example in an exo position or an endo position. Bicycloalkyl and bicycloalkenyl and their hetero analogs are optionally substituted as indicated above, for example by substituents chosen from the series consisting of ($C_1$-$C_4$)-alkyl, ($C_2$-$C_8$)-alkenyl, HO—, HO—$CH_2$— (hydroxymethyl-) and oxo, in any positions. Examples of bicycloalkyl and bicycloalkenyl groups and hetero analogs thereof are norbornyl(bicyclo[2.2.1]heptyl), bicyclo[3.1.1]heptyl, bicyclo[3.1.1]hept-2-enyl, bicyclo[2.2.2]octyl, bicyclo[2.2.2]oct-2-enyl, bicyclo[3.2.1]octyl, 7-azabicyclo[2.2.1]heptyl, 1-azabicyclo[2.2.2]octyl, bicyclo[2.2.2.]oct-2-en-yl.

Halogen is fluorine, chlorine, bromine or iodine. In one embodiment of the invention, halogen is fluorine, chlorine or bromine, in another embodiment fluorine or chlorine, in another embodiment fluorine.

An oxo group, i.e. an oxygen atom which is bonded via a double bond, when bonded to a carbon atom, replaces two hydrogen atoms on the carbon atom of the parent system to which it is bonded. Thus, if a $CH_2$ group is substituted by oxo, it becomes a carbonyl group (C(O), C=O). An oxo group cannot occur as a substituent on a carbon atom in an aromatic ring such as in a phenyl group. Similarly, a methylene group which can occur as a substituent on the ring A and in this case is a group $CH_2$ bonded via a double bond, replaces two hydrogen atoms on the carbon atom of the parent system to which it is bonded, thus forming the group $C=CH_2$.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups, can all independently of each other have the S configuration or the R configuration. The invention relates to enantiomers, both the levorotatory and the dextrorotatory antipode, in enantiomerically pure form and essentially enantiomerically pure form, for example with a molar ratio of the two enantiomers of 99:1 or greater, and in the form of racemates and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 99:1 or greater, and in the form of mixtures of the cis isomer and the trans isomer in all ratios. Cis/trans isomerism can occur in substituted rings, such as the ring A, and on double bonds, for example. The preparation of individual stereoisomers, if desired, can be carried out by resolution of a mixture according to customary methods, for example, by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts, including pharmaceutically utilizable salts, of the compounds of the formula I generally comprise a nontoxic salt component. They can contain inorganic or organic salt components. Such salts can be formed, for example, from compounds of the formula I which contain an acidic group, for example a carboxylic acid group (hydroxycarbonyl group, HO—C(O)—), and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formula I with bases for the preparation of the salts are in general carried out according to customary procedures in a solvent or diluent. Examples of salts of acidic groups thus are sodium, potassium, magnesium or calcium salts or ammonium salts which can also carry one or more organic groups on the nitrogen atom. Compounds of the formula I which contain a basic, i.e. protonatable, group, for example an amino group or a basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formula I by reaction with an acid in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange. The present invention also comprises active metabolites of compounds of the formula I and prodrugs of the compounds of the formula I, i.e. compounds which in vitro may not necessarily exhibit pharmacological activity but which in vivo are converted into pharmacologically active compounds of the formula I, for example compounds which are converted by metabolic hydrolysis into a compound of the formula I, such as compounds in which a carboxylic acid group is present in esterified form or in the form of an amide.

The ring A can be monocyclic, i.e. comprise one ring only, or bicyclic, i.e. comprise two rings which have two or more ring members and one or more bonds in common and can thus be bridged or fused, or spirocyclic, i.e. comprise two rings which have one ring member in common. The number of ring members in the ring A can be 3, 4, 5, 6, 7, 8, 9, 10, 11 or 12. In one embodiment of the invention, the ring A is 3-membered to 11-membered, in another embodiment 3-membered to 10-membered, in another embodiment 3-membered to 8-membered, in another embodiment 3-membered to 7-membered, in another embodiment 5-membered to 10-membered, in another embodiment 5-membered to 8-membered, in another embodiment 5-membered to 7-membered, in another embodiment 6-membered to 8-membered, in another embodiment 6-membered or 7-membered. In one embodiment of the invention, a monocyclic ring representing A is 3-membered to 8-membered, in another embodiment 3-membered to 7-membered, in another embodiment 5-membered to 8-membered, in another embodiment 5-membered to 7-membered, in another embodiment 6-membered to 8-membered, in another embodiment 6-membered or 7-membered, in another embodiment 3-membered, 6-membered or 7-membered. In one embodiment of the invention, a bicyclic ring representing A is 6-membered to 12-membered, in another embodiment 7-membered to 12-membered, in another embodiment 6-membered to 10-membered, in another embodiment 7-membered to 10-membered, in another embodiment 6-membered to 8-membered, in another embodiment 7-membered or 8-membered. In one embodiment of the invention, a spirocyclic ring representing A is 7-membered to 12-membered, in another embodiment 8-membered to 12-membered, in another embodiment 7-membered to 11-membered, in another embodiment 8-membered to 11-membered. In all these embodiments can the number of ring members in the ring A have all those values from the general number of ring members, i.e. 3, 4, 5, 6, 7, 8, 9, 10, 11 and 12, which are comprised by the respective embodiment. In case the ring A is a spiro-fused ring, in one embodiment of the invention comprises the ring which does not carry the groups $N(R^{20})$ and $C(O)—R^{50}$, 3, 4, 5 or 6 ring members including the spiro atom, in another embodiment 3, 4 or 5 ring members including the spiro atom. In one embodiment of the invention, the ring A is a monocyclic or bicyclic ring, in another embodiment a monocyclic or spirocyclic ring, in another embodiment it is a monocyclic ring, in another embodiment it is a bicyclic ring, in another embodiment it is a spirocyclic ring, wherein in all these embodiments the rings are as indicated above or below herein.

The carbon atom in the ring A which carries the two groups N(R$^{20}$) and C(O)—R$^{50}$, can be present in any ring position which allows for the binding of two groups. The hetero ring members in the ring A can be present in any combination and can be located in any suitable position, wherein generally the two ring members in the ring A which are adjacent to the ring carbon atom carrying the groups N(R$^{20}$) and C(O)—R$^{50}$ are carbon atoms, as is also depicted in formula I by the two vertices (corners) in the circumferential line of ring A which, like the vertex in the circumferential line representing the carbon atom which carries the two groups N(R$^{20}$) and C(O)—R$^{50}$, represent carbon atoms as usual in such structural formulae. In bicyclic rings representing A, the hetero ring members can be present in the bridges and, in the case of nitrogen atoms, at the bridgeheads. Likewise as mentioned with respect to heterocyclic rings in the compounds of the formula I in general, in one embodiment of the invention two hetero ring members from the series consisting of N(R$^0$), O and S are not present in adjacent ring positions, in another embodiment two hetero ring members from the series consisting of N(R$^0$), O and S are separated by at least two ring carbon atoms, in another embodiment two hetero ring members are not present in adjacent ring positions, in another embodiment two hetero ring members are separated by at least two ring carbon atoms. In one embodiment of the invention, the number of hetero ring members in the ring A is 0 or 1, in another embodiment it is 1, and in another embodiment it is 0, i.e. in this latter embodiment the ring A is a carbocyclic ring. In one embodiment of the invention, the hetero ring members in a heterocyclic ring representing A are chosen from O, S, S(O) and S(O)$_2$, in another embodiment from S, S(O) and S(O)$_2$, in another embodiment from S(O) and S(O)$_2$, in another embodiment from O and S, in another embodiment from O and N(R$^0$), in another embodiment they are O atoms, in another embodiment they are S atoms, in another embodiment they are N(R$^0$) groups. The double bond which can be present in the ring A, can be located in any suitable position. In one embodiment of the invention, the ring A is a 3-membered to 12-membered ring in case it is saturated, and a 5-membered to 12-membered ring in case it comprises a double bond, wherein in these embodiments all other features of the rings are as indicated above or below.

In one embodiment of the invention, the ring A is saturated and thus does not comprise a double bond in the ring, in another embodiment the ring A comprises one double bond.

Examples of rings A from any one or more of which the ring A is chosen in one embodiment of the invention, are (C$_3$-C$_8$)-cycloalkane rings, (C$_5$-C$_8$)-cycloalkane rings, cyclopropane, cyclobutane, cyclopentane, cyclohexane, cycloheptane, cyclooctane, cyclononane, (C$_5$-C$_8$)-cycloalkene rings, cyclopent-3-ene wherein the carbon atom carrying the two groups N(R$^{20}$) and C(O)—R$^{50}$ is in position 1, cyclohex-3-ene wherein the carbon atom carrying the two groups N(R$^{20}$) and C(O)—R$^{50}$ is in position 1, cyclohept-3-ene wherein the carbon atom carrying the two groups N(R$^{20}$) and C(O)—R$^{50}$ is in position 1, cyclohept-4-ene wherein the carbon atom carrying the two groups N(R$^{20}$) and C(O)—R$^{50}$ is in position 1, tetrahydrofuran with binding position 3, tetrahydrothiophene and 1-oxo-tetrahydrothiophene and 1,1-dioxo-tetrahydrothiophene all with binding position 3, pyran with binding position 3, pyran with binding position 4, tetrahydrothiopyran and 1-oxo-tetrahydrothiopyran and 1,1-dioxo-tetrahydrothiopyran all with binding position 3, tetrahydrothiopyran and 1-oxo-tetrahydrothiopyran and 1,1-dioxo-tetrahydrothiopyran all with binding position 4, oxepane with binding position 3, oxepane with binding position 4, thiepane and 1-oxo-thiepane and 1,1-dioxo-thiepane all with binding position 3, thiepane and 1-oxo-thiepane and 1,1-dioxo-thiepane all with binding position 4, bicyclo[2.2.1]heptane with binding position 2, bicyclo[3.1.1]heptane with binding position 3, bicyclo[3.2.1]octane with binding position 3, bicyclo[5.1.0]octane with binding position 4, bicyclo[2.2.1]hept-5-ene with binding position 2,7-oxabicyclo[2.2.1]heptane with binding position 2, spiro[2.4]heptane with binding position 5, spiro[2.5]octane with binding position 6, spiro[2,6]nonane with binding position 5, spiro[2.6]nonane with binding position 6, 1,4-dioxa-spiro[4,4]nonane with binding position 7, 1,4-dioxa-spiro[4.5]decane with binding position 8, 1,4-dioxa-spiro[4.6]undecane with binding position 7, or 1,4-dioxa-spiro[4.6]undecane with binding position 8, which all are optionally substituted as indicated above or below including, for example, substituted cyclohexane rings such as 2-fluoro-cyclohexane, 3-fluoro-cyclohexane, 4-fluoro-cyclohexane, 4-[(C$_1$-C$_4$)-alkyl]-cyclohexane, 4-methyl-cyclohexane, 4-ethyl-cyclohexane, 4-propyl-cyclohexane, 4-[(C$_1$-C$_4$)-alkyl-O]-cyclohexane, 4-methoxy-cyclohexane or 4-ethoxy-cyclohexane, wherein in all these substituted cyclohexane ring the carbon atom carrying the two groups N(R$^{20}$) and C(O)—R$^{50}$ is in position 1, and wherein the statement "with binding position" means with respect to all listed groups that the carbon atom carrying the two groups N(R$^{20}$) and C(O)—R$^{50}$ is in the specified position of the respective ring.

The number of the substituents which are optionally present on the ring A, depends on the size and the kind of the ring A and the number of hetero ring members. In one embodiment of the invention the number of optional substituents on ring carbon atoms in ring A is 1, 2, 3 4 or 5, in another embodiment 1, 2, 3 or 4, in another embodiment 1, 2 or 3, in another embodiment 1 or 2, in another embodiment 1. In all positions on ring carbon atoms in ring A which do not carry a substituent, hydrogen atoms are present. Substituents on the ring A can be present in any suitable position. In case ring A is a 4-membered to 12-membered ring, in one embodiment of the invention substituents are optionally present only on ring carbon atoms which are not adjacent to the carbon atom carrying the group N(R$^{20}$) and C(O)—R$^{50}$, but not in the positions adjacent to the said carbon atom. In one embodiment of the invention, the substituents which are optionally present on carbon atoms in the ring A, are chosen from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, H$_2$N—, R$^1$—NH—, R$^1$—N(R$^1$)—, R$^1$—C(O)—NH—, R$^1$—C(O)—N(R$^1$)—, R$^1$—S(O)$_2$—NH—, R$^1$—S(O)$_2$—N(R$^1$)—, R$^1$—C(O)—, HO—C(O)—, R$^1$—O—C(O)—, H$_2$N—C(O)—, R$^1$—NH—C(O)—, R$^1$—N(R$^1$)—C(O)—, NC—, oxo and methylene, in another embodiment from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, R$^1$—C(O)—, HO—C(O)—, R$^1$—O—C(O)—, H$_2$N—C(O)—, R$^1$—NH—C(O)—, R$^1$—N(R$^1$)—C(O)—, NC—, oxo and methylene, in another embodiment from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, H$_2$N—, R$^1$—NH—, R$^1$—N(R$^1$)—, R$^1$—C(O)—NH—, R$^1$—C(O)—N(R$^1$)—, R$^1$—S(O)$_2$—NH—, R$^1$—S(O)$_2$—N(R$^1$)—, oxo and methylene, in another embodiment from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, R$^1$—C(O)—, HO—C(O)—, R$^1$—O—C(O)—, H$_2$N—C(O)—, R$^1$—NH—C(O)—, R$^1$—N(R$^1$)—C(O)—, oxo and methylene, in another embodiment from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, HO—C(O)—, R$^1$—O—C(O)—, H$_2$N—C(O)—, R$^1$—NH—C(O)—, R$^1$—N(R$^1$)—C(O)—, oxo and methylene, in another embodiment from the series consisting of halogen, R$^1$, R$^2$, (C$_2$-C$_6$)-alkenyl, HO—, R$^1$—O—, phenyl- (C$_1$-C$_4$)-alkyl-O—, R$^1$—C(O)—O—, R$^1$—S(O)$_2$—O—, HO—C(O)—, R$^1$—O—C(O)—, H$_2$N—C(O)—, R$^1$—NH—C(O)—, R$^1$—N(R$^1$)—C(O)— and oxo, in another embodiment from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, HO—C(O)—, R$^1$—O—C(O)—, oxo and methylene, in another embodiment from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, HO—C(O)—, R$^1$—O—C(O)— and oxo, in another embodiment from the series consisting of halogen, R$^1$, R$^2$, HO—, R$^1$—O—, phenyl-(C$_1$-C$_4$)-alkyl-O—, R$^1$—C(O)—O—, HO—C(O)—, R$^1$—O—C(O)—, oxo and methylene, in another embodiment from the series consisting of halogen, R$^1$, R$^2$, HO—, R$^1$—O—, R$^1$—C(O)—O— and oxo, in another embodiment from the series consisting of halogen, R$^1$, R$^2$, HO—, R$^1$—O— and oxo, in another embodiment from the series consisting of halogen, R$^1$, R$^2$, HO— and R$^1$—O—, in another embodiment from the series consisting of halogen, R$^1$, R$^2$ and R$^1$—O—, in another embodiment from the series consisting of halogen, R$^1$ and R$^2$, in another embodiment from the series consisting of halogen, R$^1$, HO— and R$^1$—O—, in another embodiment from the series consisting of halogen, R$^1$ and R$^1$—O— in another embodiment from the series consisting of halogen, HO— and R$^1$—O—, in another embodiment from the series consisting of halogen and R$^1$, and in another embodiment the substituents which are optionally present on carbon atoms in the ring A are substituents R$^1$, wherein all substituents can be identical or different, and wherein all alkyl, alkenyl and cycloalkyl groups in the substituents on the ring A are optionally substituted by one or more fluorine substituents and cycloalkyl groups additionally are optionally substituted by one or more (C$_1$-C$_4$)-alkyl substituents, as applies in general to alkyl, alkenyl and cycloalkyl groups in the compounds of the formula I. In one embodiment of the invention, an individual carbon atom in the ring A does not carry more than one substituent chosen from the series consisting of HO—, R$^1$—O—, phenyl-(C$_1$-C$_4$)-alkyl-O—, R$^1$—C(O)—O—, R$^1$—S(O)$_2$—O—, R$^1$—S(O)$_m$—, H$_2$N—, R$^1$—NH—, R$^1$—N(R$^1$)—, R$^1$—C(O)—NH—, R$^1$—C(O)—N(R$^1$)—, R$^1$—S(O)$_2$—NH—, R$^1$—S(O)$_2$—N(R$^1$)—, H$_2$N—S(O)$_2$—, R$^1$—NH—S(O)$_2$—, R$^1$—N(R$^1$)—S(O)$_2$— and F$_5$S—. In one embodiment of the invention, the number of F$_5$S— substituents on the ring A is not greater than one. In one embodiment of the invention, the number of oxo substituents on the ring A is not greater than two, and in another embodiment it is not greater than one. In one embodiment of the invention, the number of methylene substituents on the ring A is not greater than two, and in another embodiment it is not greater than one. In one embodiment of the invention, halogen substituents on the ring A are fluorine substituents.

In case the ring A is a cyclohexane ring or cycloheptane ring, for example, the compounds of the formula I can also be represented by the formulae Ia and Ib, respectively,

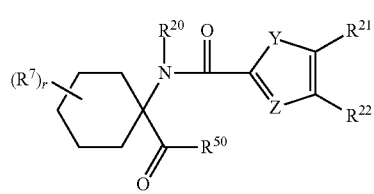

Ia

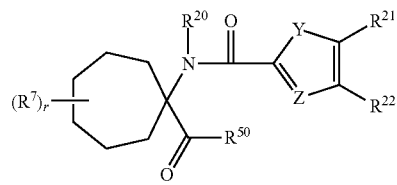

Ib wherein Y, Z, R$^{20}$ to R$^{22}$ and R$^{50}$ are defined as in the compounds of the formula I, R$^7$ is defined as the substituents which are optionally present in the ring A in the compounds of the formula I, i.e. R$^7$ is chosen from the series consisting of halogen, R$^1$, R$^2$, (C$_2$-C$_6$)-alkenyl, HO—, R$^1$—O—, phenyl-(C$_1$-C$_4$)-alkyl-O—, R$^1$—C(O)—O—, R$^1$—S(O)$_2$—O—, R$^1$—S(O)$_m$—, H$_2$N—, R$^1$—NH—, R$^1$—N(R$^1$)—, R$^1$—C(O)—NH—, R$^1$—C(O)—N(R$^1$)—, R$^1$—S(O)$_2$—NH—, R$^1$—S(O)$_2$—N(R$^1$)—, R$^1$—C(O)—, HO—C(O)—, R$^1$—O—C(O)—, H$_2$N—C(O)—, R$^1$—NH—C(O)—, R$^1$—N(R$^1$)—C(O)—, H$_2$N—S(O)$_2$—, R$^1$—NH—S(O)$_2$—, R$^1$—N(R$^1$)—S(O)$_2$—, F$_5$S—, NC—, oxo and methylene, or from any of the other series of substituents indicated herein, for example from the series consisting of halogen, R$^1$, R$^2$, HO—, R$^1$—O— and oxo, or from the series consisting of halogen and R$^1$, and the number r can be up to 10 in the compounds of the formula Ia and up to 12 in the compounds of the formula Ib, such as in case the cyclohexane or cycloheptane ring is perfluorinated. In one embodiment of the invention, the number r in the compounds of the formulae Ia and Ib is 0, 1, 2, 3, 4 or 5, in another embodiment 0, 1, 2, 3 or 4, in another embodiment 0, 1, 2 or 3, in another embodiment 0, 1 or 2, in another embodiment 0 or 1, in another embodiment the number r is 1, and in another embodiment the number r is 0, i.e. in this latter embodiment the cyclohexane ring or cycloheptane ring depicted in formulae and Ib does not carry a substituent R$^7$ but only hydrogen atoms. The substituents R$^7$ can be present on any of the carbon atoms of the cyclohexane and cycloheptane ring depicted in formulae Ia and Ib.

In the group C(R$^{12}$)=C(R$^{13}$) representing the divalent group Y, the carbon atom carrying the group R$^{13}$ is bonded to the ring carbon atom carrying the group R$^{21}$ and the carbon atom carrying the group R$^{12}$ is bonded to the ring carbon atom carrying the group C(O)—N(R$^{20}$). In the group N=C(R$^{14}$), the carbon atom carrying the group R$^{14}$ is bonded to the ring carbon atom carrying the group R$^{21}$ and the nitrogen atom is bonded to the ring carbon atom carrying the group C(O)—N(R$^{20}$). In the group C(R$^{15}$)=N, the nitrogen atom is bonded to the ring carbon atom carrying the group R$^{21}$ and the carbon atom carrying the group R$^{15}$ is bonded to the ring carbon atom carrying the group C(O)—N(R$^{20}$). In one embodiment of the invention, Y is chosen from the series consisting of S, C(R$^{12}$)=C(R$^{13}$), N=C(R$^{14}$) and C(R$^{15}$)=N, in another embodiment from the series consisting of S, C(R$^{12}$)=C(R$^{13}$) and C(R$^{15}$)=N. In one embodiment of the invention Y is chosen from the series consisting of S and C(R$^{12}$)=C(R$^{13}$), in another embodiment from the series consisting of C(R$^{12}$)=C(R$^{13}$) and C(R$^{15}$)=N. In another embodiment of the invention, Y is C(R$^{12}$)=C(R$^{13}$). In another embodiment of the invention, Y is C(R$^{15}$)=N.

In one embodiment of the invention, the trivalent group Z is C(R$^{16}$). In another embodiment Z is C(R$^{16}$) and Y is chosen from the series consisting of S, C(R$^{12}$)=C(R$^{13}$) and C(R$^{15}$)=N. In another embodiment Z is C(R$^{16}$) and Y is chosen from the series consisting of S and C(R$^{12}$)=C(R$^{13}$). In another embodiment Z is C(R$^{16}$) and Y is chosen from the series consisting of $C(R^{15})=N$ and $C(R^{12})=C(R^{13})$. In this latter embodiment, the aromatic ring in the compounds of the formula I comprising the ring members Y and Z is a pyridine ring or a benzene ring, respectively, and the compounds of the formula I are compounds of the formula Ic or of the formula Id,

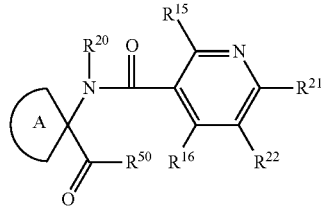

Ic

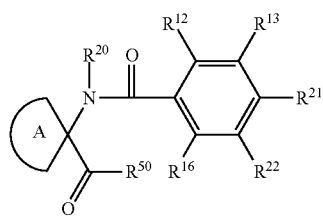

Id wherein A, $R^{12}$, $R^{13}$, $R^{15}$, $R^{16}$, $R^{20}$ to $R^{22}$ and $R^{50}$ are defined as in the compounds of the formula I or have any of their other indicated meanings. In one embodiment of the invention the group Z is $C(R^{16})$ and the group Y is S. In another embodiment of the invention the group Z is $C(R^{16})$ and the group Y is $C(R^{15})=N$. In another embodiment of the invention the group Z is $C(R^{16})$ and the group Y is $C(R^{12})=C(R^{13})$, i.e., in this embodiment the compounds of the formula I are compounds of the formula Id.

In one embodiment of the invention, in the compounds of the formula Ia the group Z is $C(R^{16})$ and the group Y is $C(R^{12})=C(R^{13})$, i.e., compounds of this embodiment are compounds of the formula Ie, in another embodiment in the compounds of the formula Ib the group Z is $C(R^{16})$ and the group Y is $C(R^{12})=C(R^{13})$, i.e., compounds of this embodiment are compounds of the formula If, in another embodiment in the compounds of the formula Ia the group Z is $C(R^{16})$ and the group Y is $C(R^{15})=N$, i.e., compounds of this embodiment are compounds of the formula Ig, and in another embodiment in the compounds of the formula Ib the group Z is $C(R^{16})$ and the group Y is $C(R^{15})=N$, i.e., compounds of this embodiment are compounds of the formula Ih,

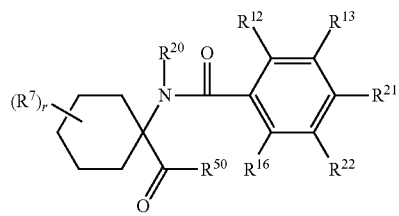

Ie

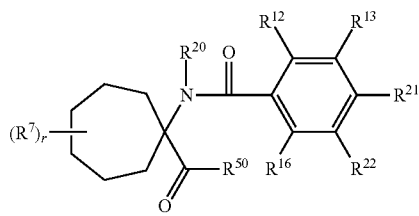

If

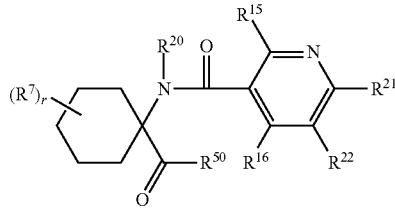

Ig

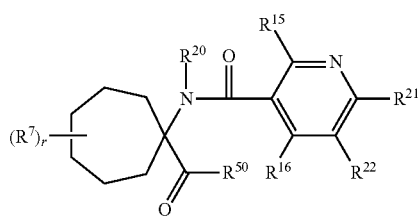

Ih wherein $R^{12}$, $R^{13}$, $R^{15}$, $R^{16}$, $R^{20}$ to $R^{22}$ and $R^{50}$ in these compounds are defined as in the compounds of the formula I or have any of their other indicated meanings, and $R^7$ and r are defined as in the compounds of the formulae Ia and Ib and, like in the compounds of the formulae Ia and Ib, the substituents $R^7$ can be present on any of the carbon atoms of the cyclohexane and cycloheptane rings depicted in formulae Ie, If, Ig and Ih. All explanations on groups and all definitions and embodiments specified above or below with respect to the compounds of the formula I apply correspondingly to the compounds of all formulae which represent subgroups of the compounds of the formula I, including the compounds of the formulae Ia to Ih.

In one embodiment of the invention, $R^0$ is chosen from the series consisting of hydrogen and $(C_1-C_4)$-alkyl, in another embodiment from the series consisting of hydrogen and methyl. In one embodiment of the invention, $R^0$ is hydrogen. In another embodiment of the invention $R^0$ is $(C_1-C_4)$-alkyl, for example methyl.

In one embodiment of the invention, $R^1$ is chosen from the series consisting of $(C_1-C_6)$-alkyl, $(C_3-C_7)$-cycloalkyl and $(C_3-C_7)$-cycloalkyl-$(C_1-C_2)$-alkyl-, in another embodiment from the series consisting of $(C_1-C_6)$-alkyl, $(C_3-C_6)$-cycloalkyl and $(C_3-C_6)$-cycloalkyl-$(C_1-C_2)$-alkyl-, in another embodiment from the series consisting of $(C_1-C_6)$-alkyl, $(C_3-C_6)$-cycloalkyl and $(C_3-C_6)$-cycloalkyl-$CH_2$—, in another embodiment from the series consisting of $(C_1-C_6)$-alkyl, $(C_3-C_4)$-cycloalkyl and $(C_3-C_4)$-cycloalkyl-$CH_2$—, in another embodiment from the series consisting of $(C_1-C_6)$-alkyl and $(C_3-C_6)$-cycloalkyl, in another embodiment from the series consisting of $(C_1-C_6)$-alkyl and $(C_3-C_4)$-cycloalkyl, in another embodiment from the series consisting of $(C_1-C_6)$-alkyl, in another embodiment from the series consisting of $(C_1-C_4)$-alkyl, wherein all these groups are all optionally substituted by one or more fluorine substituents and in the case of cycloalkyl groups by one or more identical or different $(C_1-C_4)$-alkyl substituents, and thus can also be groups such as fluoromethyl, difluoromethyl, trifluoromethyl, 2,2,2-trifluoroethyl, 1-methyl-cyclopropyl or 2,2-dimethyl-cyclopropyl, for example.

In one embodiment of the invention, the $(C_1-C_4)$-alkyl group representing $R^2$ is a $(C_1-C_3)$-alkyl group, in another embodiment a $(C_1-C_2)$-alkyl group, in another embodiment a methyl group. In one embodiment of the invention, the number of substituents HO— and $(C_1-C_4)$alkyl-O— in $R^2$ is 1, 2 or 3, in another embodiment 1 or 2, in another embodiment 1. In one embodiment of the invention, an individual carbon atom in $R^2$ does not carry more than one substituent chosen from the series consisting of HO— and $(C_1-C_4)$alkyl-O—. Examples of $R^2$, from any one or more of which $R^2$ is chosen in one embodiment of the invention, are hydroxymethyl, 1-hydroxyethyl, 2-hydroxyethyl, 3-hydroxypropyl, 1,2-dihydroxyethyl, methoxymethyl, propoxymethyl, 2-methoxyethyl or 3-methoxypropyl.

In one embodiment of the invention, $R^{11}$, $R^{30}$, $R^{33}$, $R^{35}$, $R^{54}$, $R^{55}$, $R^{57}$ and $R^{58}$ are, independently of each other group $R^{11}$, $R^{30}$, $R^{33}$, $R^{35}$, $R^{54}$, $R^{55}$, $R^{57}$ and $R^{58}$, chosen from the series consisting of $(C_1-C_6)$-alkyl, $(C_2-C_4)$-alkenyl, $(C_2-C_4)$-alkynyl, $(C_3-C_7)$-cycloalkyl and $(C_3-C_7)$-cycloalkyl-$(C_1-C_2)$-alkyl-, in another embodiment from the series consisting of $(C_1-C_4)$-alkyl, $(C_2-C_4)$-alkenyl, $(C_2-C_4)$-alkynyl, $(C_3-C_7)$-cycloalkyl and $(C_3-C_7)$-cycloalkyl-$(C_1-C_2)$-alkyl-, in another embodiment from the series consisting of $(C_1-C_6)$-alkyl, $(C_3-C_7)$-cycloalkyl and $(C_3-C_7)$-cycloalkyl-$(C_1-C_2)$-alkyl-, in another embodiment from the series consisting of $(C_1-C_4)$-alkyl, $(C_3-C_7)$-cycloalkyl and $(C_3-C_7)$-cycloalkyl-$(C_1-C_2)$-alkyl-, in another embodiment from the series consisting of $(C_1-C_6)$-alkyl, $(C_3-C_7)$-cycloalkyl and $(C_3-C_7)$-cycloalkyl-$CH_2$-alkyl-, in another embodiment from the series consisting of $(C_1-C_6)$-alkyl and $(C_3-C_7)$-cycloalkyl, in another embodiment from the series consisting of $(C_1-C_4)$-alkyl and $(C_3-C_7)$-cycloalkyl, which are all optionally substituted by one or more identical or different substituents $R^{70}$, wherein in these groups besides any substituents $R^{70}$ one or more fluorine substituents are optionally present and in cycloalkyl groups one or more $(C_1-C_4)$-alkyl substituents are optionally present as applies to alkyl, alkenyl, alkynyl and cycloalkyl groups in general. In one embodiment of the invention $R^{11}$, $R^{30}$, $R^{33}$, $R^{35}$, $R^{54}$, $R^{55}$, $R^{57}$ and $R^{58}$ are, independently of each other group $R^{11}$, $R^{30}$, $R^{33}$, $R^{35}$, $R^{54}$, $R^{55}$, $R^{57}$ and $R^{58}$, chosen from the series consisting of $(C_1-C_6)$-alkyl, in another embodiment from the series consisting of $(C_1-C_4)$-alkyl, which are all optionally substituted by one or more identical or different substituents $R^{70}$. In one embodiment of the invention, $(C_3-C_7)$-cycloalkyl groups occurring in $R^{11}$, $R^{30}$, $R^{33}$, $R^{35}$, $R^{54}$, $R^{55}$, $R^{57}$ and $R^{58}$ are, independently of each other group $R^{11}$, $R^{30}$, $R^{33}$, $R^{35}$, $R^{54}$, $R^{55}$, $R^{57}$ and $R^{58}$, $(C_3-C_6)$-cycloalkyl, in another embodiment $(C_3-C_4)$-cycloalkyl, for example cyclopropyl, in another embodiment $(C_5-C_6)$-cycloalkyl, for example cyclohexyl. In one embodiment of the invention, the number of substituents $R^{70}$ in any of the groups $R^{11}$, $R^{30}$, $R^{33}$, $R^{35}$, $R^{54}$, $R^{55}$, $R^{57}$ and $R^{58}$ is, independently of each other group $R^{11}$, $R^{30}$, $R^{33}$, $R^{35}$, $R^{54}$, $R^{55}$, $R^{57}$ and $R^{58}$, 0, 1, 2, 3 or 4, in another embodiment 0, 1, 2 or 3, in another embodiment 0, 1 or 2, in another embodiment 0 or 1. In one embodiment of the invention, any of the groups $R^{11}$, $R^{30}$, $R^{33}$, $R^{35}$, $R^{54}$, $R^{55}$, $R^{57}$ and $R^{58}$, independently of each other group $R^{11}$, $R^{30}$, $R^{33}$, $R^{35}$, $R^{54}$, $R^{55}$, $R^{57}$ and $R^{58}$, does not carry a substituent $R^{70}$, but merely is optionally substituted by one or more fluorine substituents and, in the case of cycloalkyl groups, one or more $(C_1-C_4)$-alkyl substituents. In another embodiment of the invention, any of the groups $R^{11}$, $R^{30}$, $R^{33}$, $R^{35}$, $R^{54}$, $R^{55}$, $R^{57}$ and $R^{58}$, independently of each other group $R^{11}$, $R^{30}$, $R^{33}$, $R^{35}$, $R^{54}$, $R^{55}$, $R^{57}$ and $R^{58}$, does neither carry a substituent $R^{70}$ nor fluorine substituents nor, in the case of cycloalkyl groups, $(C_1-C_4)$-alkyl substituents. As examples of $R^{11}$, $R^{30}$, $R^{33}$, $R^{35}$, $R^{54}$, $R^{55}$, $R^{57}$ and $R^{58}$ which examplarily carry a hydroxy or alkyl-O— group as a substituent $R^{70}$, from any one or more of which examples any of the groups $R^{11}$, $R^{30}$, $R^{33}$, $R^{35}$, $R^{54}$, $R^{55}$, $R^{57}$ and $R^{58}$ is chosen in one embodiment of the invention, HO—$(C_1-C_4)$-alkyl-, HO—$(C_2-C_3)$-alkyl-, HO—$CH_2$—$CH_2$—, $CH_3$—CH(OH)—, HO—$CH_2$—, $(C_1-C_4)$-alkyl-O—$(C_1-C_4)$-alkyl-, $(C_1-C_3)$-alkyl-O—$(C_1-C_3)$-alkyl-, $(C_1-C_2)$-alkyl-O—$(C_2-C_3)$-alkyl-, $(C_1-C_2)$-alkyl-O—$(C_1-C_2)$-alkyl-, $CH_3$—O—$CH_2$—$CH_2$—, $(C_1-C_4)$-alkyl-O—$CH_2$—, $CH_3$—O—$CH_2$— may be mentioned.

In one embodiment of the invention, $R^{10}$ is chosen from the series consisting of hydrogen and methyl. In another embodiment $R^{10}$ is hydrogen. In another embodiment of the invention $R^{10}$ is $(C_1-C_4)$-alkyl, for example methyl.

In case $R^{13}$ or $R^{14}$, together with the one of the groups $R^{21}$ and $R^{22}$ which is not the group of the formula II, forms a chain consisting of 3 to 5 chain members of which 0, 1 or 2 chain members are identical or different hetero chain members chosen from the series consisting of $N(R^{17})$, O and S, but two hetero chain members cannot be present in adjacent positions, and the other chain members are identical or different groups $C(R^{18})(R^{18})$, the group $R^{22}$ is the group of the formula II and the group $R^{21}$ forms a chain together with $R^{13}$ or $R^{14}$. The formed chain, together with the carbon atom carrying $R^{21}$ and the carbon atom carrying $R^{13}$ or $R^{14}$ forms a 5-membered to 7-membered ring, which is fused to the aromatic ring comprising the groups Y and Z depicted in formula I and which has the bond between the group Y and the carbon atom carrying $R^{21}$ in common with the said ring comprising Y and Z. In one embodiment of the invention, the said chain consists of 3 to 4 chain members and the formed ring thus is 5-membered to 6-membered, and in another embodiment the said chain consists of 3 chain members and the formed ring thus is 5-membered. The hetero chain members can be present in any position in the said chain, provided that two hetero chain members cannot be present in adjacent positions. If hetero chain members are present, in one embodiment of the invention one hetero chain member is present in a terminal position of the said chain, in another embodiment one hetero chain member is present in the terminal position of the said chain which is attached to the carbon atom in the ring comprising Y and Z depicted in formula I which carries the group $R^{21}$, in another embodiment one hetero chain member is present in the terminal position of the said chain which is attached to the carbon atom in the group $CR^{12}$=$CR^{13}$ or the group N=$CR^{14}$ representing Y which carries the group $R^{13}$ or $R^{14}$, respectively, in another embodiment two hetero chain members are present in the two terminal positions of the said chain which are attached to the carbon atom in the ring comprising Y and Z depicted in formula I which carries the group $R^{21}$, and to the carbon atom in the group $CR^{12}$=$CR^{13}$ or the group N=$CR^{14}$ representing Y which carries the group $R^{13}$ or $R^{14}$, respectively. In one embodiment of the invention, 0 (zero) hetero chain members are present in the said chain, in another embodiment 0 or 1 hetero chain members are present, in another embodiment 1 or 2 hetero chain members are present, and in another embodiment 2 hetero chain members are present. In one embodiment of the invention, hetero chain members in the said chain are chosen from $N(R^{17})$ and O, in another embodiment from O and S, and in another embodiment they are O (oxygen atoms). Examples of chains formed by $R^{13}$ or $R^{14}$ together with the one of the groups $R^{21}$ and $R^{22}$ which is not the group of the formula II, from any one or more of which the said chain is chosen in one embodiment of the invention, are —$CH_2$—$CH_2$—$CH_2$—, —$CH_2$—$CH_2$—

$CH_2$—$CH_2$—, —$CH_2$—$CH_2$—$CH_2$—$CH_2$—$CH_2$—, —O—$CH_2$—$CH_2$— and —O—$CH_2$—$CH_2$—$CH_2$— wherein in the latter two chains the oxygen atom is attached to the carbon atom in the group $CR^{12}$=$CR^{13}$ or the group N=$CR^{14}$ representing Y which carries the group $R^{13}$ or $R^{14}$, respectively, —$CH_2$—$CH_2$—O— and —$CH_2$—$CH_2$—$CH_2$—O— wherein in the latter two chains the oxygen atom is attached to the carbon atom in the ring comprising Y and Z depicted in formula I which carries the group $R^{21}$, —$CH_2$—O—$CH_2$—, —O—$C(R^{18})(R^{18})$—O-including —O—$CH_2$—O—, —O—$CF_2$—O— and —O—$C(CH_3)_2$—O—, —O—$C(R^{18})(R^{18})$—$C(R^{18})(R^{18})$—O-including —O—$CH_2$—$CH_2$—O—, —O—$CH_2$—$CH_2$—$CH_2$—O—, or —$N(CH_3)$—$CH_2$—$CH_2$—O— wherein in the latter chain the nitrogen atom is attached to the carbon atom in the group $CR^{12}$=$CR^{13}$ or the group N=$CR^{14}$ representing Y which carries the group $R^{13}$ or $R^{14}$ respectively.

In one embodiment of the invention, $R^{12}$, $R^{13}$, $R^{14}$, $R^{15}$ and $R^{16}$ are independently of each other chosen from the series consisting of hydrogen, halogen, $(C_1$-$C_4)$-alkyl, HO—$(C_1$-$C_4)$-alkyl-, $(C_1$-$C_4)$-alkyl-O—, $H_2N$—, $(C_1$-$C_4)$-alkyl-NH—, $(C_1$-$C_4)$-alkyl-N$((C_1$-$C_4)$-alkyl)- and NC—, in another embodiment from the series consisting of hydrogen, halogen, $(C_1$-$C_4)$-alkyl, $(C_1$-$C_4)$-alkyl-O—, $H_2N$—, $(C_1$-$C_4)$-alkyl-NH—, $(C_1$-$C_4)$-alkyl-N$((C_1$-$C_4)$-alkyl)- and NC—, in another embodiment from the series consisting of hydrogen, halogen, $(C_1$-$C_4)$-alkyl and $(C_1$-$C_4)$-alkyl-O—, in another embodiment from the series consisting of hydrogen, halogen and $(C_1$-$C_4)$-alkyl-O—, in another embodiment from the series consisting of hydrogen and halogen, or in all these embodiments $R^{13}$ or $R^{14}$, together with the one of the groups $R^{21}$ and $R^{22}$ which is not the group of the formula II, forms a chain consisting of 3 to 5 chain members of which 0, 1 or 2 chain members are identical or different hetero chain members chosen from the series consisting of $N(R^{17})$, O and S, but two hetero chain members cannot be present in adjacent positions, and the other chain members are identical or different groups $C(R^{18})(R^{18})$. In one embodiment of the invention, $R^{12}$ and $R^{13}$ are independently of each other chosen from the series consisting of hydrogen, halogen, $(C_1$-$C_4)$-alkyl and $(C_1$-$C_4)$-alkyl-O—, in another embodiment from the series consisting of hydrogen, halogen and $(C_1$-$C_4)$-alkyl-O—, in another embodiment from the series consisting of hydrogen and halogen, in another embodiment from the series consisting of hydrogen, chlorine and fluorine, in another embodiment from the series consisting of hydrogen and fluorine, or in all these embodiments $R^{13}$, together with the one of the groups $R^{21}$ and $R^{22}$ which is not the group of the formula II, forms a chain consisting of 3 to 5 chain members of which 0, 1 or 2 chain members are identical or different hetero chain members chosen from the series consisting of $N(R^{17})$, O and S, but two hetero chain members cannot be present in adjacent positions, and the other chain members are identical or different groups $C(R^{18})(R^{18})$. In one embodiment of the invention, $R^{12}$ and $R^{13}$ are independently of each other chosen from the series consisting of hydrogen, halogen, $(C_1$-$C_4)$-alkyl and $(C_1$-$C_4)$-alkyl-O—, in another embodiment from the series consisting of hydrogen, halogen and $(C_1$-$C_4)$-alkyl-O—, in another embodiment from the series consisting of hydrogen and halogen, in another embodiment from the series consisting of hydrogen, chlorine and fluorine, in another embodiment from the series consisting of hydrogen and fluorine, and $R^{13}$, together with the one of the groups $R^{21}$ and $R^{22}$ which is not the group of the formula II, forms a chain consisting of 3 to 5 chain members of which 0, 1 or 2 chain members are identical or different hetero chain members chosen from the series consisting of $N(R^{17})$, O and S, but two hetero chain members cannot be present in adjacent positions, and the other chain members are identical or different groups $C(R^{18})(R^{18})$. In one embodiment of the invention, $R^{12}$ is hydrogen and $R^{13}$ is fluorine, or $R^{12}$ is fluorine and $R^{13}$ is hydrogen. In another embodiment $R^{12}$ and $R^{13}$ are hydrogen. In one embodiment of the invention, $R^{14}$ and $R^{15}$ are independently of each other chosen from the series consisting of hydrogen, halogen, $(C_1$-$C_4)$-alkyl and $(C_1$-$C_4)$-alkyl-O—, in another embodiment from the series consisting of hydrogen, halogen and $(C_1$-$C_4)$-alkyl, in another embodiment from the series consisting of hydrogen and halogen, in another embodiment from the series consisting of hydrogen, chlorine and fluorine. In another embodiment of the invention, $R^{14}$ and $R^{15}$ are hydrogen. In one embodiment of the invention, $R^{16}$ is chosen from the series consisting of hydrogen, halogen, $(C_1$-$C_4)$-alkyl and $(C_1$-$C_4)$-alkyl-O—, in another embodiment from the series consisting of hydrogen, halogen and $(C_1$-$C_4)$-alkyl, in another embodiment from the series consisting of hydrogen and halogen, in another embodiment from the series consisting of hydrogen, chlorine and fluorine. In another embodiment of the invention, $R^{16}$ is hydrogen.

In one embodiment of the invention, $R^{17}$ and $R^{25}$ are independently of each other chosen from the series consisting of hydrogen and methyl, in another embodiment they are hydrogen. In another embodiment of the invention, $R^{17}$ and $R^{25}$ are independently of each other chosen from the series consisting of $(C_1$-$C_4)$-alkyl, and in another embodiment they are methyl.

In case two groups $R^{18}$ bonded to the same carbon atom, together with the carbon atom carrying them, form a 3-membered to 6-membered cycloalkane ring, the formed cycloalkane ring is spiro-fused to the ring which is optionally formed by $R^{13}$ or $R^{14}$ together with the one of the groups $R^{21}$ and $R^{22}$ which is not the group of the formula II, and the carbon atom carrying $R^{21}$ and the carbon atom carrying $R^{13}$ or $R^{14}$. In one embodiment of the invention, the cycloalkane ring formed by two of the groups $R^{18}$ is 3-membered to 5-membered, in another embodiment it is 3-membered or 4-membered, in another embodiment it is 3-membered, i.e. in this latter embodiment a cyclopropane ring is formed. In one embodiment of the invention, $R^{18}$, independently of each other group $R^{18}$, is chosen from the series consisting of hydrogen, fluorine and $(C_1$-$C_2)$-alkyl, in another embodiment from the series consisting of hydrogen, fluorine and methyl, in another embodiment from the series consisting of hydrogen and fluorine, and in another embodiment the groups $R^{18}$ are hydrogen, or in all these embodiments two of the groups $R^{18}$ bonded to the same carbon atom, together with the carbon atom carrying them, form a 3-membered to 6-membered cycloalkane ring which is optionally substituted as indicated. In one embodiment of the invention, $R^{18}$, independently of each other group $R^{18}$, is chosen from the series consisting of hydrogen, fluorine and $(C_1$-$C_2)$-alkyl, in another embodiment from the series consisting of hydrogen, fluorine and methyl, in another embodiment from the series consisting of hydrogen and fluorine, and in another embodiment the groups $R^{18}$ are hydrogen. In one embodiment of the invention, not more than one cycloalkane ring which is formed by two of the groups $R^{18}$ bonded to the same carbon atom together with the carbon atom carrying them, is present in the compounds of the formula I. In one embodiment of the invention, the number of substituents chosen from the series consisting of fluorine and $(C_1-C_4)$-alkyl, which are optionally present on a cycloalkane ring formed by two of the groups $R^{18}$ bonded to the same carbon atom together with the carbon atom carrying them, is 1, 2, 3 or 4, in another embodiment it is 1, 2 or 3, in another embodiment it is 1 or 2, and in another embodiment such a cycloalkane ring does not carry any substituents, i.e. in this latter embodiment it is unsubstituted. In one embodiment of the invention, the substituents which are optionally present on a cycloalkane ring formed by two of the groups $R^{18}$ bonded to the same carbon atom together with the carbon atom carrying them, are chosen from fluorine and methyl, and in another embodiment they are fluorine substituents.

In one embodiment of the invention, $R^{20}$ is chosen from the series consisting of hydrogen and methyl. In another embodiment $R^{20}$ is hydrogen. In another embodiment $R^{20}$ is $(C_1-C_4)$-alkyl, for example methyl.

In one embodiment of the invention the group $R^{21}$ is the one of the groups $R^{21}$ and $R^{22}$ which is a group of the formula II, i.e. a group of the formula $R^{24}$—$R^{23}$— which is bonded to the remainder of the molecule through the moiety $R^{23}$ as is symbolized with respect to this group and in general by a terminal hyphen representing the free bond, and the group $R^{22}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, H$_2$N—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, H$_2$N—C(O)—, $R^{30}$—NH—C(O)—, $R^{30}$—N($R^{30}$)—C(O)—, H$_2$N—S(O)$_2$—, $R^{30}$—NH—S(O)$_2$—, $R^{30}$—N($R^{30}$)—S(O)$_2$—, NC—, O$_2$N— and Het$^1$. In another embodiment, the group $R^{22}$ is the one of the groups $R^{21}$ and $R^{22}$ which is a group of the formula II and the group $R^{21}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, H$_2$N—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, H$_2$N—C(O)—, $R^{30}$—NH—C(O)—, $R^{30}$—N($R^{30}$)—C(O)—, H$_2$N—S(O)$_2$—, $R^{30}$—NH—S(O)$_2$—, $R^{30}$—N($R^{30}$)—S(O)$_2$—, NC—, O$_2$N— and Het$^1$, or together with $R^{13}$ or $R^{14}$ forms a chain as specified in the definition of $R^{13}$ and $R^{14}$.

In one embodiment of the invention, the one of the groups $R^{21}$ and $R^{22}$ which is not a group of the formula II, is chosen from the series consisting of hydrogen, halogen, $R^{30}$, $R^{30}$—O—, $R^{30}$—C(O)—O—, $R^{30}$—S(O)$_m$—, H$_2$N—, $R^{30}$—NH—, $R^{30}$—N($R^{30}$)—, $R^{30}$—C(O)—NH—, $R^{30}$—C(O)—, NC— and Het$^1$, in another embodiment from the series consisting of hydrogen, halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-S(O)$_m$—, H$_2$N—, $(C_1-C_4)$-alkyl-NH—, di($(C_1-C_4)$-alkyl)N—, $(C_1-C_4)$-alkyl-C(O)—, Het$^1$ and NC—, in another embodiment from the series consisting of hydrogen, halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-S(O)$_m$—, $(C_1-C_4)$-alkyl-C(O)—, Het$^1$ and NC—, in another embodiment from the series consisting of hydrogen, halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—$(C_1-C_4)$-alkyl-, HO—$(C_1-C_4)$-alkyl-O—, $(C_1-C_4)$-alkyl-O—$(C_1-C_4)$-alkyl-O—, $(C_1-C_4)$-alkyl-S(O)$_m$—, $(C_1-C_4)$-alkyl-C(O)— and Het$^1$, in another embodiment from the series consisting of hydrogen, halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-C(O)— and Het$^1$, in another embodiment from the series consisting of hydrogen, halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O— and Het$^1$, in another embodiment from the series consisting of hydrogen, halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O— and $(C_1-C_4)$-alkyl-O—$(C_1-C_4)$-alkyl-O—, in another embodiment from the series consisting of halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-C(O)— and Het$^1$, in another embodiment from the series consisting of halogen, $(C_1-C_4)$-alkyl, HO—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-C(O)— and Het$^1$, in another embodiment from the series consisting of halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O— and Het$^1$, in another embodiment from the series consisting of halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O— and $(C_1-C_4)$-alkyl-O—$(C_1-C_4)$-alkyl-O—, in another embodiment from the series consisting of $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-C(O)— and Het$^1$, in another embodiment from the series consisting of $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O—, $(C_1-C_4)$-alkyl-O—$(C_1-C_4)$-alkyl-O—, $(C_1-C_4)$-alkyl-C(O)— and Het$^1$, in another embodiment from the series consisting of $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, HO—$(C_1-C_4)$-alkyl-O— and $(C_1-C_4)$-alkyl-O—$(C_1-C_4)$-alkyl-O—, in another embodiment from the series consisting of $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—, $(C_1-C_4)$-alkyl-C(O)— and Het$^1$, in another embodiment from the series consisting of $(C_1-C_4)$-alkyl, HO—$(C_1-C_4)$-alkyl-, $(C_1-C_4)$-alkyl-O— and $(C_1-C_4)$-alkyl-C(O)—, in another embodiment from the series consisting of $(C_1-C_4)$-alkyl and $(C_1-C_4)$-alkyl-O—, in another embodiment from the series consisting of $(C_1-C_4)$-alkyl-O—, or in all these embodiments together with $R^{13}$ or $R^{14}$ forms a chain as specified in the definition of $R^{13}$ and $R^{14}$. In one embodiment of the invention, the one of the groups $R^{21}$ and $R^{22}$ which is not a group of the formula II, is chosen from the series consisting of $(C_1-C_4)$-alkyl and $(C_1-C_4)$-alkyl-O—. In another embodiment, the one of the groups $R^{21}$ and $R^{22}$ which is not a group of the formula II, is $(C_1-C_4)$-alkyl-O—, for example methoxy or ethoxy.

In one embodiment of the invention, in case the group $R^{21}$ is the one of the groups $R^{21}$ and $R^{22}$ which is a group of the formula II, the group $R^{22}$ is chosen from the series consisting of $(C_1-C_4)$-alkyl and $(C_1-C_4)$-alkyl-O—, and in another embodiment it is $(C_1-C_4)$-alkyl-O—, and in case the group $R^{22}$ is the one of the groups $R^{21}$ and $R^{22}$ which is the group of the formula II, the group $R^{21}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, H$_2$N—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, H$_2$N—C(O)—, $R^{30}$—NH—C(O)—, $R^{30}$—N($R^{30}$)—C (O)—, $H_2N$—$S(O)_2$—, $R^{30}$—NH—$S(O)_2$—, $R^{30}$—N($R^{30}$)—$S(O)_2$—, NC—, $O_2N$— and $Het^1$, or together with $R^{13}$ or $R^{14}$ forms a chain as specified in the definition of $R^{13}$ and $R^{14}$, or is defined as in any of the embodiments or other definitions of $R^{21}$ specified herein.

The chain members in a chain representing $R^{23}$ are connected to each other by single bonds. The number of chain members in a chain representing $R^{23}$ can be 1, 2, 3, 4 or 5. In one embodiment of the invention, the divalent group $R^{23}$ is a direct bond, i.e. the group $R^{24}$ is directly bonded to the ring comprising the groups Y and Z which is depicted in formula I. In another embodiment $R^{23}$ is a direct bond or a chain consisting of 1, 2, 3 or 4 chain members. In another embodiment $R^{23}$ is a direct bond or a chain consisting of 2, 3 or 4 chain members, in another embodiment a direct bond or a chain consisting of 2 or 3 chain members, in another embodiment a direct bond or a chain consisting of 3 chain members, wherein in these embodiments the chain members are defined as above or below. In another embodiment $R^{23}$ is a chain consisting of 1, 2, 3, 4 or 5 chain members, in another embodiment a chain consisting of 1, 2, 3 or 4 chain members, in another embodiment a chain consisting of 2, 3 or 4 chain members, in another embodiment a chain consisting of 2 or 3 chain members, in another embodiment a chain consisting of 3 chain members, wherein in these embodiments the chain members are defined as above or below. In one embodiment of the invention, zero or one of the chain members in a chain representing $R^{23}$ are hetero chain members, in another embodiment one of the chain members in a chain representing $R^{23}$ is a hetero chain member, and in another embodiment zero of the chain members in a chain representing $R^{23}$ is a hetero chain member, wherein in these embodiments the hetero chain members are defined as above or below. In one embodiment of the invention, the hetero chain members in a chain representing $R^{23}$ are chosen from the series consisting of $N(R^{25})$, O, S and $S(O)_2$. In another embodiment of the invention, the hetero chain members in a chain representing $R^{23}$ are chosen from the series consisting of $N(R^{25})$, O and S, in another embodiment from the series consisting of $N(R^{25})$ and O, in another embodiment from the series consisting of O and S, in another embodiment from the series consisting of $N(R^{25})$, O and $S(O)_2$, in another embodiment from the series consisting of $N(R^{25})$ and $S(O)_2$, in another embodiment from the series consisting of O and $S(O)_2$. In another embodiment of the invention, the hetero chain members which can be present in a chain representing $R^{23}$, are O (oxygen), and in another embodiment the hetero chain members which can be present in a chain representing $R^{23}$, are S. In another embodiment of the invention, zero or one hetero chain member is present in a chain representing $R^{23}$ which is O (oxygen), and in another embodiment one hetero chain member is present which is O. In another embodiment of the invention, zero or one hetero chain member is present in a chain representing $R^{23}$ which is S, and in another embodiment one hetero chain member is present which is S.

Hetero chain members in a chain representing $R^{23}$ can be present in any positions of the chain provided that the resulting moiety complies with the prerequisites specified above with respect to $R^{23}$ and the compounds of the invention in general. Hetero chain members can be present in any one of the terminal positions of the chain or in both terminal positions of the chain, and can thus be directly bonded to the group $R^{24}$ and/or the ring comprising the groups Y and Z which is depicted in formula I, and/or they can be present inside the chain. In case one or two hetero chain members are present in a chain representing $R^{23}$, in one embodiment of the invention at least one of the terminal chain members is a hetero chain member, and in another embodiment the terminal chain member which is bonded to the group $R^{24}$ is a hetero chain member, and in another embodiment the terminal chain member which is bonded to the ring comprising the groups Y and Z is a hetero chain member. In one embodiment of the invention, one of the chain members in a chain representing $R^{23}$ is a hetero chain member and this hetero chain member is the terminal chain member bonded to the group $R^{24}$. In another embodiment, one of the chain members in a chain representing $R^{23}$ is a hetero chain member and this hetero chain member is the terminal chain member bonded to the ring comprising the groups Y and Z which is depicted in formula I.

In one embodiment of the invention $R^{23}$ is chosen from a direct bond and from any one or more of the chains which are present in the following examples of groups of the formula II, which groups are bonded to the ring comprising the groups Y and Z which is depicted in formula I by the free bond represented by the terminal hyphen, and from which groups of the formula II the groups $R^{23}$ themselves are obtained by removing the group $R^{24}$:

$R^{24}$—$C(R^{26})(R^{26})$—, $R^{24}$—$C(R^{26})(R^{26})C(R^{26})(R^{26})$—, $R^{24}$—$C(R^{26})(R^{26})$—O—, $R^{24}$—$C(R^{26})(R^{26})$—S—, $R^{24}$—$C(R^{26})(R^{26})$—$N(R^{25})$—, $R^{24}$—$S(O)_2$—O—, $R^{24}$—$C(R^{26})(R^{26})$—$C(R^{26})(R^{26})$—$C(R^{26})(R^{26})$—$R^{24}$—$C(R^{26})(R^{26})$—$C(R^{26})(R^{26})$—O—, $R^{24}$—O—$C(R^{26})(R^{26})$—$C(R^{26})(R^{26})$—, $R^{24}$—$C(R^{26})(R^{26})$—O—$C(R^{26})(R^{26})$—, $R^{24}$—$C(R^{26})(R^{26})$—$C(R^{26})(R^{26})$—S—, $R^{24}$—$C(R^{26})(R^{26})$—S—$C(R^{26})(R^{26})$—, $R^{24}$—S—$C(R^{26})(R^{26})$—$C(R^{26})(R^{26})$—, $R^{24}$—$C(R^{26})(R^{26})$—$C(R^{26})(R^{26})$—$N(R^{25})$—, wherein in these groups of the formula II the groups $R^{24}$, $R^{25}$ and $R^{26}$ are defined as above or below.

In one embodiment of the invention, a 3-membered to 10-membered, monocyclic or bicyclic ring representing $R^{24}$ is a monocyclic ring, which is all optionally substituted as indicated above or below. In one embodiment of the invention, a monocyclic ring representing $R^{24}$ is 3-membered to 7-membered, in another embodiment 3-membered or 5-membered to 7-membered, in another embodiment 3-membered, 5-membered or 6-membered, in another embodiment 5-membered or 6-membered, in another embodiment 6-membered, which rings are all optionally substituted as indicated above or below. In one embodiment of the invention, a bicyclic ring representing $R^{24}$ is 7-membered to 10-membered which is optionally substituted as indicated above or below. In one embodiment of the invention, a ring representing $R^{24}$ is a saturated ring or an unsaturated ring including a partially unsaturated, i.e. non-aromatic, ring which contains zero, one, two or three, for example zero, one or two, double bonds, within the ring, or an aromatic ring, which rings are all optionally substituted as indicated above or below. In another embodiment, a ring representing $R^{24}$ is a saturated ring or a partially unsaturated ring which contains zero, one, two or three, for example zero, one or two, double bonds within the ring, which rings are all optionally substituted as indicated above or below. In another embodiment of the invention, a ring representing $R^{24}$ is an aromatic ring, in another embodiment an aromatic ring chosen from benzene, aromatic 5-membered and 6-membered monocyclic heterocycles, naphthalene and aromatic 9-membered and 10-membered bicyclic heterocycles, in another embodiment an aromatic ring chosen from benzene and aromatic 5-membered and 6-membered monocyclic heterocycles, in another embodiment an aromatic ring chosen from benzene and thiophene, which rings are all optionally substituted as indicated above or below. In another embodiment, a ring representing $R^{24}$ is a benzene ring which is optionally substituted as indicated above or below, i.e. by the substituents specified above or below with respect to the 3-membered to 10-membered ring representing $R^{24}$. In terms of residues, in this latter embodiment $R^{24}$ is a phenyl group which is optionally substituted as indicated above or below, i.e. by the substituents specified above or below with respect to the 3-membered to 10-membered ring representing $R^{24}$.

In one embodiment of the invention, the number of hetero ring members which can be present in a saturated 3-membered to 10-membered ring representing $R^{24}$ is 0, in another embodiment it is 1. In one embodiment of the invention, the number of hetero ring members which can be present in an unsaturated 3-membered to 10-membered ring representing $R^{24}$ is 0 or 1, and in another embodiment it is 1 or 2, in another embodiment it is 1, and in another embodiment the number of hetero ring members is 0 (zero), i.e., in this latter embodiment a 3-membered to 10-membered ring representing $R^{24}$ is a carbocyclic ring, which rings are all optionally substituted as indicated above or below. In one embodiment of the invention, the hetero ring members which can be present in a 3-membered to 10-membered ring representing $R^{24}$ are chosen from N, N($R^{32}$), O, S and S(O)$_2$, in another embodiment from N, N($R^{32}$), O and S, in another embodiment from N, O and S, in another embodiment from N($R^{32}$), O and S, in another embodiment from N and S, in another embodiment they are N (nitrogen), and in another embodiment they are S (sulfur).

In one embodiment of the invention, the number of substituents which are optionally present on ring carbon atoms in a 3-membered to 10-membered ring representing $R^{24}$ is 1, 2, 3, 4, or 5, in another embodiment the number of substituents which are optionally present on ring carbon atoms is 1, 2, 3 or 4, in another embodiment the number of substituents which are optionally present on ring carbon atoms is 1, 2 or 3, in another embodiment the number of substituents which are optionally present on ring carbon atoms is 1 or 2, and in another embodiment the number of substituents which are optionally present on ring carbon atoms is 1.

In one embodiment of the invention, the substituents which are optionally present on ring carbon atoms in a 3-membered to 10-membered ring representing $R^{24}$, including a benzene ring or a phenyl group, respectively, representing $R^{24}$, are chosen from the series consisting of halogen, $R^{33}$, oxetanyl, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, HO—C(O)—, $R^{33}$—O—C(O)—, H$_2$N—C(O)—, $R^{33}$—NH—C(O)—, $R^{33}$—N($R^{33}$)—C(O)—, NC— and oxo, in another embodiment from the series consisting of halogen, $R^{33}$, oxetanyl, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, HO—C(O)—, $R^{33}$—O—C(O)—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—S(O)$_2$—NH—, H$_2$N—S(O)$_2$—NH—, $R^{33}$—NH—S(O)$_2$—NH—, $R^{33}$—N($R^{33}$)—S(O)$_2$—NH—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—S(O)$_2$—NH—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, HO—, $R^{33}$—O—, $R^{33}$—S(O)$_m$—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, HO—, $R^{33}$—O—, $R^{33}$—S(O)$_m$—, $R^{33}$—C(O)—NH—, $R^{33}$—S(O)$_2$—NH—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, HO—, $R^{33}$—O—, $R^{33}$—C(O)—NH—, $R^{33}$—S(O)$_2$—NH—, H$_2$N—C(O)—, $R^{33}$—NH—C(O)—, $R^{33}$—N($R^{33}$)—C(O)— and NC—, in another embodiment from the series consisting of halogen, $R^{33}$, oxetanyl, $R^{33}$—O— and NC—, in another embodiment from the series consisting of halogen, $R^{33}$, oxetanyl, and $R^{33}$—O—, in another embodiment from the series consisting of halogen, $R^{33}$ and oxetanyl, in another embodiment from the series consisting of halogen, $R^{33}$, $R^{33}$—O— and NC—, in another embodiment from the series consisting of halogen, $R^{33}$, and $R^{33}$—O—, in another embodiment from the series consisting of halogen and $R^{33}$, wherein in all these embodiments $R^{33}$ and $R^{71}$ are defined as indicated above or below and $R^{33}$ is optionally substituted by one or more identical or different substituents $R^{70}$. In one embodiment of the invention, the groups $R^{33}$ in these substituents on a ring representing $R^{24}$ are independently of each other chosen from the series consisting of (C$_1$-C$_6$)-alkyl, (C$_3$-C$_7$)-cycloalkyl and (C$_3$-C$_7$)-cycloalkyl-(C$_1$-C$_4$)-alkyl-, in another embodiment from the series consisting of (C$_1$-C$_6$)-alkyl, (C$_3$-C$_6$)-cycloalkyl and (C$_3$-C$_6$)-cycloalkyl-(C$_1$-C$_2$)-alkyl-, in another embodiment from the series consisting of (C$_1$-C$_6$)-alkyl, (C$_3$-C$_6$)-cycloalkyl and (C$_3$-C$_6$)-cycloalkyl-CH$_2$—, in another embodiment from the series consisting of (C$_1$-C$_6$)-alkyl, cyclopropyl and cyclopropyl-CH$_2$—, for example from the series consisting of (C$_1$-C$_6$)-alkyl, in another embodiment from the series consisting of (C$_1$-C$_4$)-alkyl, cyclopropyl and cyclopropyl-CH$_2$—, for example from the series consisting of (C$_1$-C$_4$)-alkyl. In one embodiment of the invention, the number of substituents $R^{70}$, which are optionally present in these groups $R^{33}$ besides any fluorine substituents and, in the case of cycloalkyl groups, any (C$_1$-C$_4$)-alkyl substituents, is independently of each other 0, 1, 2 or 3, in another embodiment 0, 1 or 2, in another embodiment 0 or 1, in another embodiment 0. In one embodiment of the invention, the substituents $R^{70}$ in these groups $R^{33}$ are independently of each other chosen from the series consisting of HO—, $R^{71}$—O—, $R^{71}$—C(O)—O—, H$_2$N—, $R^{71}$—NH—, $R^{71}$—N($R^{71}$)—, $R^{71}$—C(O)—NH—, $R^{71}$—C(O)—N($R^{71}$)—, $R^{71}$—S(O)$_2$—NH— and $R^{71}$—S(O)$_2$—N($R^{71}$)—, in another embodiment from the series consisting of HO—, $R^{71}$—C(O)—O—, $H_2N$—, $R^{71}$—C(O)—NH— and $R^{71}$—S(O)$_2$—NH—, in another embodiment from the series consisting of HO—, $R^{71}$—C(O)—O— and $R^{71}$—C(O)—NH—, in another embodiment from the series consisting of HO— and $R^{71}$—C(O)—NH—, in another embodiment from the series consisting of HO— and $R^{71}$—O—, and in another embodiment of the invention substituents $R^{70}$ in these groups $R^{33}$ are HO—. In one embodiment of the invention, the groups $R^{71}$ present in these groups $R^{33}$ are independently of each other chosen from the series consisting of ($C_1$-$C_4$)-alkyl, cyclopropyl and cyclopropyl-$CH_2$—, in another embodiment from the series consisting of ($C_1$-$C_4$)-alkyl and cyclopropyl, in another embodiment from the series consisting of ($C_1$-$C_4$)-alkyl. In one embodiment of the invention, the number of nitro substituents ($O_2N$—) on the ring $R^{24}$ is not greater than two, in another embodiment not greater than one. In one embodiment of the invention, the total number of nitro groups in a compound of the formula I is not greater than two. In one embodiment of the invention, $R^{24}$ is a benzene ring or a thiophene ring, for example a benzene ring, or, in terms of the respective residues, $R^{24}$ is a phenyl group or a thiophenyl(thienyl) group, for example a phenyl group, which are all optionally substituted as indicated afore.

Examples of specific residues of benzene and thiophene rings, i.e. of specific phenyl and thiophenyl groups, representing $R^{24}$, from any one or more of which examples the group $R^{24}$ is chosen in one embodiment of the invention, are phenyl, 2-fluoro-phenyl, 3-fluoro-phenyl, 2-chloro-phenyl, 3-chloro-phenyl, 4-chloro-phenyl, 3-bromo-phenyl, 2,3-dichloro-phenyl, 3,4-dichloro-phenyl, 2,5-difluoro-phenyl, 2,5-dichloro-phenyl, 2-chloro-6-fluoro-phenyl, 3,4,5-trifluoro-phenyl, 3-methyl-phenyl(m-tolyl), 3-ethyl-phenyl, 3-isopropyl-phenyl, 3-cyclopropyl-phenyl, 3-tert-butyl-phenyl, 3-trifluoromethyl-phenyl, 3-(2-hydroxyethyl)-phenyl, 3-(2-hydroxy-2-methyl-propyl)-phenyl, 3-(2-acetylaminoethyl)-phenyl, 2-fluoro-5-methyl-phenyl, 3-chloro-2-methyl-phenyl, 5-chloro-2-methyl-phenyl, 5-chloro-2-fluoro-3-methyl-phenyl, 2-fluoro-3-trifluoromethyl-phenyl, 2-fluoro-5-trifluoromethyl-phenyl, 4-fluoro-3-trifluoromethyl-phenyl, 5-fluoro-3-trifluoromethyl-phenyl, 3-chloro-4-trifluoromethyl-phenyl, 5-chloro-2-trifluoromethyl-phenyl, 5-chloro-3-trifluoromethyl-phenyl, 3-ethoxy-phenyl, 2-propoxy-phenyl, 3-isopropoxy-phenyl, 3-trifluoromethoxy-phenyl, 3-(2,2,2-trifluoroethoxy)-phenyl, 5-chloro-2-methoxy-phenyl, 3-chloro-4-methoxy-phenyl, 5-fluoro-3-isopropoxy-phenyl, 2-fluoro-3-trifluoromethoxy-phenyl, 4-methoxy-3,5-dimethyl-phenyl, 3-methoxy-5-trifluoromethyl-phenyl, 3-methylsulfanyl-phenyl, 3-ethylsulfanyl-phenyl, 3-trifluoromethylsulfanyl-phenyl, 3-ethanesulfonyl-phenyl, 3-acetylamino-phenyl, 3-methanesulfonylamino-phenyl, 3-dimethylaminosulfonylamino-phenyl, 3-cyano-phenyl, 2-thienyl, 3-thienyl, 4-methyl-2-thienyl, 5-methyl-3-thienyl.

In one embodiment of the invention, $R^{26}$, independently of each other group $R^{26}$, is chosen from the series consisting of hydrogen, fluorine, methyl and HO—, in another embodiment from the series consisting of hydrogen, fluorine and ($C_1$-$C_4$)-alkyl, in another embodiment from the series consisting of hydrogen, fluorine and methyl, in another embodiment from the series consisting of hydrogen and fluorine, in another embodiment from the series consisting of hydrogen and methyl, and in another embodiment $R^{26}$ is hydrogen, or in all these embodiments two groups $R^{26}$ bonded to the same carbon atom together are oxo, or two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, N($R^{34}$), O, S, S(O) and S(O)$_2$, which ring is optionally substituted on ring carbon atoms by one or more identical or different substituents chosen from the series consisting of fluorine and ($C_1$-$C_4$)-alkyl. In another embodiment of the invention, $R^{26}$, independently of each other group $R^{26}$, is chosen from the series consisting of hydrogen, fluorine, methyl and HO—, in another embodiment from the series consisting of hydrogen, fluorine and ($C_1$-$C_4$)-alkyl, in another embodiment from the series consisting of hydrogen, fluorine and methyl, in another embodiment from the series consisting of hydrogen and fluorine, in another embodiment from the series consisting of hydrogen and methyl, and in another embodiment $R^{26}$ is hydrogen, or in all these embodiments two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, N($R^{34}$), O, S, S(O) and S(O)$_2$, which ring is optionally substituted on ring carbon atoms by one or more identical or different substituents chosen from the series consisting of fluorine and ($C_1$-$C_4$)-alkyl. In another embodiment of the invention, $R^{26}$, independently of each other group $R^{26}$, is chosen from the series consisting of hydrogen, fluorine, methyl and HO—, in another embodiment from the series consisting of hydrogen, fluorine and ($C_1$-$C_4$)-alkyl, in another embodiment from the series consisting of hydrogen, fluorine and methyl, in another embodiment from the series consisting of hydrogen and fluorine, in another embodiment from the series consisting of hydrogen and methyl, and in another embodiment all groups $R^{26}$ are hydrogen.

In one embodiment of the invention, the number of groups $R^{26}$ in a chain representing $R^{23}$ which are HO—, is zero, one or two, in another embodiment zero or one, in another embodiment zero, in another embodiment one. In one embodiment of the invention, a HO— group representing $R^{26}$ is not present on a carbon atom which is adjacent to a hetero chain member in a chain representing $R^{23}$. In one embodiment of the invention the number of groups $R^{26}$ in a chain representing $R^{23}$ which are ($C_1$-$C_4$)-alkyl such as methyl, is zero, one or two, in another embodiment zero or one, in another embodiment zero, in another embodiment one, in another embodiment two. In one embodiment of the invention the number of groups $R^{26}$ in a chain representing $R^{23}$ which are fluorine, is zero, one, two, three or four, in another embodiment zero, one, two or three, in another embodiment zero, one or two, in another embodiment zero or one, in another embodiment zero, in another embodiment one, in another embodiment two. In one embodiment of the invention, the number of oxo substituents in a chain representing $R^{23}$ which are formed by two groups $R^{26}$ bonded to the same carbon atom, is zero, one or two, in another embodiment zero or one, in another embodiment zero, in another embodiment one. In one embodiment of the invention, an oxo substituent in a chain representing $R^{23}$ is not present on a carbon atom which is adjacent to a hetero chain member chosen from the series consisting of S(O) and S(O)$_2$, in another embodiment from the series consisting of S, S(O) and S(O)$_2$, in another embodiment from the series consisting of O, S, S(O) and S(O)$_2$.

In one embodiment of the invention, the number of rings which are formed by two of the groups $R^{26}$ or one group $R^{25}$ and one group $R^{26}$, together with the comprised chain members, is zero, one or two, in another embodiment zero or one, in another embodiment one, in another embodiment zero. In one embodiment of the invention a ring formed by two of the groups $R^{26}$ or one group $R^{25}$ and one group $R^{26}$, together with the comprised chain members, is a 3-membered, 4-membered, 5-membered or 6-membered ring, in another embodiment a 3-membered, 5-membered or 6-membered ring, in another embodiment a 3-membered ring, in another embodiment a 5-membered or 6-membered ring. In one embodiment of the invention, it is possible for two of the groups $R^{26}$, together with the comprised chain members, to form a ring, but not for one group $R^{25}$ and one group $R^{26}$. In one embodiment of the invention the number of chain members which is comprised by a ring formed by two of the groups $R^{26}$ or one group $R^{25}$ and one group $R^{26}$, is one, two, three or four, in another embodiment it is one, two or three, in another embodiment it is one or two, in another embodiment it is one. In case such ring comprises only one chain member, the two of the groups $R^{26}$ forming the ring are bonded to the same carbon atom in the chain and the said one chain member is the carbon atom carrying the two groups $R^{26}$. Examples of rings, which are formed by two groups $R^{26}$ bonded to the same carbon atom and the one comprised chain member, are cycloalkane rings such as cyclopropane, cyclobutane, cyclopentane or cyclohexane, and heterocyclic rings such as tetrahydrothiophene, tetrahydrothiopyran, oxetane, tetrahydrofuran, tetrahydropyran, azetidine, pyrrolidine or piperidine, for example cyclopropane, which carry any adjacent chain members of a chain representing $R^{23}$ and/or the group $R^{24}$ and/or the ring comprising the groups Y and Z which is depicted in formula I, on the same ring carbon atom, and which rings can all be substituted as indicated. In case a ring formed by two of the groups $R^{26}$ or one group $R^{25}$ and one group $R^{26}$, together with the comprised chain members, comprises two chain members, the two groups $R^{26}$ forming the ring are bonded to two adjacent carbon atoms in the chain or the one group $R^{26}$ is bonded to a carbon atom which is adjacent to the group $N(R^{25})$, respectively. Examples of rings, which are formed in such case, are likewise cycloalkane rings such as cyclopropane, cyclobutane, cyclopentane or cyclohexane, and heterocyclic rings such as tetrahydrothiophene, tetrahydrothiopyran, oxetane, tetrahydrofuran, tetrahydropyran, azetidine, pyrrolidine or piperidine, for example cyclopropane, which carry any adjacent chain members of a chain representing $R^{23}$ and/or the group $R^{24}$ and/or the ring comprising the groups Y and Z which is depicted in formula I, on two adjacent ring carbon atoms or on the ring nitrogen atom and an adjacent ring carbon atom, and which rings can all be substituted as indicated.

In case a ring formed by two of the groups $R^{26}$ or one group $R^{25}$ and one group $R^{26}$, together with the comprised chain members, comprises more than one chain members, besides being the group $C(R^{26})(R^{26})$ the comprised chain members can also be hetero chain members including the group $N(R^{25})$, which then are hetero ring members of the formed ring, wherein at least one group $C(R^{26})(R^{26})$ is present. In one embodiment of the invention, the total number of hetero ring members in such a ring is zero, one or two, in another embodiment zero or one, in another embodiment zero, in another embodiment one. In one embodiment of the invention, hetero ring members in such a ring are chosen from the series consisting of N, $N(R^{34})$, O and S, in another embodiment form the series consisting of N, $N(R^{34})$ and O, in another embodiment from the series consisting of N and $N(R^{34})$, in another embodiment from the series consisting of $N(R^{34})$ and O, in another embodiment from the series consisting of $N(R^{34})$, and in another embodiment hetero ring members in such a ring are N, and in still another embodiment hetero ring members in such a ring are O, wherein a hetero ring member N in a ring formed by two of the groups $R^{26}$ or one group $R^{25}$ and one group $R^{26}$, together with the comprised chain members, is the nitrogen atom of a hetero chain member $N(R^{25})$.

In one embodiment of the invention, the number of substituents which are optionally present in a ring formed by two of the groups $R^{26}$ or one group $R^{25}$ and one group $R^{26}$, together with the comprised chain members, is 0, 1, 2, 3 or 4, in another embodiment 0, 1, 2 or 3, in another embodiment 0, 1 or 2, in another embodiment 0 or 1, in another embodiment 0. In one embodiment of the invention, $(C_1-C_4)$-alkyl substituents which are present in a ring formed by two of the groups $R^{26}$ or one group $R^{25}$ and one group $R^{26}$, together with the comprised chain members, are methyl. In one embodiment of the invention substituents present in a ring formed by two of the groups $R^{26}$ or one group $R^{25}$ and one group $R^{26}$, together with the comprised chain members, are fluorine, in another embodiment they are identical or different $(C_1-C_4)$-alkyl groups, for example methyl.

Examples of specific groups $R^{23}$ including specific groups $R^{26}$ contained therein are given in the following examples of groups of the formula II, which groups are bonded to the ring comprising the groups Y and Z which is depicted in formula I by the free bond represented by the terminal hyphen or the terminal line in the structural formula, and from which groups of the formula II the groups $R^{23}$ themselves are obtained by removing the group $R^{24}$, wherein in these groups of the formula II the group $R^{24}$ is defined as above or below:

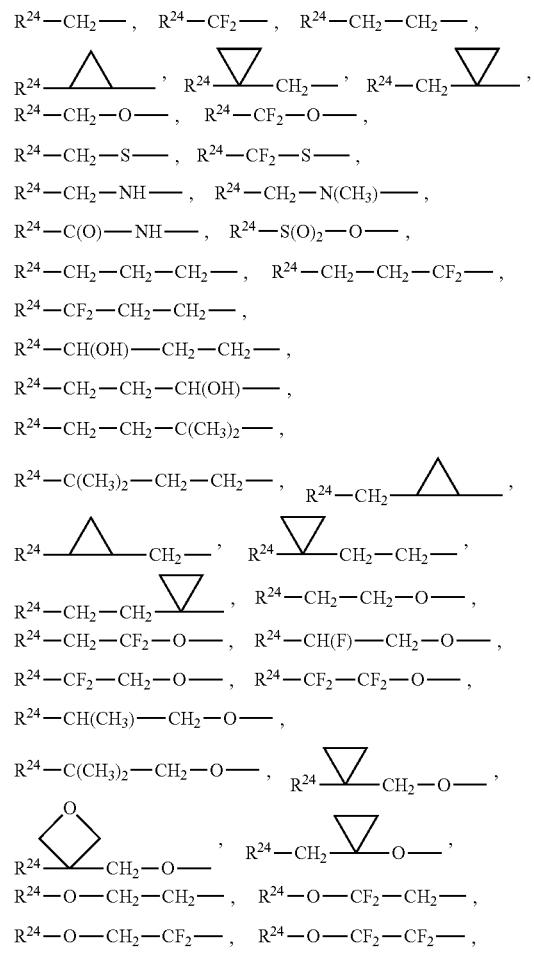

-continued

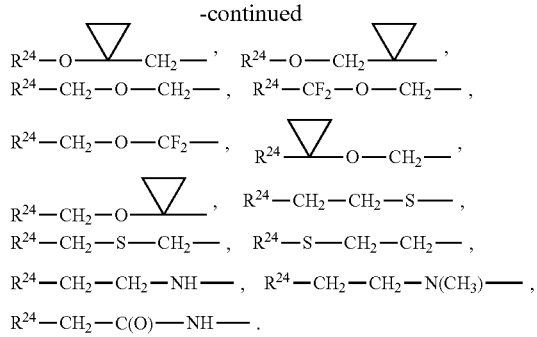

In one embodiment of the invention, $R^{23}$ is chosen from a direct bond and any one or more of the chains $R^{23}$ in the preceding examples of groups of the formula II and, likewise, the group of the formula II is chosen from the group $R^{24}$ and any one or more of the preceding examples of the groups of the formula II.

In one embodiment of the invention, $R^{32}$ and $R^{34}$ are independently of each other chosen from the series consisting of hydrogen, $R^{35}$, $R^{35}$—C(O)—, $R^{35}$—O—C(O)— and phenyl, in another embodiment from the series consisting of hydrogen, $R^{35}$, $R^{35}$—C(O)— and $R^{35}$—O—C(O)—, in another embodiment from the series consisting of hydrogen, $R^{35}$ and $R^{35}$—C(O)—, in another embodiment from the series consisting of hydrogen, $R^{35}$ and phenyl, in another embodiment from the series consisting of hydrogen and $R^{35}$. In one embodiment of the invention, the groups $R^{35}$ occurring in $R^{32}$ and $R^{34}$ are independently of each other chosen from ($C_1$-$C_6$)-alkyl, ($C_3$-$C_7$)-cycloalkyl and ($C_3$-$C_7$)-cycloalkyl-($C_1$-$C_4$)-alkyl-, in another embodiment from ($C_1$-$C_6$)-alkyl, ($C_3$-$C_7$)-cycloalkyl and ($C_3$-$C_7$)-cycloalkyl-($C_1$-$C_2$)-alkyl-, in another embodiment from ($C_1$-$C_6$)-alkyl, ($C_3$-$C_7$)-cycloalkyl and ($C_3$-$C_7$)-cycloalkyl-$CH_2$—, in another embodiment from ($C_1$-$C_6$)-alkyl and ($C_3$-$C_7$)-cycloalkyl, in another embodiment from ($C_1$-$C_6$)-alkyl, in another embodiment from ($C_1$-$C_4$)-alkyl, which are all optionally substituted by one or more identical or different substituents $R^{70}$ and wherein in these groups besides any substituents $R^{70}$ one or more fluorine substituents are optionally present and in cycloalkyl groups one or more ($C_1$-$C_4$)-alkyl substituents are optionally present as applies to alkyl and cycloalkyl groups in general.

In one embodiment of the invention, the number of substituents $R^{70}$ which are optionally present in a group $R^{35}$ occurring in $R^{32}$ and $R^{34}$ besides any fluorine substituents and, in the case of a cycloalkyl group, alkyl substituents, is, independently of each other group, 0, 1, 2, 3 or 4, in another embodiment 0, 1, 2 or 3, in another embodiment 0, 1 or 2, in another embodiment 0 or 1, in another embodiment 0. In one embodiment of the invention, substituents $R^{70}$ which are optionally present in a group $R^{35}$ occurring in $R^{32}$ and $R^{34}$ are, independently of each other group, chosen from the series consisting of HO— and $R^{71}$—O—.

In one embodiment of the invention, $R^{50}$ is chosen from $R^{51}$—O— and $R^{52}$—NH—, in another embodiment from $R^{51}$—O— and $H_2N$—. In another embodiment $R^{50}$ is $R^{51}$—O—.

In one embodiment of the invention, $R^{51}$ is hydrogen. In another embodiment of the invention, $R^{51}$ is $R^{54}$.

In one embodiment of the invention, $R^{52}$ is chosen from the series consisting of hydrogen, $R^{55}$ and $R^{56}$—S(O)$_2$—, in another embodiment from the series consisting of hydrogen, ($C_1$-$C_4$)-alkyl which is optionally substituted by one or more identical or different substituents $R^{70}$, and $R^{56}$—S(O)$_2$—, in another embodiment from the series consisting of hydrogen, unsubstituted ($C_1$-$C_4$)-alkyl and $R^{56}$—S(O)$_2$—, in another embodiment from the series consisting of hydrogen, unsubstituted methyl and $R^{56}$—S(O)$_2$—, in another embodiment from the series consisting of hydrogen and ($C_1$-$C_4$)-alkyl which is optionally substituted by one or more identical or different substituents $R^{70}$, in another embodiment from the series consisting of hydrogen and unsubstituted ($C_1$-$C_4$)-alkyl, in another embodiment from the series consisting of hydrogen and unsubstituted methyl. In another embodiment of the invention, $R^{52}$ is hydrogen.

In one embodiment of the invention, $R^{53}$ is chosen from the series consisting of hydrogen and ($C_1$-$C_4$)-alkyl which is optionally substituted by one or more identical or different substituents $R^{70}$, in another embodiment from the series consisting of hydrogen and unsubstituted ($C_1$-$C_4$)-alkyl, in another embodiment from the series consisting of hydrogen and unsubstituted methyl. In another embodiment of the invention, $R^{53}$ is hydrogen. In one embodiment of the invention, $R^{51}$, $R^{52}$ and $R^{53}$ are independently of each other chosen from the series consisting of hydrogen and unsubstituted ($C_1$-$C_4$)-alkyl, in another embodiment from the series consisting of hydrogen and unsubstituted ($C_1$-$C_3$)-alkyl, in another embodiment from the series consisting of hydrogen and unsubstituted ($C_1$-$C_2$)-alkyl.

In one embodiment of the invention, $R^{54}$ is chosen from ($C_1$-$C_6$)-alkyl, ($C_3$-$C_7$)-cycloalkyl and ($C_3$-$C_7$)-cycloalkyl-($C_1$-$C_4$)-alkyl-, in another embodiment from ($C_1$-$C_6$)-alkyl, ($C_3$-$C_7$)-cycloalkyl and ($C_3$-$C_7$)-cycloalkyl-($C_1$-$C_2$)-alkyl-, in another embodiment from ($C_1$-$C_6$)-alkyl, ($C_3$-$C_7$)-cycloalkyl and ($C_3$-$C_7$)-cycloalkyl-$CH_2$—, in another embodiment from ($C_1$-$C_6$)-alkyl and ($C_3$-$C_7$)-cycloalkyl, in another embodiment from ($C_1$-$C_6$)-alkyl, in another embodiment from ($C_1$-$C_4$)-alkyl, in another embodiment from ($C_1$-$C_3$)-alkyl, which are all optionally substituted by one or more identical or different substituents $R^{70}$ and wherein in these groups besides any substituents $R^{70}$ one or more fluorine substituents are optionally present and in cycloalkyl groups one or more ($C_1$-$C_4$)-alkyl substituents are optionally present as applies to alkyl and cycloalkyl groups in general. In one embodiment of the invention, the number of substituents $R^{70}$ which are optionally present in a group $R^{54}$ besides any fluorine substituents and, in the case of a cycloalkyl group, any alkyl substituents, is 0, 1 or 2, in another embodiment 0 or 1, in another embodiment 1, in another embodiment 0. In another embodiment of the invention, a group $R^{54}$ is neither substituted by $R^{70}$ nor by fluorine substituents nor, in the case of a cycloalkyl group, by alkyl substituents, and $R^{54}$ in this embodiment thus is chosen, for example, from the series consisting of $C_1$-$C_6$)-alkyl, ($C_2$-$C_6$)-alkenyl, ($C_2$-$C_6$)-alkynyl, ($C_3$-$C_7$)-cycloalkyl and ($C_3$-$C_7$)-cycloalkyl-($C_1$-$C_4$)-alkyl-, or from the series consisting of ($C_1$-$C_6$)-alkyl, ($C_3$-$C_7$)-cycloalkyl and ($C_3$-$C_7$)-cycloalkyl-$CH_2$—, or from the series consisting of ($C_1$-$C_6$)-alkyl, or from the series consisting of ($C_1$-$C_4$)-alkyl, or from the series consisting of ($C_1$-$C_3$)-alkyl, which are all unsubstituted. In one embodiment of the invention, substituents $R^{70}$ which are optionally present in a group $R^{54}$, are independently of each other chosen from the series consisting of HO—, $R^{71}$—O—, $R^{71}$—C(O)—O—, HO—C(O)— and $R^{71}$—O—C(O)—, in another embodiment from the series consisting of HO—, $R^{71}$—O— and $R^{71}$—C(O)—O—, in another embodiment from the series consisting of HO— and $R^{71}$—C(O)—O—.

In one embodiment of the invention, $R^{56}$ is chosen from the series consisting of phenyl which is optionally substituted as indicated above or below, and unsubstituted ($C_1$-$C_4$)-alkyl, in another embodiment from the series consisting of phenyl which is optionally substituted as indicated above or below, and unsubstituted methyl, in another embodiment from unsubstituted $(C_1-C_4)$-alkyl, in another embodiment from unsubstituted $(C_1-C_3)$-alkyl. In another embodiment $R^{56}$ is unsubstituted methyl, in another embodiment phenyl which is optionally substituted as indicated.

In one embodiment of the invention, $R^{60}$ is chosen from the series consisting of hydrogen and methyl. In another embodiment $R^{60}$ is hydrogen. In another embodiment $R^{60}$ is $(C_1-C_4)$-alkyl, for example methyl.

In one embodiment of the invention, a group $R^{70}$ in any of its occurrences is, independently of groups $R^{70}$ in other occurrences and unless specified otherwise, chosen from the series consisting of HO—, $R^{71}$—O—, $R^{71}$—C(O)—O—, $R^{71}$—S(O)$_m$—, H$_2$N—, $R^{71}$—NH—, $R^{71}$—N($R^{71}$)—, $R^{71}$—C(O)—NH—, $R^{71}$—C(O)—N($R^{71}$)—, $R^{71}$—S(O)$_2$—NH—, $R^{71}$—S(O)$_2$—N($R^{71}$)—, HO—C(O)—, $R^{71}$—O—C(O)—, H$_2$N—C(O)—, $R^{71}$—NH—C(O)—, $R^{71}$—N($R^{71}$)—C(O)— and oxo, in another embodiment from the series consisting of HO—, $R^{71}$—O—, $R^{71}$—C(O)—O—, $R^{71}$—S(O)$_m$—, H$_2$N—, $R^{71}$—NH—, $R^{71}$—N($R^{71}$)—, $R^{71}$—C(O)—NH—, $R^{71}$—S(O)$_2$—NH—, HO—C(O)—, $R^{71}$—O—C(O)—, H$_2$N—C(O)—, $R^{71}$—NH—C(O)—, $R^{71}$—N($R^{71}$)—C(O)— and oxo, in another embodiment from the series consisting of HO—, $R^{71}$—O—, $R^{71}$—C(O)—O—, $R^{71}$—S(O)$_m$—, HO—C(O)—, $R^{71}$—O—C(O)—, H$_2$N—C(O)—, $R^{71}$—NH—C(O)—, $R^{71}$—N($R^{71}$)—C(O)— and oxo, in another embodiment from the series consisting of HO—, $R^{71}$—O—, $R^{71}$—C(O)—O—, $R^{71}$—S(O)$_m$—, H$_2$N—, $R^{71}$—NH—, $R^{71}$—N($R^{71}$)—, $R^{71}$—C(O)—NH—, $R^{71}$—S(O)$_2$—NH— and oxo, in another embodiment from the series consisting of HO—, $R^{71}$—O—, $R^{71}$—C(O)—O—, $R^{71}$—S(O)$_m$— and oxo, in another embodiment from the series consisting of HO—, $R^{71}$—O—, $R^{71}$—S(O)$_m$— and oxo, in another embodiment from the series consisting of HO—, $R^{71}$—O—, $R^{71}$—C(O)—O— and $R^{71}$—S(O)$_m$—, in another embodiment from the series consisting of HO— and $R^{71}$—O—, in another embodiment from the series consisting of HO— and $R^{71}$—C(O)—O—, in another embodiment from the series consisting of HO—C(O)—, $R^{71}$—O—C(O)—, H$_2$N—C(O)—, $R^{71}$—NH—C(O)—, $R^{71}$—N($R^{71}$)—C(O)—, in another embodiment from the series consisting of HO—C(O)—, and $R^{71}$—O—C(O)—, and in another embodiment $R^{70}$ is HO—, wherein $R^{71}$ is defined as indicated above or below. In the latter embodiment, in which $R^{70}$ is HO—, a $(C_1-C_6)$-alkyl group, for example, which is optionally substituted by the said $R^{70}$, can among others be a group such as $(C_1-C_6)$-alkyl, HO—$(C_1-C_6)$-alkyl-, i.e. hydroxy-$(C_1-C_6)$-alkyl-, (HO)$_2$($C_2-C_6$)-alkyl-, i.e. dihydroxy-($C_2-C_6$)-alkyl-, and a $(C_1-C_4)$-alkyl group which is optionally substituted by $R^{70}$, can among others be a group such as $(C_1-C_4)$-alkyl, HO—$(C_1-C_4)$-alkyl-, i.e. hydroxy-$(C_1-C_4)$-alkyl-, (HO)$_2$($C_2-C_4$)-alkyl-, i.e. dihydroxy-($C_2-C_4$)-alkyl-, wherein the alkyl groups are optionally substituted by one or more fluorine substituents. In one embodiment of the invention, a carbon atom does not carry more than one HO— group.

In one embodiment of the invention, $R^{71}$ is chosen from $(C_1-C_4)$-alkyl, cyclopropyl and cyclopropyl-CH$_2$—, in another embodiment from $(C_1-C_4)$-alkyl and cyclopropyl, in another embodiment from $(C_1-C_4)$-alkyl, in another embodiment from $(C_1-C_3)$-alkyl, unless specified otherwise.

A subject of the invention are all compounds of the formula I wherein any one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratios, and their physiologically acceptable salts are a subject of the present invention.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that all their stereoisomeric forms and mixtures of stereoisomeric forms in any ratio, and their physiologically acceptable salts are a subject of the present invention. A subject of the invention also are all specific compounds disclosed herein, irrespective thereof whether they are disclosed as a free compound and/or as a specific salt, both in the form of the free compound and in the form of all its physiologically acceptable salts. Thus, a subject of the invention also is a compound of the formula I which is chosen from any of the specific compounds of the formula I which are disclosed herein, or is any one of the specific compounds of the formula I which are disclosed herein, irrespective thereof whether they are disclosed as a free compound and/or as a specific salt, or a physiologically acceptable salt thereof, wherein the compound of the formula I is a subject of the invention in any of its stereoisomeric forms or a mixture of stereoisomeric forms in any ratio where applicable.

As an example of compounds of the invention which with respect to any structural elements are defined as in specified embodiments of the invention or definitions of such elements, compounds of the formula I may be mentioned wherein ring A is a 3-membered to 8-membered monocyclic ring which comprises 0, 1 or 2 identical or different hetero ring members chosen from the series consisting of N, N($R^0$), O, S, S(O) and S(O)$_2$, and which is saturated or comprises 1 double bond, wherein ring A is optionally substituted on ring carbon atoms by one or more identical or different substituents chosen from the series consisting of halogen, $R^1$, $R^2$, $(O_2-C_6)$-alkenyl, HO—, $R^1$—O—, phenyl-$(C_1-C_4)$-alkyl-O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^1$)—, $R^1$—S(O)$_2$—NH—, $R^1$—S(O)$_2$—N($R^1$)—, $R^1$—C(O)—, HO—C(O)—, $R^1$—O—C(O)—, H$_2$N—C(O)—, R—NH—C(O)—, $R^1$—N(R)—C(O)—, H$_2$N—S(O)$_2$—, $R^1$—NH—S(O)$_2$—, $R^1$—N($R^1$)—S(O)$_2$—, F$_5$S—, NC—, oxo and methylene;
Y is chosen from the series consisting of S, C($R^{12}$)=C($R^{13}$), and C($R^{15}$)=N;
Z is C($R^{16}$);
$R^{20}$ is hydrogen;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts.

As another such example compounds of the formula I may be mentioned, wherein ring A is a cyclohexane ring or cycloheptane ring which is optionally substituted on ring carbon atoms by one or more identical or different substituents chosen from the series consisting of halogen, $R^1$, $R^2$, $(C_2-C_6)$-alkenyl, HO—, $R^1$—O—, phenyl-$(C_1-C_4)$-alkyl-O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^1$)—, $R^1$—S(O)$_2$—NH—, $R^1$—S(O)$_2$—N($R^1$)—, $R^1$—C(O)—, HO—C(O)—, $R^1$—O—C(O)—, $H_2N$—C(O)—, $R^1$—NH—C(O)—, $R^1$—N($R^1$)—C(O)—, $H_2N$—S(O)$_2$—, $R^1$—NH—S(O)$_2$—, $R^1$—N($R^1$)—S(O)$_2$—, $F_5S$—, NC—, oxo and methylene;

Y is chosen from the series consisting of S, C($R^{12}$)=C($R^{13}$) and C($R^{15}$)=N;

Z is C($R^{16}$);

$R^{20}$ is hydrogen;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts.

As another such example compounds of the formula I may be mentioned, wherein $R^{21}$ is chosen from the series consisting of hydrogen, halogen, (C$_1$-C$_4$)-alkyl, HO—(C$_1$-C$_4$)-alkyl-, (C$_1$-C$_4$)-alkyl-O—(C$_1$-C$_4$)-alkyl-, (C$_1$-C$_4$)-alkyl-O—, HO—(C$_1$-C$_4$)-alkyl-O—, (C$_1$-C$_4$)-alkyl-O—(C$_1$-C$_4$)-alkyl-O—, (C$_1$-C$_4$)-alkyl-S(O)$_m$—, (C$_1$-C$_4$)-alkyl-C(O)—, NC— and Het$^1$, or together with $R^{13}$ or $R^{14}$ forms a chain as specified in the definition of $R^{13}$ and $R^{14}$;

$R^{22}$ is a group of the formula II $$R^{24}\text{—}R^{23}\text{—} \qquad \text{II}$$

$R^{23}$ is a direct bond or a chain consisting of 2, 3 or 4 chain members of which 0 or 1 chain members are hetero chain members chosen from the series consisting of N($R^{25}$), O, S, S(O) and S(O)$_2$ and the other chain members are identical or different groups C($R^{26}$)($R^{26}$);

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts.

As another such example compounds of the formula I may be mentioned, wherein ring A is a cyclohexane ring or a cycloheptane ring which is optionally substituted by one or two identical or different substituents chosen from the series consisting of halogen, (C$_1$-C$_4$)-alkyl and (C$_1$-C$_4$)-alkyl-O—;

Y is chosen from the series consisting of C($R^{12}$)=C($R^{13}$) and C($R^{15}$)=N;

Z is C($R^{16}$);

$R^{12}$, $R^{13}$, $R^{15}$ and $R^{16}$ are independently of each other chosen from the series consisting of hydrogen, halogen, (C$_1$-C$_4$)-alkyl; or $R^{13}$ forms together with $R^{21}$ a chain which is chosen from the series consisting of —O—C($R^{18}$)($R^{18}$)—O—, —CH$_2$—CH$_2$—CH$_2$—, —CH$_2$—O—CH$_2$—, —CH$_2$—CH$_2$—CH$_2$—CH$_2$— and —O—C($R^{18}$)($R^{18}$)—C($R^{18}$)($R^{18}$)—O;

$R^{18}$ is chosen from the series consisting of hydrogen or fluorine;

$R^{21}$ is chosen from the series consisting of hydrogen, halogen, (C$_1$-C$_4$)-alkyl, HO—(C$_1$-C$_4$)-alkyl-, (C$_1$-C$_4$)-alkyl-O—, (C$_1$-C$_4$)-alkyl-C(O)—, (C$_1$-C$_4$)-alkyl-O—(C$_1$-C$_4$)alkyl-, HO—(C$_1$-C$_4$)-alkyl-O—, (C$_1$-C$_4$)-alkyl-O—(C$_1$-C$_4$)-alkyl-O—, NC— and oxetanyl, or together with $R^{13}$ forms a chain as specified in the definition of $R^{13}$;

$R^{22}$ is a group of the formula II $$R^{24}\text{—}R^{23}\text{—} \qquad \text{II}$$

$R^{23}$ is a direct bond or a chain consisting of 2, 3 or 4 chain members of which 0 or 1 chain members are hetero chain members chosen from the series consisting of O and S, and the other chain members are identical or different groups C($R^{26}$)($R^{26}$);

$R^{24}$ is a benzene ring which is optionally substituted by one or more identical or different substituents chosen from the series consisting of halogen, $R^{33}$, oxetanyl, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—S(O)$_2$—NH—, HO—C(O)—, $R^{33}$—O—C(O)—, $H_2N$—C(O)—, $R^{33}$—NH—C(O)—, $R^{33}$—N($R^{33}$)—C(O)— and NC—;

$R^{26}$, independently of each other group $R^{26}$, is chosen from the series consisting of hydrogen, fluorine, (C$_1$-C$_4$)-alkyl, or two of the groups $R^{26}$ which are bonded to the same carbon atom in the chain, together with the carbon atom carrying them, form a cyclopropane ring or an oxetane ring;

$R^{33}$, independently of each other group $R^{33}$, is chosen from the series consisting of (C$_1$-C$_4$)-alkyl, (C$_3$-C$_7$)-cycloalkyl and (C$_3$-C$_7$)-cycloalkyl-(C$_1$-C$_2$)-alkyl-, which are all optionally substituted by one or more identical or different substituents $R^{70}$;

$R^{50}$ is chosen from the series consisting of $R^{51}$O— and $R^{52}$($R^{53}$)N—;

$R^{51}$, $R^{52}$ and $R^{53}$ are independently of each other chosen from the series consisting of hydrogen and (C$_1$-C$_4$)-alkyl;

$R^{70}$ is chosen from the series consisting of HO— and $R^{71}$—O—;

$R^{71}$ is (C$_1$-C$_4$)-alkyl;

m, independently of each other number m, is an integer chosen from the series consisting of 0 and 2;

cycloalkyl, independently of each other group cycloalkyl, and independently of any other substituents on cycloalkyl, is optionally substituted by one or more identical or different substituents chosen from fluorine and (C$_1$-C$_4$)-alkyl;

alkyl, independently of each other group alkyl, and independently of any other substituents on alkyl, is optionally substituted by one or more fluorine substituents;

in any of their stereoisomeric forms or a mixture of stereoisomeric forms in any ratio, and their physiologically acceptable salts.

A subject of the present invention is a compound of the formula I, which is trans-1-({5-[2-(3-Chloro-phenyl)-ethoxy]-6-methoxy-pyridine-3-carbonyl}-amino)-4-methyl-cyclohexanecarboxylic acid, cis-1-[(5-{2-[3-(2-Hydroxy-ethyl)-phenyl]-ethoxy}-6-methoxy-pyridine-3-carbonyl)-amino]-4-methyl-cyclohexanecarboxylic acid, trans-1-[(5-{2-[3-(2-Hydroxy-ethyl)-phenyl]-ethoxy}-6-methoxy-pyridine-3-carbonyl)-amino]-4-methyl-cyclohexanecarboxylic acid, cis-4-Ethyl-1-{[6-methoxy-5-(3-trifluoromethoxy-phenyl)-pyridine-3-carbonyl]-amino}-cyclohexanecarboxylic acid, cis-4-Ethyl-1-{[6-methoxy-5-(3-trifluoromethyl-phenyl)-pyridine-3-carbonyl]-amino}-cyclohexanecarboxylic acid, trans-4-Ethyl-1-{[6-methoxy-5-(3-trifluoromethoxy-phenyl)-pyridine-3-carbonyl]-amino}-cyclohexanecarboxylic acid, trans-4-Ethyl-1-{[6-methoxy-5-(3-trifluoromethyl-phenyl)-pyridine-3-carbonyl]-amino}-cyclohexanecarboxylic acid, cis-1-{[5-(3-Chloro-4-methoxy-phenyl)-6-methoxy-pyridine-3-carbonyl]-amino}-4-methyl-cyclohexanecarboxylic acid, trans-1-{[5-(3-Chloro-4-methoxy-phenyl)-6-methoxy-pyridine-3-carbonyl]-amino}-4-methyl-cyclohexanecarboxylic acid, cis-1-[(3'-Chloro-6,4'-dimethoxy-biphenyl-3-carbonyl)-amino]-4-ethyl-cyclohexanecarboxylic acid, trans-1-[(3'-Chloro-6,4'-dimethoxy-biphenyl-3-carbonyl)-amino]-4-ethyl-cyclohexanecarboxylic acid,
trans-4-Ethyl-1-[(6-methoxy-5-phenethyloxy-pyridine-3-carbonyl)-amino]-cyclohexanecarboxylic acid,
cis-1-({5-[2-(3-Chloro-phenyl)-ethoxy]-6-methoxy-pyridine-3-carbonyl}-amino)-4-methyl-cyclohexanecarboxylic acid,
cis-1-({5-[2-(3-Chloro-phenyl)-ethoxy]-6-methoxy-pyridine-3-carbonyl}-amino)-4-ethyl-cyclohexanecarboxylic acid,
cis-4-Ethyl-1-[(6-methoxy-5-phenethyloxy-pyridine-3-carbonyl)-amino]-cyclohexanecarboxylic acid,
trans-4-Ethyl-1-{[6-(2-hydroxy-ethoxy)-3'-trifluoromethyl-biphenyl-3-carbonyl]-amino}-cyclohexanecarboxylic acid,
trans-1-({5-[2-(3-Chloro-phenyl)-ethoxy]-6-methoxy-pyridine-3-carbonyl}-amino)-4-ethyl-cyclohexanecarboxylic acid,
trans-1-[3-[2-(3-Chloro-phenyl)-ethoxy]-4-(2-hydroxy-ethoxy)-benzoylamino]-4-ethyl-cyclohexanecarboxylic acid,
cis-1-[3-[2-(3-Chloro-phenyl)-ethoxy]-4-(2-hydroxy-ethoxy)-benzoylamino]-4-ethyl-cyclohexanecarboxylic acid,
Trans-1-[(3'-Chloro-5-fluoro-6,4'-dimethoxy-biphenyl-3-carbonyl)-amino]-4-methyl-cyclohexanecarboxylic acid,
Cis-1-[(3'-chloro-5-fluoro-6,4'-dimethoxy-biphenyl-3-carbonyl)-amino]-4-ethyl-cyclohexanecarboxylic acid,
Cis-1-[(3'-Chloro-5-fluoro-6,4'-dimethoxy-biphenyl-3-carbonyl)-amino]-4-trifluoromethyl-cyclohexanecarboxylic acid, or
cis-4-Ethyl-1-{[6-(2-hydroxy-ethoxy)-5-(3-trifluoromethoxy-phenyl)-pyridine-3-carbonyl]-amino}-cyclohexanecarboxylic acid,
in any of their stereoisomeric forms or a mixture of stereoisomeric forms in any ratio, and their physiologically acceptable salts.

Another subject of the present invention are processes for the preparation of the compounds of the formula I which are outlined below and by which the compounds are obtainable. For example, the preparation of the compounds of the formula I can be carried out by reacting a compound of the formula III with a compound of the formula IV with formation of an amide bond.

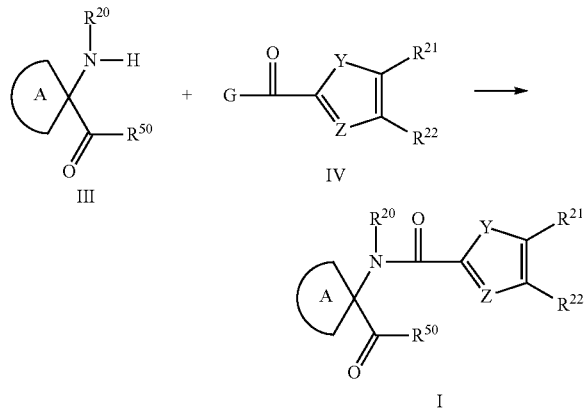

The ring A and the groups Y, Z, $R^{20}$ to $R^{22}$ and $R^{50}$ in the compounds of the formulae III and IV are defined as in the compounds of the formula I and additionally functional groups can be present in protected form or in the form of a precursor group which is later converted into the final group. As an example of a precursor group which can favorably be employed in the reaction of the compounds of the formulae III and IV, the carbonitrile group NC— (cyano group) may by mentioned as a precursor of the group —C(O)—$R^{50}$. Thus, compounds of the formula I can also be prepared by reacting a compound of the formula V, which carries a NC— group in the position of the group —C(O)—$R^{50}$, with a compound of the formula IV to give a compound of the formula VI which likewise carries a NC— group in the position of the group —C(O)—$R^{50}$ in the compounds of the formula I, and then converting the NC— group into the desired group —C(O)—$R^{50}$, for example into a carboxylic acid group or a carboxamide group by the well-known techniques for hydrolyzing carbonitriles. For example, the NC— group can be converted into the group —C(O)—$R^{50}$ in a two step, one pot procedure by initial alcoholysis of the nitrile to the imino ester in a alcohol like ethanol or methanol in the presence of an acid such as hydrogen chloride under anhydrous conditions, and the formed imino ester converted into a carboxylic acid ester, i.e. a compound of the formula I in which $R^{50}$ is $R^{51}$O, by subsequent addition of water. The ring A and the groups Y, Z, $R^{20}$ to $R^{22}$ in the compounds of the formulae V and VI are defined as in the compounds of the formula I, and additionally can functional groups be present in protected form or in the form of a precursor group.

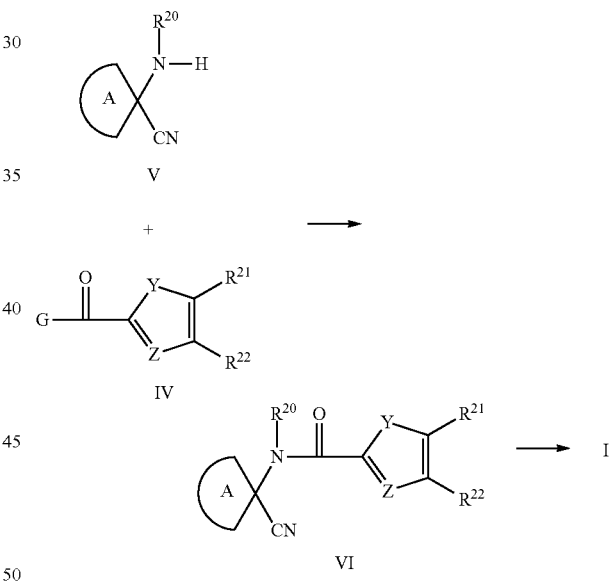

The group G in the compounds of the formula IV can be HO— (hydroxy), i.e. the compound of the formula IV can thus be a carboxylic acid, or another group which can be replaced by the group N($R^{20}$) in the compound of the formula III or V in a substitution reaction, for example an aryloxy group such as optionally substituted phenoxy or an alkyloxy group such as a ($C_1$-$C_4$)-alkyl-O— group, for example a ($C_1$-$C_3$)-alkyl-O— group like methoxy or ethoxy, or halogen, for example chlorine or bromine, and the compound of the formula IV can thus be a reactive ester like an aryl ester or alkyl ester, for example a methyl ester or ethyl ester, or an acid halide, for example an acid chloride or acid bromide, of the respective carboxylic acid. The compound of the formula III and V and/or the compound of the formula IV can also be employed, and the compounds of the formulae I and VI obtained, in the form of a salt, for example an acid addition salt such as an hydrohalide, for example a hydrochloride, of the compound of the formulae III and V and/or an alkaline metal salt, for example a sodium salt, of a compound of the formula IV in which G is HO—. Likewise, in all other reactions in the preparation of the compounds of the formula I, including the preparation of starting compounds, compounds can also be employed and/or products obtained in the form a salt.

In case a compound of the formula IV is employed in which G is HO—, the carboxylic acid group HO—C(O)— is generally activated in situ by means of a customary amide coupling reagent or converted into a reactive carboxylic acid derivative which can be prepared in situ or isolated. For example, the compound of the formula IV in which G is HO— can be converted into an acid halide, e.g. the compound of the formula IV in which G is Cl or Br, by treatment with thionyl chloride, phosphorus pentachloride, phosphorus tribromide or oxalyl chloride, or treated with an alkyl chloroformate like ethyl chloroformate or isobutyl chloroformate to give a mixed anhydride. Customary coupling reagents which can be employed, are propanephosphonic anhydride, N,N'-carbonyldiazoles like N,N'-carbonyldiimidazole (CDI), carbodiimides like 1,3-diisopropylcarbodiimide (DIC), 1,3-dicyclohexylcarbodiimide (DCC) or 1-(3-dimethylaminopropyl)-3-ethylcarbodiimide hydrochloride (EDC), carbodiimides together with additives like 1-hydroxy-benzotriazole (HOBT) or 1-hydroxy-7-azabenzotriazole (HOAT), uronium-based coupling reagents like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), and phosphonium-based coupling reagents like (benzotriazol-1-yloxy)tris (dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP).

The reaction conditions for the preparation of the compounds of the formulae I and VI from compounds of the formulae III and V and compounds of the formula IV depend on the particulars of the specific case, for example the meaning of the group G or the employed coupling reagent, and are well known to a skilled person in view of the general knowledge in the art. For example, in case a compound of the formula IV in which G is alkyl-O—, like methoxy or ethoxy, is reacted with a compound of the formula III or V, generally the reaction is carried out in an inert solvent, for example a hydrocarbon or chlorinated hydrocarbon like benzene, toluene, xylene, chlorobenzene, dichloromethane, chloroform or dichloroethane, an ether like tetrahydrofuran (THF), dioxane, dibutyl ether, diisopropyl ether or dimethoxyethane (DME), or a mixture of solvents, at elevated temperatures, for example at temperatures from about 40° C. to about 140° C., in particular at temperatures from about 50° C. to about 120° C., for example at about the boiling temperature of the solvent. In case a compound of the formula IV in which G is halogen, like chlorine or bromine, is reacted with a compound of the formula III or V, generally the reaction is likewise carried out in an inert solvent, for example a hydrocarbon or chlorinated hydrocarbon or ether like the aforementioned ones, an ester like ethyl acetate or butyl acetate, a nitrile like acetonitrile, or water, or a mixture of solvents including a mixture of water and an organic solvent which is miscible or immiscible with water, at temperatures from about −10° C. to about 100° C., in particular at temperatures from about 0° C. to about 80° C., for example at about room temperature.

Favorably, the reaction of a compound of the formula IV in which G is halogen with a compound of the formula III or V is carried out in the presence of a base such as a tertiary amine, like triethylamine, ethyldiisopropylamine, N-methylmorpholine or pyridine, or an inorganic base such as an alkaline metal hydroxide, carbonate or hydrogencarbonate, like sodium hydroxide, potassium hydroxide, sodium carbonate or sodium hydrogencarbonate.

In case a compound of the formula IV in which G is HO— is reacted with a compound of the formula III or V and the carboxylic acid group is activated by means of an amide coupling reagent such as, for example, a carbodiimide or TOTU, the reaction is generally carried out under anhydrous conditions in an inert aprotic solvent, for example an ether like THF, dioxane or DME, an amide like N,N-dimethylformamide (DMF) or N-methylpyrrolidone (NMP), at temperatures from about −10° C. to about 40° C., in particular at temperatures from about 0° C. to about 30° C. in the presence of a base such as a tertiary amine, like triethylamine, ethyldiisopropylamine or N-methylmorpholine. In case the compound of the formula III or V is employed in the form of an acid addition salt in the reaction with the compound of the formula IV, usually a sufficient amount of a base is added in order to liberate the free compound of the formula III or V.

As indicated above, during the formation of the amide bond between the compounds of the formulae III and V and compounds of the formula IV functional groups in the compounds of the formulae III, IV and V can be present in protected form or in the form of a precursor group. Depending on the particulars of the specific case, it may be necessary or advisable for avoiding an undesired course of the reaction or side reactions to temporarily block any functional groups by protective groups and remove them later, or to let functional groups be present in the form of a precursor group which is later converted into the desired final group. This applies correspondingly to all reactions in the course of the synthesis of the compounds of the formula I including the synthesis of intermediates outlined below and the synthesis of starting compounds and building blocks. Respective synthetic strategies are commonly used in the art. Details about protective groups and their introduction and removal are found in P. G. M. Wuts and T. W. Greene, Greene's Protective Groups in Organic Synthesis, 4. ed. (2007), John Wiley & Sons, for example. Examples of protective groups which may be mentioned, are benzyl protective groups which may occur in the form of benzyl ethers of hydroxy groups and benzyl esters of carboxylic acid groups from which the benzyl group can be removed by catalytic hydrogenation in the presence of a palladium catalyst, tert-butyl protective groups which may occur in the form of tert-butyl esters of carboxylic acid groups from which the tert-butyl group can be removed by treatment with trifluoroacetic acid, acyl protective groups which may be used to protect hydroxy groups and amino groups in the form of esters and amides and which can be cleaved by acidic or basic hydrolysis, and alkyloxycarbonyl protective groups which may occur in the form of tert-butoxycarbonyl derivatives of amino groups which can be cleaved by treatment with trifluoroacetic acid. Undesired reactions of carboxylic acid groups, for example the carboxylic acid group present in the compound of the formula III in case $R^{50}$ is HO—, can also be avoided by employing them in the reaction of the compounds of the formulae III and IV in the form of other esters, for example in the form of alkyl esters like the methyl or ethyl ester which can be cleaved by hydrolysis, for example by means of an alkaline metal hydroxide like sodium hydroxide or lithium hydroxide. Another example of precursor groups besides cyano groups (NC—, N≡C—), which were already mentioned, are nitro groups which can be converted into amino groups by catalytic hydrogenation or by reduction with sodium dithionite, for example. A further example of a precursor group is an oxo group, which may initially be present in the course of the synthesis of compounds of the formula I containing a hydroxy group, and which can be reduced, for example with a complex hydride such as sodium borohydride, or reacted with an organometallic compound, for example a Grignard compound. If any protective groups or precursor groups are present in the compounds of the formulae III, IV and V and the direct product of the reaction of the compound of the formula III or V with the compound of the formula IV is not yet the desired final compound, the removal of the protective group or conversion into the desired compound can in general also be carried out in situ.

The compounds of the formula IV are commercially available or can be obtained according to, or analogously to, procedures described in the literature. Customarily, in synthetic procedures for the preparation of compounds of the formula IV compounds are prepared in which the group G in the compounds of the formula IV is a group like $(C_1\text{-}C_4)$-alkyl-O— and the group G-C(O)— thus is a $(C_1\text{-}C_4)$-alkyl ester group, or the group G-C(O)— is any other ester group such as a benzyl ester phenyl-$CH_2$—O—C(O)— and the group G thus is a benzyloxy group. Compounds of the formula IV in which G is HO—, can be obtained from such compounds of the formula IV by acidic or basic hydrolysis of alkyl esters or by hydrogenation of benzyl esters under standard conditions. Compounds of the formula IV in which G is HO— can then be converted into compounds of the formula IV in which G is halogen as already explained above, which latter compounds can be converted into compounds in which G is aryloxy, for example by reaction with a hydroxyarene such as phenol. In the following, various synthetic procedures for the preparation of compounds of the formula IV in which the group $R^{23}$ in the group $R^{24}$—$R^{23}$—, i.e. in the group of the formula II which represents one of the groups $R^{21}$ and $R^{22}$, has different meanings, are exemplarily outlined.

In a procedure for the preparation of compounds of the formula IV in which the group $R^{23}$ is a chain wherein the terminal chain member which is bonded to the ring comprising the groups Y and Z, is a hetero chain member, a compound of the formula VII is reacted with a compound of the formula VIII to give a compound of the formula IVa.

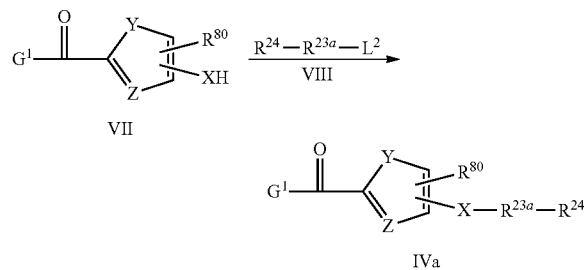

In the compounds of the formulae IVa, VII and VIII the groups Y, Z and $R^{24}$ are defined as in the compounds of the formula I. The group $R^{80}$ is chosen from the series consisting of hydrogen, halogen, $R^{30}$, HO—, $R^{30}$—O—, $R^{30}$—C(O)—O—, $R^{30}$—$S(O)_2$—O—, $R^{30}$—$S(O)_m$—, $H_2N$—, $R^{30}$—NH—, $R^{30}$—$N(R^{30})$—, $R^{30}$—C(O)—NH—, $R^{30}$—C(O)—$N(R^{71})$—, $R^{30}$—$S(O)_2$—NH—, $R^{30}$—$S(O)_2$—$N(R^{71})$—, $R^{30}$—C(O)—, HO—C(O)—, $R^{30}$—O—C(O)—, $H_2N$—C(O)—, $R^{30}$—NH—C(O)—, $R^{30}$—$N(R^{30})$—C(O)—, $H_2N$—$S(O)_2$—, $R^{30}$—NH—$S(O)_2$—, $R^{30}$—$N(R^{30})$—$S(O)_2$—, NC—, $O_2N$— and $Het^1$; or together with $R^{13}$ or $R^{14}$ forms a chain as specified in the definition of $R^{13}$ and $R^{14}$; i.e. $R^{80}$ has the meaning of the one of the groups $R^{21}$ and $R^{22}$ in the compounds of the formula I which is not a group of the formula II. Additionally, functional groups in the compounds of the formulae IVa, VII and VIII can be present in protected form or in the form of a precursor group which is later converted into the final group. The group $G^1$-C(O)— is an ester group and the group $G^1$ a group such as $(C_1\text{-}C_4)$-alkyl-O— or benzyloxy. The group X is a hetero chain member as specified in the definition of $R^{23}$, i.e. a group chosen from the series consisting of $N(R^{25})$, O, S, S(O) and $S(O)_2$, in particular from the series consisting of $N(R^{25})$, O and S. The groups $R^{23a}$ and X together represent the group $R^{23}$ as specified above wherein a terminal chain member which is a hetero chain member, is bonded to the ring comprising the groups Y and Z. $R^{23a}$ thus is a direct bond or a chain consisting of 1 to 4 chain members of which 0 or 1 chain member is a hetero chain member chosen from the series consisting of $N(R^{25})$, O, S, S(O) and $S(O)_2$, provided that the terminal chain member adjacent to the group $L^2$ can only be a hetero chain member which leads to the formation of compound of the formula IVa in which one of the group X and the said terminal chain member is chosen from the series consisting of S(O) and $S(O)_2$ and the other is chosen from the series consisting of $N(R^{25})$, O and S, and the other chain members are identical or different groups $C(R^{26})(R^{26})$. As is symbolized by the bonds connecting the groups $R^{80}$ and XH in the compounds of the formula VII, as well as the groups $R^{80}$ and X—$R^{23a}$—$R^{24}$ in the compounds of the formula IVa, which bonds are not directed to a specific ring carbon atom, each of the said two groups can be located in each of the two positions of the moiety C=C in the ring comprising the groups Y and Z which is depicted in the formulae. I.e., $R^{80}$ can be located on the ring carbon which is adjacent to the group Y and the other of the two groups on the ring carbon atom which is adjacent to the group Z, as well as $R^{80}$ can be located on the ring carbon which is adjacent to the group Z and the other of the two groups on the ring carbon atom which is adjacent to the group Y. This applies to all compounds defined below containing a group $R^{80}$ and a second group in which the bonds connecting the group to the ring comprising the groups Y and Z are not directed to a specific ring carbon atoms. The group $L^2$ in the compounds of the formula VIII is a leaving group which can be replaced with the group X, such as halogen, fore example chlorine or bromine, a sulfonyloxy group, for example methanesulfonyloxy, trifluoromethanesulfonyloxy or toluene-4-sulfonyloxy, or hydroxy, for example.

The reaction of a compound of the formula VII with a compound of the formula VIII is a nucleophilic substitution reaction which can be carried out under standard conditions for such reactions which are well known to a person skilled in the art. Generally, the reaction is performed in an inert solvent, for example a hydrocarbon or chlorinated hydrocarbon like benzene, toluene, xylene, chlorobenzene, dichloromethane, chloroform or dichloroethane, an ether like THF, dioxane, dibutyl ether, diisopropyl ether or DME, an alcohol like methanol, ethanol or isopropanol, a ketone like acetone or butan-2-one, an ester like ethyl acetate or butyl acetate, a nitrile like acetonitrile, an amide like DMF or NMP, a sulfoxide like DMSO or a sulfone like sulfolane, or a mixture of solvents, at temperatures from about –10° C. to about 120° C., in particular at temperatures from about 0° C. to about 100° C., depending on the particulars of the specific case. In many cases it is favorable for enhancing the nucleophilicity of the compound of the formula VII and/or binding an acid which is liberated during the reaction, to add a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula VII can also be treated with a base and converted into a salt in a separate step. Compounds of the formula VIII in which the group $L^2$ is hydroxy can favorably be reacted with compounds of the formula VII under the conditions of the Mitsunobu reaction in the presence of an azodicarboxylate like diethyl azodicarboxylate or diisopropyl azodicarboxylate and a phosphine like triphenylphosphine or tributylphosphine in an inert aprotic solvent such as an ether like THF or dioxane (cf. O. Mitsunobu, Synthesis (1981), 1-28).

In another procedure, compounds of the formula IVa can be obtained by reacting a compound of the formula IX with a compound of the formula X.

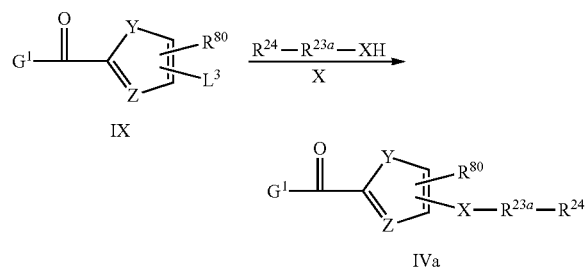

IX

IVa

In the compounds of the formulae IX and X the groups Y, Z and $R^{24}$ are defined as in the compounds of the formula I. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IX and X can be present in protected form or in the form of a precursor group which is later converted into the final group. The group $G^1$-C(O)— is an ester group and the group $G^1$ a group such as $(C_1$-$C_4)$-alkyl-O— or benzyloxy. The group X is a hetero chain member as specified in the definition of $R^{23}$, i.e. a group chosen from the series consisting of $N(R^{25})$, O, S, S(O) and $S(O)_2$, in particular from the series consisting of $N(R^{25})$, O and S. In the compound of the formula X the groups $R^{23a}$ and X together represent the group $R^{23}$ as specified above wherein a terminal chain member which is a hetero chain member, is bonded to the ring comprising the groups Y and Z in the obtained compounds of the formula IVa. $R^{23a}$ thus is a direct bond or a chain consisting of 1 to 4 chain members of which 0 or 1 chain member is a hetero chain member chosen from the series consisting of $N(R^{25})$, O, S, S(O) and $S(O)_2$, provided that the terminal chain member adjacent to the group X can only be a hetero chain member if one of the group X and the said terminal chain member is chosen from the series consisting of S(O) and $S(O)_2$ and the other is chosen from the series consisting of $N(R^{25})$, O and S, and the other chain members are identical or different groups $C(R^{26})(R^{26})$. The group $L^3$ in the compounds of the formulae IX is a leaving group which can be replaced with the group X, such as halogen like fluorine, chlorine, bromine or iodine, or a sulfonyloxy group like methanesulfonyloxy or trifluoromethanesulfonyloxy, for example. The reaction of a compound of the formula IX with a compound of the formula X formally is a nucleophilic substitution reaction at the ring comprising the groups Y and Z which can in particular be performed in case of compounds of the formulae IX which are susceptible to such a reaction because of the presence of electron-withdrawing substituents or ring hetero atoms. The reaction can be carried out under standard conditions for such reactions which are well known to a person skilled in the art. The explanations on the reaction conditions such as solvents or bases which are favorably added, which are given above with respect to the reaction of a compound of the formula VII with a compound of the formula VIII apply correspondingly to the reaction of a compound of the formula IX with a compound of the formula X.

The explanations on the reaction of a compound of the formula VII with a compound of the formula VIII also apply correspondingly to reactions for the preparation of compounds of the formula I in which a hetero chain member in the group $R^{23}$ is not present in the terminal position of the chain which is adjacent to the ring comprising the groups Y and Z, but is separated from the said ring by one or more groups $C(R^{26})(R^{26})$, which reactions are of the same type as the reactions outlined above. As an example, the preparation of a compound of the formula IVb from a compound of the formula XI and a compound of the formula XII may be illustrated.

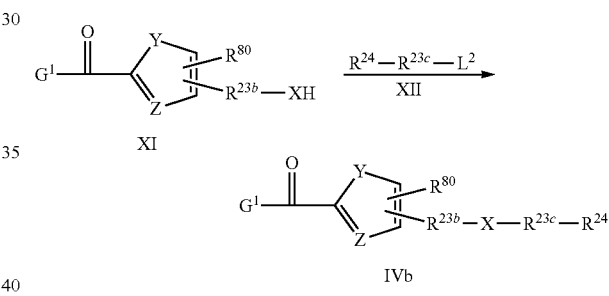

XI

IVb

In the compounds of the formulae IVb, XI and XII the groups Y, Z and $R^{24}$ are defined as in the compounds of the formula I. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IX and X can be present in protected form or in the form of a precursor group which is later converted into the final group. Additionally, functional groups in the compounds of the formulae IVb, XI and XII can be present in protected form or in the form of a precursor group which is later converted into the final group. The group $G^1$-C(O)— is an ester group and the group $G^1$ a group such as $(C_1$-$C_4)$-alkyl-O— or benzyloxy. The group X is a hetero chain member as specified in the definition of $R^{23}$, i.e. a group chosen from the series consisting of $N(R^{25})$, O, S, S(O) and $S(O)_2$, in particular from the series consisting of $N(R^{25})$, O and S. The groups $R^{23b}$, $R^{23c}$ and X in the compounds of the formulae IVb together represent the group $R^{23}$ as specified above wherein X is a said hetero chain member. In case $R^{23}$ comprises only one hetero chain member, the group $R^{23b}$ in the compounds of the formulae IVb and XI is a chain consisting of 1 to 4 identical or different groups $C(R^{26})(R^{26})$ and the group $R^{23c}$ in the compounds of the formulae IVb and XII is a direct bond or a chain consisting of 1 to 3 identical or different groups $C(R^{26})(R^{26})$, provided that the total number of groups $C(R^{26})(R^{26})$ is not greater than 4. In the group $R^{23c}$ in the compounds of the formulae IVb and XII a further hetero chain member chosen from the series consisting of $N(R^{25})$, O, S, S(O) and $S(O)_2$ can be present instead of one of the groups $C(R^{26})(R^{26})$, provided that such further hetero chain member can only be present in the terminal position adjacent to the group $L^2$ if one of the group X and the said chain member in the terminal position is chosen from the series consisting of S(O) and $S(O)_2$ and the other is chosen from the series consisting of $N(R^{25})$, O and S. The leaving group $L^2$ in the compounds of the formula XII is defined as in the compounds of the formula VIII. Correspondingly as outlined above with respect to the synthesis of the compounds of the formula IVa, which can be prepared by reacting a compound of the formula VII with a compound of the formula VIII as well as by reacting a compound of the formula IX with a compound of the formula X, compounds of the formula IVb can also be prepared by reacting a compound which is defined as the compound of the formula XI but contains a group $L^2$ instead of the group XH, with a compound which is defined as the compound of the formula XII but contains a group XH instead of the group $L^2$.

In a procedure for the preparation of compounds of the formula IV in which the group $R^{23}$ is a chain which does not comprise any hetero chain member, a carbonyl compound of the formula XIII is condensed with a compound of the formula XIV to give an olefin of the formula IVc which can subsequently be hydrogenated to give a compound of the formula IVd, respectively, or reacted with an organometallic compound of the formula XV to give an alcohol of the formula IVe which likewise can subsequently be hydrogenated to give a compound of the formula IVf.

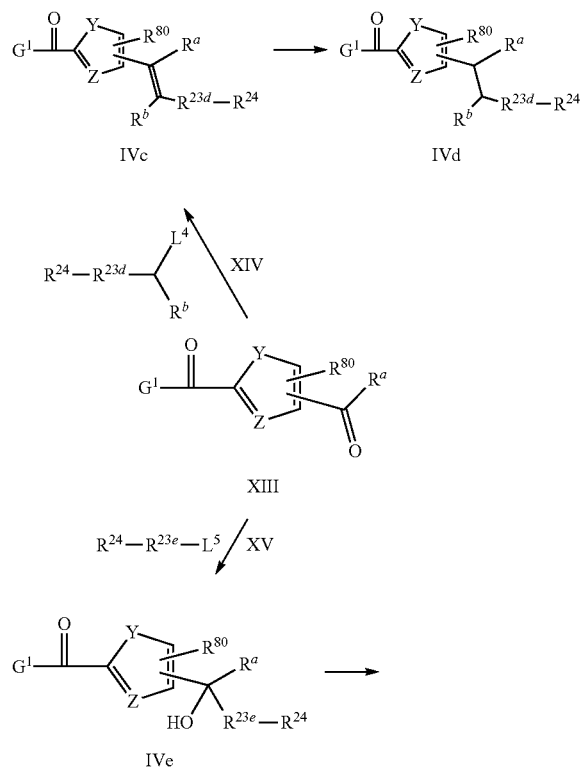

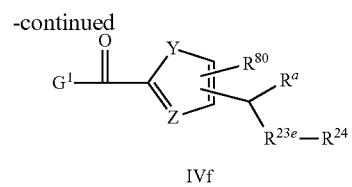

IVf

In the compounds of the formulae IVc to IVf, XIII, XIV and XV the groups Y, Z and $R^{24}$ are defined as in the compounds of the formula I. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IVc to IVf, XIII, XIV and XV can be present in protected form or in the form of a precursor group which is later converted into the final group. The group $G^1$-C(O)— is an ester group and the group $G^1$ a group such as $(C_1$-$C_4)$-alkyl-O— or benzyloxy. The groups $R^a$ and $R^b$ are independently of each other chosen from hydrogen and $(C_1$-$C_4)$-alkyl. The group $R^{23d}$ is a direct bond or a chain consisting of 1 to 3 identical or different groups $C(R^{26})(R^{26})$, the group $R^{23e}$ a direct bond or a chain consisting of 1 to 4 identical or different groups $C(R^{26})(R^{26})$. The group $L^4$ in the compounds of the formula XIV is group which allows for the formation of a double bond between the carbon atom carrying the group $L^4$ and the carbon atom of the aldehyde group or ketone group carrying the group $R^a$ in the compound of the formula XIII in a condensation reaction. Examples of suitable condensation reactions are the Wittig reaction and the Wittig-Horner reaction, and examples of suitable groups $L^4$ thus are trisubstituted phosphonio groups, such as the triphenylphosphonio group, having an anion, such as a halide anion, as counterion, and $di((C_1$-$C_4)$-alkyl)phosphonyl groups, such as the diethylphosphonyl group. The group $L^5$ in the compounds of the formula XV is a metal such as lithium or a magnesium halide group like MgCl, MgBr or MgI, and the compound of the formula XV thus an organolithium compound or a Grignard compound. The Wittig reaction and Wittig-Horner reaction and the addition of the organometallic compound of the formula XV to the compound of the formula XIII can be performed under standard conditions in an inert solvent such as a hydrocarbon like benzene or toluene or an ether like diethyl ether, THF, dioxane or DME. The Wittig reaction and the Wittig-Horner reaction are performed in the presence of a base such as a hydride like sodium hydride, an amide like sodium amide or lithium diisopropylamide, or an alkoxide like potassium tert-butoxide. Depending on the particular case, instead of employing a phosphonium salt and deprotonating it, also stable phosphorus ylides can directly be employed in the reaction. The hydrogenation of the double bond in the compounds of the formula IVc to give the compounds of the formulae IVd, or of the benzylic hydroxy group in the compounds of the formulae IVe to give the compounds of the formulae IVf, can be performed in the presence of a hydrogenation catalyst such as palladium on charcoal.

Depending on the particulars of the specific case, various other reactions can be used for preparing compounds of the formula IV. As an example of the preparation of compounds in which the group $R^{23}$ is a chain comprising three groups $C(R^{26})(R^{26})$ and no hetero chain members, an aldol-type reaction of a compound of the formula XIIIa, which is a compound of the formula XIII in which the group $R^a$ is methyl, with an aldehyde of the formula XVI may be mentioned which leads to a compound of the formula IVg or the formula IVm which can be reduced to a compound of the formula IVh, IVk or IVn, for example.

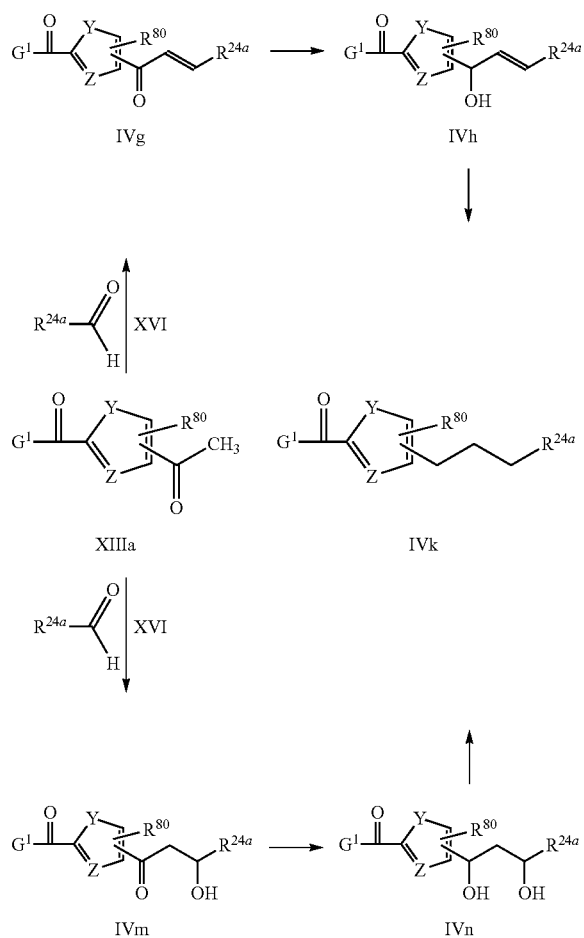

In the compounds of the formulae IVg to IVn and XIIIa the groups Y and Z are defined as in the compounds of the formula I. The group $R^{24a}$ in the compounds of the formulae IVg to IVn and XVI is a group $R^{31}$ or a 3-membered to 10-membered ring as it can represent the group $R^{24}$ in the compounds of the formula I which is bonded via a ring carbon atom, in particular an aromatic ring such as an optionally substituted phenyl, naphthyl or heteroaryl group. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IVg to IVn, XIIIa and XVI can be present in protected form or in the form of a precursor group which is later converted into the final group. The group $G^1$-C(O)— is an ester group and the group $G^1$ a group such as $(C_1\text{-}C_4)$-alkyl-O— or benzyloxy.

The reaction of a compound of the formula XIIIa with a compound of the formula XIV to give an aldol addition product of the formula IVm or a condensation product of the formula IVg can be carried under standard conditions for the aldol reaction in the presence of a base, such as an alkaline metal hydroxide like sodium hydroxide or potassium hydroxide, an alkoxide like sodium methoxide or sodium ethoxide or an amide like lithium diisopropylamide, in a solvent such as an alcohol like methanol or ethanol or an ether like diethyl ether, THF or dioxane. At lower temperatures, for example at temperatures from about −80° C. to about −30° C., the compound of the formula IVm can be obtained, at higher temperatures, for example at temperatures from about 10° C. to about 60° C., or by treatment of the compound of the formula IVm with an acid, the compound of the formula IVg can be obtained. The ketone function in the compounds of the formulae IVg and IVm can be reduced to an alcohol function, for example with a complex hydride such as a borohydride like lithium borohydride or sodium borohydride, to give a compound of the formula IVh or IVn, respectively, which can be converted into a compound of the formula IVk by dehydration in the presence of an acid and/or hydrogenation in the presence of a catalyst such as palladium on charcoal, for example.

As a further example of reactions which can be used for preparing compounds of the formula IV, transition metal-catalyzed C—C coupling reactions may be mentioned by which compounds can be obtained wherein the group $R^{23}$ is a direct bond. Such compounds can be obtained from a compound of the formula IX and a boronic acid, for example an optionally substituted phenylboronic acid, cycloalkylboronic acid or heteroarylboronic acid. As catalyst in such reactions, a palladium compound such as bis(triphenylphosphine)palladium(II) chloride or tetrakis(triphenylphosphine)palladium(0) and a copper compound such as copper(I) iodide can be used. Further details on such reactions are found in N. Miyaura et al., Chem. Rev. 95 (1995), 2457-2483; and R. Chinchilla et al., Chem. Rev. 107 (2007), 874-922, for example.

The order in which groups are introduced in the course of the synthesis of a compound of the formula I, can also be different from the ones outlined above. For example, instead of first preparing a compound of the formula IVa from a compound of the formula VII and a compound of the formula VIII, or from a compound of the formula IX and a compound of the formula X, and then reacting the compound of the formula IVa with a compound of the formula III to give a compound of the formula I, a compound of the formula III can also be reacted with a compound of the formula VII or a compound of the formula IX and the obtained compound of the formula XVII or XVIII reacted with a compound of the formula VIII or X, respectively, to give a compound of the formula Ik. This reaction sequence can also be performed with compounds of the formula V instead of with compounds of the formula III, and in the obtained compounds the nitrile group converted into the group —C(O)—$R^{50}$ to give compounds of the formula Ik.

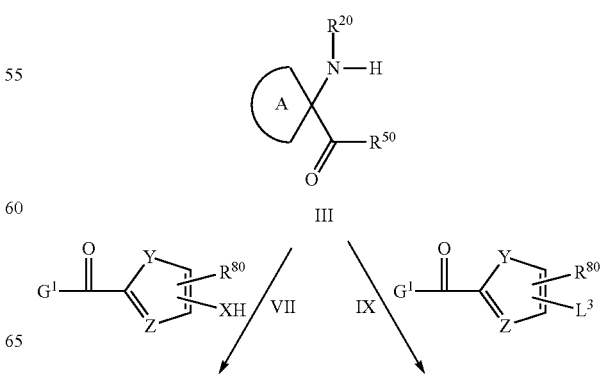

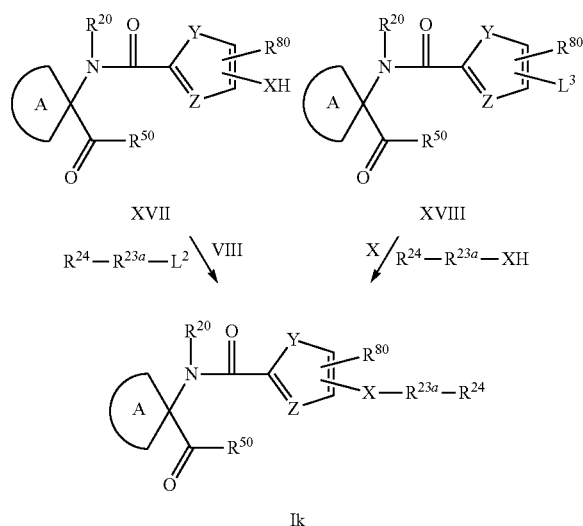

In the compounds of the formulae Ik, XVII and XVIII the ring A and the groups Y, Z, $R^{20}$, $R^{24}$ and $R^{50}$ are defined as in the compounds of the formula I. The groups X, $R^{23a}$ and $R^{80}$ are defined as in the compounds of the formula IVa. Thus, $R^{80}$ has the meaning of the one of the groups $R^{21}$ and $R^{22}$ in the compounds of the formula I which is not a group of the formula II. The group X is a hetero chain member as specified in the definition of $R^{23}$, i.e. a group chosen from the series consisting of $N(R^{25})$, O, S, S(O) and $S(O)_2$, in particular from the series consisting of $N(R^{25})$, O and S. The groups $R^{23a}$ and X together represent the group $R^{23}$ as specified above wherein a terminal chain member which is a hetero chain member, is bonded to the ring comprising the groups Y and Z. $R^{23a}$ thus is a direct bond or a chain consisting of 1 to 4 chain members of which 0 or 1 chain member is a hetero chain member chosen from the series consisting of $N(R^{25})$, O, S, S(O) and $S(O)_2$, provided that the terminal chain member adjacent to the group X can only be a hetero chain member if one of the group X and the said terminal chain member is chosen from the series consisting of S(O) and $S(O)_2$ and the other is chosen from the series consisting of $N(R^{25})$, O and S, and the other chain members are identical or different groups $C(R^{26})(R^{26})$. Additionally, functional groups in the compounds of the formulae Ik, XVII and XVIII can be present in protected form or in the form of a precursor group which is later converted into the final group. As indicated above and as applies to all compounds which contain a group $R^{80}$ and another group which are connected to the ring comprising the groups Y and Z by bonds which are not directed to a specific ring carbon atom, the groups $R^{80}$ and X in the compounds of the formula XVII, the groups $R^{80}$ and $L^3$ in the compounds of the formula XVIII, and the groups $R^{80}$ and $X-R^{23a}-R^{24}$ in the compounds of the formula Ik can be located in each of the two positions of the moiety C=C in the ring comprising the groups Y and Z. The explanations given above with respect to the reaction of a compound of the formula III with a compound of the formula IV, the reaction of a compound of the formula VII with a compound of the formula VIII, and the reaction of a compound of the formula IX with a compound of the formula X apply correspondingly to the reaction of a compound of the formula III with a compound of the formula VII or a compound of the formula IX, the reaction of a compound of the formula XVII with a compound of the formula VIII, and the reaction of a compound of the formula XVIII with a compound of the formula X. The order in which groups are introduced in the course of the synthesis of a compound of the formula I, can also be varied with respect to other reactions. For example, a compound of the formula XVIII can be employed in a transition-metal catalyzed C—C coupling reaction as referred to above, or a compound of the formula XIIIa can be reacted with a compound of the formula III and the obtained compound modified at the $CH_3$—C(O)— group to give a compound of the formula I.

Like the compounds of the formula IV, the compounds of the formulae III and V are commercially available or can be obtained according to, or analogously to, procedures described in the literature, for example according to the Bucherer-Bergs hydantoin procedure or the Strecker procedure for the preparation of amino acids and amino acid nitriles, respectively. The following scheme illustrates the Bucherer-Bergs hydantoin procedure for the synthesis of amino acids.

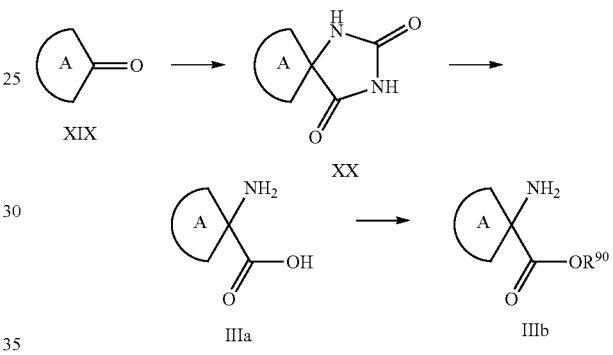

In the Bucherer-Bergs procedure, a ketone of the formula XIX is converted into a hydantoin of the formula XX by reaction with a cyanide source, such as an alkaline metal cyanide like sodium cyanide (NaCN), and ammonium carbonate $((NH_4)_2CO_3)$ in an inert solvent like a mixture of an alcohol such as a $(C_1-C_3)$-alkanol and water, for example a mixture of ethanol and water, at temperatures from about 0° C. to about 150° C., in particular at temperatures from about 20° C. to about 120° C., for example at the reflux temperature of the employed solvent. The obtained hydantoin can be converted into the respective amino acid of the formula IIIa by hydrolysis, for example by hydrolysis with an aqueous acid like sulfuric acid or hydrochloric acid or by hydrolysis with an aqueous bases like sodium hydroxide or potassium hydroxide, at elevated temperatures, for example at the reflux temperature of the reaction mixture. For the reaction with the compound of the formula IV, the amino acid of the formula IIIa can be protected by conversion into an amino acid ester of the formula IIIb in which $R^{90}$ is a group such as $(C_1-C_4)$-alkyl, for example methyl or ethyl, or benzyl, by standard methods which are well known to a person skilled in the art, for example by esterification with an alcohol like methanol or ethanol in the presence of an acid like hydrogen chloride. The group A in the compounds of the formulae XIX, XX, IIIa and IIIb is defined as in the compounds of the formula I and additionally functional groups can be present in protected form or in the form of a precursor group which is later converted into the final group.

The following scheme illustrates the Strecker procedure for the synthesis of amino acid nitriles.

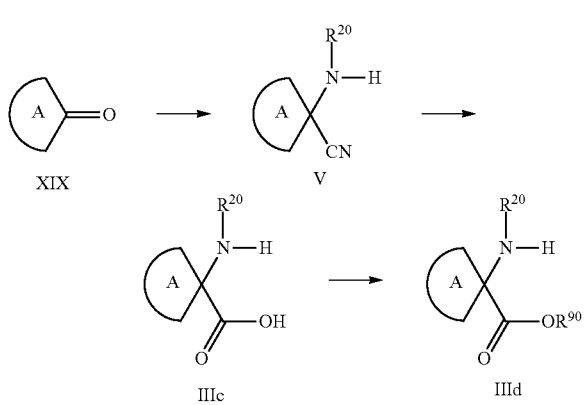

In the Strecker procedure, a ketone of the formula XIX is converted into the corresponding amino acid nitrile of the formula V by reaction with a cyanide source, such as an alkaline metal cyanide like potassium cyanide (KCN), and a salt of an amine of the formula $R^{20}$—$NH_2$, wherein $R^{20}$ is defined as in the compounds of the formula I, for example ammonium chloride ($NH_4Cl$) in case $R^{20}$ is hydrogen or methylammonium chloride ($CH_3$—$NH_3Cl$) in case $R^{20}$ is methyl, in an inert solvent like water or an alcohol such as a ($C_1$-$C_3$)-alkanol like methanol or ethanol or a mixture thereof with water, for example a mixture of ethanol and water, at temperatures from about 0° C. to about 150° C., in particular at temperatures from about 20° C. to about 120° C. or at temperatures from room temperature to the reflux temperature of the employed solvent. The obtained amino acid nitrile of the formula V can be hydrolyzed to the amino acid of the formula IIIc, for example by hydrolysis with an aqueous acid like sulfuric acid or hydrochloric acid, or by hydrolysis with an aqueous base like sodium hydroxide or potassium hydroxide, at elevated temperature, for example at temperatures from about 50° C. to about 150° C., for example at the reflux temperature of the reaction mixture, and the amino acid then esterified to give a compound of the formula IIId, for use in the reaction with the compound of the formula IV, as mentioned above with respect to the amino acids of the formula IIIa. Alternatively, the amino acid nitrile of the formula V can directly be reacted with a compound of the formula IV and the nitrile group hydrolyzed subsequently, as outlined above. The groups A and $R^{20}$ in the compounds of the formulae IIIc and IIId and in the amines of the formula $R^{20}$—$NH_2$ are defined as in the compounds of the formula I and additionally functional groups can be present in protected form or in the form of a precursor group which is later converted into the final group. The group $R^{90}$ in the compounds of the formula IIId is defined as in the compounds of the formula IIIb.

The Bucherer-Bergs procedure and the Strecker procedure were found to give different results with respect to the stereochemistry in case the prepared amino acid or amino acid nitriles contain additional substituents in the ring A. It was described in the literature (cf. L. Munday, J. Chem. Soc. (1961), 4372-79) that, if the ring A is a substituted cyclohexane ring, the Bucherer-Bergs procedure delivers products in which the substituent is in cis position with respect to the amino group in the obtained amino acid in case the substituent is in 2-position or 4-position of the ring, but products in which the substituent is in trans position with respect to the amino group in case the substituent is in the 3-position of the ring, whereas the Strecker procedure delivers products in which the substituent is in trans position with respect to the amino group in case the substituent is in 2-position or 4-position, but products in which the substituent is in cis position with respect to the amino group in case the substituent is in the 3-position.

The cyclic ketones of the formula XIX which are employed in the Bucherer-Bergs procedure and the Strecker procedure, are commercially available or can be synthesized by a broad variety of synthetic methods which are well known to a person skilled in the art. For example, a cyclic ketone of the formula XIX can be synthesized by ring expansion of the respective ketone of smaller ring size of the formula XXI, which contains one ring carbon less, with diazomethane ($CH_2N2$), for example according to the procedure described in F. Alonso et al., Tetrahedron 51 (1995), 10259-10280.

The ring expansion reaction with diazomethane is generally carried out in an inert solvent, for example an ether like diethyl ether, tetrahydrofuran (THF), dioxane, dibutyl ether, diisopropyl ether or dimethoxyethane (DME), ethanol, methanol, a hydrocarbon, dichloromethane, chloroform or dichloroethane, or a mixture of solvents, at temperatures from about −78° C. to 50° C., in particular at temperatures from about −40° C. to about room temperature, for example at about 0° C. Diazomethane can be used as solution in an inert solvent, for example diethyl ether or THF, or can be generated in situ from an appropriate source for diazomethane like N-methyl-N-nitroso-p-toluenesulfonamide (Diazald®) or N-methyl-N-nitrosourea. For example, N-methyl-N-nitroso-p-toluenesulfonamide can be added to a solution of the ketone in an inert solvent like a mixture of ethanol, methanol and water containing a base like potassium hydroxide to generate diazomethane in situ. Alternatively, trimethylsilyl diazomethane can be added to a solution of the ketone and an acid or silyl scavenger like boron trifluoride etherate in an inert solvent like dichloromethane to generate a diazomethane equivalent and to perform the ring enlargement reaction. As applies in general and is well known to a person skilled in the art, the reaction conditions for ring enlargement of a ketone depend on the particulars of the specific case, for example on the substituents on the ring A.

An alternative synthetic approach to amino acid derivatives of the formulae IIIa and IIIb starts from malonic acid derivatives of the formula XXIII which can be dialkylated with a divalent alkylating compound of the formula XXII to give a cyclic dicarboxylic acid derivative of the formula XXIV analogously as described in V. Prelog et al., Helv. Chim. Acta 65 (1982), 2622-2644, and illustrated in the following scheme.

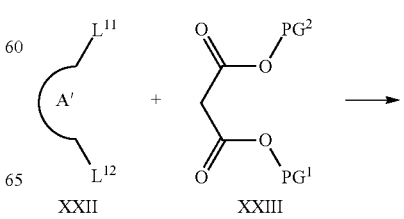

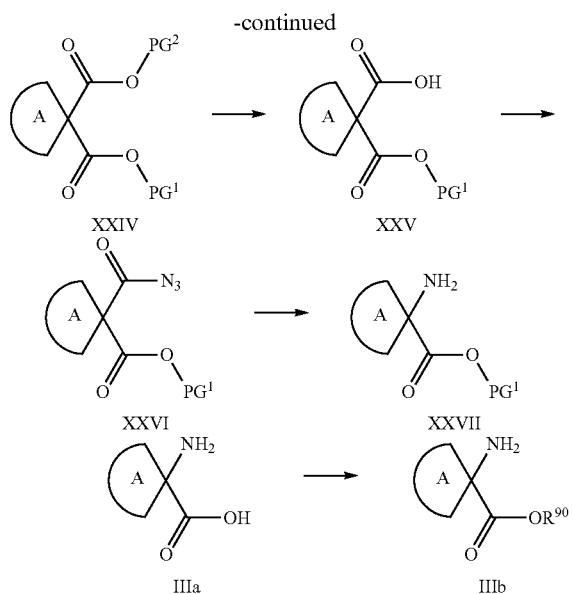

The moiety A' in the divalent alkylating compound of the formula XXII corresponds to the ring A in the compounds of the formula I except that it does not contain the ring carbon atom present in A which carries the groups $N(R^{20})$ and $C(O)$—$R^{50}$, and is defined accordingly, and the groups $L^{11}$ and $L^{12}$ are leaving groups such as halogen, for example chlorine or bromine, or sulfonyloxy groups, for example methanesulfonyloxy or trifluoromethanesulfonyloxy. The groups $PG^1$ and $PG^2$ in the malonic acid derivative of the formula XXIII and the compounds of the formulae XXIV, XXV, XXVI and XXVII have the function of protective groups of the carboxylic acid groups and can be identical or different groups such as $(C_1\text{-}C_4)$-alkyl, for example methyl, ethyl or tert-butyl, or benzyl. The alkylation reaction of the compounds of the formulae XXII and XXXIII is generally carried out in the presence of a base, for example an alkaline metal hydride such as sodium hydride or an alkaline metal alkoxide such as potassium tert-butoxide, in an inert solvent such as an ether like THF or diethyl ether or an amide like DMF or NMP or a nitrile like acetonitrile at temperatures from about 0° C. to about 100° C., depending on the particulars of the specific case. Subsequent to the alkylation reaction, one of the protective groups, for example $PG^2$, is cleaved, for example by treatment with an aqueous base like sodium hydroxide or potassium hydroxide in the case of methyl or ethyl group. In the obtained compound of the formula XXV can the free carboxylic acid group be degraded to an amino group by degradation reactions which are well known to a person skilled in the art. For example, the carboxylic acid can be activated by formation of a mixed anhydride, for example by reaction with a chloroformic acid ester like isobutyl chloroformate in the presence of a base like triethylamine or N-methylmorpholine in an inert solvent like acetone, the mixed anhydride reacted in situ with an alkaline metal azide like sodium azide to give the acid azide of the formula XXVI, which is subsequently heated in an inert solvent, for example a hydrocarbon like toluene or xylene, to give the degraded isocyanate which can be hydrolyzed, for example with aqueous acid like hydrochloric acid to give the amino acid derivative of the formula XXVII which already constitutes a compound of the formula IIIb or in which the protective group $PG^1$ can be cleaved to give a compound of the formula IIIa which can in turn be esterified as mentioned above to give a compound of the formula IIIb. Alternatively, the free carboxylic acid group in the compound of the formula XXV can be reacted with an azide transfer reagent like diphenylphosphoryl azide to yield the acid azide of the formula XXVI which can be degraded as indicated. Further details on the degradation procedures and the hydrolysis of the intermediary isocyanate can be found in T. N. Wheeler, Synth. Commun. 18 (1988), 141-149, and M. Oba et al., Tetrahedron 61 (2005), 593-598, for example. The group A in the compounds of the formulae XXIV, XXV, XXVI and XXVII is defined as in the compounds of the formula I and additionally can functional groups be present in protected form or in the form of a precursor group which is later converted into the final group.

The starting compounds and building blocks for the synthesis of the compounds of the formula I can generally be prepared according to procedures described in the literature or analogously to such procedures, or are commercially available. Exemplarily the preparation of compounds of the formula VIII in which $R^{24}$ is an optionally substituted phenyl or naphthyl group, $R^{23a}$ is an optionally alkyl-substituted $CH_2CH_2$ group and $L^2$ is a hydroxy group, may be mentioned in which use can be made of the procedure for the coupling of aryl halides with ester enolates described by M. Jørgensen et al., J. Am. Chem. Soc. 124 (2002), 12557-12565. In the said procedure an optionally alkyl-substituted acetic acid ester, for example acetic acid tert-butyl ester or isobutyric acid methyl ester, is deprotonated with a base such as lithium dicyclohexylamide and reacted with an optionally substituted aryl bromide in the presence of a palladium compound such as bis(dibenzylideneacetone)palladium or tris(dibenzylideneactone)dipalladium and tri(tert-butyl)phosphine to give a 2-(optionally substituted aryl)acetic acid ester which is optionally alkyl-substituted in the 2-position of the acetic acid moiety. Reduction of the ester function under standard conditions, for example with lithium aluminium hydride, then affords the 2-(optionally substituted aryl)ethanol which is optionally alkyl-substituted in the 2-position.

For obtaining further compounds of the formula I, various transformations of functional groups can be carried out under standard conditions in compounds of the formula I or intermediates or starting compounds in the synthesis of the compounds of the formula I. For example, a hydroxy group can be esterified to give a carboxylic acid ester or a sulfonic acid ester, or etherified. Etherifications of hydroxy groups can favorably be performed by alkylation with the respective halogen compound, for example a bromide or iodide, in the presence of a base such an alkali metal carbonate like potassium carbonate or cesium carbonate in an inert solvent such as an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with an activated carboxylic acid or a carboxylic acid derivate like an acid chloride or anhydride or a sulfonic acid chloride. A carboxylic ester group can be hydrolyzed under acidic or basic conditions to give a carboxylic acid. A carboxylic acid group can be activated or converted into a reactive derivative as outlined above with respect to the compounds of the formula IX and reacted with an alcohol or an amine or ammonia to give an ester or amide. A primary amide can be dehydrated to give a nitrile. A sulfur atom in an alkyl-S— group or in a heterocyclic ring or a sulfur atom occurring in a chain representing the group $R^{23}$ can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example with a complex hydride such al lithium aluminium hydride, lithium borohydride or sodium borohydride. All reactions in the preparation of the compounds of the formula I are known per se and can be carried out in a manner familiar to a person skilled in the art according to, or analogously, to procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein. Furthermore, besides by techniques of solution chemistry, the compounds of the formula I can also be obtained by solid phase chemistry.

Another subject of the present invention are the novel starting compounds and intermediates occurring in the synthesis of the compounds of the formula I, including the compounds of the formulae III, IIIa, IIIb, IIIc, IIId, IV, IVb, IVc, IVd, IVe, IVf, IVg, IVh, IVk, IVm, IVn, V, VI, VII, VIII, IX, X, XI, XII, XIII, XIV, XV, XVI, XVII, XVIII, XIX, XX, XXI, XXII, XXIII, XXIV, XXV, XXVI and XXVII wherein the ring A and the groups G, $G^1$, $L^2$, $L^3$, $L^{11}$, $L^{12}$, $PG^1$, $PG^2$, X, Y, Z, $R^{20}$ to $R^{23}$, $R^{23a}$, $R^{23b}$, $R^{23}$, $R^{24}$, $R^{24a}$, $R^{50}$, $R^{80}$, $R^a$ and $R^b$ are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit the Edg-2 receptor ($LPA_1$ receptor) as can be demonstrated in the pharmacological test described below and in other tests which are known to a person skilled in the art. The compounds of the formula I and their physiologically acceptable salts are valuable pharmaceutical active compounds. The compounds of the formula I and their physiologically acceptable salts can be used for the treatment of cardiovascular diseases such as heart failure including systolic heart failure, diastolic heart failure, diabetic heart failure and heart failure with preserved ejection fraction, cardiomyopathy, myocardial infarction, myocardial remodeling including myocardial remodeling after infarction or after cardiac surgery, vascular remodeling including vascular stiffness, hypertension including pulmonary hypertension, portal hypertension and systolic hypertension, atherosclerosis, peripheral arterial occlusive disease (PAOD), restenosis, thrombosis or vascular permeability disorders, for cardioprotection such as cardioprotection after myocardial infarction or after cardiac surgery, for renoprotection, or for the treatment of inflammation or inflammatory diseases such as rheumatoid arthritis, osteoarthritis, renal diseases such as renal papillary necrosis or renal failure including renal failure after ischemia/reperfusion, pulmonary diseases such as chronic obstructive pulmonary disease (COPD), asthma or acute respiratory dystress syndrome (ARDS), immunological diseases, allergic diseases, tumor growth, metastasis, metabolic diseases, fibrotic diseases such as pulmonary fibrosis including idiopathic lung fibrosis, cardiac fibrosis, vascular fibrosis, perivascular fibrosis, renal fibrosis including renal tubulointerstitial fibrosis, liver fibrosis, fibrosing skin conditions including keloid formation, collagenosis, scleroderma, progressive systemic sclerosis and nephrogenic fibrosing dermopathy, or other types of fibrosis including Dupuytren's contracture, psoriasis, pain such as neuropathic pain, diabetic pain or inflammatory pain, pruritus, retinal ischemia/reperfusion damage, macular degeneration, psychiatric disorders, neurodegenerative diseases, cerebral nerve disorders, peripheral nerve disorders, endocrinic disorders such as hyperthyroidism, scarring disorders or wound healing disorders, for example. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarction can be prevented or its extent and sequelae decreased, or in patients who are susceptible to disturbed wound healing, by means of the prophylactic or preventive medicinal treatment wound healing after surgery can favorably be influenced. The treatment of diseases can occur both in acute cases and in chronic cases. The efficacy of the compounds of the formula I can be demonstrated in the pharmacological tests described below and in other tests which are known to a person skilled in the art The compounds of the formula I and their physiologically acceptable salts can therefore be used in animals, in particular in mammals and specifically in humans, as a pharmaceutical or medicament on their own, in mixtures with one another or in the form of pharmaceutical compositions. A subject of the present invention also are the compounds of the formula I and their physiologically acceptable salts for use as a pharmaceutical, as well as pharmaceutical compositions and medicaments which comprise an efficacious dose of at least one compound of the formula I and/or a physiologically acceptable salt thereof as an active ingredient and a pharmaceutically acceptable carrier, i.e. one or more pharmaceutically innocuous, or nonhazardous, vehicles and/or excipients, and optionally one or more other pharmaceutical active compounds. A subject of the present invention furthermore are the compounds of the formula I and their physiologically acceptable salts for use in the treatment of the diseases mentioned above or below, including the treatment of any one of the mentioned diseases, for example heart failure or fibrotic diseases such as pulmonary fibrosis, cardiac fibrosis, vascular fibrosis, perivascular fibrosis, renal fibrosis, liver fibrosis or fibrosing skin conditions, the use of the compounds of the formula I and their physiologically acceptable salts for the manufacture of a medicament for the treatment of the diseases mentioned above or below, including the treatment of any one of the mentioned diseases, for example heart failure or fibrotic diseases such as pulmonary fibrosis, cardiac fibrosis, vascular fibrosis, perivascular fibrosis, renal fibrosis, liver fibrosis or fibrosing skin conditions, wherein the treatment of diseases comprises their therapy and prophylaxis as mentioned above, as well as their use for the manufacture of a medicament for the inhibition of the Edg-2 receptor ($LPA_1$ receptor). A subject of the invention also are methods for the treatment of the diseases mentioned above or below, including the treatment of any one of the mentioned diseases, for example heart failure or fibrotic diseases such as pulmonary fibrosis, cardiac fibrosis, vascular fibrosis, perivascular fibrosis, renal fibrosis, liver fibrosis or fibrosing skin conditions, which comprise administering an efficacious amount of at least one compound of the formula I and/or a physiologically acceptable salt thereof to a human or an animal which is in need thereof. The compounds of the formula I and pharmaceutical compositions and medicaments comprising them can be administered enterally, for example by oral, sublingual or rectal administration, parenterally, for example by intravenous, intramuscular, subcutaneous or intraperitoneal injection or infusion, or by another type of administration such as topical, percutaneous, transdermal, intra-articular, intranasal or intraocular administration.

The compounds of the formula I and their physiologically acceptable salts can also be used in combination with other pharmaceutical active compounds, wherein in such a combination use the compounds of the formula I and/or their physiologically acceptable salts and one or more other pharmaceutical active compounds can be present in one and the same pharmaceutical composition or in two or more pharmaceutical compositions for separate, simultaneous or sequential administration. Examples of such other pharmaceutical active compounds are angiotensin converting enzyme (ACE) inhibitors, ramipril, angiotensin II receptor subtype 1 (AT1) antagonists, irbesartan, antiarrhythmics, dronedarone, peroxisome proliferator-activated receptor-alpha (PPAR-α) activators, peroxisome proliferator-activated receptor-gamma (PPAR-γ) activators, pioglitazone, rosiglitazone, prostanoids, endothelin receptor antagonists, bosentan, elastase inhibitors, calcium antagonists, beta blockers, diuretics, aldosterone receptor antagonists, eplerenone, renin inhibitors, rho kinase inhibitors, soluble guanylate cyclase (sGC) activators, sGC sensitizers, phosphodiesterase (PDE) inhibitors, phosphodiesterase type 5 (PDE5) inhibitors, NO donors, digitalis drugs, angiotensin converting enzyme/neutral endopeptidase (ACE/NEP) inhibitors, statins, bile acid reuptake inhibitors, platelet derived growth factor (PDGF) receptor antagonists, vasopressin antagonists, aquaretics, sodium hydrogen exchanger subtype 1 (NHE1) inhibitors, factor II/factor IIa antagonists, factor IX/factor IXa antagonists, factor X/factor Xa antagonists, factor XIII/factor XIIIa antagonists, anticoagulants, antithrombotics, platelet inhibitors, profibrinolytics, thrombin-activatable fibrinolysis inhibitors (TAFI), plasminogen activator inhibitor-1 (PAI 1), coumarins, heparins, thromboxane antagonists, serotonin antagonists, cyclooxygenase inhibitors, acetylsalicylic acid, therapeutic antibodies, glycoprotein IIb/IIIa (GPIIb/IIIa) antagonists including abciximab, chymase inhibitors, cytostatics, taxanes, paclitaxel, docetaxel, aromatase inhibitors, estrogen receptor antagonists, selective estrogen receptor modulators (SERM), tyrosine kinase inhibitors, imatinib, receptor tyrosine kinase inhibitors, RAF kinase inhibitors, p38 mitogen-activated protein kinase (p38 MAPK) inhibitors, pirfenidone, multi-kinase inhibitors, and sorafenib. A subject of the present invention also is the said combination use of any one or more of the compounds of the formula I disclosed herein and their physiologically acceptable salts, with any one or more, for example one or two, of the mentioned other pharmaceutical active compounds.

The pharmaceutical compositions and medicaments according to the invention normally contain from about 0.5 to about 90 percent by weight of compounds of the formula I and/or physiologically acceptable salts thereof, and an amount of active ingredient of the formula I and/or its physiologically acceptable salt which in general is from about 0.2 mg to about 1000 mg, in particular from about 0.2 mg to about 500 mg, for example from about 1 mg to about 300 mg, per unit dose. Depending on the kind of the pharmaceutical composition and other particulars of the specific case, the amount may deviate from the indicated ones. The production of the pharmaceutical compositions and medicaments can be carried out in a manner known per se. For this, the compounds of the formula I and/or their physiologically acceptable salts are mixed together with one or more solid or liquid vehicles and/or excipients, if desired also in combination with one or more other pharmaceutical active compounds such as those mentioned above, and brought into a suitable form for dosage and administration, which can then be used in human medicine or veterinary medicine.

As vehicles, which may also be looked upon as diluents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of vehicles and excipients are water, vegetable oils, waxes, alcohols such as ethanol, isopropanol, 1,2-propanediol, benzyl alcohols, glycerol, polyols, polyethylene glycols or polypropylene glycols, glycerol triacetate, polyvinylpyrrolidone, gelatin, cellulose, carbohydrates such as lactose or starch like corn starch, sodium chloride, stearic acid and its salts such as magnesium stearate, talc, lanolin, petroleum jelly, or mixtures thereof, for example saline or mixtures of water with one or more organic solvents such as mixtures of water with alcohols. For oral and rectal use, pharmaceutical forms such as, for example, tablets, film-coated tablets, sugar-coated tablets, granules, hard and soft gelatin capsules, suppositories, solutions, including oily, alcoholic or aqueous solutions, syrups, juices or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Further suitable pharmaceutical forms are, for example, implants and patches and forms adapted to inhalation. The compounds of the formula I and their physiologically acceptable salts can also be lyophilized and the obtained lyophilizates used, for example, for the production of injectable compositions. In particular for topical application, also liposomal compositions are suitable. The pharmaceutical compositions and medicaments can also contain one or more other active ingredients and/or, for example, one or more vitamins.

As usual, the dosage of the compounds of the formula I depends on the circumstances of the specific case and is adjusted by the physician according to the customary rules and procedures. It depends, for example, on the compound of the formula I administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 10 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in-vitro diagnoses of biological samples, if an inhibition of the Edg-2 receptor is intended. The compounds of the formula I and their salts can also be used as intermediates for the preparation of further pharmaceutical active substances.

The following examples illustrate the invention.

ABBREVIATIONS

ACN acetonitrile
DCM dichloromethane
DIAD diisopropyl azodicarboxylate
DMF dimethylformamide
DMSO dimethyl sulfoxide
EA ethyl acetate
EDIA N-ethyldiisopropylamine
EDC 1-(3-dimethylaminopropyl)-3-ethylcarbodiimide hydrochloride
HEP heptane
HOBT 1-hydroxy-benzotriazole
TFA trifluoroacetic acid
THF tetrahydrofuran In general, reactions were carried out under argon. When example compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the workup such as evaporation or lyophilization conditions. In the names of the example compounds and the structural formulae such contained trifluoroacetic acid is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or thin layer chromatography (TLC) Rf values, and/or nuclear magnetic resonance (NMR) spectra. Unless specified otherwise, $^1$H-NMR spectra were recorded at 500 MHz in $D_6$-DMSO as solvent at 298 K. In the NMR characterization, the chemical shift δ (in ppm), the number of hydrogen atoms (H) and the multiplicity (s: singlet, d: doublet, dd: doublet of doublets, ddd: doublet of doublets of doublets, t: triplet, dt: doublet of triplets, tt: triplet of triplets, q: quartet, dq: doublet of quartets, m: multiplet; br: broad) of the peaks as determined on printouts are given. In the MS characterization, in general the mass number (m/z) of the peak of the molecular ion [M], e.g. [M$^+$], or of a related ion such as the ion [M+1], e.g. [(M+1)$^+$], i.e. the protonated molecular ion [(M+H)$^+$] abbreviated as [MH$^+$], or the ion [M−1], e.g. [(M−1)$^-$], i.e. the deprotonated molecular ion [(M−H)$^-$], which was formed depending on the ionization method used, is given. Generally, the ionization method was electrospray ionization (ESI). The particulars of the LC/MS methods used are as follows.

Method LC1
Column: Merck Chromolith FastGradient RP-18e, 50×2 mm; flow: 2 ml/min; 50° C.; eluent A: ACN+0.05% TFA; eluent B: water+0.05% TFA; gradient: 2% A+98% B for 0.2 min, then to 98% A+2% B within 2.2 min, then 98% A+2% B for 0.8 min; MS ionization method: ESI$^+$ Method LC2
Column: Merck Chromolith FastGradient RP-18e, 50×2 mm; flow: 2.4 ml/min; 50° C.; eluent A: ACN+0.05% TFA; eluent B: water+0.05% TFA; gradient: 2% A+98% B for 0.2 min, then to 98% A+2% B within 2.2 min, then 98% A+2% B for 0.8 min; MS ionization method: ESI$^+$ Method LC3
Column: YMC J'sphere H80, 33×2.1 mm, 4 µm; flow: 1 ml/min; eluent A: methanol+0.05% TFA; eluent B: water+0.05% TFA; gradient: 2% A+98% B for 1 min, then to 95% A+5% B within 4 min, then 95% A+5% B for 1.25 min; MS ionization method: ESI$^+$ Method LC4
Column: Waters Acquity UPLC BEH C18, 50×2.1 mm; 1.7 µm; flow: 0.9 ml/min; 55° C.; eluent A: ACN+0.08% formic acid; eluent B: water+0.1% formic acid; from gradient: 5% A+95% B to 95% A+5% B within 1.1 min, then 95% A+5% B for 0.6 min; MS ionization method: ESI$^+$ or ESI$^-$ Method LC5
Column: Waters XBridge C18, 50×4.6 mm, 2.5 µm; flow: 1.3 ml/min; eluent A: ACN+0.08% formic acid; eluent B: water+0.1% formic acid; gradient: from 3% A+97% B to 60% A+40% B within 3.5 min, then to 98% A+2% B within 0.5 min, then 98% A+2% B for 1 min; MS ionization method: ESI$^-$ Method LC6
Column: Waters XBridge C18, 50×4.6 mm, 2.5 µm; flow: 1.3 ml/min; 45° C.; eluent A: ACN+0.1% formic acid; eluent B: water+0.1% formic acid; gradient: from 3% A+97% B to 60% A+40% B within 3.5 min, then to 98% A+2% B within 0.5 min, then 98% A+2% B for 1 min; MS ionization method: ESI$^+$ or ESI$^-$ Method LC7
Column: Waters XBridge C18, 50×4.6 mm, 2.5 µm; flow: 1.7 ml/min; 40° C.; eluent A: ACN+0.05% TFA; eluent B: water+0.05% TFA; gradient: 5% A+95% B for 0.2 min, then to 95% A+5% B within 2.2 min, then 95% A+5% B for 0.8 min; MS ionization method: ESI$^+$ Method LC8
Column: Waters XBridge C18, 50×4.6 mm, 2.5 µm; flow: 1.7 ml/min; 50° C.; eluent A: ACN+0.05% TFA; eluent B: water+0.05% TFA; gradient: 5% A+95% B for 0.2 min, then to 95% A+5% B within 2.2 min, then 95% A+5% B for 1.1 min; MS ionization method: ESI$^+$ Method LC9
Column: Waters XBridge C18, 50×4.6 mm, 2.5 µm; flow: 1.3 ml/min; 40° C.; eluent A: ACN+0.05% TFA; eluent B: water+0.05% TFA; gradient: 5% A+95% B for 0.3 min, then to 95% A+5% B within 3.2 min, then 95% A+5% B for 0.5 min; MS ionization method: ESI$^+$ Method LC10
Column: YMC J'sphere H80, 33×2.1 mm, 4 µm; flow: 1 ml/min; eluent A: ACN+0.05% TFA; eluent B: water+0.05%

TFA; gradient: 2% A+98% B for 1 min, then to 95% A+5% B within 4 min, then 95% A+5% B for 1.25 min; MS ionization method: ESI+

Method LC11

Column: Thermo Javelin C18, 40×2.1 mm, 5 μm; flow: 1 ml/min; eluent A: ACN+0.1% TFA; eluent B: water+0.1% TFA; gradient: from 2% A+98% B to 80% A+20% B within 7 min, then to 100% A+0% B within 0.2 min; MS ionization method: ESI+

Method LC12

Column: Zorbax Eclipse XDB-C18, 50×4.6 mm, 1.8 μm; flow: 1.5 ml/min; 40° C.; eluent A: ACN+0.1% TFA; eluent B: water+0.1% TFA; gradient: from 2% A+98% B to 100% A+0% B within 2 min; MS ionization method: ESI+

Method LC13

Column: YMC J'sphere H80, 20×2.1 mm, 4 μm; 30° C.; flow: 1.0 ml/min; eluent A: ACN; eluent B: water+0.05% TFA; gradient: from 4% A+96% B to 95% A+5% B within 2.4 min, then to 4% A+96% B within 0.05 min, then 4% A+96% B for 0.05 min; MS ionization method: ESI+

EXAMPLE 1

1-{3-[2-(2-Fluoro-5-methyl-phenyl)-ethoxy]-4-methoxy-benzoylamino}-cycloheptanecarboxylic acid

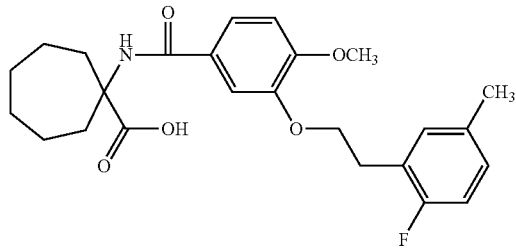 [SMILES: COc1ccc(C(=O)NC2(C(=O)O)CCCCCC2)cc1OCCc1cc(C)ccc1F]

Step 1: 3-[2-(2-Fluoro-5-methyl-phenyl)-ethoxy]-4-methoxy-benzoic acid methyl ester 2-(2-Fluoro-5-methyl-phenyl)-ethanol (508 mg, 3.29 mmol) was dissolved in THF (23 ml). Triphenylphosphine (1.08 g, 4.12 mmol) and 3-hydroxy-4-methoxy-benzoic acid methyl ester (500 mg, 2.75 mmol) were added, the mixture was cooled in an ice bath, and DIAD (832 mg, 4.12 mmol) was added slowly with stirring. The ice bath was removed and stirring was continued overnight at room temperature. The volatiles were evaporated in vacuo, and the residue was purified by RP HPLC (water/ACN gradient) to give 530 mg of the title compound.

$^1$H-NMR: δ=7.59 (dd, 1H); 7.45 (d, 1H); 7.24 (d, 1H); 7.10-7.02 (m, 3H); 4.20 (t, 2H); 3.82 (s, 3H); 3.80 (s, 3H); 3.04 (t, 2H); 2.26 (s, 3H)

Step 2: 3-[2-(2-Fluoro-5-methyl-phenyl)-ethoxy]-4-methoxy-benzoic acid

The compound of step 1 (530 mg, 1.66 mmol) was dissolved in dioxane (8.3 ml). Lithium hydroxide (8.3 ml of an aqueous 1 M solution) was added and the mixture was kept for 20 min at 60° C. After cooling, the mixture was partitioned between an excess of 2 N hydrochloric acid and EA and the aqueous phase extracted with EA. The combined organic phases were dried over sodium sulfate, filtered and evaporated to dryness in vacuo. The residue was stirred overnight with a mixture of diethyl ether and HEP, filtered, and the solid was dried in vacuo to give 500 mg of the title compound.

$^1$H-NMR: δ=12.5 (br s, 1H); 7.56 (dd, 1H); 7.44 (d, 1H); 7.23 (d, 1H); 7.10-7.02 (m, 3H); 4.20 (t, 2H); 3.82 (s, 3H); 3.04 (t, 2H); 2.26 (s, 3H)

Step 3: 1-{3-[2-(2-Fluoro-5-methyl-phenyl)-ethoxy]-4-methoxy-benzoylamino}-cycloheptanecarboxylic acid methyl ester The compound of step 2 (285 mg, 0.937 mmol) was dissolved in an excess of thionyl chloride (0.7 ml) and stirred for 20 min at 60° C. The solution was evaporated to dryness in vacuo. The residue was dissolved in a little DCM and added to a well-stirred mixture of 1-amino-cycloheptanecarboxylic acid methyl ester hydrochloride (195 mg, 0.937 mmol), EA and an excess of a saturated aqueous sodium hydrogencarbonate solution. The mixture was stirred for 30 min at room temperature. The layers were separated, the aqueous phase was extracted with EA, the combined organic phases were washed with brine, dried over sodium sulfate, filtered and evaporated to dryness. This residue was purified by preparative RP HPLC (water/ACN gradient) to give 160 mg of the title compound.

Step 4: 1-{3-[2-(2-Fluoro-5-methyl-phenyl)-ethoxy]-4-methoxy-benzoylamino}-cycloheptanecarboxylic acid The compound of step 3 (160 mg, 0.35 mmol) was dissolved in dioxane (1.8 ml). 1 M aqueous lithium hydroxide (1.8 ml) was added, the mixture was stirred at 60° C. for 30 min, cooled, and partitioned between 2 N hydrochloric acid and EA. The aqueous phase was extracted with EA, the combined organic phases were dried over sodium sulfate, filtered and evaporated to dryness. The residue was stirred in ether and the solid material which formed was filtered and dried in vacuo to yield the title compound (126 mg).

$^1$H-NMR: δ=12 (br s, 1H); 8.07 (s, 1H); 7.50 (dd, 1H); 7.41 (d, 1H); 7.24 (d, 1H); 7.10-7.00 (m, 3H); 4.20 (t, 2H); 3.80 (s, 3H); 3.04 (t, 2H); 2.26 (s, 3H); 2.13-2.01 (m, 4H); 1.58-1.42 (m, 8H)

EXAMPLE 2

1-[4-Methoxy-3-(2-m-tolyl-ethoxy)-benzoylamino]-cycloheptanecarboxylic acid

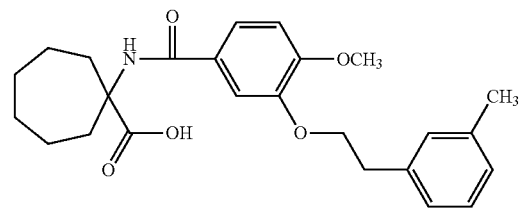 [SMILES: COc1ccc(C(=O)NC2(C(=O)O)CCCCCC2)cc1OCCc1cccc(C)c1]

Step 1: 4-Methoxy-3-(2-m-tolyl-ethoxy)-benzoic acid

From 3-hydroxy-4-methoxy-benzoic acid methyl ester, the title compound was obtained by reaction with 2-m-tolylethanol (2-(3-methyl-phenyl)-ethanol) in analogy to step 1 of example 1 and hydrolysis of the ester group in analogy to step 2 of example 1.

¹H-NMR: δ=12.65 (br s, 1H); 7.56 (dd, 1H); 7.44 (d, 1H); 7.19 (t, 1H); 7.17-7.15 (m, 1H); 7.12 (d, 1H); 7.06-7.02 (m, 2H); 4.19 (t, 2H); 3.83 (s, 3H); 3.01 (t, 2H); 2.29 (s, 3H)

Step 2: 1-[4-Methoxy-3-(2-m-tolyl-ethoxy)-benzoylamino]-cycloheptanecarboxylic acid The title compound was synthesized in analogy to example 1, steps 3 and 4.
LC/MS (Method LC10): Rt=3.67 min; m/z=426.23 [MH⁺]

EXAMPLE 3

1-{3-[2-(5-Chloro-2-fluoro-phenyl)-ethoxy]-4-methoxy-benzoylamino}-cycloheptanecarboxylic acid

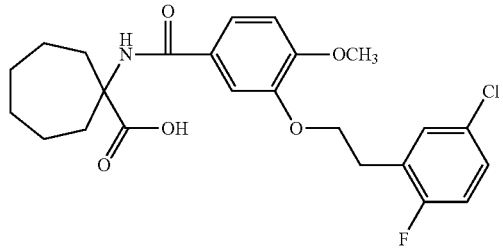 [SMILES: COc1ccc(C(=O)NC2(C(=O)O)CCCCCC2)cc1OCCc1cc(Cl)ccc1F]

Step 1: 1-(3-Acetoxy-4-methoxy-benzoylamino)-cycloheptanecarboxylic acid methyl ester 3-Acetoxy-4-methoxy-benzoic acid (7.10 g, 33.8 mmol) was dissolved in DMF (70 ml). The solution was cooled in an ice bath and 1-amino-cycloheptanecarboxylic acid methyl ester hydrochloride (7.72 g, 37.2 mmol), EDIA (24.4 ml, 135 mmol) and TOTU (16.6 g, 50.7 mmol) were added sequentially. Stirring was continued at room temperature for 1 h. Water was added and stirring was continued for 1 h. The solid material which formed was collected by filtration, washed with water and dried in vacuo. The obtained material was stirred with a diethyl ether/HEP mixture, filtered and dried in vacuo to yield the title compound (9.03 g).

¹H-NMR: δ=8.81 (s, 1H); 7.78 (dd, 1H); 7.62 (d, 1H); 7.19 (d, 1H); 3.82 (s, 3H); 3.55 (s, 3H); 2.28 (s, 3H); 2.13-2.02 (m, 4H); 1.60-1.41 (m, 8H)

Step 2: 1-(3-Hydroxy-4-methoxy-benzoylamino)-cycloheptanecarboxylic acid methyl ester The compound of step 1 (10.6 g, 29.4 mmol) was dissolved in methanol (100 ml), potassium carbonate (812 mg, 5.88 mmol) was added and the mixture was stirred overnight at room temperature. An excess of 2 N hydrochloric acid was added, the methanol was evaporated in vacuo and the residue partitioned between EA and water. The aqueous phase was extracted with EA, the combined organic phases were dried over sodium sulfate and evaporated to dryness to give the title compound (6.81 g).

¹H-NMR: δ=9.15 (s, 1H); 8.17 (s, 1H); 7.31 (dd, 1H); 7.28 (d, 1H); 6.95 (d, 1H); 3.81 (s, 3H); 3.54 (s, 3H); 2.10-2.00 (m, 4H); 1.57-1.40 (m, 8H)

Step 3: 1-{3-[2-(5-Chloro-2-fluoro-phenyl)-ethoxy]-4-methoxy-benzoylamino}-cycloheptanecarboxylic acid methyl ester The compound of step 2 (80 mg, 0.249 mmol) and triphenylphosphine (98 mg, 0.374 mmol) were dissolved in THF. 2-(5-Chloro-2-fluoro-phenyl)-ethanol (48 mg, 0.274 mmol) and DIAD (80.3 mg, 0.374 mmol) were added and the mixture was stirred at room temperature for 2 h. The volatiles were evaporated in vacuo and the residue was purified by preparative RP HPLC (water/ACN gradient) to give 85 mg of the title compound.

¹H-NMR: δ=8.21 (s, 1H); 7.58 (dd, 1H); 7.51 (dd, 1H); 7.41 (d, 1H); 7.38-7.33 (m, 1H); 7.25 (t, 1H); 7.02 (d, 1H); 4.23 (t, 2H); 3.80 (s, 3H); 3.54 (s, 3H); 3.09 (t, 2H); 2.12-2.01 (m, 4H); 1.57-1.40 (m, 8H)

Step 4: 1-{3-[2-(5-Chloro-2-fluoro-phenyl)-ethoxy]-4-methoxy-benzoylamino}-cycloheptanecarboxylic acid The compound of step 3 was hydrolyzed in analogy to step 4 of example 1 to yield the title compound.

¹H-NMR: δ=8.07 (s, 1H); 7.58 (dd, 1H); 7.51 (dd, 1H); 7.42 (d, 1H); 7.38-7.33 (m, 1H); 7.24 (t, 1H); 7.01 (d, 1H); 4.22 (t, 2H); 3.80 (s, 3H); 3.10 (t, 2H); 2.12-2.02 (m, 4H); 1.59-1.42 (m, 8H)

In analogy to example 3, the example compounds of the formula I-1 listed in table 1 were prepared. The compounds can be named as 1-[3-(R¹⁰¹-oxy)-4-methoxy-benzoylamino]-cycloheptanecarboxylic acid, for example as 1-{3-[2-(thiophen-3-yl)-ethoxy]-4-methoxy-benzoylamino]-cycloheptanecarboxylic acid in the case of example 11.

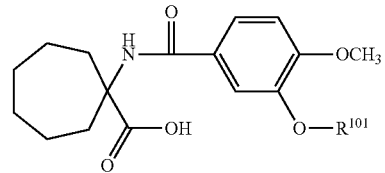

I-1

TABLE 1

Example compounds of the formula I-1

| Example | R¹⁰¹ | LC/MS Method | m/z [MH⁺] | Retention time [min] |
|---|---|---|---|---|
| 4 | 2-(3,5-dimethyl-1H-pyrazol-4-yl)-ethyl | LC10 | 430.18 | 2.57 |
| 5 | 2-(2-fluoro-5-trifluoromethoxy-phenyl)-ethyl | LC10 | 514.11 | 3.87 |
| 6 | 2-(thiophen-2-yl)-ethyl | LC8 | 418.17 | 2.36 |
| 7 | 2-(3-methoxy-phenyl)-ethyl | LC8 | 442.23 | 2.39 |
| 8 | 2-phenyl-ethyl | LC8 | 412.22 | 2.41 |
| 9 | 2-phenyl-propyl | LC8 | 426.22 | 2.49 |
| 10 | 2-(3-chloro-phenyl)-ethyl | LC8 | 446.17 | 2.51 |
| 11 | 2-(thiophen-3-yl)-ethyl | LC8 | 418.16 | 2.37 |
| 12 | (cyclohex-3-enyl)-methyl | LC8 | 402.22 | 2.49 |
| 13 | 2-(2-fluoro-phenyl)-ethyl | LC8 | 430.17 | 2.41 |
| 14 | 2-phenyl-butyl | LC8 | 440.21 | 2.59 |
| 15 | 2-(2,4-dichloro-phenyl)-ethyl | LC8 | 480.11 | 2.66 |
| 16 | 2-(2-chloro-6-fluoro-phenyl)-ethyl | LC8 | 464.12 | 2.50 |
| 17 | 2-(2,5-dichloro-phenyl)-ethyl | LC8 | 480.1 | 2.62 |
| 18 | 2-(2,5-dimethyl-phenyl)-ethyl | LC8 | 440.2 | 2.58 |

TABLE 1-continued

Example compounds of the formula I-1

| Example | R[101] | LC/MS Method | m/z [MH+] | Retention time [min] |
|---|---|---|---|---|
| 19 | 2-(2-methyl-phenyl)-ethyl | LC8 | 426.2 | 2.49 |
| 20 | 2-(2,5-difluoro-phenyl)-ethyl | LC8 | 448.15 | 2.42 |
| 21 | 2-(3-chloro-2-fluoro-phenyl)-ethyl | LC8 | 464.13 | 2.51 |
| 22 | (3-phenyl-oxetan-3-yl)-methyl | LC2 | 454.3 | 1.55 |

EXAMPLE 23

1-[4-Methoxy-3-(2-m-tolyl-ethoxy)-benzoylamino]-cyclooctanecarboxylic acid

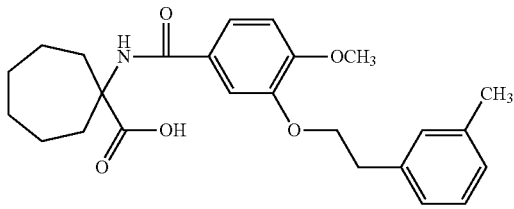

The title compound was synthesized in analogy to example 3 using 1-amino-cyclooctanecarboxylic acid methyl ester hydrochloride instead of 1-amino-cycloheptanecarboxylic acid methyl ester hydrochloride.

LC/MS (Method LC9): Rt=3.56 min; m/z=440.21 [MH+]

EXAMPLE 24

1-{3-[2-(2-Fluoro-5-methyl-phenyl)-ethoxy]-4-methoxy-benzoylamino}-cyclooctanecarboxylic acid

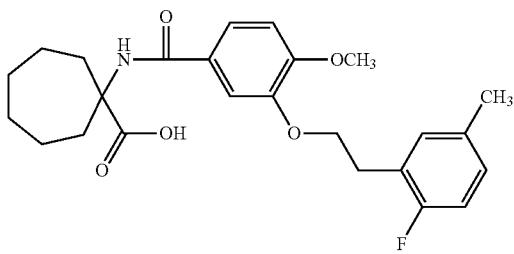 [SMILES: COc1ccc(C(=O)NC2(C(=O)O)CCCCCC2)cc1OCCc1cc(C)ccc1F]

The title compound was synthesized in analogy to example 23.

LC/MS (Method LC9): Rt=3.58 min; m/z=458.2 [MH+]

EXAMPLE 25

4-[4-Methoxy-3-(2-m-tolyl-ethoxy)-benzoylamino]-oxepane-4-carboxylic acid

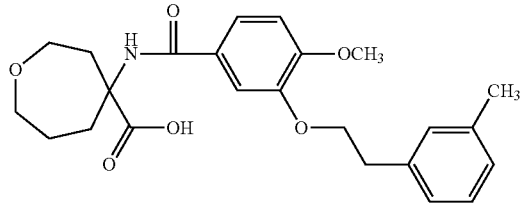 [SMILES: COc1ccc(C(=O)NC2(C(=O)O)CCCOCC2)cc1OCCc1cccc(C)c1]

4-Amino-oxepane-4-carboxylic acid methyl ester hydrochloride (synthesized from oxepan-4-one via the Bucherer-Bergs hydantoin route in analogy to the procedure described in J. W. Tsang et al., J. Med. Chem. 27 (1984), 1663-1668; oxepan-4-one was synthesized from tetrahydropyran-4-one by the in-situ diazomethane route described in F. Alonso et al., Tetrahedron 51 (1995), 10259-10280) was reacted with 4-methoxy-3-(2-m-tolyl-ethoxy)-benzoic acid and the obtained methyl ester hydrolyzed in analogy to steps 3 and 4 of example 1.

$^1$H-NMR: δ=12.15 (br s, 1H); 8.19 (s, 1H); 7.50 (dd, 1H); 7.41 (d, 1H); 7.21-7.15 (m, 2H); 7.12 (d, 1H); 7.06-6.99 (m, 2H); 4.20 (t, 2H); 3.80 (s, 3H); 3.65-3.55 (m, 4H); 3.01 (t, 2H); 2.35-2.22 (m, 5H, therein 2.29 (s, 3H)); 2.15-2.01 (m, 2H); 1.81-1.71 (m, 1H); 1.65-1.57 (m, 1H)

By coupling 4-methoxy-3-(2-m-tolyl-ethoxy)-benzoic acid to the respective amino acid methyl ester via the carboxylic acid chloride route as described in step 3 of example 1 or the TOTU coupling route as described in step 1 of example 3, the example compounds of the formula I-2 listed in table 2 were prepared. The amino acid methyl esters or the amino acids were commercially available or were prepared from the respective ketone in analogy to example 25. In the formulae of the groups R[102] in table 2 the line crossed with the symbol ~~ represents the free bond via which the group R[102] is bonded to the nitrogen atom of the amide group depicted in formula I-2. I.e., in the formula of the complete molecule the terminal endpoint of the line crossed with the said symbol ends on the nitrogen atom of the amide group.

I-2

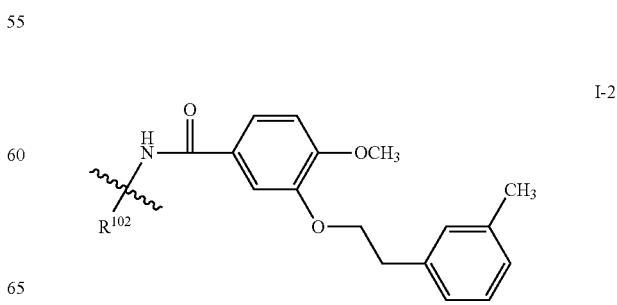

TABLE 2

Example compounds of the formula I-2

| Example | R¹⁰² | Starting material | LC/MS Method | m/z [MH⁺] | Retention time [min] |
|---|---|---|---|---|---|
| 26 | (4-methylcycloheptyl carboxylic acid) | (a) | LC2 | 440.33 | 1.77 |
| 27 | (4-methylcyclohexyl carboxylic acid) | (a) | LC10 | 426.14 | 3.72 |
| 28 | (4-trifluoromethylcyclohexyl carboxylic acid) | (a) | LC2 | 480.25 | 1.28 |
| 29 | (4-isopropylcyclohexyl carboxylic acid) | (a) | LC10 | 454.39 | 3.99 |
| 30 | (4-ethylcyclohexyl carboxylic acid) | (a) | LC1 | 440.27 | 1.89 |
| 31 | (bicyclic carboxylic acid) | (a) | LC2 | 438.31 | 1.29 |
| 32 | (1-methylcyclohexyl carboxylic acid) | (a) | LC2 | 426.27 | 1.31 |
| 33 | (3-methylcyclopentyl carboxylic acid) | (a) | LC2 | 412.26 | 1.29 |
| 34 | (cyclobutyl carboxylic acid) | (b) | LC12 | 384.2 | 1.97 |
| 35 | (cyclopentyl carboxylic acid) | (b) | LC12 | 398.2 | 2.02 |
| 36 | (tetrahydrothiopyranyl carboxylic acid) | (b) | LC11 | 430.2 | 4.29 |
| 37 | (tetrahydropyranyl carboxylic acid) | (b) | LC11 | 414.2 | 3.7 |
| 38 | (cyclohexyl carboxylic acid) | (b) | LC1 | 412.21 | 1.75 |
| 39 | (camphanyl carboxylic acid) | (b) | LC1 | 466.17 | 1.87 |
| 40 | (vinylcyclopropyl carboxylic acid) | (b) | LC2 | 396.27 | 1.24 |
| 41 | (ethylcyclopropyl carboxylic acid) | Example 42 | LC2 | 398.29 | 1.25 |

(a) The amino acid ester was prepared from the respective ketone.
(b) The amino acid ester or amino acid was commercially available.

EXAMPLE 42

1-Amino-2-ethylcyclopropanecarboxylic acid ethyl ester (starting compound)

1-tert-Butoxycarbonylamino-2-vinyl-cyclopropanecarboxylic acid ethyl ester (50 mg, 0.196 mmol) was dissolved in methanol (3 ml), azodicarboxylic acid dipotassium salt (D. J. Pasto et al., Organic Reactions 40 (1991), 91-155; 229 mg, 1.16 mmol) was added, the mixture was cooled in an ice bath and acetic acid (141 mg, 2.35 mmol) was added slowly. This mixture was warmed to 30° C. and stirred for 1 h. The addition of azodicarboxylic acid dipotassium salt and acetic acid and stirring at 30° C. was repeated until completion of the reduction. The mixture was evaporated to dryness and partitioned between EA and an aqueous sodium hydrogencarbonate solution. The aqueous phase was extracted with EA, the combined organic phases were dried over sodium chloride and evaporated to dryness. The residue was dissolved in a mixture of DCM and TFA (1:1) and stirred for 1 h. The mixture was evaporated to dryness and the obtained crude title compound (obtained in the form of the trifluoroacetic acid salt) used in the amide coupling step.

EXAMPLE 43 trans-1-[4-Methoxy-3-(2-m-tolyl-ethoxy)-benzoylamino]-4-methyl-cyclohexanecarboxylic acid

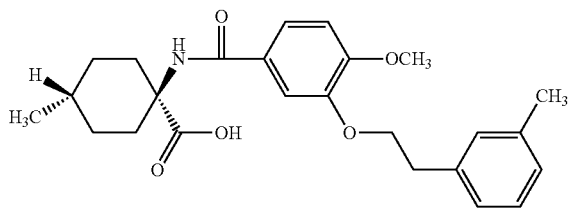 [SMILES: COc1ccc(C(=O)N[C@]2(C(=O)O)CC[C@@H](C)CC2)cc1OCCc1cccc(C)c1]

Step 1: N-(trans-1-Cyano-4-methyl-cyclohexyl)-4-methoxy-3-(2-m-tolyl-ethoxy)-benzamide 4-Methyl-cyclohexanone was reacted in a Strecker aminonitrile synthesis in analogy to the procedure described in I. L. Munday, J. Chem. Soc. (1961), 4372-4379 to yield trans-1-amino-4-methyl-cyclohexanecarbonitrile which was coupled with 4-methoxy-3-(2-m-tolyl-ethoxy)-benzoic acid via the TOTU coupling route as described in step 1 of example 3.

$^1$H-NMR: δ=8.42 (s, 1H); 7.50 (dd, 1H); 7.41 (d, 1H); 7.21-7.15 (m, 2H); 7.12 (d, 1H); 7.04 (d, 2H); 4.19 (t, 2H); 3.81 (s, 3H); 3.02 (t, 2H); 2.50-2.43 (m, 2H); 2.28 (s, 3H); 1.80-1.71 (m, 2H); 1.65-1.55 (m, 2H); 1.48-1.38 (m, 1H); 1.27-1.14 (m, 2H); 0.91 (d, 3H)

Step 2: trans-1-[4-Methoxy-3-(2-m-tolyl-ethoxy)-benzoylamino]-4-methyl-cyclohexanecarboxylic acid ethyl ester The compound of step 1 (810 mg, 1.99 mmol) was dissolved in ethanol (10 ml). The solution was cooled in an acetone/dry ice bath, acetyl chloride (2.3 ml, 30 mmol) was added and the mixture was warmed to room temperature and stirred for 3 days. Then 2 N hydrochloric acid was added and the mixture was stirred overnight to hydrolyze the imino ester. After evaporation of the ethanol, the residue was partitioned between EA and 2 N hydrochloric acid. The phases were separated, the aqueous phase was extracted with EA, the combined organic phases were dried over sodium sulfate and evaporated to dryness. The residue was purified by silica gel chromatography (DCM/EA gradient) to yield the title compound (0.78 g).

$^1$H-NMR: δ=8.20 (s, 1H); 7.45 (dd, 1H); 7.39 (d, 1H); 7.22-7.15 (m, 2H); 7.12 (d, 1H); 7.05-6.99 (m, 2H); 4.18 (t, 2H); 4.03 (q, 2H); 3.80 (s, 3H); 3.01 (t, 2H); 2.31-2.25 (m, 5H, therein 2.29 (s, 3H)); 1.65-1.54 (m, 4H); 1.52-1.41 (m, 1H); 1.30-1.18 (m, 2H); 1.10 (t, 3H); 0.88 (d, 3H)

Step 3: trans-1-[4-Methoxy-3-(2-m-tolyl-ethoxy)-benzoylamino]-4-methyl-cyclohexanecarboxylic acid The compound of step 2 was hydrolyzed in analogy to step 4 of example 1 to yield the title compound.

$^1$H-NMR: δ=12.0 (s, 1H); 8.09 (s, 1H); 7.48 (dd, 1H); 7.40 (d, 1H); 7.21-7.13 (m, 2H); 7.12 (d, 1H); 7.04 (d, 1H); 7.00 (d, 1H); 4.19 (t, 2H); 3.80 (s, 3H); 3.02 (t, 2H); 2.32-2.22 (m, 5H, therein 2.29 (s, 3H)); 1.65-1.51 (m, 4H); 1.51-1.40 (m, 1H); 1.31-1.20 (m, 2H); 0.86 (d, 3H)

In analogy to example 43, by employing the respective ketone instead of 4-methyl-cyclohexanone in the initial Strecker aminonitrile step, the example compounds of the formula I-3 listed in table 3 were prepared. In the formulae of the groups $R^{103}$ in table 3 the line crossed with the symbol ∿ represents the free bond via which the group $R^{103}$ is bonded to the nitrogen atom of the amide group depicted in formula I-3. I.e., in the formula of the complete molecule the terminal endpoint of the line crossed with the said symbol ends on the nitrogen atom of the amide group.

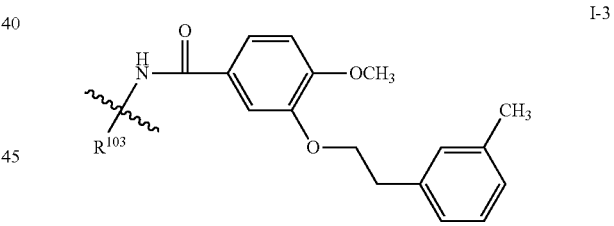

I-3

TABLE 3

Example compounds of the formula I-3

| Example | $R^{103}$ | LC/MS Method | m/z [MH⁺] | Retention time [min] |
|---|---|---|---|---|
| 44 | ![structure with F-cyclohexane-OH] | LC2 | 430.18 | 1.58 |

TABLE 3-continued

Example compounds of the formula I-3

| Example | R103 | LC/MS Method | m/z [MH+] | Retention time [min] |
|---|---|---|---|---|
| 45 | H3C, H3C— cyclohexyl-COOH | LC1 | 440.25 | 1.85 |
| 46 | H3C— cycloheptyl-COOH | (a) LC1 | 440.24 | 1.85 |
| 47 | bicyclic-COOH | (a) LC1 | 438.25 | 1.78 |
| 48 | CH3 cyclohexyl-COOH | (a) LC2 | 426.38 | 1.30 |
| 49 | CH3 cyclopentyl-COOH | LC2 | 412.33 | 1.30 |
| 50 | H3C— cyclohexyl-COOH | (a) LC1 | 440.25 | 1.87 |

(a) Other diastereomer than in example 26, example 30, example 31 and example 32, respectively.

EXAMPLE 51

8-[4-Methoxy-3-(2-m-tolyl-ethoxy)-benzoylamino]-1,4-dioxa-spiro[4.6]undecane-8-carboxylic acid

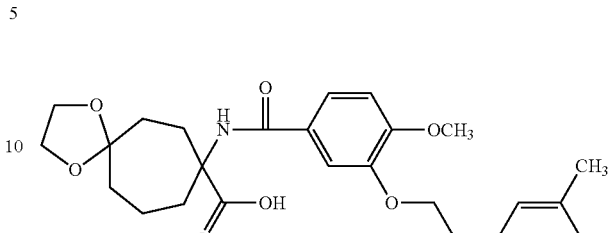

Step 1: 8-Benzyloxycarbonylamino-1,4-dioxa-spiro[4.6]undecane-8-carboxylic acid and 1-benzyloxycarbonylamino-4-oxo-cycloheptanecarboxylic acid 8-Amino-1,4-dioxa-spiro[4.6]undecane-8-carboxylic acid was synthesized from 1,4-dioxa-spiro[4.6]undecan-8-one (F. Alonso et al., Tetrahedron 51 (1995), 10259-10280) via the Bucherer-Bergs route in analogy to the procedure described in J. W. Tsang et al., J. Med. Chem. 27 (1984), 1663-1668. The intermediate was suspended in dioxane/water (2.5 ml/5 ml), sodium carbonate (0.732 g, 6.90 mmol) was added, the mixture was cooled in an ice bath and benzyl chloroformate (0.392 ml, dissolved in 2.5 ml of dioxane) was added with stirring. After 4 h, the mixture was partitioned between 2 N hydrochloric acid and EA, the aqueous phase was extracted with EA, the combined organic phrases were washed with water, dried over sodium sulfate and evaporated to dryness to yield a mixture of 8-benzyloxycarbonylamino-1,4-dioxa-spiro[4.6]undecane-8-carboxylic acid and 1-benzyloxycarbonylamino-4-oxo-cycloheptanecarboxylic acid.

Step 2: 8-Benzyloxycarbonylamino-1,4-dioxa-spiro[4.6]undecane-8-carboxylic acid methyl ester and 1-benzyloxycarbonylamino-4-oxo-cycloheptanecarboxylic acid methyl ester The mixture obtained in step 1 (200 mg) was dissolved in DMF (2 ml), cesium carbonate (280 mg, 0.86 mmol), EDIA (149 mg, 1.14 mmol) and iodomethane (121 mg, 0.858 mmol) were added and the mixture was stirred at room temperature for 2 h. The volatiles were evaporated in vacuo, the residue was partitioned between EA and saturated aqueous sodium hydrogencarbonate solution. The aqueous phase was extracted with EA, and the combined organic phases were dried over sodium sulfate and evaporated to dryness. The residue was purified by RP HPLC (water/ACN gradient) to yield 66 mg of 8-benzyloxycarbonylamino-1,4-dioxa-spiro[4.6]undecane-8-carboxylic acid methyl ester and 83 mg of 1-benzyloxycarbonylamino-4-oxo-cycloheptanecarboxylic acid methyl ester.

8-Benzyloxycarbonylamino-1,4-dioxa-spiro[4.6]undecane-8-carboxylic acid methyl ester $^1$H-NMR: δ=7.75 (s, 1H); 7.45-7.25 (m, 5H); 5.00 (s, 2H); 3.85-3.75 (m, 4H); 3.56 (s, 3H); 2.5-1.4 (m, 10H)

1-Benzyloxycarbonylamino-4-oxo-cycloheptanecarboxylic acid methyl ester $^1$H-NMR: δ=7.76 (s, 1H); 7.40-7.28 (m, 5H); 5.02 (s, 2H); 3.60 (s, 3H); 2.6-1.6 (m, 10H)

Step 3: 8-Amino-1,4-dioxa-spiro[4.6]undecane-8-carboxylic acid methyl ester 66 mg of 8-benzyloxycarbonylamino-1,4-dioxa-spiro[4.6]undecane-8-carboxylic acid methyl ester was dissolved in methanol and hydrogenated in an H-cube™ hydrogenation reactor (ThalesNano, Budapest, Hungary) at a hydrogen pressure of 100 bar at 40° C. over a cartridge with 10% palladium on charcoal. The mixture was evaporated to dryness to yield the crude title compound (32 mg).

Step 4: 8-[4-Methoxy-3-(2-m-tolyl-ethoxy)-benzoylamino]-1,4-dioxa-spiro[4.6]undecane-8-carboxylic acid The title compound was prepared from the compound of step 3 and 4-methoxy-3-(2-m-tolyl-ethoxy)-benzoic acid in analogy to steps 3 and 4 of example 1.

$^1$H-NMR: δ=12.1 (br s, 1H); 8.5-8.1 (br s, 1H); 7.45-7.33 (m, 2H); 7.22-7.15 (m, 2H), 7.11 (d, 1H); 7.03 (d, 1H); 6.98 (d, 1H); 4.20 (t, 2H); 3.84-3.76 (m, 7H); 3.01 (t, 2H), 2.29 (s, 3H); 2.27-1.90 (m, 4H); 1.86-1.50 (m, 6H)

EXAMPLE 52

1-[4-Methoxy-3-(2-m-tolyl-ethoxy)-benzoylamino]-4-oxo-cycloheptanecarboxylic acid

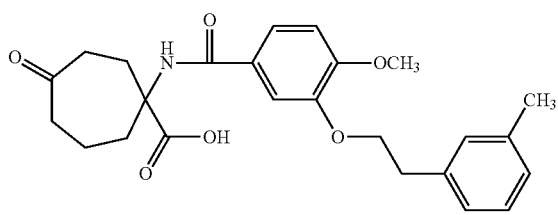 [SMILES: COc1ccc(C(=O)NC2(C(=O)O)CCCC(=O)CC2)cc1OCCc1cccc(C)c1]

1-Benzyloxycarbonylamino-4-oxo-cycloheptanecarboxylic acid methyl ester (83 mg) was hydrogenated in analogy to step 3 of example 51 and transformed into the title compound in analogy to step 4 of example 51.

$^1$H-NMR: δ=12.35 (s, 1H); 8.15 (s, 1H); 7.45 (dd, 1H); 7.39 (d, 1H); 7.21-7.15 (m, 2H), 7.11 (d, 1H); 7.05-7.00 (m, 2H); 4.20 (t, 2H); 3.81 (s, 3H); 3.01 (t, 2H), 2.65-2.50 (m, 2H); 2.42-2.11 (m, 8H, therein 2.30 (s, 3H)); 1.92-1.69 (m, 3H)

EXAMPLE 53

4-Hydroxy-1-[4-methoxy-3-(2-m-tolyl-ethoxy)-benzoylamino]-cycloheptanecarboxylic acid

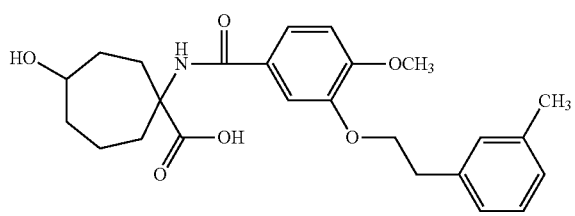 [SMILES: COc1ccc(C(=O)NC2(C(=O)O)CCCC(O)CC2)cc1OCCc1cccc(C)c1]

Step 1: 1-[4-Methoxy-3-(2-m-tolyl-ethoxy)-benzoylamino]-4-oxo-cycloheptanecarboxylic acid methyl ester 1-Benzyloxycarbonylamino-4-oxo-cycloheptanecarboxylic acid methyl ester was hydrogenated in analogy to step 3 of example 51 and transformed into the title compound by reaction with 4-methoxy-3-(2-m-tolyl-ethoxy)-benzoic acid in analogy to step 3 of example 1.

LC/MS (Method LC5): Rt=4.62 min; m/z=454.32 [MH$^+$]

Step 2: 4-Hydroxy-1-[4-methoxy-3-(2-m-tolyl-ethoxy)-benzoylamino]-cycloheptanecarboxylic acid methyl ester The compound of step 1 (67 mg, 0.148 mmol) was dissolved in THF (1 ml) and cooled in an ice bath. Sodium borohydride (5.7 mg, 0.148 mmol) was added. Subsequently methanol (0.3 ml) was added dropwise. The ice bath was removed and after stirring for 45 min at room temperature the mixture was partitioned between EA and 2 N hydrochloric acid. The aqueous phase was extracted with EA, and the combined organic phases were dried over sodium sulfate and evaporated to dryness to yield the title compound (65 mg).

LC/MS (Method LC6): Rt=4.27 min; m/z=456.36 [MH$^+$]

Step 3: 4-Hydroxy-1-[4-methoxy-3-(2-m-tolyl-ethoxy)-benzoylamino]-cycloheptanecarboxylic acid The compound of step 2 (63 mg, 0.138 mmol) was hydrolyzed in analogy to step 4 of example 1 to yield the title compound (49 mg) as mixture of diastereomers.

$^1$H-NMR: δ=12.0 (s, 1H); 8.12/8.06 (2s, 1H); 7.49 (dd, 1H); 7.40 (d, 1H); 7.22-7.10 (m, 3H), 7.08-6.99 (m, 2H); 4.46/4.40 (2d, 1H); 4.22-4.15 (m, 2H); 3.80 (s, 3H); 3.67-3.58 (m, 1H); 3.01 (t, 2H); 2.28 (s, 3H); 2.30-1.25 (m, 10H)

EXAMPLE 54

8-[4-Methoxy-3-(2-m-tolyl-ethoxy)-benzoylamino]-1,4-dioxa-spiro[4.5]decane-8-carboxylic acid

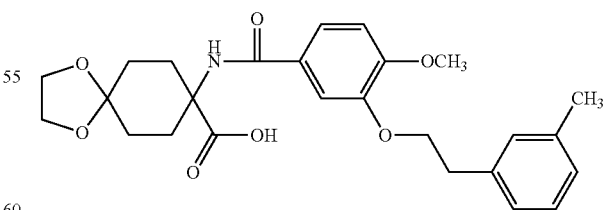

The title compound was synthesized in analogy to example 51 starting from commercially available 8-amino-1,4-dioxa-spiro[4.5]decane-8-carboxylic acid.

LC/MS (Method LC1): Rt=1.63 min; m/z=470.2 [MH$^+$]

EXAMPLE 55

1-[4-Methoxy-3-(2-m-tolyl-ethoxy)-benzoylamino]-4-oxo-cyclohexanecarboxylic acid

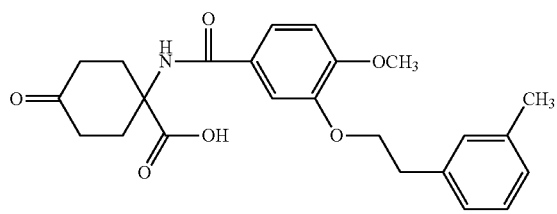 [SMILES: COc1ccc(C(=O)NC2(C(=O)O)CCC(=O)CC2)cc1OCCc1cccc(C)c1]

Step 1: 1-[4-Methoxy-3-(2-m-tolyl-ethoxy)-benzoylamino]-4-oxo-cyclohexanecarboxylic acid methyl ester 8-[4-Methoxy-3-(2-m-tolyl-ethoxy)-benzoylamino]-1,4-dioxa-spiro[4.5]decane-8-carboxylic acid methyl ester (4.7 g, 9.7 mmol; intermediate in the synthesis of example 54) was dissolved in dioxane (70 ml), 2 N aqueous hydrochloric acid (10 ml) was added and the mixture was stirred at room temperature overnight. The material was partitioned between EA and saturated aqueous sodium chloride solution, the aqueous phase was extracted with EA, the combined organic phases were dried over sodium sulfate and evaporated to dryness to yield the title compound.
LC/MS (Method LC1): Rt=1.66 min; m/z=440.21 [MH+]

Step 2: 1-[4-Methoxy-3-(2-m-tolyl-ethoxy)-benzoylamino]-4-oxo-cyclohexanecarboxylic acid The compound of step 1 was hydrolyzed in analogy to step 4 of example 1 to yield the title compound.
LC/MS (Method LC4): Rt=1.15 min; m/z=425.74 [MH+]

EXAMPLE 56

1-[4-Methoxy-3-(2-m-tolyl-ethoxy)-benzoylamino]-4-methylene-cyclohexanecarboxylic acid

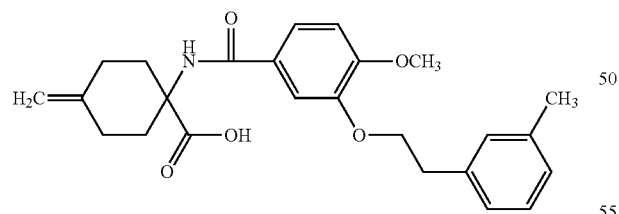

Step 1: 1-[4-Methoxy-3-(2-m-tolyl-ethoxy)-benzoylamino]-4-methylene-cyclohexanecarboxylic acid methyl ester Methyltriphenylphosphonium bromide (4.88 g, 13.7 mmol) was suspended in THF. Potassium bis(trimethylsilyl)amide (13.6 mmol, solution in toluene) was added slowly and the mixture was stirred at room temperature for 1 h. The mixture was cooled in a acetone/dry ice bath and the compound of step 1 of example 55 (3.00 g, 6.83 mmol) was added. The mixture was warmed to room temperature and stirred overnight. Methanol and an aqueous sodium dihydrogenphosphate solution were added. The mixture was extracted with diethyl ether, the combined extracts were dried over sodium sulfate and evaporated to dryness. The residue was purified by silica gel chromatography (HEP/EA gradient) to yield the title compound (1.40 g).
LC/MS (Method LC1): Rt=1.91 min; m/z=438.22 [MH+]

Step 2: 1-[4-Methoxy-3-(2-m-tolyl-ethoxy)-benzoylamino]-4-methylene-cyclohexanecarboxylic acid The compound of step 1 was hydrolyzed in analogy to step 4 of example 1 to yield the title compound.
LC/MS (Method LC10): Rt=3.70 min; m/z=424.25 [MH+]

EXAMPLE 57

6-[4-Methoxy-3-(2-m-tolyl-ethoxy)-benzoylamino]-spiro[2.5]octane-6-carboxylic acid

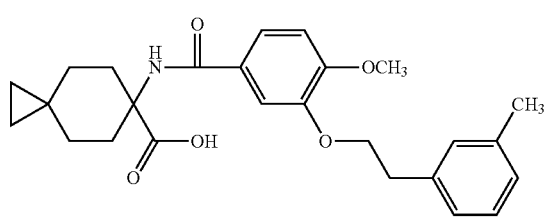 [SMILES: COc1ccc(C(=O)NC2(C(=O)O)CCC3(CC3)CC2)cc1OCCc1cccc(C)c1]

The compound of step 1 of example 56 (400 mg, 0.91 mmol) was dissolved in toluene (8 ml) and diethylzinc (2.7 ml, 2.7 mmol, solution in hexane) was added. The mixture was heated to 60° C. and diiodomethane (1.10 g, 4.11 mmol) was added with stirring. This mixture was reacted at 60° C. overnight, the addition of diethyl zinc and diiodomethane was repeated and stirring continued for another night. The mixture was partitioned between EA and 2 N hydrochloric acid, the aqueous phase was extracted with EA, the combined organic phases were washed with aqueous sodium hydrogencarbonate solution, dried over sodium sulfate and evaporated to dryness. The obtained methyl ester was hydrolyzed in analogy to step 4 of example 1 to yield the title compound (15 mg).
LC/MS (Method LC10): Rt=3.70 min; m/z=438.29 [MH+]

EXAMPLE 58

4-Hydroxymethyl-1-[4-methoxy-3-(2-m-tolyl-ethoxy)-benzoylamino]-cyclohexanecarboxylic acid

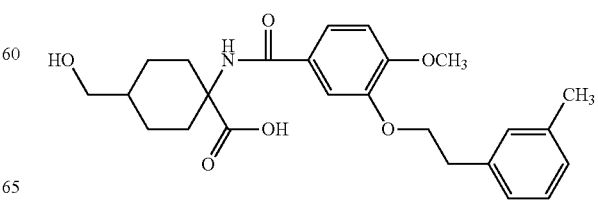

Step 1: 4-Hydroxymethyl-1-[4-methoxy-3-(2-m-tolyl-ethoxy)-benzoylamino]-cyclohexanecarboxylic acid methyl ester The compound of step 1 of example 56 (500 mg, 1.14 mmol) was dissolved in THF (5 ml) and cooled to −25° C. Borane-tetrahydrofuran complex (2.29 ml of a 1 M solution in THF, 2.29 mmol) was added and the mixture was kept overnight at 0° C. Hydrogen peroxide (2.5 ml, 30% in water) and sodium hydroxide (2.5 ml, 20% in water) were added sequentially and stirring was continued at room temperature. The mixture was partitioned between water and EA, the aqueous phase extracted with EA, and the combined organic phases were dried over sodium sulfate and evaporated to dryness. The residue was purified by silica gel chromatography (HEP/EA gradient) to yield the title compound.

LC/MS (Method LC1): Rt=1.62 min; m/z=456.18 [MH$^+$]

Step 2: 4-Hydroxymethyl-1-[4-methoxy-3-(2-m-tolyl-ethoxy)-benzoylamino]-cyclohexanecarboxylic acid The compound of step 1 was hydrolyzed in analogy to step 4 of example 1 to yield the title compound as mixture of the cis isomer and the trans isomer.

$^1$H-NMR: δ=12.0 (s, 1H); 8.09/7.96 (2s, 1H); 7.52-7.46 (m, 1H); 7.41 (s, 1H); 7.22-7.16 (m, 2H); 7.12 (d, 1H); 7.08-6.98 (m, 2H); 4.42-4.36 (m, 1H); 4.24-4.18 (m, 2H); 3.81 (s, 3H); 3.22/3.20 (2t, 2H); 3.01 (t, 2H); 2.32-2.22 (m, 5H, therein 2.28 (s, 3H)); 1.68-1.50 (m, 4H); 1.48-1.33 (m, 1H); 1.32-1.22 (m, 1H); 1.22-1.11 (m, 1H)

EXAMPLE 59

4-Fluoromethyl-1-[4-methoxy-3-(2-m-tolyl-ethoxy)-benzoylamino]-cyclohexanecarboxylic acid

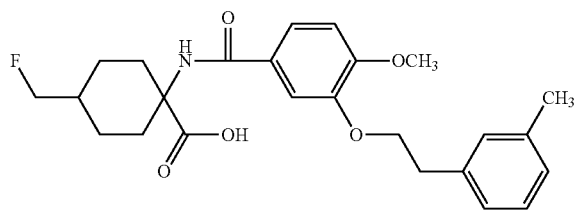 [SMILES: COc1ccc(C(=O)NC2(C(=O)O)CCC(CF)CC2)cc1OCCc1cccc(C)c1]

The compound of step 1 of example 58 (100 mg, 0.220 mmol) was dissolved in DCM (2 ml), diethylaminosulfur trifluoride (35 mg, 0.22 mmol) was added and the mixture was stirred at room temperature for 72 h. The mixture was partitioned between EA and aqueous sodium hydrogencarbonate solution. The aqueous phase was extracted with EA, the combined organic phases were dried over sodium sulfate and evaporated to dryness. The residue was purified by silica gel chromatography (HEP/EA gradient) and hydrolyzed in analogy to step 4 of example 1 to yield the title compound.

$^1$H-NMR: δ=12.15 (s, 1H); 8.15/8.02 (2s, 1H); 7.53-7.48 (m, 1H); 7.41 (s, 1H); 7.23-7.16 (m, 2H); 7.12 (d, 1H); 7.09-7.00 (m, 2H); 4.35-4.26 (m, 3H); 3.81 (s, 3H); 3.02 (t, 2H); 2.39-2.30 (m, 2H); 2.29 (s, 3H); 1.80-1.53 (m, 5H); 1.48-1.22 (m, 2H)

EXAMPLE 60

1-[4-Acetyl-3-(2-m-tolyl-ethoxy)-benzoylamino]-cycloheptanecarboxylic acid

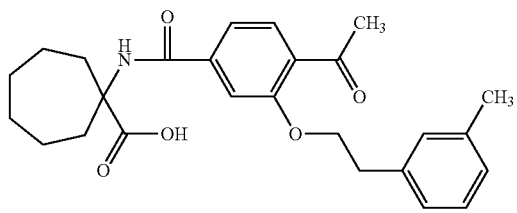 [SMILES: CC(=O)c1ccc(C(=O)NC2(C(=O)O)CCCCCC2)cc1OCCc1cccc(C)c1]

Step 1: 1-(4-Acetyl-3-hydroxy-benzoylamino)-cycloheptanecarboxylic acid methyl ester 1-Amino-cycloheptanecarboxylic acid methyl ester hydrochloride (968 mg, 4.66 mmol), HOBT (105 mg, 0.78 mmol) and 4-acetyl-3-hydroxy-benzoic acid (700 mg, 3.89 mmol) were dissolved in DMF (5 ml). EDIA (3.01 g, 23.3 mmol) and EDC were added and the mixture was stirred at room temperature for 72 h. Then the mixture was partitioned between EA and saturated sodium chloride solution, the aqueous phase was extracted with EA, the combined organic phases were dried over sodium sulfate and evaporated to dryness. The residue was purified by RP HPLC (water/ACN gradient) to yield the title compound.

LC/MS (Method LC9): Rt=3.19 min; m/z=334.17 [MH$^+$]

Step 2: 1-[4-Acetyl-3-(2-m-tolyl-ethoxy)-benzoylamino]-cycloheptanecarboxylic acid methyl ester The compound of step 1 and 2-m-tolylethanol were reacted in analogy to step 1 of example 1 to yield the title compound.

LC/MS (Method LC9): Rt=3.98 min; m/z=452.21 [MH$^+$]

Step 3: 1-[4-Acetyl-3-(2-m-tolyl-ethoxy)-benzoylamino]-cycloheptanecarboxylic acid The compound of step 2 was hydrolyzed in analogy to step 4 of example 1 to yield the title compound.

LC/MS (Method LC9): Rt=3.53 min; m/z=438.18 [MH$^+$]

EXAMPLE 61

1-[4-(1-Hydroxy-ethyl)-3-(2-m-tolyl-ethoxy)-benzoylamino]-cycloheptanecarboxylic acid

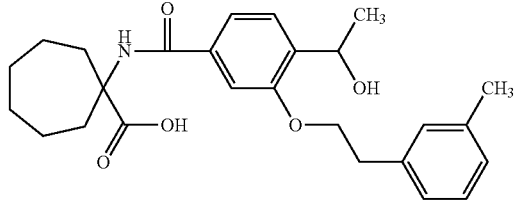 [SMILES: Cc1cccc(CCOc2cc(C(=O)NC3(C(=O)O)CCCCCC3)ccc2C(C)O)c1]

The compound of example 60 (300 mg, 0.686 mmol) was dissolved in methanol (6 ml) and cooled in an ice bath. Sodium borohydride (79 mg, 2.06 mmol) was added, the mixture was kept at 0° C. for 72 h, and then evaporated to dryness. The residue was partitioned between EA and 2 N hydrochloric acid, the aqueous phase was extracted with EA, the combined organic phases were dried over sodium sulfate and evaporated to dryness. The residue was stirred with diethyl ether and the solidified material was filtered and dried in vacuo to yield the title compound (50 mg). From the mother liquor a further batch of the title compounds was isolated by RP HPLC (water/ACN gradient).

LC/MS (Method LC9): Rt=3.32 min; m/z=440.23 [MH$^+$]

EXAMPLE 62

1-[4-Ethyl-3-(2-m-tolyl-ethoxy)-benzoylamino]-cycloheptanecarboxylic acid

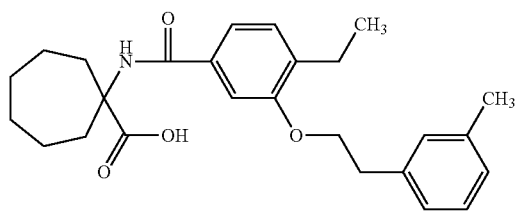 [SMILES: CCc1ccc(C(=O)NC2(C(=O)O)CCCCCC2)cc1OCCc1cccc(C)c1]

The compound of example 61 (100 mg) was dissolved in ethanol (10 ml) and hydrogenated in an H-cube™ hydrogenation reactor at a hydrogen pressure of 10 bar at 35° C. over a cartridge with 10% palladium on charcoal. The reaction mixture was evaporated to dryness and purified by RP HPLC (water/ACN gradient) to yield the title compound (60 mg).

$^1$H-NMR: δ=12.00 (s, 1H); 8.12 (s, 1H); 7.38 (dd, 1H); 7.32 (d, 1H); 7.22-7.13 (m, 3H); 7.11 (d, 1H); 7.03 (d, 1H); 4.23 (t, 2H); 3.03 (t, 2H); 2.53 (q, 2H); 2.28 (s, 3H); 2.10-2.04 (m, 4H); 1.57-1.43 (m, 8H); 1.03 (t, 3H)

EXAMPLE 63

1-[4-(1-Fluoro-ethyl)-3-(2-m-tolyl-ethoxy)-benzoylamino]-cycloheptanecarboxylic acid

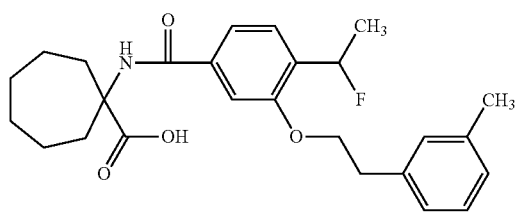 [SMILES: Cc1cccc(CCOc2cc(C(=O)NC3(C(=O)O)CCCCCC3)ccc2C(C)F)c1]

The compound of step 2 of example 60 (110 mg, 0.244 mmol) was dissolved in methanol (1.1 ml) and cooled in an ice bath. Sodium borohydride (9.2 mg, 0.244 mmol) was added and stirring continued for 1 h. This mixture was partitioned between EA and saturated sodium hydrogencarbonate solution, the aqueous phase was extracted with EA, the combined organic phases were dried over sodium sulfate and evaporated to dryness. The residue (100 mg) was dissolved in DCM (2 ml) and diethylaminosulfur trifluoride (36 mg, 0.22 mmol) was added. The mixture was stirred for 3 h, partitioned between EA and saturated sodium hydrogencarbonate solution, the aqueous phase was extracted with EA, the combined organic phases were dried over sodium sulfate and evaporated to dryness. The obtained ester was hydrolyzed in analogy to step 4 of example 1 to yield the title compound.

$^1$H-NMR: δ=12.05 (s, 1H); 8.24 (s, 1H); 7.48 (d, 1H); 7.41-7.36 (m, 2H); 7.20 (t, 1H); 7.15 (s, 1H); 7.12 (d, 1H); 7.03 (d, 1H); 5.81 (dq, 1H); 4.28 (t, 2H); 3.03 (t, 2H); 2.30 (s, 3H); 2.12-2.02 (m, 4H); 1.56-1.42 (m, 8H); 1.40 (dd, 3H)

EXAMPLE 64

1-[4-Chloro-3-(2-m-tolyl-ethoxy)-benzoylamino]-cycloheptanecarboxylic acid

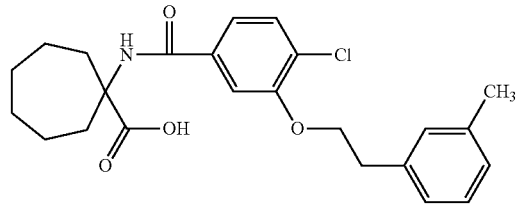 [SMILES: Cc1cccc(CCOc2cc(C(=O)NC3(C(=O)O)CCCCCC3)ccc2Cl)c1]

Step 1: 3-Acetoxy-4-chlorobenzoic acid

4-Chloro-3-hydroxybenzoic acid (1.00 g, 5.80 mmol) was suspended in acetic anhydride (11 ml) and heated to reflux for 3 h. After cooling, water (11 ml) was added and the mixture was refluxed again for 1 h. After cooling, crystals formed overnight which were collected by suction filtration and dried in vacuo to yield the title compound (630 mg).

$^1$H-NMR: δ=13.5 (br s, 1H); 7.88-7.81 (m, 2H); 7.71 (d, 1H); 2.34 (s, 3H)

Step 2: 1-(3-Acetoxy-4-chloro-benzoylamino)-cycloheptanecarboxylic acid methyl ester The compound of step 1 (200 mg, 0.932 mmol) was dissolved in DCM (16 ml), DMF (12 mg) and oxalyl chloride (362 mg, 2.80 mmol) were added and the mixture was stirred at room temperature until completion of the reaction. The volatiles were evaporated in vacuo and the residue dissolved in DCM. The solution was added to a stirred mixture of 1-amino-cycloheptanecarboxylic acid methyl ester hydrochloride (194 mg, 0.932 mmol) in EA/saturated sodium hydrogencarbonate solution with cooling in an ice bath. Stirring continued at room temperature for 2 h. The phases were separated, aqueous phase was extracted with EA, the combined organic phases were dried over sodium sulfate and evaporated to dryness. The residue was purified by silica gel chromatography (HEP/EA gradient) to yield the title compound (430 mg).

LC/MS (Method LC9): Rt=3.48 min; m/z=368.12 [MH$^+$]

Step 3: 1-(4-Chloro-3-hydroxy-benzoylamino)-cycloheptanecarboxylic acid methyl ester The compound of step 2 (400 mg, 1.088 mmol) was dissolved in methanol (3.5 ml), potassium carbonate (3 mg, 0.02 mmol) was added, and the mixture was stirred at room temperature for 6 h and evaporated to dryness to yield the title compound (300 mg).

LC/MS (Method LC9): Rt=3.05 min; m/z=326.22 [MH$^+$]

Step 4: 1-[4-Chloro-3-(2-m-tolyl-ethoxy)-benzoylamino]-cycloheptanecarboxylic acid The compound of step 3 was etherified with 2-m-tolylethanol in analogy to step 1 of example 1, and the intermediate was hydrolyzed in analogy to step 4 of example 1 to yield the title compound.

LC/MS (Method LC9): Rt=3.78 min; m/z=430.16 [MH$^+$]

EXAMPLE 65

1-[4-Bromo-3-(2-m-tolyl-ethoxy)-benzoylamino]-cycloheptanecarboxylic acid

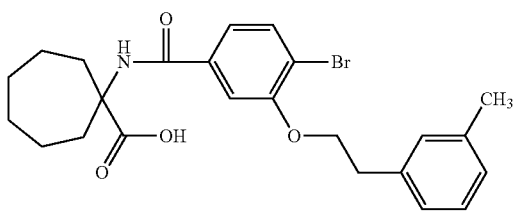 [SMILES: Cc1cccc(CCOc2cc(C(=O)NC3(C(=O)O)CCCCCC3)ccc2Br)c1]

The title compound was synthesized in analogy to example 64 starting with 4-bromo-3-hydroxybenzoic acid in step 1.
LC/MS (Method LC9): Rt=3.83 min; m/z=474.11 [MH$^+$]

EXAMPLE 66

2-Benzyloxy-1-[4-methoxy-3-(2-m-tolyl-ethoxy)-benzoylamino]-cyclopentanecarboxylic acid, diastereomer 1 and diastereomer 2

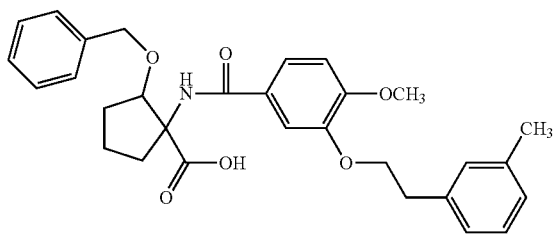 [SMILES: COc1ccc(C(=O)NC2(C(=O)O)CCCC2OCc2ccccc2)cc1OCCc1cccc(C)c1]

Step 1:
1-Amino-2-benzyloxy-cyclopentanecarbonitrile, diastereomer 1 and diastereomer 2

2-Benzyloxycyclopentanone (A. B. Smith et al., J. Am. Chem. Soc. 108 (1986), 3040-3048; 310 mg, 1.63 mmol) was reacted in a Strecker aminonitrile synthesis in analogy to step 1 of example 43 to give the two racemic diastereomers of the title compound which were separated by silica gel chromatography (HEP/EA gradient).
Diastereomer 1
$^1$H-NMR: δ=7.40-7.32 (m, 4H); 7.31-7.25 (m, 1H); 4.60 (d, 1H); 4.56 (d, 1H); 3.75-3.72 (m, 1H); 2.07-1.92 (m, 2H); 1.83-1.77 (m, 1H); 1.77-1.67 (m 3H)
Diastereomer 2
$^1$H-NMR: δ=7.40-7.32 (m, 4H); 7.31-7.25 (m, 1H); 4.68 (d, 1H); 4.61 (d, 1H); 4.02 (dd, 1H); 1.98-1.62 (m, 5H); 1.62-1.51 (m, 1H)

Step 2a: 2-Benzyloxy-1-[4-methoxy-3-(2-m-tolyl-ethoxy)-benzoylamino]-cyclopentanecarboxylic acid, diastereomer 1

The compound of step 1, diastereomer 1, was coupled with 4-methoxy-3-(2-m-tolyl-ethoxy)-benzoic acid via the carboxylic acid chloride in analogy to step 3 of example 1. The obtained nitrile was reacted with ethanol in analogy to step 2 of example 43, and the obtained ethyl ester was hydrolyzed in analogy to step 4 of example 1 to yield the title compound.
LC/MS (Method LC6): Rt=4.81 min; m/z=502.16 [M−H$^+$]

Step 2b: 2-Benzyloxy-1-[4-methoxy-3-(2-m-tolyl-ethoxy)-benzoylamino]-cyclopentanecarboxylic acid, diastereomer 2

The compound of step 1, diastereomer 2, was reacted in analogy to step 2a to yield the title compound.
LC/MS (Method LC1): Rt=1.91 min; m/z=504.18 [MH$^+$]

EXAMPLE 67

2-Hydroxy-1-[4-methoxy-3-(2-m-tolyl-ethoxy)-benzoylamino]-cyclopentanecarboxylic acid, diastereomer 1 and diastereomer 2

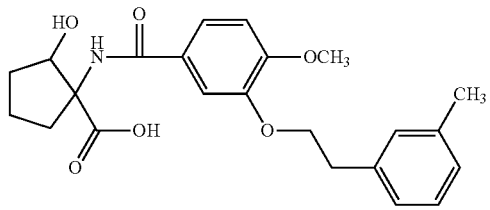 [SMILES: COc1ccc(C(=O)NC2(C(=O)O)CCCC2O)cc1OCCc1cccc(C)c1]

Diastereomer 1 and diastereomer 2 of the compound of example 66 were separately dissolved in ethanol and hydrogenated with palladium 10% on charcoal at room temperature with 1 bar hydrogen pressure until completion of the reaction. After filtration, the solutions were evaporated to dryness and the residues purified by RP HPLC (water/ACN gradient) to yield the two diastereomers of the title compound separately.
Diastereomer 1
$^1$H-NMR: δ=8.52 (br s, 1H); 7.36-7.30 (m, 1H); 7.22-7.15 (m, 2H); 7.12 (d, 1H); 7.06-7.00 (m, 2H); 4.60 (br s, 1H); 4.18 (t, 2H); 4.14-4.09 (m, 1H); 3.80 (s, 3H); 3.01 (t, 2H); 2.29 (s, 3H); 2.20-2.11 (m, 1H); 2.09-1.93 (m, 2H); 1.77-1.65 (m, 2H); 1.62-1.52 (m, 1H)
Diastereomer 2
$^1$H-NMR: δ=12.0 (br s, 1H); 8.11 (s, 1H); 7.45 (dd, 1H); 7.40 (d, 1H); 7.23-7.14 (m, 2H); 7.11 (d, 1H); 7.06-7.00 (m, 2H); 5.11 (br s, 1H); 4.29 (t, 1H); 4.19 (t, 2H); 3.80 (s, 3H); 3.01 (t, 2H); 2.29 (s, 3H); 2.03-1.95 (m, 1H); 1.94-1.85 (m, 1H); 1.80-1.68 (m, 1H); 1.58-1.50 (m, 2H)

EXAMPLE 68

2-Methoxy-1-[4-methoxy-3-(2-m-tolyl-ethoxy)-benzoylamino]-cyclopentanecarboxylic acid

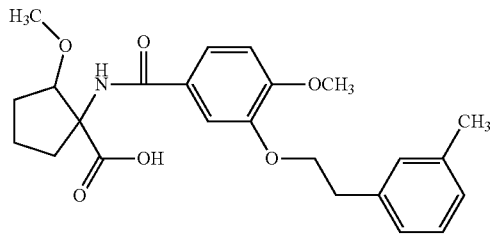 [SMILES: COc1ccc(C(=O)NC2(C(=O)O)CCCC2OC)cc1OCCc1cccc(C)c1]

The title compound was synthesized in analogy to example 60 starting with 2-methoxy-cyclopentanone (B. Foehlisch et al., Chem. Ber. 120 (1987), 1951-1960) and obtained as a mixture of diastereomers which was not separated.

LC/MS (Method LC4): Rt=1.21 min; m/z=428.25 [MH+]

EXAMPLE 69

1-[2-Fluoro-4-methoxy-3-(2-m-tolyl-ethoxy)-benzoylamino]-cycloheptanecarboxylic acid

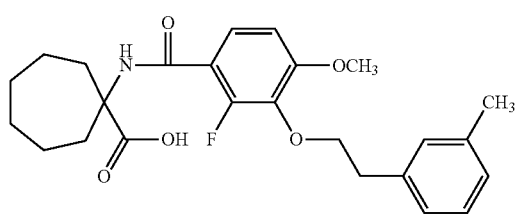 [SMILES: COc1ccc(C(=O)NC2(C(=O)O)CCCCCC2)c(F)c1OCCc1cccc(C)c1]

Step 1: 3-Fluoro-5-hydroxy-4-methoxybenzoic acid methyl ester and 2-Fluoro-3-hydroxy-4-methoxybenzoic acid methyl ester 3-Acetoxy-4-methoxybenzoic acid methyl ester (WO 2005/009389; 3.58 g, 16.0 mmol) and 1-chloromethyl-4-fluoro-1,4-diazoniabicyclo[2.2.2]octane bis(tetrafluoroborate) (Selectfluor®; 14.1 g, 39.9 mmol) were suspended in ACN (50 ml) and heated in a microwave oven for 7 min at 170° C. After cooling, water was added and the mixture was repeatedly extracted with diethyl ether. The combined extracts were dried over sodium sulfate and evaporated to dryness. The residue was purified by RP HPLC (water/ACN gradient). The obtained mixture of fluorinated species, which were partially deacetylated, was dissolved in methanol (20 ml), potassium carbonate (80 mg) was added and the mixture was stirred for 3 h at 60° C. The methanol was evaporated, the residue was partitioned between EA and 2 N hydrochloric acid, the aqueous phase was extracted with EA, the combined organic phases were dried over sodium sulfate and evaporated to dryness. This residue was purified by RP HPLC (water/ACN gradient) to yield two regioisomers.

3-Fluoro-5-hydroxy-4-methoxybenzoic acid methyl ester $^1$H-NMR: δ=10.2 (s, 1H); 7.30 (d, 1H); 7.21 (dd, 1H); 3.88 (s, 3H); 3.81 (s, 3H)

2-Fluoro-3-hydroxy-4-methoxybenzoic acid methyl ester $^1$H-NMR: δ=10.55 (s, 1H); 7.61 (d, 1H); 6.80 (dd, 1H); (d, 1H); 3.94 (d, 3H); 3.84 (s, 3H); 2.32 (s, 3H)

Step 2: 1-[2-Fluoro-4-methoxy-3-(2-m-tolyl-ethoxy)-benzoylamino]-cycloheptanecarboxylic acid 2-Fluoro-3-hydroxy-4-methoxybenzoic acid methyl ester was coupled to 2-m-tolylethanol, the intermediate hydrolyzed, coupled to 1-amino-cycloheptanecarboxylic acid methyl ester hydrochloride and the obtained ester hydrolyzed in analogy to steps 1 to 4 of example 1 to yield the title compound.

LC/MS (Method LC7): Rt=2.74 min; m/z=444.24 [MH+]

EXAMPLE 70

1-[3-Fluoro-4-methoxy-5-(2-m-tolyl-ethoxy)-benzoylamino]-cycloheptanecarboxylic acid

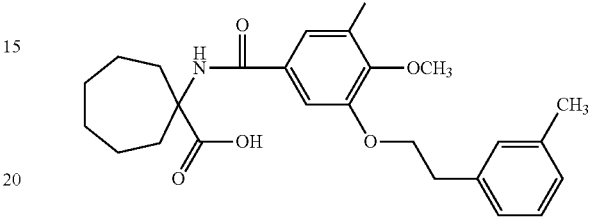

The title compound was synthesized in analogy to step 2 of example 69 from 3-fluoro-5-hydroxy-4-methoxybenzoic acid methyl ester (prepared in step 1 of example 69).

LC/MS (Method LC7): Rt=2.64 min; m/z=444.22 [MH+]

EXAMPLE 71

1-[3-(2,2-Difluoro-2-phenyl-ethoxy)-4-methoxy-benzoylamino]-cycloheptanecarboxylic acid

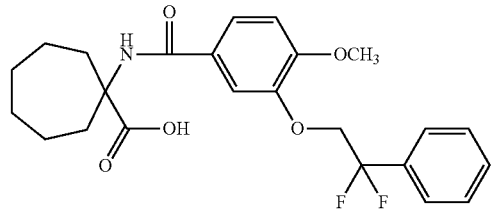 [SMILES: COc1ccc(C(=O)NC2(C(=O)O)CCCCCC2)cc1OCC(F)(F)c1ccccc1]

Step 1: Trifluoromethanesulfonic acid 2,2-difluoro-2-phenyl-ethyl ester 2,2-Difluoro-2-phenyl-ethanol (200 mg, 1.27 mmol) was dissolved in DCM (2 ml) and treated at 0° C. with EDIA (0.27 ml, 1.52 mmol) and trifluoromethanesulfonic acid anhydride (0.43 g, 1.52 mmol). After completion of the reaction (monitored by TLC (silica gel, DCM/methanol 98:2)), the mixture was partitioned between water and EA. The aqueous phase was extracted with EA, the combined organic phases were washed with saturated sodium chloride solution, dried over sodium sulfate and evaporated to dryness. This intermediate was used without further purification.

Step 2: 1-[3-(2,2-Difluoro-2-phenyl-ethoxy)-4-methoxy-benzoylamino]-cycloheptanecarboxylic acid methyl ester To a mixture of 1-(3-hydroxy-4-methoxy-benzoylamino)-cycloheptanecarboxylic acid methyl ester (80 mg, 0.249 mmol) and potassium carbonate (83 mg, 0.60 mmol) in 0.5 ml of acetone and 0.5 ml of DMF was added slowly a solution of the compound of step 1 (0.22 g, 0.374 mmol) as solution in acetone. The mixture was stirred for 3 d at room temperature and then evaporated. The residue was purified by preparative RP HPLC (water/ACN gradient) to give the title compound (87 mg).

LC/MS (Method LC10): Rt=3.90 min; m/z=462.12 [MH⁺]

Step 3: 1-[3-(2,2-Difluoro-2-phenyl-ethoxy)-4-methoxy-benzoylamino]-cycloheptanecarboxylic acid The compound of step 2 was hydrolyzed in analogy to step 4 of example 1 to yield the title compound.
LC/MS (Method LC8): Rt=2.41 min; m/z=448.19 [MH⁺]

EXAMPLE 72

1-[4-Methoxy-3-(3-m-tolyl-propyl)-benzoylamino]-cycloheptanecarboxylic acid

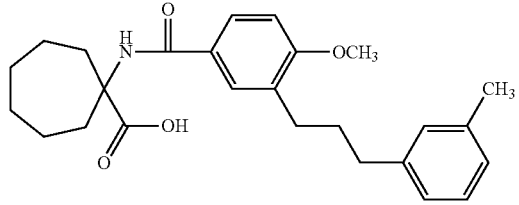

Step 1: 1-[3-(1,3-Dihydroxy-3-m-tolyl-propyl)-4-methoxy-benzoylamino]-cycloheptanecarboxylic acid methyl ester 3-Acetyl-4-methoxy-benzoic acid methyl ester (150 mg, 0.720 mmol) was dissolved in THF (3 ml), cooled to −78° C., and a freshly prepared solution of lithium diisopropylamide (obtained by addition of n-butyllithium in n-hexane (0.317 ml, 2.5 M solution) to diisopropylamine (80.1 mg, 0.792 mmol) in THF (3 ml) at 0° C. and stirring for 10 min) was slowly added with stirring. After 10 min, 3-methylbenzaldehyde (86.5 mg, 0.720 mmol) was added at −78° C. After 30 min at −78° C., 2 N hydrochloric acid and EA were added, the cooling bath was removed, the mixture was brought to room temperature. The phases were separated, the aqueous phase was extracted three times with EA, the combined organic phases were dried over sodium chloride, decanted and evaporated to dryness. The residue was dissolved in methanol (5 ml), sodium borohydride (28.7 mg, 0.761 mmol) was added, and the mixture was stirred at room temperature for 30 min. The mixture was evaporated to dryness and the residue was purified by silica gel chromatography (HEP/EA gradient) to give 140 mg of the title compound as a mixture of diastereomers.

LC/MS (Method LC13): Rt=1.32 min; m/z=353.1 [MNa⁺], 683.2 [2MNa⁺]

Step 2: 4-Methoxy-3-(3-m-tolyl-propyl)-benzoic acid methyl ester

The compound of step 1 (140 mg, 0.424 mmol) was dissolved in ethanol (10 ml), 12 N hydrochloric acid (0.2 ml) and palladium on charcoal (10%) was added, and the mixture was hydrogenated at a hydrogen pressure of 6 bar at room temperature overnight. After filtration and evaporation, the residue was purified by silica gel chromatography (HEP/EA gradient) to give 80 mg of the title compound.

¹H-NMR: δ=7.83 (dd, 1H); 7.72 (d, 1H); 7.16 (dd, 1H); 7.06 (d, 1H); 7.03-6.96 (m, 3H); 3.85 (s, 3H); 3.80 (s, 3H); 2.65-2.53 (m, 4H); 2.27 (s, 3H); 1.82 (m, 2H)

Step 3: 1-[4-Methoxy-3-(3-m-tolyl-propyl)-benzoylamino]-cycloheptanecarboxylic acid From the compound of step 2, the title compound was obtained by hydrolysis of the ester group in analogy to example 1 step 2, reaction of the obtained carboxylic acid with 1-amino-cycloheptanecarboxylic acid methyl ester hydrochloride in analogy to step 3 of example 1, and hydrolysis of the ester group in analogy to step 4 of example 1.

¹H-NMR: δ=11.95 (br s, 1H); 8.03 (s, 1H); 7.73 (dd, 1H); 7.64 (d, 1H); 7.14 (t, 1H); 7.03-6.95 (m, 4H); 3.83 (s, 3H); 2.63-2.55 (m, 4H); 2.27 (s, 3H); 2.12-2.03 (m, 4H); 1.83 (tt, 2H); 1.56-1.45 (m 8H)

EXAMPLE 73

1-[3-(2-Hydroxy-2-m-tolyl-ethoxy)-4-methoxy-benzoylamino]-cycloheptanecarboxylic acid

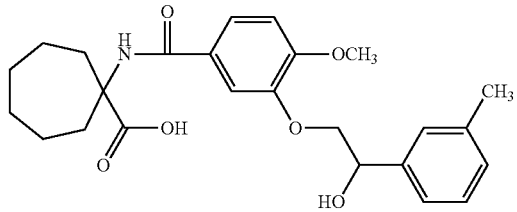 [SMILES: COc1ccc(C(=O)NC2(C(=O)O)CCCCCC2)cc1OCC(O)c1cccc(C)c1]

Step 1: 4-Methoxy-3-(2-oxo-2-m-tolyl-ethoxy)-benzoic acid methyl ester

3-Hydroxy-4-methoxybenzoic acid methyl ester (2.50 g, 13.7 mmol) was dissolved in methanol (20 ml), potassium carbonate (3.72 g, 27.4 mmol) and 2-bromo-1-m-tolyl-ethanone (2.92 g, 13.7 mmol) were added and the mixture was stirred overnight at room temperature. The volatiles were evaporated, the crude material was partitioned between EA and water, the aqueous phase was extracted with EA, the combined organic phases were dried over sodium sulfate and evaporated to dryness. The residue was purified by preparative RP HPLC (water/ACN gradient) to yield the title compound.

LC/MS (Method LC2): Rt=1.57 min; m/z=315.17 [MH⁺]

Step 2: 1-[4-Methoxy-3-(2-oxo-2-m-tolyl-ethoxy)-benzoylamino]-cycloheptanecarboxylic acid ethyl ester The compound of step 2 was hydrolyzed in analogy to step 2 of example 1, and the carboxylic acid intermediate was coupled to 1-amino-cycloheptanecarboxylic acid ethyl ester hydrochloride in analogy to step 1 of example 3 to yield the title compound.

LC/MS (Method LC2): Rt=1.74 min; m/z=468.23 [MH⁺]

Step 3: 1-[3-(2-Hydroxy-2-m-tolyl-ethoxy)-4-methoxy-benzoylamino]-cycloheptanecarboxylic acid The compound of step 2 was reduced with sodium borohydride in analogy to step 2 of example 53, the ester intermediate purified by RP HPLC (water/ACN gradient) and hydrolyzed in analogy to step 4 of example 1 to yield the title compound.

LC/MS (Method LC2): Rt=1.51 min; m/z=442.29 [MH+]

EXAMPLE 74

1-[4-Methoxy-3-(2-m-tolyl-ethoxy)-benzoylamino]-cyclohept-4-enecarboxylic acid

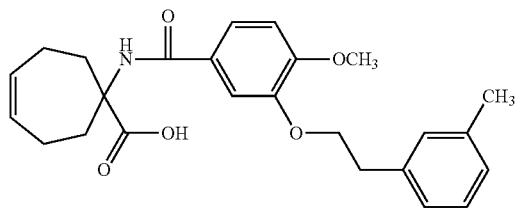

1-Amino-cyclohept-4-enecarboxylic acid methyl ester (K. Hammer et al., Tetrahedron 53 (1997), 2309-2322) was coupled to 4-methoxy-3-(2-m-tolyl-ethoxy)-benzoic acid analogy to step 1 of example 3. The ester intermediate was hydrolyzed in analogy to step 4 of example 1 to yield the title compound.

LC/MS (Method LC1): Rt=1.76 min; m/z=424.29 [MH+]

EXAMPLE 75

4-[4-Methyl-3-(2-m-tolyl-ethoxy)-benzoylamino]-bicyclo[5.1.0]octane-4-carboxylic acid

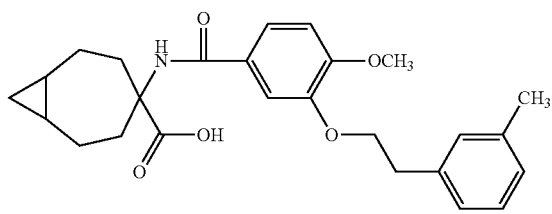 [SMILES: COc1ccc(C(=O)NC2(C(=O)O)CCC3CC3CC2)cc1OCCc1cccc(C)c1]

1-[4-Methoxy-3-(2-m-tolyl-ethoxy)-benzoylamino]-cyclohept-4-enecarboxylic acid methyl ester (0.418 g, 0.955 mmol) was dissolved in toluene (4.5 ml), diethylzinc (2.86 mmol, 1.5 M solution in toluene) was added and the mixture was warmed to 60° C. Diiodomethane (1.16 g, 4.30 mmol) was added dropwise and the mixture was stirred overnight at 60° C. The addition of diethyl zinc and diiodomethane was repeated until completion of the reaction. The mixture was partitioned between EA and 2 N hydrochloric acid, the aqueous phase extracted with EA, and the combined organic phases were dried over sodium sulfate and evaporated to dryness. The obtained ester was hydrolyzed in analogy to step 4 of example 1. The title compound was purified by preparative RP HPLC (water/ACN gradient).

LC/MS (Method LC4): Rt=1.32 min; m/z=438.35 [MH+]

EXAMPLE 76

1-[4-Methoxy-3-(2-m-tolyl-ethoxy)-benzoylamino]-3-methyl-cyclobutanecarboxylic acid

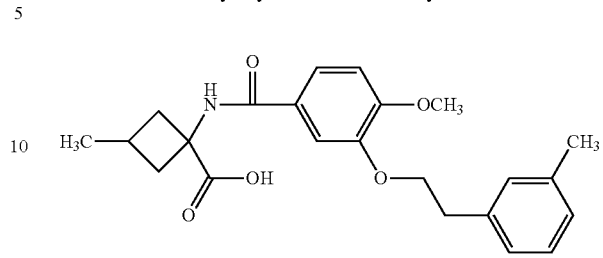

Step 1: 1-Amino-3-methyl-cyclobutanecarboxylic acid ethyl ester hydrochloride

3-Methyl-cyclobutane-1,1-dicarboxylic acid ethyl ester (V. Prelog et al., Helv. Chim. Acta 65 (1982), 2622-2644; 200 mg, 1.074 mmol) was suspended in acetone (20 ml) and stirred in an ice bath. Triethylamine (152 mg, 1.50 mmol) and isobutyl chloroformate (191 mg, 1.40 mmol) were added, the mixture was stirred at 0° C. for 30 min, then sodium azide (129 mg, 1.99 mmol) as solution in water (10 ml) was added, and stirring was continued for 15 min. Then diethyl ether (50 ml) was added, the phases were separated. The organic layer was washed with water, dried over sodium sulfate, filtered and added to refluxing toluene in a flask with distillation bridge. The toluene solution was refluxed for 4 h, the volatiles were evaporated in vacuo, the residue was dissolved in dioxane, 2 N hydrochloric acid was added in excess, and the mixture was stirred until the isocyanate was completely decomposed (approximately 20 min). The volatiles were evaporated and the obtained amino acid ester hydrochloride was used without further purification.

Step 2: 1-[4-Methoxy-3-(2-m-tolyl-ethoxy)-benzoylamino]-3-methyl-cyclobutanecarboxylic acid The compound of step 1 (65 mg, 0.413 mmol) was coupled to 4-methoxy-3-(2-m-tolyl-ethoxy)-benzoic acid in analogy to step 1 of example 3. The ester intermediate was hydrolyzed in analogy to step 4 of example 1 to yield the title compound as mixture of the cis isomer and the trans isomer.

$^1$H-NMR: δ=12.2 (s, 1H); 8.75/8.70 (2 s, 1H); 7.55-7.45 (m, 2H); 7.23-7.11 (m, 3H); 7.08-6.98 (m, 2H); 4.23-4.14 (m, 2H); 3.81 (2s, 3H); 3.02 (t, 2H); 2.73-2.68 (m, 1H); 2.55-2.25 (m, 5H, therein 2.29 (s, 3H)); 2.20-2.12 (m, 1H); 1.90-1.80 (m, 1H); 1.05 (d, 3H)

EXAMPLE 77

1-{[6-Methoxy-5-(2-m-tolyl-ethoxy)-pyridine-3-carbonyl]-amino}-cycloheptanecarboxylic acid

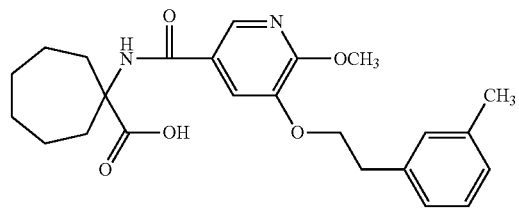

6-Chloro-5-nitro-nicotinic acid methyl ester was prepared according to the procedure described in WO 2005/021544 and transformed into 5-hydroxy-6-methoxy-nicotinic acid methyl ester according to the procedure described in WO 95/04045. The intermediate was transformed into the title compound by etherification with 2-m-tolyl-ethanol in analogy to step 1 of example 1, hydrolysis of the ester group in analogy to step 2 of example 1, reaction of the obtained carboxylic acid with 1-amino-cycloheptanecarboxylic acid methyl ester hydrochloride in analogy to step 3 of example 1 and hydrolysis in analogy to step 4 of example 1.

$^1$H-NMR: δ=12.0 (s, 1H); 8.21 (d, 1H); 8.20 (s, 1H); 7.63 (d, 1H); 7.23-7.17 (m, 2H); 7.12 (d, 1H); 7.03 (d, 1H); 4.23 (t, 2H); 3.91 (s, 3H); 3.02 (t, 2H); 2.29 (s, 3H); 2.13-2.00 (m, 4H); 1.55-1.45 (m, 8H)

EXAMPLE 78

1-{[6-Methoxy-5-(2-m-tolyl-ethoxy)-pyridine-3-carbonyl]-amino}-cyclooctanecarboxylic acid

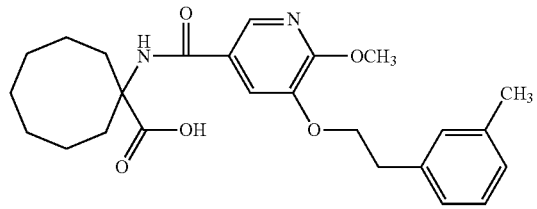 [SMILES: COc1ncc(C(=O)NC2(C(=O)O)CCCCCCC2)cc1OCCc1cccc(C)c1]

The title compound was synthesized in analogy to example 77 using 1-amino-cyclooctanecarboxylic acid methyl ester hydrochloride instead of 1-amino-cycloheptanecarboxylic acid methyl ester hydrochloride.

LC/MS (Method LC9): Rt=3.66 min; m/z=441.19 [MH$^+$]

EXAMPLE 79 cis-1-{[6-Methoxy-5-(2-m-tolyl-ethoxy)-pyridine-3-carbonyl]-amino}-4-methyl-cyclohexanecarboxylic acid

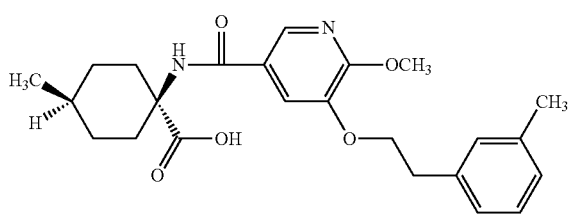 [SMILES: COc1ncc(C(=O)N[C@]2(C(=O)O)CC[C@@H](C)CC2)cc1OCCc1cccc(C)c1]

The title compound was synthesized in analogy to example 77 using cis-1-amino-4-methyl-cyclohexanecarboxylic acid methyl ester hydrochloride (prepared in analogy to example 25) instead of 1-amino-cycloheptanecarboxylic acid methyl ester hydrochloride.

$^1$H-NMR: δ=12.2 (s, 1H); 8.23 (s, 1H); 8.11 (s, 1H); 7.61 (s, 1H); 7.22-7.15 (m, 2H); 7.12 (d, 1H); 7.03 (d, 1H); 4.26 (t, 2H); 3.91 (s, 3H); 3.02 (t, 2H); 2.30-2.22 (m, 5H, therein 2.28 (s, 3H)); 1.70-1.61 (m, 2H); 1.54-1.48 (m, 2H); 1.42-1.32 (m, 1H); 1.25-1.12 (m, 2H); 0.88 (d, 3H)

EXAMPLE 80 trans-1-{[6-Methoxy-5-(2-m-tolyl-ethoxy)-pyridine-3-carbonyl]-amino}-4-methyl-cyclohexanecarboxylic acid

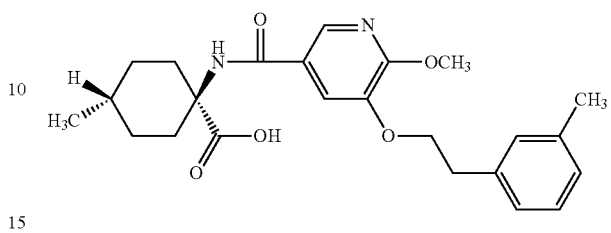

The title compound was synthesized in analogy to example 77 using trans-1-amino-1-cyclohexanecarbonitrile (step 1 of example 43) instead of 1-amino-cycloheptanecarboxylic acid methyl ester hydrochloride and hydrolysis of the carbonitrile in analogy to example 43, steps 2 and 3.

$^1$H-NMR: δ=12.1 (s, 1H); 8.22 (s, 1H); 8.20 (s, 1H); 7.62 (s, 1H); 7.22-7.15 (m, 2H); 7.12 (d, 1H); 7.05 (d, 1H); 4.22 (t, 2H); 3.91 (s, 3H); 3.04 (t, 2H); 2.31-2.24 (m, 5H, therein 2.28 (s, 3H)); 1.62-1.53 (m, 4H); 1.51-1.40 (m, 1H); 1.32-1.22 (m, 2H); 0.88 (d, 3H)

EXAMPLE 81 trans-1-({5-[2-(5-Chloro-2-fluoro-phenyl)-ethoxy]-6-methoxy-pyridine-3-carbonyl}-amino)-4-methyl-cyclohexanecarboxylic acid

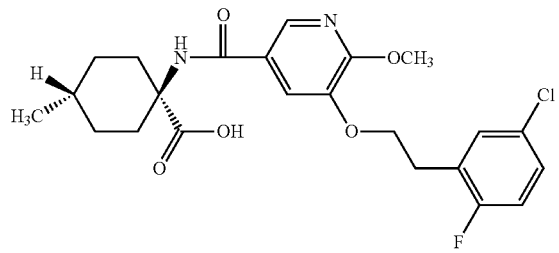 [SMILES: COc1ncc(C(=O)N[C@]2(C(=O)O)CC[C@@H](C)CC2)cc1OCCc1cc(Cl)ccc1F]

The title compound was synthesized in analogy to example 80 using 2-(5-chloro-2-fluoro-phenyl)-ethanol in the etherification step.

LC/MS (Method LC1): Rt=1.81 min; m/z=464.16 [MH$^+$]

EXAMPLE 82 trans-1-({5-[2-(2-Fluoro-5-trifluoromethoxy-phenyl)-ethoxy]-6-methoxy-pyridine-3-carbonyl}-amino)-4-methyl-cyclohexanecarboxylic acid

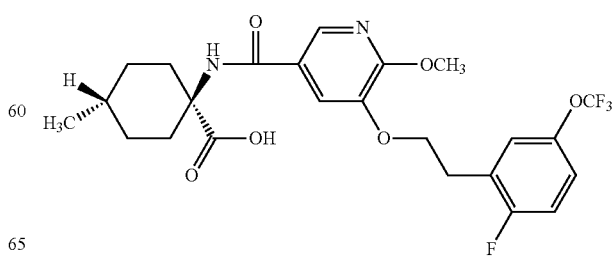

The title compound was synthesized in analogy to example 80 using 2-(2-fluoro-5-trifluoromethoxy-phenyl)-ethanol in the etherification step.
LC/MS (Method LC4): Rt=1.31 min; m/z=513.76 [MH⁺]

EXAMPLE 83 trans-1-{[6-Methoxy-5-(2-phenyl-ethoxy)-pyridine-3-carbonyl]-amino}-4-methyl-cyclohexanecarboxylic acid

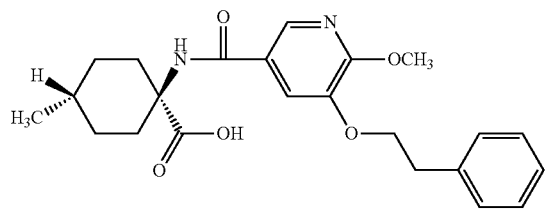 [SMILES: COc1ncc(C(=O)N[C@]2(C(=O)O)CC[C@@H](C)CC2)cc1OCCc1ccccc1]

The title compound was synthesized in analogy to example 80 using 2-phenyl-ethanol in the etherification step.
LC/MS (Method LC4): Rt=1.27 min; m/z=413.24 [MH⁺]

EXAMPLE 84 trans-1-({5-[2-(2,5-Dimethyl-phenyl)-ethoxy]-6-methoxy-pyridine-3-carbonyl}-amino)-4-methyl-cyclohexanecarboxylic acid

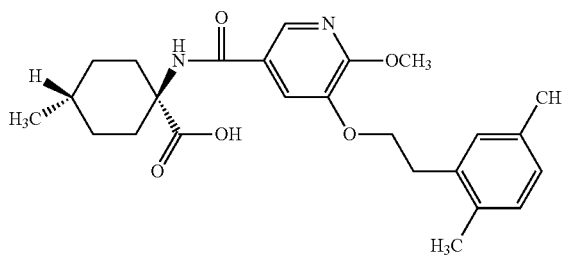 [SMILES: COc1ncc(C(=O)N[C@]2(C(=O)O)CC[C@@H](C)CC2)cc1OCCc1cc(C)ccc1C]

The title compound was synthesized in analogy to example 80 using 2-(2,5-dimethyl-phenyl)-ethanol in the etherification step.
LC/MS (Method LC4): Rt=1.34 min; m/z=441.26 [MH⁺]

EXAMPLE 85 trans-1-({5-[2-(3-chloro-phenyl)-ethoxy]-6-methoxy-pyridine-3-carbonyl}-amino)-4-methyl-cyclohexanecarboxylic acid

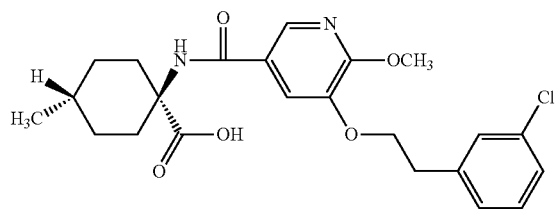 [SMILES: COc1ncc(C(=O)N[C@]2(C(=O)O)CC[C@@H](C)CC2)cc1OCCc1cccc(Cl)c1]

The title compound was synthesized in analogy to example 80 using 2-(3-chloro-phenyl)-ethanol in the etherification step.
LC/MS (Method LC4): Rt=1.31 min; m/z=447.18 [MH⁺]

EXAMPLE 86 cis-1-({5-[2-(2,5-Dimethyl-phenyl)-ethoxy]-6-methoxy-pyridine-3-carbonyl}-amino)-4-methyl-cyclohexanecarboxylic acid

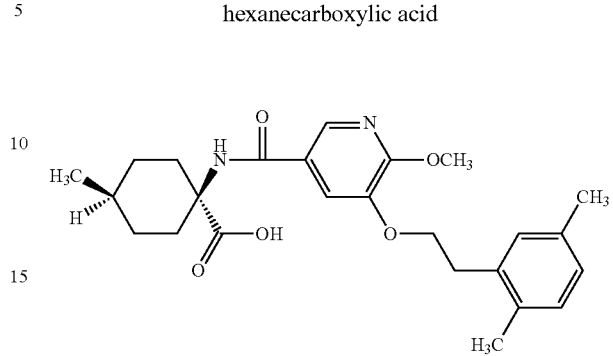

The title compound was synthesized in analogy to example 79 using 2-(2,5-dimethyl-phenyl)-ethanol in the etherification step.
LC/MS (Method LC4): Rt=1.34 min; m/z=441.3 [MH⁺]

EXAMPLE 87

1-({5-[2-(2,5-Dimethyl-phenyl)-ethoxy]-6-methoxy-pyridine-3-carbonyl}-amino)-cycloheptanecarboxylic acid

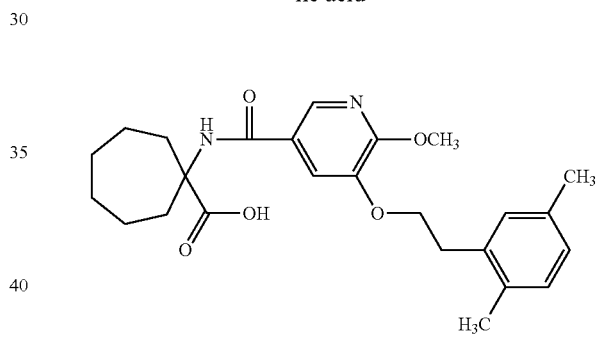

The title compound was synthesized in analogy to example 77 using 2-(2,5-dimethyl-phenyl)-ethanol in the etherification step.
LC/MS (Method LC4): Rt=1.33 min; m/z=439.29 [M−H⁺]

EXAMPLE 88

1-{[5-(2-Phenyl-ethoxy)-6-methoxy-pyridine-3-carbonyl]-amino}-cycloheptanecarboxylic acid

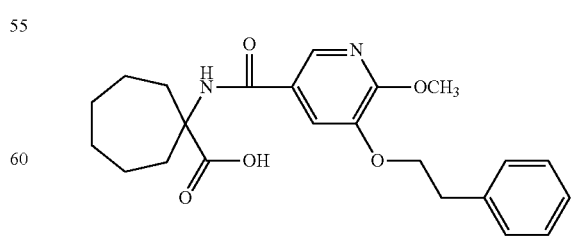

The title compound was synthesized in analogy to example 77 using 2-phenyl-ethanol in the etherification step.
LC/MS (Method LC4): Rt=1.26 min; m/z=413.3 [MH⁺]

EXAMPLE 89 trans-4-tert-Butyl-1-{[6-methoxy-5-(2-m-tolyl-ethoxy)-pyridine-3-carbonyl]-amino}-cyclohexanecarboxylic acid

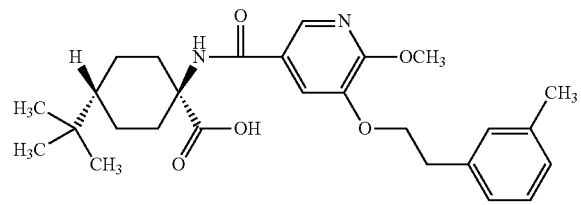 [SMILES: COc1ncc(C(=O)N[C@]2(C(=O)O)CC[C@@H](C(C)(C)C)CC2)cc1OCCc1cccc(C)c1]

The title compound was synthesized in analogy to example 80 using 1-amino-4-tert-butyl-cyclohexanecarbonitrile in the amide coupling step.

LC/MS (Method LC4): Rt=1.36 min; m/z=469.4 [MH$^+$]

EXAMPLE 90 trans-1-[(5-{2-[3-(2-Hydroxy-ethyl)-phenyl]-ethoxy}-6-methoxy-pyridine-3-carbonyl)-amino]-4-methyl-cyclohexanecarboxylic acid

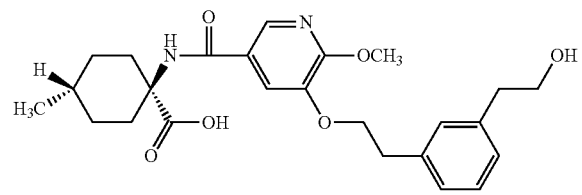 [SMILES: COc1ncc(C(=O)N[C@]2(C(=O)O)CC[C@@H](C)CC2)cc1OCCc1cccc(CCO)c1]

5-Hydroxy-6-methoxy-nicotinic acid methyl ester was etherified with 2-[3-(2-hydroxy-ethyl)-phenyl]-ethanol in analogy to step 1 of example 1. Hydrolysis of the ester group in analogy to step 2 of example 1, coupling of the obtained carboxylic acid to trans-1-amino-4-methyl-cyclohexanecarboxylic acid methyl ester hydrochloride in analogy to step 1 of example 3 and hydrolysis of the methyl ester in analogy to step 4 of example 1 yielded the title compound.

LC/MS (Method LC1): Rt=1.53 min; m/z=457.24 [MH$^+$]

EXAMPLE 91 cis-1-[(5-{2-[3-(2-Hydroxy-ethyl)-phenyl]-ethoxy}-6-methoxy-pyridine-3-carbonyl)-amino]-4-methyl-cyclohexanecarboxylic acid

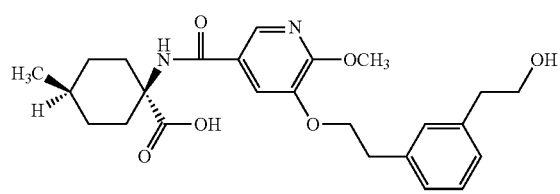 [SMILES: COc1ncc(C(=O)N[C@]2(C(=O)O)CC[C@H](C)CC2)cc1OCCc1cccc(CCO)c1]

The title compound was synthesized in analogy to example 90 using cis-1-amino-4-methyl-cyclohexanecarboxylic acid methyl ester hydrochloride instead of trans-1-amino-4-methyl-cyclohexanecarboxylic acid methyl ester hydrochloride.

LC/MS (Method LC4): Rt=1.16 min; m/z=457.37 [MH$^+$]

EXAMPLE 92

1-{[5-(3-Cyano-phenyl)-6-methoxy-pyridine-3-carbonyl]-amino}-cycloheptanecarboxylic acid

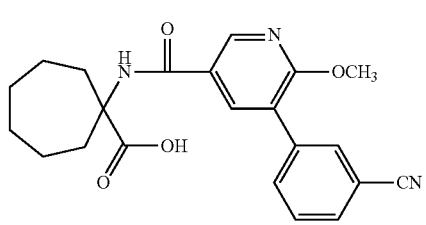 [SMILES: COc1ncc(C(=O)NC2(C(=O)O)CCCCCC2)cc1-c1cccc(C#N)c1]

Step 1: 5-Bromo-6-methoxy-nicotinic acid

5-Bromo-6-methoxy-nicotinic acid methyl ester (W. J. Thompson et al., J. Org. Chem. 49 (1984), 5237-5243; 2.00 g, 8.13 mmol) was dissolved in dioxane (40 ml), lithium hydroxide (40 ml of a 1 M solution in water) was added and subsequently sufficient methanol to achieve complete dissolution. The mixture was stirred at 60° C. for 2 h. The methanol was evaporated in vacuo and the remaining mixture was acidified with 2 N hydrochloric acid and extracted with EA. The combined extracts were dried over sodium sulfate, filtered and evaporated to dryness to yield the title compound.

$^1$H-NMR: δ=13.3 (s, 1H); 8.68 (d, 1H); 8.35 (d, 1H); 4.01 (s, 3H)

Step 2: 1-{[5-Bromo-6-methoxy-pyridine-3-carbonyl]-amino}-cycloheptanecarboxylic acid methyl ester The compound of step 1 (1.85 g, 7.97 mmol) was dissolved in thionyl chloride (6 ml) and stirred for 30 min at 60° C. The volatiles were evaporated in vacuo, the residue was dissolved in DCM and added to a stirred mixture of 1-amino-cycloheptanecarboxylic acid methyl ester hydrochloride, EA and saturated sodium hydrogencarbonate solution with ice cooling. The mixture was stirred at room temperature overnight, the phases were separated and the aqueous phase was extracted with EA. The combined organic phases were dried over sodium sulfate and evaporated to dryness to yield the title compound (2.80 g).

$^1$H-NMR: δ=8.62 (d, 1H); 8.52 (s, 1H); 8.48 (d, 1H); 3.99 (s, 3H); 3.57 (s, 3H); 2.15-2.01 (m, 4H); 1.65-1.43 (m, 8H)

Step 3: 1-{[5-(3-Cyano-phenyl)-6-methoxy-pyridine-3-carbonyl]-amino}-cycloheptanecarboxylic acid methyl ester The compound of step 2 (300 mg, 0.779 mmol), 3-cyanophenylboronic acid (171 mg, 1.17 mmol), tris(dibenzylideneacetone)dipalladium(0) (214 mg, 0.234 mmol), potassium fluoride (149 mg, 2.57 mmol) and tri-tert-butylphosphonium tetrafluoroborate (136 mg, 0.47 mmol) in a flask were thoroughly flushed with argon, dioxane (3 ml) was added and the mixture was stirred for 2 h at 50° C. The mixture was filtered over silica gel and evaporated to dryness. This residue was purified by RP HPLC (water/ACN gradient) to yield 200 mg of the title compound.

LC/MS (Method LC9): Rt=3.44 min; m/z=408.6 [MH$^+$]

Step 4: 1-{[5-(3-Cyano-phenyl)-6-methoxy-pyridine-3-carbonyl]-amino}-cycloheptanecarboxylic acid The compound of step 3 was hydrolyzed in analogy to step 4 of example 1 at a hydrolysis temperature of 40° C. The residue obtained after evaporation of the EA extracts was purified by RP HPLC (water/ACN gradient) to yield the title compound.

$^1$H-NMR: δ=12.1 (s, 1H); 8.68 (d, 1H); 8.32 (s, 1H); 8.24 (d, 1H); 8.09 (s, 1H); 7.96 (d, 1H); 7.88 (d, 1H); 7.69 (t, 1H); 3.95 (s, 3H); 2.15-2.04 (m, 4H); 1.60-1.45 (m, 8H)

In analogy to example 92, the example compounds of the formula I-4 listed in table 4 were prepared by using the respective substituted phenylboronic acid instead of 3-cyano-phenylboronic acid. The compounds of the formula I-4 listed in table 4 can be named as 1-[(5-R$^{104}$-6-methoxy-pyridine-3-carbonyl)-amino]-cycloheptanecarboxylic acid, for example as 1-{[5-(3-chloro-phenyl)-6-methoxy-pyridyl-3-carbonyl]-amino}-cycloheptanecarboxylic acid in the case of example 94.

I-4

TABLE 4

Example compounds of the formula I-4

| Example | R$^{104}$ | LC/MS Method | m/z | Retention time [min] |
|---|---|---|---|---|
| 93 | 3-dimethylamino-sulfonylamino-phenyl | LC9 | 491.17 [MH$^+$] | 2.99 |
| 94 | 3-chloro-phenyl | LC9 | 403.16 [MH$^+$] | 3.44 |
| 95 | 3-isopropyl-phenyl | LC5 | 409.22 [M − H]$^-$ | 5.04 |
| 96 | 3-trifluoromethoxy-phenyl | LC4 | 453.22 [MH$^+$] | 1.34 |
| 97 | 2,3-dichloro-phenyl | LC4 | 437.16 [MH$^+$] | 1.32 |
| 98 | 3,4,5-trifluoro-phenyl | LC4 | 423.2 [MH$^+$] | 1.33 |
| 99 | 3-chloro-5-tri-fluoromethyl-phenyl | LC4 | 471.2 [MH$^+$] | 1.39 |
| 100 | 3-trifluoromethyl-phenyl | LC4 | 437.23 [MH$^+$] | 1.34 |

EXAMPLE 101

1-{[5-(3-Chloro-4-methoxy-phenyl)-6-methoxy-pyridine-3-carbonyl]-amino}-cycloheptanecarboxylic acid

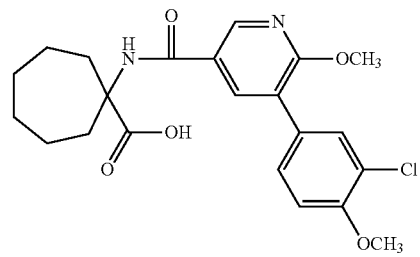 [SMILES: COc1ccc(-c2cc(C(=O)NC3(C(=O)O)CCCCCC3)cnc2OC)cc1Cl]

The compound can be prepared in analogy to example 92.

EXAMPLE 102

1-{[5-(2-Fluoro-3-trifluoromethyl-phenyl)-6-methoxy-pyridine-3-carbonyl]-amino}-cycloheptanecarboxylic acid

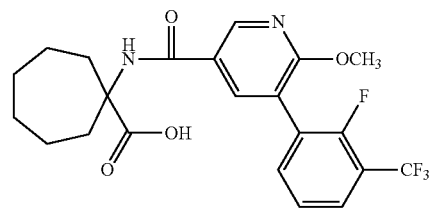 [SMILES: COc1ncc(C(=O)NC2(C(=O)O)CCCCCC2)cc1-c1cccc(C(F)(F)F)c1F]

The compound can be prepared in analogy to example 92.

In analogy to example 92, the example compounds of the formula I-5 listed in table 5 were prepared by synthesizing the intermediate 1-(3-bromo-4-methoxy-benzoylamino)-cycloheptanecarboxylic acid methyl ester in analogy to step 2 of example 92 using 3-bromo-4-methoxybenzoic acid instead of 5-bromo-6-methoxy-nicotinic acid. The intermediate was transformed into the example compounds in analogy to example 92, steps 3 and 4, using the appropriate phenylboronic acid. The compounds can be named as 1-[(substituted biphenyl-3-carbonyl)-amino]-cycloheptanecarboxylic acid, for example as 1-[(3'-cyano-6-methoxy-biphenyl-3-carbonyl)-amino]-cycloheptanecarboxylic acid in the case of example 104 in which the group R$^{105}$ is 3-chloro-phenyl and the group 3-(R$^{105}$)-4-methoxy-phenyl-C(O) depicted in formula I-5 thus is the group 3'-cyano-6-methoxy-biphenyl-3-carbonyl.

I-5

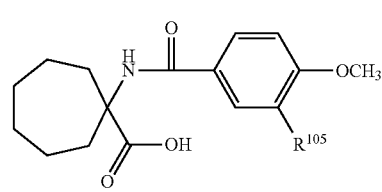

TABLE 5

Example compounds of the formula I-5

| Example | R[105] | LC/MS Method | m/z [MH+] | Retention time [min] |
|---|---|---|---|---|
| 103 | 3-dimethylaminosulfonylamino-phenyl | LC10 | 490.27 | 3.29 |
| 104 | 3-chloro-phenyl | LC9 | 402.14 | 3.49 |
| 105 | 3-isopropyl-phenyl | LC10 | 410.29 | 3.93 |
| 106 | 3-cyano-phenyl | LC9 | 393.17 | 3.28 |

EXAMPLE 107

1-(3-{2-[3-(2-Hydroxy-ethyl)-phenyl]-ethoxy}-4-methoxy-benzoylamino)-cycloheptanecarboxylic acid

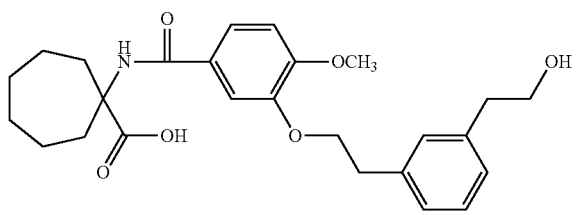 [SMILES: COc1ccc(C(=O)NC2(C(=O)O)CCCCCC2)cc1OCCc1cccc(CCO)c1]

Step 1: 3-{2-[3-(2-Hydroxy-ethyl)-phenyl]-ethoxy}-4-methoxy-benzoic acid

2-[3-(2-Hydroxy-ethyl)-phenyl]-ethanol and 3-hydroxy-4-methoxybenzoic acid methyl ester were coupled in analogy to step 1 of example 1 and the methyl ester was hydrolyzed in analogy to step 2 of example 1 to yield the title compound.
LC/MS (Method LC9): Rt=2.69 min; m/z=317.18 [MH+]

Step 2: 1-(3-{2-[3-(2-Hydroxy-ethyl)-phenyl]-ethoxy}-4-methoxy-benzoylamino)-cycloheptanecarboxylic acid methyl ester The compound of step 1 (280 mg, 0.885 mmol) was dissolved in DMF (1.3 ml) and HOBT (24 mg), 1-amino-cycloheptanecarboxylic acid methyl ester hydrochloride (221 mg, 1.06 mmol) and EDIA (578 mg, 4.43 mmol) were added. The mixture was cooled in an ice bath and EDC (254 mg, 1.33 mmol) was added. The mixture was stirred at room temperature for 3 days and partitioned between EA and water. The aqueous phase was extracted with EA, the combined organic phases were dried over sodium sulfate and evaporated to dryness. The residue was purified by RP HPLC (water/ACN gradient) to yield the title compound (120 mg).
LC/MS (Method LC9): Rt=3.29 min; m/z=470.25 [MH+]

Step 3: 1-(3-{2-[3-(2-Hydroxy-ethyl)-phenyl]-ethoxy}-4-methoxy-benzoylamino)-cycloheptanecarboxylic acid The compound of step 2 was hydrolyzed in analogy to step 4 of example 1 to yield the title compound (89 mg).
$^1$H-NMR: δ=12.0 (s, 1H); 8.07 (s, 1H); 7.50 (dd, 1H); 7.40 (s, 1H); 7.23-7.18 (m, 2H); 7.15 (d, 1H); 7.06 (d, 1H); 7.01 (d, 1H); 4.61 (t, 1H); 4.21 (t, 2H); 3.80 (s, 3H); 3.59 (dt, 2H); 3.02 (t, 2H); 2.70 (t, 2H); 2.12-2.02 (m, 4H); 1.57-1.42 (m, 8H)

EXAMPLE 108

1-(3-{2-[3-(2-Hydroxy-ethyl)-phenyl]-ethoxy}-4-methoxy-benzoylamino)-cyclooctanecarboxylic acid

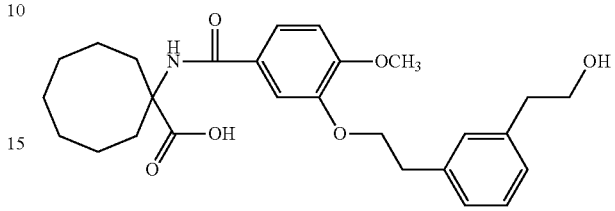

The title compound was synthesized in analogy to example 107 using 1-amino-cyclooctanecarboxylic acid methyl ester hydrochloride instead of 1-amino-cycloheptanecarboxylic acid methyl ester hydrochloride.
LC/MS (Method LC9): Rt=3.21 min; m/z=470.25 [MH+]

EXAMPLE 109 cis-1-(3-{2-[3-(2-Hydroxy-ethyl)-phenyl]-ethoxy}-4-methoxy-benzoylamino)-4-methyl-cyclohexanecarboxylic acid

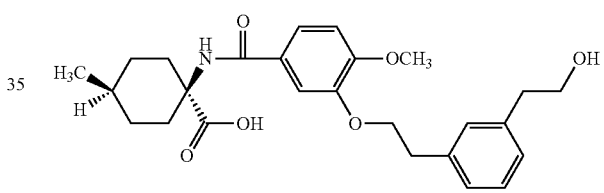

The title compound was synthesized in analogy to example 107 using cis-1-amino-4-methyl-cyclohexanecarboxylic acid methyl ester hydrochloride instead of 1-amino-cycloheptanecarboxylic acid methyl ester hydrochloride.
LC/MS (Method LC4): Rt=1.21 min; m/z=456.34 [MH+]

EXAMPLE 110 trans-1-(3-{2-[3-(2-Hydroxy-ethyl)-phenyl]-ethoxy}-4-methoxy-benzoylamino)-4-methyl-cyclohexanecarboxylic acid

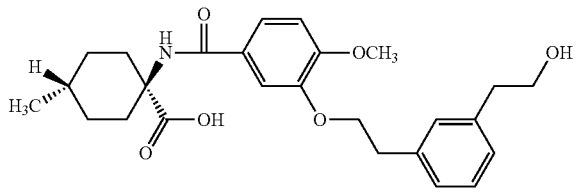

The title compound was synthesized in analogy to example 107 using trans-1-amino-4-methyl-cyclohexanecarboxylic acid methyl ester hydrochloride instead of 1-amino-cycloheptanecarboxylic acid methyl ester hydrochloride.
LC/MS (Method LC4): Rt=1.21 min; m/z=456.33 [MH+]

EXAMPLE 111 cis-4-Ethyl-1-(3-{2-[3-(2-hydroxy-ethyl)-phenyl]-ethoxy}-4-methoxy-benzoylamino)-cyclohexanecarboxylic acid

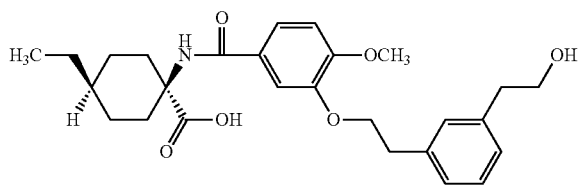 [SMILES: CC[C@H]1CC[C@](NC(=O)c2ccc(OC)c(OCCc3cccc(CCO)c3)c2)(C(=O)O)CC1]

The title compound was synthesized in analogy to example 107 using cis-1-amino-4-ethyl-cyclohexanecarboxylic acid methyl ester hydrochloride instead of 1-amino-cycloheptanecarboxylic acid methyl ester hydrochloride.

LC/MS (Method LC4): Rt=1.25 min; m/z=470.36 [MH$^+$]

EXAMPLE 112 trans-4-Ethyl-1-(3-{2-[3-(2-hydroxy-ethyl)-phenyl]-ethoxy}-4-methoxy-benzoylamino)-cyclohexanecarboxylic acid

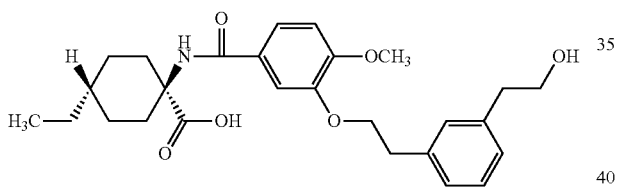

The title compound was synthesized in analogy to example 107 using trans-1-amino-4-ethyl-cyclohexanecarboxylic acid methyl ester hydrochloride instead of 1-amino-cycloheptanecarboxylic acid methyl ester hydrochloride.

LC/MS (Method LC3): Rt=4.30 min; m/z=470.36 [MH$^+$]

EXAMPLE 113 cis-1-[3-[2-(3-Chloro-phenyl)-ethoxy]-4-(2-methoxy-ethoxy)-benzoylamio]-4-methyl-cyclohexanecarboxylic acid

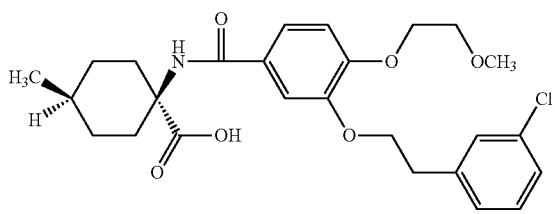

Step 1: 3-Acetoxy-4-hydroxy-benzoic acid ethyl ester 3,4-Dihydroxy-benzoic acid ethyl ester (550 mg, 3.02 mmol) was dissolved in DMF (5 ml), potassium tert-butylate (210 mg, 2.87 mmol) was added and the mixture stirred for 10 min. Acetic anhydride (339 mg, 3.32 mmol) was added and stirring continued for 10 min. The mixture was partitioned between EA and 2 N hydrochloric acid, the aqueous phase extracted with EA, the combined organic phases were dried over sodium chloride, decanted and evaporated to dryness. The residue was purified by RP HPLC (water/ACN gradient) to yield the title compound.

$^1$H-NMR: δ=10.6 (s, 1H); 7.71 (dd, 1H); 7.58 (d, 1H); 7.00 (d, 1H); 4.25 (q, 2H); 2.27 (s, 3H); 1.29 (t, 3H)

Step 2: 3-Acetoxy-4-benzyloxy-benzoic acid ethyl ester

The compound of step 1 (20 g, 89.2 mmol) was dissolved in DMF (100 ml) and cooled in an ice bath. Potassium carbonate (18.4 g, 134 mmol) and, immediately thereafter, benzyl bromide (15.2 g, 89.2 mmol) were added. This mixture was stirred for 30 min at room temperature, poured on a mixture of 2 N hydrochloric acid and diethyl ether, filtered and washed repeatedly with diethyl ether. The combined ethereal phases were washed with water, dried over sodium chloride, decanted and evaporated to dryness. The residue was purified by silica gel chromatography (HEP/EA gradient) to yield the title compound (21 g).

$^1$H-NMR: δ=7.82 (dd, 1H); 7.67 (d, 1H); 7.43-7.37 (m, 5H); 7.30 (d, 1H); 5.24 (s, 2H); 4.27 (q, 2H); 2.26 (s, 3H); 1.30 (t, 3H)

Step 3: 4-Benzyloxy-3-hydroxy-benzoic acid ethyl ester

The compound of step 2 (10 g, 31.8 mmol) was dissolved in methanol, potassium carbonate (88 mg, 0.636 mmol) was added and the mixture was stirred for 2 h under reflux. The solution was evaporated to dryness and the residue used without further purification.

$^1$H-NMR: δ=9.7 (br s, 1H); 7.48 (d, 2H); 7.42-7.30 (m, 5H); 7.06 (d, 1H); 5.19 (s, 2H); 4.22 (q, 2H); 1.28 (t, 3H)

Step 4: 4-Benzyloxy-3-[2-(3-chloro-phenyl)-ethoxy]-benzoic acid ethyl ester

The compound of step 3 was coupled to 2-(3-chloro-phenyl)-ethanol in analogy to step 1 of example 1 to yield the title compound.

$^1$H-NMR: δ=7.57 (dd, 1H); 7.49-7.24 (m, 10H); 7.17 (d, 1H); 5.17 (s, 2H), 4.31-4.21 (m. 4H); 3.06 (t, 2H); 1.29 (t, 3H)

Step 5: 4-Benzyloxy-3-[2-(3-chloro-phenyl)-ethoxy]-benzoic acid

The compound of step 4 was hydrolyzed in analogy to step 2 of example 1 to yield the title compound.

$^1$H-NMR: δ=12.7 (s, 1H); 7.53 (dd, 1H); 7.48-7.26 (m, 9H); 7.12 (d, 1H); 5.17 (s, 2H); 4.26 (t, 2H); 3.07 (t, 2H)

Step 6: cis-1-{4-Benzyloxy-3-[2-(3-chloro-phenyl)-ethoxy]-benzoylamino}-4-methyl-cyclohexanecarboxylic acid methyl ester The compound of step 5 was coupled to cis-1-amino-4-methyl-cyclohexanecarboxylic acid methyl ester hydrochloride in analogy to step 2 of example 64 to yield the title compound.

¹H-NMR: δ=8.12 (s, 1H); 7.49-7.25 (m, 11H); 7.08 (d, 1H); 5.12 (s, 2H); 4.28 (t, 2H); 3.55 (s, 3H); 3.08 (t, 2H); 2.22 (d, 2H); 1.69-1.59 (m, 2H); 1.53-1.44 (m, 2H); 1.41-1.30 (m, 1H); 1.24-1.12 (m, 2H); 0.87 (d, 3H)

Step 7: cis-1-{3-[2-(3-Chloro-phenyl)-ethoxy]-4-hydroxy-benzoylamino}-4-methyl-cyclohexanecarboxylic acid methyl ester The compound of step 6 (410 mg, 0.765 mmol) was dissolved in methanol (3 ml), cooled in an acetone/dry ice bath, and acetyl chloride (2.7 ml, 38.2 mmol) was added with stirring. This mixture was stirred for 72 h at room temperature and evaporated to dryness.

¹H-NMR: δ=9.58 (s, 1H); 8.01 (s, 1H); 7.49-7.27 (m, 6H); 6.82 (d, 1H); 4.22 (t, 2H); 3.55 (s, 3H); 3.08 (t, 2H); 2.26-2.19 (m, 2H); 1.68-1.59 (m, 2H); 1.52-1.48 (m, 2H); 1.42-1.32 (m, 1H); 1.23-1.12 (m, 2H); 0.85 (d, 3H)

Step 8: cis-1-[3-[2-(3-Chloro-phenyl)-ethoxy]-4-(2-methoxy-ethoxy)-benzoylamino]-4-methyl-cyclohexanecarboxylic acid methyl ester The compound of step 7 (150 mg, 0.337 mmol) was dissolved in DMF (7 ml), and potassium carbonate (233 mg, 1.68 mmol) and 2-bromoethyl methyl ether (70 mg, 0.51 mmol) were added subsequently. The mixture was stirred for 48 h and then partitioned between water and EA. The aqueous phase was extracted with EA, the combined organic phases were dried over sodium sulfate and evaporated to dryness to yield the title compound (145 mg).

¹H-NMR: δ=8.11 (s, 1H); 7.48-7.26 (m, 6H); 7.02 (d, 1H); 4.29-4.20 (m, 2H); 4.13 (t, 2H); 3.69 (t, 2H); 3.56 (s, 3H); 3.30 (s, 3H); 3.08 (t, 2H); 2.27-2.20 (m, 2H); 1.69-1.61 (m, 2H); 1.53-1.49 (m, 2H); 1.42-1.33 (m, 1H); 1.25-1.15 (m, 2H); 0.88 (d, 3H)

Step 9: cis-1-[3-[2-(3-Chloro-phenyl)-ethoxy]-4-(2-methoxy-ethoxy)-benzoylamio]-4-methyl-cyclohexanecarboxylic acid The compound of step 8 was hydrolyzed on analogy to step 4 of example 1.

¹H-NMR: δ=12.1 (br s, 1H); 7.98 (s, 1H); 7.49-7.38 (m, 3H); 7.37-7.21 (m, 3H); 7.02 (d, 1H); 4.23 (t, 2H); 4.11 (t, 2H); 3.68 (t, 2H); 3.32 (s, 3H); 3.08 (t, 2H); 2.28 (d, 2H); 1.68-1.59 (m, 2H); 1.51 (d, 2H); 1.42-1.32 (m, 1H); 1.24-1.12 (m, 2H); 0.86 (d, 3H)

In analogy to example 113, the compounds of examples 114 and 115 were synthesized using the respective amino acid methyl ester hydrochloride in the amide coupling step 6.

EXAMPLE 114 trans-1-[3-[2-(3-Chloro-phenyl)-ethoxy]-4-(2-methoxy-ethoxy)-benzoylamino]-4-methyl-cyclohexanecarboxylic acid

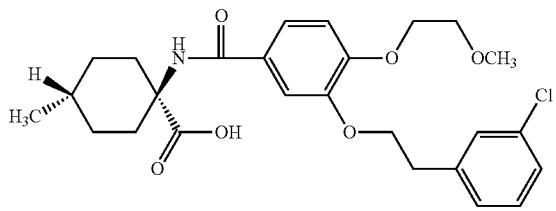 [SMILES: COCCOc1ccc(C(=O)N[C@]2(C(=O)O)CC[C@@H](C)CC2)cc1OCCc1cccc(Cl)c1]

¹H-NMR: δ=12.0 (s, 1H); 8.09 (s, 1H); 7.48-7.38 (m, 3H); 7.36-7.24 (m, 3H); 7.01 (d, 1H); 4.21 (t, 2H); 4.11 (dd, 2H); 3.68 (dd, 2H); 3.32 (s, 3H); 3.07 (t, 2H); 2.30-2.22 (m, 2H); 1.65-1.51 (m, 4H); 1.50-1.38 (m, 1H); 1.32-1.19 (m, 2H); 0.89 (d, 3H)

EXAMPLE 115

1-[3-[2-(3-Chloro-phenyl)-ethoxy]-4-(2-methoxy-ethoxy)-benzoylamino]-cycloheptanecarboxylic acid

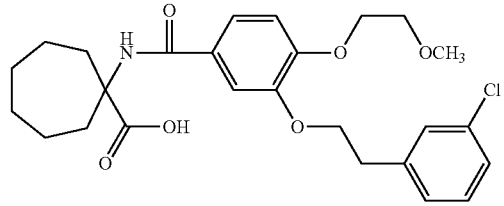 [SMILES: COCCOc1ccc(C(=O)NC2(C(=O)O)CCCCCC2)cc1OCCc1cccc(Cl)c1]

¹H-NMR: δ=11.98 (s, 1H); 8.07 (s, 1H); 7.50-7.42 (m, 2H); 7.41 (s, 1H); 7.38-7.25 (m, 3H); 7.01 (d, 1H); 4.22 (t, 2H); 4.11 (dd, 2H); 3.69 (dd, 2H); 3.30 (s, 3H); 3.07 (t, 2H); 2.12-2.02 (m, 4H); 1.60-1-42 (m, 8H)

In analogy to example 113, the compounds of examples 116 to 118 were synthesized using the respective alcohol in the etherification step 4 and the respective amino acid methyl ester hydrochloride in the amide coupling step 6. In step 7, cleavage of the benzyl ether was accomplished by dissolution of the starting material in methanol, addition of palladium on charcoal (10%), hydrogenation under 1 bar hydrogen pressure for 1 h, filtration and evaporation to dryness.

EXAMPLE 116

1-[4-(2-Methoxy-ethoxy)-3-(2-m-tolyl-ethoxy)-benzoylamino]-cycloheptanecarboxylic acid

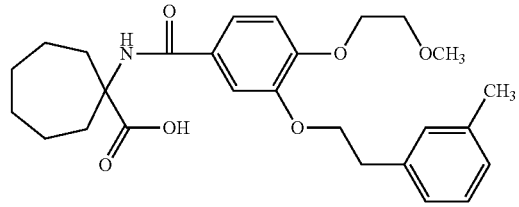

¹H-NMR: δ=11.9 (s, 1H); 8.07 (s, 1H); 7.46 (dd, 1H); 7.41 (s, 1H); 7.19-7.11 (m, 3H); 7.02 (t, 2H); 4.19 (t, 2H); 4.11 (t,

2H); 3.68 (t, 2H); 3.31 (s, 3H); 3.00 (t, 2H); 2.29 (s, 3H); 2.10-2.00 (m, 4H); 1.58-1.42 (m, 8H)

EXAMPLE 117 trans-1-[4-(2-Methoxy-ethoxy)-3-(2-m-tolyl-ethoxy)-benzoylamino]-4-methyl-cyclohexane-carboxylic acid

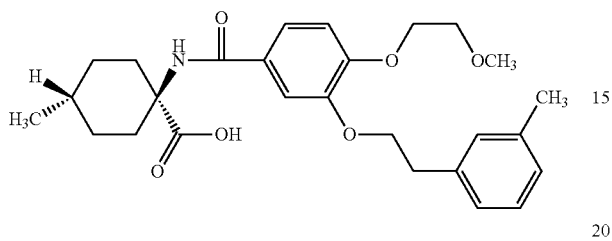

$^1$H-NMR: δ=12.00 (s, 1H); 8.08 (s, 1H); 7.44 (dd, 1H); 7.40 (d, 1H); 7.20-7.11 (m, 3H); 7.01 (d, 1H); 6.99 (d, 1H); 4.20 (t, 2H); 4.11 (ddd, 2H); 3.68 (ddd, 2H); 3.30 (s, 3H); 3.00 (t, 2H); 2.30 (s, 3H); 2.30-2.23 (m, 2H); 1.62-1.52 (m, 4H); 1.50-1.41 (m, 1H); 1.31-1.20 (m, 2H); 0.89 (d, 3H)

EXAMPLE 118 cis-1-[4-(2-Methoxy-ethoxy)-3-(2-m-tolyl-ethoxy)-benzoylamino]-4-methyl-cyclohexane-carboxylic acid

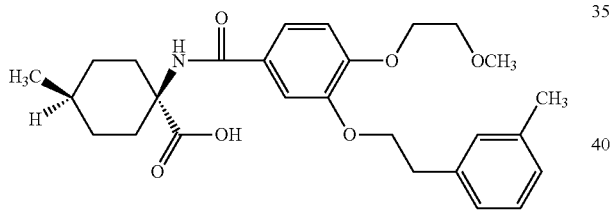

$^1$H-NMR: δ=12.1 (s, 1H); 7.99 (s, 1H); 7.46 (dd, 1H); 7.41 (s, 1H); 7.20-7.11 (m, 3H); 7.02 (d, 2H); 4.21 (t, 2H); 4.11 (ddd, 2H); 3.68 (ddd, 2H); 3.30 (s, 3H); 3.01 (t, 2H); 2.29 (s, 3H); 2.27-2.22 (m, 2H); 1.69-1.59 (m, 2H); 1.53-1.47 (m, 2H); 1.42-1.31 (m, 1H); 1.22-1.12 (m, 2H); 0.87 (d, 3H)

EXAMPLE 119 cis-1-[3-[2-(3-Chloro-phenyl)-ethoxy]-4-(2-hydroxy-ethoxy)-benzoylamino]-4-methyl-cyclohexanecarboxylic acid

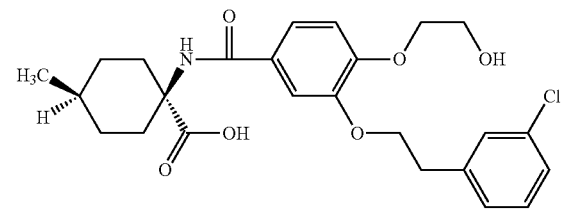 [SMILES: C[C@H]1CC[C@](NC(=O)c2ccc(OCCO)c(OCCc3cccc(Cl)c3)c2)(C(=O)O)CC1]

The title compound of step 7 of example 113 (150 mg, 0.337 mmol) was reacted in analogy to step 8 of example 113 using 2-bromoethyl acetate as alkylating agent, followed by hydrolysis in analogy to step 4 of example 1 to yield the title compound. $^1$H-NMR: δ=12.1 (s, 1H); 7.97 (s, 1H); 7.51-7.27 (m, 6H); 7.03 (d, 1H); 4.85 (t, 1H); 4.25 (t, 2H); 4.07-3.99 (m, 2H); 3.78-3.70 (m, 2H); 3.08 (t, 2H); 2.28 (d, 2H); 1.70-1.57 (m, 2H); 1.53-1.42 (m, 2H); 1.42-1.31 (m, 1H); 1.23-1.11 (m, 2H); 0.88 (d, 3H)

In analogy to example 119, the compounds of examples 120 and 121 were synthesized using the respective amino acid methyl ester hydrochloride in the amide coupling step.

EXAMPLE 120 trans-1-[3-[2-(3-Chloro-phenyl)-ethoxy]-4-(2-hydroxy-ethoxy)-benzoylamino]-4-methyl-cyclohexanecarboxylic acid

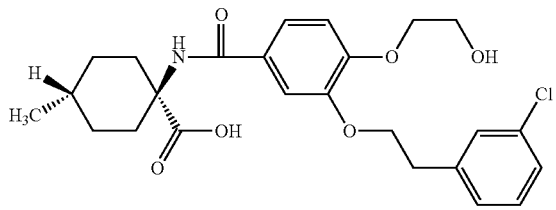

$^1$H-NMR: δ=12.0 (s, 1H); 8.08 (s, 1H); 7.49-7.26 (m, 6H); 7.02 (d, 1H); 4.82 (t, 1H); 4.22 (t, 2H); 4.02 (t, 2H); 3.80-3.70 (m, 2H); 3.08 (t, 2H); 2.29 (d, 2H); 1.63-1.40 (m, 4H); 1.32-1.18 (m, 3H); 0.88 (d, 3H)

EXAMPLE 121

1-[3-[2-(3-Chloro-phenyl)-ethoxy]-4-(2-hydroxy-ethoxy)-benzoylamino]-cycloheptane-carboxylic acid

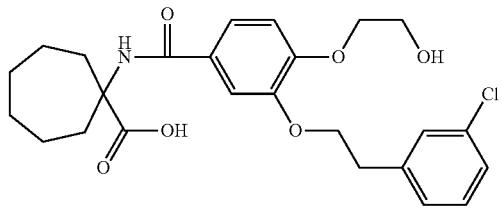

$^1$H-NMR: δ=12.0 (s, 1H); 8.08 (s, 1H); 7.50-7.25 (m, 6H); 7.02 (d, 1H); 4.82 (t, 1H); 4.22 (t, 2H); 4.01 (t, 2H); 3.78-3.70 (m, 2H); 3.09 (t, 2H); 2.12-2.02 (m, 4H); 1.58-1.42 (m, 8H)

In analogy to example 119, the compounds of examples 122 to 124 were synthesized using 2-m-tolyl-ethanol in the ether coupling step 4 of example 113 and the respective amino acid methyl ester hydrochloride in the amide coupling step 6. In step 7, cleavage of the benzyl ether was accomplished by dissolution of the starting material in methanol, addition of palladium on charcoal (10%), hydrogenation under 1 bar hydrogen pressure for 1 h, filtration and evaporation to dryness.

EXAMPLE 122 trans-1-[4-(2-Hydroxy-ethoxy)-3-(2-m-tolyl-ethoxy)-benzoylamino]-4-methyl-cyclohexanecarboxylic acid

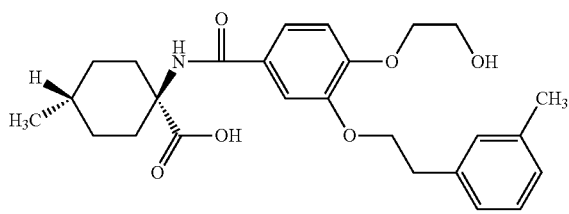 [SMILES: Cc1cccc(CCOc2cc(C(=O)N[C@]3(C(=O)O)CC[C@@H](C)CC3)ccc2OCCO)c1]

¹H-NMR: δ=12.0 (s, 1H); 8.08 (s, 1H); 7.46-7.38 (m, 2H); 7.20-7.11 (m, 3H); 7.03-6.99 (m, 2H); 4.84 (t, 1H); 4.19 (t, 2H); 4.01 (t, 2H); 3.72 (dt, 2H); 3.00 (t, 2H); 2.30 (s, 3H); 2.29-2.21 (m, 2H); 1.61-1.51 (m, 4H); 1.51-1.39 (m, 1H); 1.30-1.18 (m, 2H); 0.88 (d, 3H)

EXAMPLE 123 cis-1-[4-(2-Hydroxy-ethoxy)-3-(2-m-tolyl-ethoxy)-benzoylamino]-4-methyl-cyclohexanecarboxylic acid

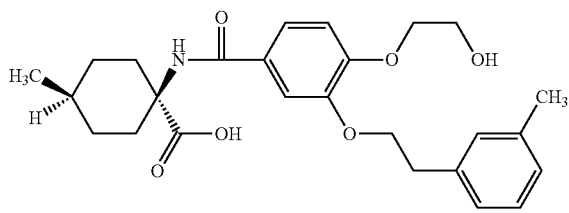

¹H-NMR: δ=12.1 (s, 1H); 7.97 (s, 1H); 7.48 (dd, 1H); 7.39 (d, 1H); 7.19-7.11 (m, 3H); 7.02 (d, 2H); 4.82 (t, 1H); 4.21 (t, 2H); 4.02 (t, 2H); 3.72 (dt, 2H); 3.01 (t, 2H); 2.29 (s, 3H); 2.29-2.22 (m, 2H); 1.68-1.59 (m, 2H); 1.51-1.44 (m, 2H); 1.41-1.31 (m, 1H); 1.21-1.11 (m, 2H); 0.88 (d, 3H)

EXAMPLE 124

1-[4-(2-Hydroxy-ethoxy)-3-(2-m-tolyl-ethoxy)-benzoylamino]-cycloheptane-carboxylic acid

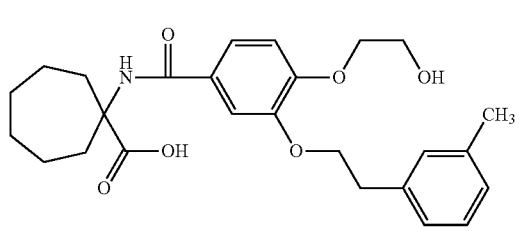 [SMILES: Cc1cccc(CCOc2cc(C(=O)NC3(C(=O)O)CCCCCC3)ccc2OCCO)c1]

¹H-NMR: δ=12.0 (s, 1H); 8.08 (s, 1H); 7.47 (dd, 1H); 7.60 (d, 1H); 7.21-7.12 (m, 3H); 7.05-7.00 (m, 2H); 4.82 (t, 1H); 4.20 (t, 1H); 4.01 (t, 2H); 3.72 (dt, 2H); 2.99 (t, 2H); 2.29 (s, 3H); 2.11-2.00 (m, 4H); 1.57-1.42 (m, 8H)

EXAMPLE 125 cis-1-[(3'-Chloro-4'-methoxy-6-trifluoromethyl-biphenyl-3-carbonyl)-amino]-4-ethyl-cyclohexanecarboxylic acid

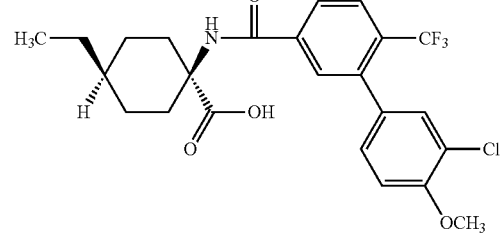

Step 1: 3'-Chloro-4'-methoxy-6-trifluoromethyl-biphenyl-3-carboxylic acid

3-Bromo-4-trifluoromethyl-benzoic acid (0.484 g, 1.80 mmol), 3-chloro-4-methoxyphenylboronic acid (0.503 g, 2.70 mmol), tri-tert-butylphosphonium tetrafluoroborate (0.313 g, 1.08 mmol), tris(dibenzylideneacetone)dipalladium (0) (0.494 g, 0.54 mmol) and potassium fluoride (0.345 g, 5.93 mmol) were weighed into a flask and dioxane (10 ml) was added under argon, and the mixture was stirred for 24 h at 50° C. The mixture was filtered over celite and evaporated to dryness. The residue was purified by preparative RP HPLC (water/ACN gradient) to yield the title compound.

Step 2: cis-1-[(3'-Chloro-4'-methoxy-6-trifluoromethyl-biphenyl-3-carbonyl)-amino]-4-ethyl-cyclohexanecarboxylic acid The compound of step 1 was coupled with cis-1-amino-4-ethyl-cyclohexanecarboxylic acid methyl ester hydrochloride in analogy to step 1 of example 3 and hydrolyzed in analogy to step 4 of example 1 to yield the title compound.

LC/MS (Method LC4): Rt=1.39 min; m/z=484.31 [MH⁺]

EXAMPLE 126

(1R,2S,4S)-2-[4-Methoxy-3-(2-m-tolyl-ethoxy)-benzoylamino]-7-oxa-bicyclo[2.2.1]heptane-2-carboxylic acid and (1S,2R,4R)-2-[4-methoxy-3-(2-m-tolyl-ethoxy)-benzoylamino]-7-oxa-bicyclo[2.2.1]heptane-2-carboxylic acid

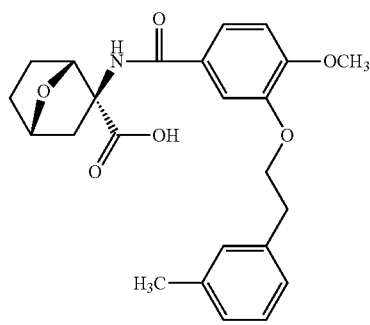

and

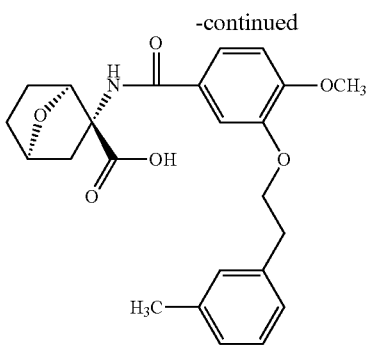

Step 1: Spiro[imidazolidine-2,4-dione-5,2'-7-oxabicyclo[2.2.1]heptane]

27.6 g of ammonium carbonate were dissolved in 200 ml of water and 200 ml of ethanol. 12.4 g of 7-oxa-bicyclo[2.2.1]heptan-2-one (A. Warm et al., Helv. Chim. Acta 70 (1987), 690-700) were added and the mixture was stirred at 50° C. for 4 h. Then a solution of 7.2 g of potassium cyanide in 55 ml of water and 55 ml of ethanol was added and the mixture stirred at 50° C. for 16 h. Afterwards the mixture was concentrated to a volume of about 100 ml, 3 g of sodium chloride were added and the mixture was stirred at room temperature for 2 h. The precipitate was filtered off, washed with water and dried to yield 10.4 g of the title compound as a racemic mixture.

Step 2: 2-Amino-7-oxa-bicyclo[2.2.1]heptane-2-carboxylic acid 9.0 g of spiro[imidazolidine-2,4-dione-5,2'-7-oxabicyclo[2.2.1]heptane] and 77.9 g of barium hydroxide octahydrate were dissolved in 135 ml of water, divided into 9 portions and treated under microwave irradiation at 190° C. for 30 min. The pooled mixture were diluted with 300 ml of water, heated to 90° C. and the precipitate was filtered off by suction. Then 4.5 g of ammonium carbonate were added to the filtrate and the mixture was heated to 90° C. 50 g of solid carbon dioxide were then added and the mixture was stirred at 90° C. for 10 min. The precipitated barium carbonate was filtered off by suction. Then another 50 g of solid carbon dioxide were added to the filtrate and the mixture was stirred at 50° C. for 1 h. The precipitated barium carbonate was filtered off by suction. The filtrate was evaporated in vacuo to yield 6.3 g of the title compound as a racemic mixture.

Step 3: 2-Amino-7-oxa-bicyclo[2.2.1]heptane-2-carboxylic acid methyl ester 3.0 g of 2-amino-7-oxa-bicyclo[2.2.1]heptane-2-carboxylic acid were suspended in 100 ml of methanol and 11.4 g of thionyl chloride were added at room temperature. The mixture was left at room temperature for 24 h. Then the volatiles were evaporated in vacuo to yield 3.9 g of the title compound as a racemic mixture.

LC/MS (Method LC6): Rt=0.53 min; m/z=172.21 [MH$^+$]

Step 4: 2-[4-Methoxy-3-(2-m-tolyl-ethoxy)-benzoylamino]-7-oxa-bicyclo[2.2.1]heptane-2-carboxylic acid methyl ester)

550 mg of O-(7-azabenzotriazol-1-yl)-1,1,3,3-tetramethyluronium hexafluorophosphate (HATU), 300 mg of 2-amino-7-oxa-bicyclo[2.2.1]heptane-2-carboxylic acid methyl ester and 410 mg of 4-methoxy-3-(2-m-tolyl-ethoxy)-benzoic acid (example 2) were stirred in 20 ml of anhydrous DMF for 15 h at room temperature. The mixture was diluted with 150 ml of EA and washed three times with 50 ml each of a saturated aqueous sodium carbonate solution and then three times with 50 ml each of a 10% aqueous sodium hydrogensulfate solution. The organic layer was dried with magnesium sulfate, evaporated to dryness and the residue purified by silica gel chromatography (HEP/EA gradient) to yield 630 mg of the title compound as a racemic mixture.

LC/MS (Method LC4): Rt=1.22 min; m/z=440.34 [MH$^+$]

Step 5: (1R,2S,4S)-2-[4-Methoxy-3-(2-m-tolyl-ethoxy)-benzoylamino]-7-oxa-bicyclo[2.2.1]heptane-2-carboxylic acid and (1S,2R,4R)-2-[4-methoxy-3-(2-m-tolyl-ethoxy)-benzoylamino]-7-oxa-bicyclo[2.2.1]heptane-2-carboxylic acid 630 mg of 2-[4-methoxy-3-(2-m-tolyl-ethoxy)-benzoylamino]-7-oxa-bicyclo[2.2.1]heptane-2-carboxylic acid methyl ester was dissolved in 10 ml of methanol, and 2.2 ml of a 1 N solution of sodium hydroxide in water were added at room temperature. The mixture was stirred at 40° C. for 5 h, then another 1.1 ml of a 1 N solution of sodium hydroxide in water were added and the mixture stirred at 40° C. for another 4 h. The mixture was then diluted with 40 ml of water, the methanol was evaporated, the pH adjusted to 2 and the mixture stirred at room temperature of 1 h. The precipitated product was filtered off and dried in vacuo to yield 400 mg of 2-[4-methoxy-3-(2-m-tolyl-ethoxy)-benzoylamino]-7-oxa-bicyclo[2.2.1]heptane-2-carboxylic acid as a racemic mixture of (1R,2S,4S)-2-[4-methoxy-3-(2-m-tolyl-ethoxy)-benzoylamino]-7-oxa-bicyclo[2.2.1]heptane-2-carboxylic acid and (1S,2R,4R)-2-[4-methoxy-3-(2-m-tolyl-ethoxy)-benzoylamino]-7-oxa-bicyclo[2.2.1]heptane-2-carboxylic acid.

LC/MS (Method LC3): Rt=4.00 min; m/z=426.18 [MH$^+$]

EXAMPLE 127 cis-4-Ethyl-1-{4-methoxy-3-[2-(3-oxetan-3-yl-phenyl)-ethoxy]-benzoylamino}-cyclohexanecarboxylic acid

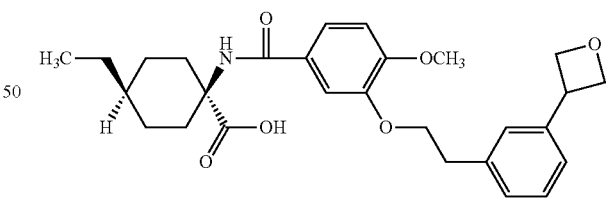

Step 1: 3-[2-(tert-Butyl-dimethyl-silanyloxy)-ethyl]-phenylboronic acid 50.0 g of [2-(3-bromo-phenyl)-ethoxy]-tert-butyl-dimethyl-silane were dissolved in 500 ml of anhydrous THF. 64.6 ml of a 2.7 M solution of n-butyllithium in n-heptane were added dropwise at −70° C. The mixture was stirred for 1 h at −70° C. Then 40.2 ml of triisopropyl borate were added dropwise at −70° C. Stirring was continued for 30 min at −70° C. and the mixture allowed to warm up to −20° C. 500 ml of water were added and the mixture was extracted three time with 500 ml each of DCM. The combined organic layers were dried with magnesium sulfate and evaporated to yield 43.6 g of the title compound.

LC/MS (Method LC4): Rt=1.32 min; m/z=325.13 [M−H+HCOOH]⁻

Step 2: tert-Butyl-dimethyl-[2-(3-oxetan-3-yl-phenyl)-ethoxy]-silane 4.6 g of 3-[2-(tert-butyl-dimethyl-silanyloxy)-ethyl]-phenylboronic acid, 130 mg of nickel iodide, 5.0 g of sodium bis(trimethylsilyl)amide and 62 mg of (1R,2R)-2-aminocyclohexanol were placed in a microwave vial and 3.5 ml of isopropanol were added. The mixture was stirred for 10 min at room temperature. Then a solution of 3-iodooxetane in 1.5 ml of isopropanol was added and the mixture treated under microwave irradiation at 80° C. for 30 min. The obtained mixture was combined with the mixtures obtained in three further runs of the synthesis, poured into 50 ml of a saturated aqueous sodium hydrogencarbonate solution and extracted three time with 50 ml each of EA. The combined organic layers were dried with magnesium sulfate and evaporated to yield 9.0 g of the title compound.

Step 3: 2-(3-Oxetan-3-yl-phenyl)-ethanol 9.0 g of tert-butyl-dimethyl-[2-(3-oxetan-3-yl-phenyl)-ethoxy]-silane and 92.3 ml of a 1 N solution of tetra-n-butylammonium fluoride were dissolved in 200 ml of anhydrous THF. The mixture was stirred for 3 h at room temperature. Then the mixture was poured into 200 ml of a saturated aqueous solution of sodium hydrogencarbonate and extracted three times with 500 ml each of EA The combined organic layers were dried with magnesium sulfate and evaporated. The residue was purified by silica gel chromatography (HEP/EA gradient) to yield 4.9 g of the title compound.

Step 4: Toluene-4-sulfonic acid 2-(3-oxetan-3-yl-phenyl)-ethyl ester 4.9 g of 2-(3-oxetan-3-yl-phenyl)-ethanol were dissolved in 30 ml of DCM and 9.5 ml of pyridine were added at room temperature. The mixture was cooled to 0° C. and 6.3 g of p-toluenesulfonyl chloride were added at 0° C. Stirring was continued for 6 h at room temperature. Then the volatiles were evaporated, the residue was dissolved in 100 ml of EA and washed with 100 ml of a saturated aqueous solution of sodium hydrogencarbonate. The aqueous layer was extracted two times with 100 ml each of EA. The combined organic layers were dried with magnesium sulfate and evaporated. Silica gel chromatography (EA/HEP 1:1) of the residue yielded 2.0 g of the title compound.

LC/MS (Method LC4): Rt=1.26 min; m/z=333.16 [MH]⁺

Step 5: 3-Acetoxy-4-methoxy-benzoic acid 17.0 g of 3-hydroxy-4-methoxy-benzoic acid and 51.6 g of acetic anhydride were combined and stirred at 140° C. for 3 h. Then 50 ml of water were added at 100° C., the mixture was heated under reflux for 30 min, another 200 ml of water were added and the mixture heated under reflux for 30 min. The mixture was cooled to 0° C., and the product was filtered off, washed with water and dried in vacuo to yield 18.8 g of the title compound.

LC/MS (Method LC4): Rt=0.93 min; m/z=209.14 [M−H]⁻

Step 6: Acetic acid 5-chlorocarbonyl-2-methoxy-phenyl ester 700 mg of 3-acetoxy-4-methoxy-benzoic acid were suspended in 6 ml of anhydrous DCM and 24 μl of DMF were added. Then 5.0 ml of a 2 M solution of oxalyl chloride in DCM were added dropwise. The mixture was stirred until the evolution of gas had ceased (about 30 min). The volatiles were removed in vacuo, the residue was dissolved in 10 ml of DCM and evaporated to yield 750 mg of the title compound which was used in the subsequent step without further purification.

Step 7: cis-1-(3-Acetoxy-4-methoxy-benzoylamino)-4-ethyl-cyclohexanecarboxylic acid methyl ester 100 mg of 1-amino-4-ethyl-cyclohexanecarboxylic acid methyl ester (prepared in analogy to example 25) were dissolved in 5 ml of EA and 10 ml of a saturated aqueous solution of sodium hydrogencarbonate were added. A solution of 103 mg of acetic acid 5-chlorocarbonyl-2-methoxy-phenyl ester in 3 ml of DCM was added dropwise at 0° C. over a period of 5 min. Stirring was continued for 1 h at room temperature. The phases were allowed to separate. The aqueous layer was extracted two times with 15 ml each of EA. The combined organic layers were dried with magnesium sulfate and evaporated to yield 109 mg of the title compound.

Step 8: cis-4-Ethyl-1-(3-hydroxy-4-methoxy-benzoylamino)-cyclohexanecarboxylic acid methyl ester 109 mg of 1-(3-acetoxy-4-methoxy-benzoylamino)-4-ethyl-cyclohexanecarboxylic acid methyl ester were dissolved in 5 ml of methanol and 8.0 mg of potassium carbonate were added. The mixture was stirred at room temperature for 1 h, then poured into 10 ml of 1 N hydrochloric acid and extracted three times with 10 ml of EA. The combined organic layers were washed two times with 10 ml each of a saturated aqueous solution of sodium hydrogencarbonate, once with 10 ml of 1 N hydrochloric acid and once with 10 ml of a saturated aqueous solution of sodium chloride. The organic layer was dried with magnesium sulfate and evaporated. Silica gel chromatography (EA/HEP 1:1) of the residue yielded 18 mg of the title compound.

LC/MS (Method LC4): Rt=1.21 min; m/z=336.22 [MH⁺]

Step 9: cis-4-Ethyl-1-{4-methoxy-3-[2-(3-oxetan-3-yl-phenyl)-ethoxy]-benzoylamino}-cyclohexanecarboxylic acid methyl ester 17.8 mg of toluene-4-sulfonic acid 2-(3-oxetan-3-yl-phenyl)-ethyl ester, 18.0 mg of 4-ethyl-1-(3-hydroxy-4-methoxy-benzoylamino)-cyclohexanecarboxylic acid methyl ester and 22.3 mg of potassium carbonate were stirred in 1 ml of DMF for 6 h at 40° C. Then 9.0 mg of toluene-4-sulfonic acid 2-(3-oxetan-3-yl-phenyl)-ethyl ester were added and the mixture was stirred for 5 h at 40° C. The reaction mixture was then diluted with 10 ml of EA and washed with 10 ml of a saturated aqueous solution of sodium chloride. The aqueous layer was extracted two times with 10 ml of EA. The combined organic layers were dried with magnesium sulfate, and evaporated. Silica gel chromatography (EA/HEP, 1:1) of the residue yielded 20 mg of the title compound.

LC/MS (Method LC4): Rt=1.34 min; m/z=496.29 [MH⁺]

Step 10: cis-4-Ethyl-1-{4-methoxy-3-[2-(3-oxetan-3-yl-phenyl)-ethoxy]-benzoylamino}-cyclohexanecarboxylic acid 20 mg of 4-ethyl-1-{4-methoxy-3-[2-(3-oxetan-3-yl-phenyl)-ethoxy]-benzoylamino}-cyclohexanecarboxylic acid methyl ester were dissolved in 1 ml of methanol and 48 µl of a 1 M aqueous solution of sodium hydroxide were added. The mixture was stirred for 7 h at 60° C. and then poured into 10 ml of water. The pH was adjusted to 5 with a 5% aqueous solution of sodium hydrogensulfate. The mixture was extracted three time with 15 ml each of EA. The combined organic layers were dried with magnesium sulfate and evaporated to yield 14 mg of the title compound.

LC/MS (Method LC4): Rt=1.28 min; m/z=480.38 [M−H]⁻

EXAMPLE 128 trans-1-{4-Methoxy-3-[2-(3-oxetan-3-yl-phenyl)-ethoxy]-benzoylamino}-4-methyl-cyclohexanecarboxylic acid

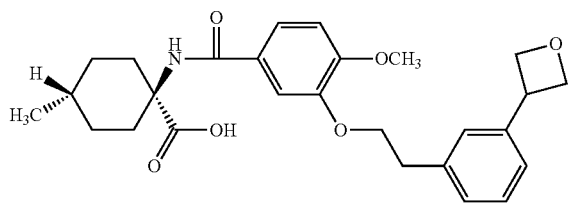 [SMILES: COc1ccc(C(=O)N[C@]2(C(=O)O)CC[C@@H](C)CC2)cc1OCCc1cccc(C2COC2)c1]

The title compound was synthesized in analogy to example 127.

LC/MS (Method LC4): Rt=1.24 min; m/z=466.2 [M−H]⁻

EXAMPLE 129

1-{4-Methoxy-3-[2-(3-oxetan-3-yl-phenyl)-ethoxy]-benzoylamino}-cycloheptanecarboxylic acid

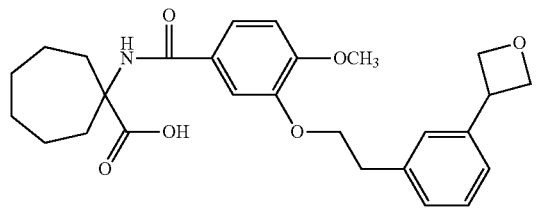 [SMILES: COc1ccc(C(=O)NC2(C(=O)O)CCCCCC2)cc1OCCc1cccc(C2COC2)c1]

The title compound was synthesized in analogy to example 127.

LC/MS (Method LC4): Rt=1.23 min; m/z=466.37 [M−H]⁻

EXAMPLE 130 cis-4-Ethyl-1-[4-oxetan-3-yl-3-(2-m-tolyl-ethoxy)-benzoylamino]-cyclohexanecarboxylic acid

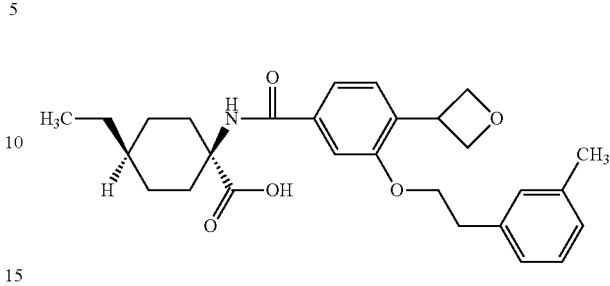

Step 1: 4-Iodo-3-(2-m-tolyl-ethoxy)-benzoic acid methyl ester 10.0 g of 3-hydroxy-4-iodo-benzoic acid methyl ester, 7.2 g of 1-(2-bromo-ethyl)-3-methyl-benzene and 10.0 g of potassium carbonate were stirred in 100 ml of anhydrous DMF for 28 h at 80° C. The solvent was evaporated and the residue dissolved in 200 ml of water and 400 ml of EA. The organic layer was separated, washed with 200 ml of water, dried with magnesium sulfate and evaporated. Silica gel chromatography (EA/HEP gradient) of the residue yielded 4.66 g of the title compound.

Step 2: 4-Borono-3-(2-m-tolyl-ethoxy)-benzoic acid methyl ester 2.3 g of bis(2-dimethylaminoethyl)ether were dissolved in 50 ml of anhydrous THF and 7.1 ml of a 2 M solution of isopropylmagnesium chloride added at 15° C. The mixture was stirred for 20 min at 15° C. Then a solution of 4.7 g of 4-iodo-3-(2-m-tolyl-ethoxy)-benzoic acid methyl ester in 20 ml of anhydrous THF was added at room temperature. The mixture was stirred for 10 min at 20° C., and then 2.4 g of trimethyl borate were added dropwise at 0° C. and the mixture stirred for 20 min at 0° C. 100 ml of 0.1 N hydrochloric acid were added, and the mixture was extracted three times with 100 ml of EA. The combined organic layers were washed with 100 ml of water, dried with magnesium sulfate and evaporated. Silica gel chromatography (EA/HEP 1:5) of the residue yielded 2.1 g of the title compound.

TLC (silica gel, EA/HEP 1:5): Rf=0.16

Step 3: 4-Oxetan-3-yl-3-(2-m-tolyl-ethoxy)-benzoic acid isopropyl ester 2.0 g of 4-borono-3-(2-m-tolyl-ethoxy)-benzoic acid methyl ester, 51 mg of nickel iodide, 2.0 g of sodium bis(trimethylsilyl)amide and 25 mg of trans-2-aminocyclohexanol hydrochloride were placed into a microwave vial and 10 ml of anhydrous 2-propanol added. The mixture was stirred for 10 min. Then a solution of 1.0 g of 3-iodo-oxetane in 3 ml of anhydrous 2-propanol was added and the mixture reacted for 40 min at 80° C. under microwave irradiation. The mixture was then poured into 150 ml of EA and washed three times with 30 ml each of a saturated aqueous sodium hydrogensulfate solution and three times with 30 ml each of a saturated aqueous sodium carbonate solution. The organic layer was dried with magnesium sulfate and evaporated. Silica gel chromatography (EA/HEP 1:5) of the residue yielded 120 mg of the title compound.

TLC (silica gel, EA/HEP 1:5): Rf=0.20

Step 4: 4-Oxetan-3-yl-3-(2-m-tolyl-ethoxy)-benzoic acid 120 mg of 4-oxetan-3-yl-3-(2-m-tolyl-ethoxy)-benzoic acid isopropyl ester were dissolved in 3 ml of methanol and 0.2 ml of a 2 N aqueous solution of sodium hydroxide added. The mixture was left at room temperature for 6 days and then evaporated. The residue was dissolved in 10 ml of water, the pH adjusted to 2 with an aqueous sodium hydrogensulfate solution, and the mixture extracted three times using 20 ml each of DCM. The combined extracts were dried with magnesium sulfate and evaporated to yield 105 mg of the title compound.

Step 5: cis-4-Ethyl-1-[4-oxetan-3-yl-3-(2-m-tolyl-ethoxy)-benzoylamino]-cyclohexanecarboxylic acid cis-4-Ethyl-1-[4-oxetan-3-yl-3-(2-m-tolyl-ethoxy)-benzoylamino]-cyclohexanecarboxylic acid methyl ester was synthesized from 4-oxetan-3-yl-3-(2-m-tolyl-ethoxy)-benzoic acid and cis-1-amino-4-ethyl-cyclohexanecarboxylic acid methyl ester hydrochloride in analogy to example 126, step 4, and the ester hydrolyzed to the title compound in analogy to example 126, step 5.
LC/MS (Method LC4): Rt=1.36 min; m/z=466.33 [MH⁺]

EXAMPLE 131 cis-1-[4-Oxetan-3-yl-3-(2-m-tolyl-ethoxy)-benzoylamino]-4-trifluoromethyl-cyclohexanecarboxylic acid

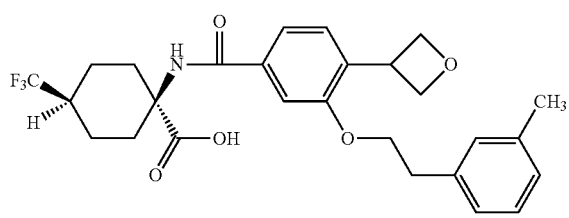 [SMILES: Cc1cccc(CCOc2cc(C(=O)N[C@]3(C(=O)O)CC[C@H](C(F)(F)F)CC3)ccc2C2COC2)c1]

The title compound was synthesized in analogy to example 130.
LC/MS (Method LC4): Rt=1.31 min; m/z=504.44 [M–H]⁻

EXAMPLE 132

1-{[7-(2-m-Tolyl-ethoxy)-benzo[1,3]dioxole-5-carbonyl]-amino}-cycloheptanecarboxylic acid

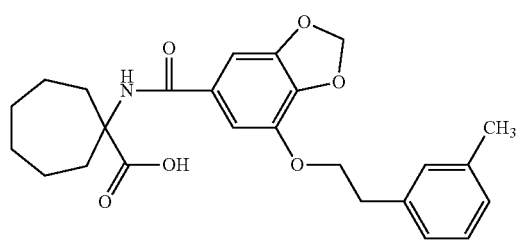 [SMILES: Cc1cccc(CCOc2cc(C(=O)NC3(C(=O)O)CCCCCC3)cc3c2OCO3)c1]

Step 1: 7-(2-m-Tolyl-ethoxy)-benzo[1,3]dioxole-5-carboxylic acid 2-m-tolyl-ethyl ester 2.5 g of 7-hydroxy-benzo[1,3]dioxole-5-carboxylic acid, 6.8 g of 1-(2-bromo-ethyl)-3-methyl-benzene and 7.6 g of potassium carbonate were stirred in 100 ml of anhydrous DMF for 10 h at 80° C. Then another 1.4 g of 1-(2-bromo-ethyl)-3-methyl-benzene and 1.5 g of potassium carbonate were added and the mixture was stirred for 5 h at 90° C. The solvent was removed in vacuo and the residue dissolved in 200 ml of water and 200 ml of EA. The organic layer was separated, washed with 100 ml of a saturated aqueous sodium carbonate solution, dried with magnesium sulfate and evaporated to yield 4.5 g of the title compound.

Step 2: 7-(2-m-Tolyl-ethoxy)-benzo[1,3]dioxole-5-carboxylic acid 4.5 g of 7-(2-m-tolyl-ethoxy)-benzo[1,3]dioxole-5-carboxylic acid 2-m-tolyl-ethyl ester and 650 mg of sodium hydroxide were dissolved in 50 ml of methanol, 50 ml of THF and 5 ml of water. The mixture was kept at room temperature for 20 h, then stirred at 50° C. for 5 h and evaporated. The residue was dissolved in 300 ml of a 0.1 M aqueous solution of sodium hydroxide and washed three times with 50 ml each of diisopropyl ether. The pH was adjusted to 2 with sodium hydrogensulfate and the mixture stirred for 30 min at room temperature. The product was collected by filtration, washed and dried in vacuo to yield 3.1 g of the title compound.
LC/MS (Method LC4): Rt=1.23 min; m/z=299.16 [M–H]⁻

Step 3: 1-{[7-(2-m-Tolyl-ethoxy)-benzo[1,3]dioxole-5-carbonyl]-amino}-cycloheptanecarboxylic acid methyl ester The title compound was synthesized from 7-(2-m-tolyl-ethoxy)-benzo[1,3]dioxole-5-carboxylic acid and 1-amino-cycloheptanecarboxylic acid methyl ester hydrochloride in analogy to example 126, step 4.
LC/MS (Method LC4): Rt=1.4 min; m/z=454.31 [MH⁺]

Step 4: 1-{[7-(2-m-Tolyl-ethoxy)-benzo[1,3]dioxole-5-carbonyl]-amino}-cycloheptanecarboxylic acid The title compound was synthesized from 1-{[7-(2-m-Tolyl-ethoxy)-benzo[1,3]dioxole-5-carbonyl]-amino}-cycloheptanecarboxylic acid methyl ester in analogy to example 126, step 5.
LC/MS (Method LC4): Rt=1.33 min; m/z=440.24 [MH⁺]

EXAMPLE 133 cis-1-{[7-(2-m-Tolyl-ethoxy)-benzo[1,3]dioxole-5-carbonyl]-amino}-4-trifluoromethyl-cyclohexanecarboxylic acid

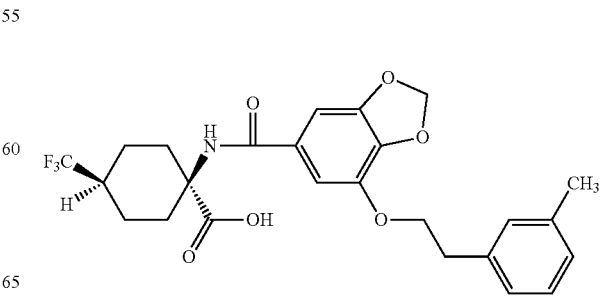

The title compound was synthesized in analogy to example 132.

LC/MS (Method LC4): Rt=1.33 min; m/z=494.25 [MH+]

EXAMPLE 134 cis-4-Ethyl-1-{[7-(2-m-tolyl-ethoxy)-benzo[1,3]dioxole-5-carbonyl]-amino}-cyclohexanecarboxylic acid

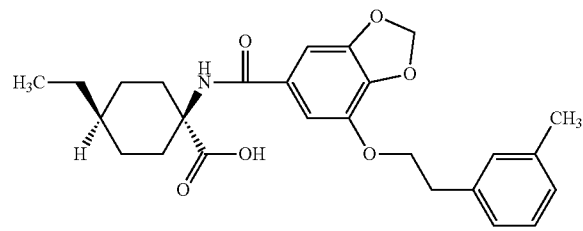 [SMILES: CC[C@H]1CC[C@](NC(=O)c2cc(OCCc3cccc(C)c3)c3c(c2)OCO3)(C(=O)O)CC1]

The title compound was synthesized in analogy to example 132.

LC/MS (Method LC4): Rt=1.37 min; m/z=454.29 [MH+]

In analogy to example 3, the example compounds of the formula I-6 listed in table 6 were prepared. The compounds can be named as cis-1-[3-($R^{106}$-oxy)-4-methoxy-benzoylamino]-4-methyl-cyclohexane-1-carboxylic acid, for example as cis-1-{3-[2-(4-methoxy-phenyl)-ethoxy]-4-methoxy-benzoylamino}-4-methyl-cyclohexane-1-carboxylic acid in the case of example 135.

I-6

![I-6 structure]

TABLE 6

Example compounds of the formula I-6

| Example | $R^{106}$ | LC/MS Method | m/z [MH+] | Retention time [min] |
|---|---|---|---|---|
| 135 | 2-(4-methoxy-phenyl)-ethyl | LC4 | 442.32 | 1.29 |
| 136 | 2-cyclohexyl-ethyl | LC4 | 418.35 | 1.39 |
| 137 | 2-(3-trifluoromethyl-phenyl)-ethyl | LC4 | 480.3 | 1.34 |
| 138 | 2-(thiophen-2-yl)-ethyl | LC4 | 418.26 | 1.28 |
| 139 | 2-(3-fluoro-phenyl)-ethyl | LC4 | 430.29 | 1.3 |
| 140 | 2-(3,4-dimethoxy-phenyl)-ethyl | LC4 | 472.34 | 1.25 |
| 141 | 2-(4-chloro-phenyl)-ethyl | LC4 | 446.27 | 1.34 |
| 142 | 2-(4-tert-butyl-phenyl)-ethyl | LC4 | 468.37 | 1.4 |
| 143 | 2-phenyl-propyl | LC4 | 426.3 | 1.33 |
| 144 | 2-(2-trifluoromethyl-phenyl)-ethyl | LC4 | 480.32 | 1.34 |
| 145 | 2-(3-chloro-phenyl)-ethyl | LC4 | 446.26 | 1.34 |
| 146 | 2-(4-cyano-phenyl)-ethyl | LC4 | 437.3 | 1.26 |
| 147 | 2-(thiophen-3-yl)-ethyl | LC4 | 418.27 | 1.28 |
| 148 | 2-(2,4-dichloro-phenyl)-ethyl | LC4 | 480.24 | 1.38 |
| 149 | 2-(2-chloro-4-fluoro-phenyl)-ethyl | LC4 | 464.26 | 1.34 |
| 150 | [1-(4-chloro-phenyl)-cyclopropyl]-methyl | LC4 | 472.29 | 1.37 |
| 151 | 2-(2-fluoro-phenyl)-ethyl | LC4 | 430.29 | 1.3 |
| 152 | 2-(2-chloro-6-fluoro-phenyl)-ethyl | LC4 | 464.25 | 1.33 |
| 153 | 2-(2-methyl-phenyl)-ethyl | LC4 | 426.32 | 1.33 |
| 154 | 2-(4-fluoro-phenyl)-ethyl | LC4 | 430.29 | 1.3 |
| 155 | 2-(3-methoxy-phenyl)-ethyl | LC4 | 442.31 | 1.29 |
| 156 | 2-(2-chloro-phenyl)-ethyl | LC4 | 446.25 | 1.33 |
| 157 | 2-(2,5-dichloro-phenyl)-ethyl | LC4 | 480.22 | 1.37 |

In analogy to example 3, the example compounds of the formula I-7 listed in table 7 were prepared. The compounds can be named as trans-1-[3-($R^{107}$-oxy)-4-methoxy-benzoylamino]-4-methyl-cyclohexane-1-carboxylic acid, for example as trans-1-{3-[2-(4-methoxy-phenyl)-ethoxy]-4-methoxy-benzoylamino]-4-methyl-cyclohexane-1-carboxylic acid in the case of example 158.

I-7

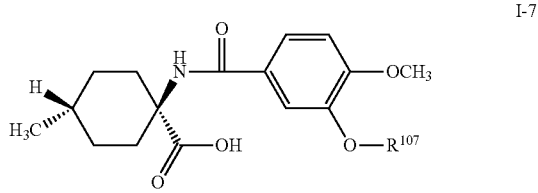

TABLE 7

Example compounds of the formula I-7

| Example | $R^{107}$ | LC/MS Method | m/z [MH+] | Retention time [min] |
|---|---|---|---|---|
| 158 | 2-(4-methoxy-phenyl)-ethyl | LC4 | 442.3 | 1.28 |
| 159 | 2-cyclohexyl-ethyl | LC4 | 418.35 | 1.38 |
| 160 | 2-(3-trifluoromethyl-phenyl)-ethyl | LC4 | 480.29 | 1.34 |
| 161 | 2-(thiophen-2-yl)-ethyl | LC4 | 418.24 | 1.28 |
| 162 | 2-(3-fluoro-phenyl)-ethyl | LC4 | 430.28 | 1.3 |
| 163 | 2-phenyl-ethyl | LC4 | 412.29 | 1.29 |
| 164 | 2-(2-methoxy-phenyl)-ethyl | LC4 | 442.3 | 1.3 |
| 165 | 2-(3,4-dimethoxy-phenyl)-ethyl | LC4 | 470.47 | 1.25 |
| 166 | 2-(4-chloro-phenyl)-ethyl | LC4 | 446.26 | 1.33 |
| 167 | 2-(4-tert-butyl-phenyl)-ethyl | LC4 | 468.39 | 1.4 |
| 168 | 2-phenyl-propyl | LC4 | 426.33 | 1.32 |
| 169 | 2-(4-methyl-phenyl)-ethyl | LC4 | 426.32 | 1.33 |
| 170 | 2-(2-trifluoromethyl-phenyl)-ethyl | LC4 | 480.29 | 1.34 |
| 171 | 2-(3-chloro-phenyl)-ethyl | LC4 | 446.27 | 1.33 |
| 172 | 2-(4-cyano-phenyl)-ethyl | LC4 | 437.3 | 1.25 |
| 173 | 2-(2,4,6-trimethyl-phenyl)-ethyl | LC4 | 454.36 | 1.38 |
| 174 | 2-(thiophen-3-yl)-ethyl | LC4 | 418.26 | 1.28 |
| 175 | 2-(2,4-dichloro-phenyl)-ethyl | LC4 | 480.23 | 1.37 |
| 176 | 2-(2-chloro-4-fluoro-phenyl)-ethyl | LC4 | 464.27 | 1.33 |
| 177 | 2-(2-fluoro-phenyl)-ethyl | LC4 | 430.28 | 1.3 |
| 178 | 2-phenyl-butyl | LC4 | 440.34 | 1.35 |
| 179 | 2-(2-chloro-6-fluoro-phenyl)-ethyl | LC4 | 464.28 | 1.32 |
| 180 | 2-(2-methyl-phenyl)-ethyl | LC4 | 426.31 | 1.32 |
| 181 | 2-(2,5-difluoro-phenyl)-ethyl | LC4 | 448.28 | 1.3 |
| 182 | 2-(3-chloro-2-fluoro-phenyl)-ethyl | LC4 | 464.27 | 1.33 |
| 183 | 2-(4-fluoro-phenyl)-ethyl | LC4 | 430.29 | 1.29 |
| 184 | 2-(indol-3-yl)-ethyl | LC4 | 451.34 | 1.26 |
| 185 | 2-(3-methoxy-phenyl)-ethyl | LC4 | 442.32 | 1.28 |
| 186 | 2-(2-chloro-phenyl)-ethyl | LC4 | 446.26 | 1.32 |
| 187 | 2-(2,5-dimethyl-phenyl)-ethyl | LC4 | 440.34 | 1.35 |
| 188 | 2-(2,5-dichloro-phenyl)-ethyl | LC4 | 480.24 | 1.36 |
| 189 | 2-(3,5-dimethyl-phenyl)-ethyl | LC4 | 440.33 | 1.36 |

TABLE 7-continued

Example compounds of the formula I-7

| Example | $R^{107}$ | LC/MS Method | m/z [MH+] | Retention time [min] |
|---|---|---|---|---|
| 190 | 1-methyl-2-phenyl-ethyl | LC4 | 426.31 | 1.31 |
| 191 | 4-methoxy-benzyl | LC4 | 442.31 | 1.3 |
| 192 | 4-trifluoromethoxy-benzyl | LC4 | 482.27 | 1.33 |
| 193 | 3-(4-methoxy-phenyl)-propyl | LC4 | 456.34 | 1.3 |
| 194 | 2-phenylsulfanyl-ethyl | LC4 | 444.27 | 1.3 |
| 195 | 3-chloro-benzyl | LC4 | 432.25 | 1.31 |
| 196 | 2-(naphthalen-1-yl)-ethyl | LC4 | 462.33 | 1.35 |
| 197 | (2,3-dihydro-benzo[1,4]dioxin-2-yl)-methyl | LC4 | 456.31 | 1.29 |
| 198 | 3-phenyl-propyl | LC4 | 426.32 | 1.32 |
| 199 | 3-fluoro-benzyl | LC4 | 416.28 | 1.28 |
| 200 | cyclohexyl-methyl | LC4 | 404.32 | 1.36 |
| 201 | 3-cyclopentyl-propyl | LC4 | 418.34 | 1.39 |
| 202 | 2,5-dimethyl-benzyl | LC4 | 426.32 | 1.33 |
| 203 | 2-(4-fluoro-phenylsulfanyl)-ethyl | LC4 | 462.29 | 1.31 |
| 204 | 2-(6,6-dimethyl-bicyclo[3.1.1]hept-2-en-2-yl)-ethyl | LC4 | 456.39 | 1.43 |

In analogy to example 3, the example compounds of the formulae I-8 and I-9 listed in table 8, in which $R^{108}$ and $R^{109}$ have the meanings given in table 8, were prepared.

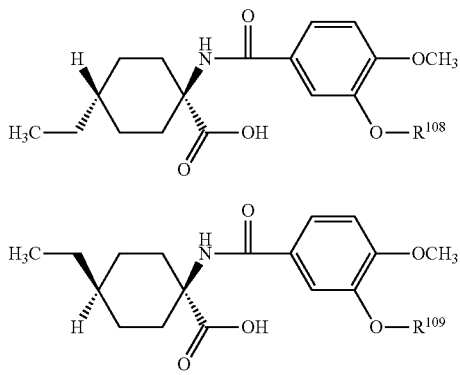

TABLE 8

Example compounds of the formulae I-8 and I-9

| Example | Formula | $R^{108}/R^{109}$ | LC/MS Method | m/z [MH+] | Retention time [min] |
|---|---|---|---|---|---|
| 205 | I-8 | 2-phenyl-ethyl | LC4 | 426.30 | 1.34 |
| 206 | I-9 | 2-phenyl-ethyl | LC4 | 426.29 | 1.22 |
| 207 | I-8 | 2-(3-chloro-phenyl)-ethyl | LC4 | 460.27 | 1.38 |
| 208 | I-9 | 2-(3-chloro-phenyl)-ethyl | LC3 | 460.29 | 4.75 |

In analogy to example 3, the compounds of the formulae I-8 and I-9 listed in table 9, in which $R^{108}$ and $R^{109}$ have the meanings given in table 9, can be prepared.

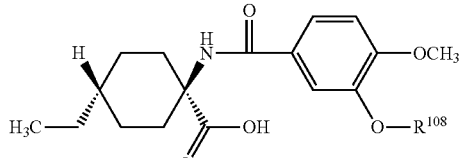

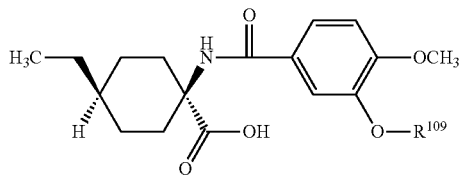

TABLE 9

Compounds of the formulae I-8 and I-9

| Example (formula) | Example (formula) | $R^{108}/R^{109}$ |
|---|---|---|
| 209 (I-8) | 210 (I-9) | 2-(4-methoxy-phenyl)-ethyl |
| 211 (I-8) | 212 (I-9) | 2-cyclohexyl-ethyl |
| 213 (I-8) | 214 (I-9) | 2-(3-trifluoromethyl-phenyl)-ethyl |
| 215 (I-8) | 216 (I-9) | 2-(thiophen-2-yl)-ethyl |
| 217 (I-8) | 218 (I-9) | 2-(3-fluoro-phenyl)-ethyl |
| 219 (I-8) | 220 (I-9) | 2-(2-methoxy-phenyl)-ethyl |
| 221 (I-8) | 222 (I-9) | 2-(3,4-dimethoxy-phenyl)-ethyl |
| 223 (I-8) | 224 (I-9) | 2-(4-chloro-phenyl)-ethyl |
| 225 (I-8) | 226 (I-9) | 2-(4-tert-butyl-phenyl)-ethyl |
| 227 (I-8) | 228 (I-9) | 2-phenyl-propyl |
| 229 (I-8) | 230 (I-9) | 2-(4-methyl-phenyl)-ethyl |
| 231 (I-8) | 232 (I-9) | 2-(2-trifluoromethyl-phenyl)-ethyl |
| 233 (I-8) | 234 (I-9) | 2-(4-cyano-phenyl)-ethyl |
| 235 (I-8) | 236 (I-9) | 2-(2,4,6-trimethyl-phenyl)-ethyl |
| 237 (I-8) | 238 (I-9) | 2-(thiophen-3-yl)-ethyl |
| 239 (I-8) | 240 (I-9) | 2-(2,4-dichloro-phenyl)-ethyl |
| 241 (I-8) | 242 (I-9) | 2-(2-chloro-4-fluoro-phenyl)-ethyl |
| 243 (I-8) | 244 (I-9) | 2-(2-fluoro-phenyl)-ethyl |
| 245 (I-8) | 246 (I-9) | 2-phenyl-butyl |
| 247 (I-8) | 248 (I-9) | 2-(2-chloro-6-fluoro-phenyl)-ethyl |
| 249 (I-8) | 250 (I-9) | 2-(2-methyl-phenyl)-ethyl |
| 251 (I-8) | 252 (I-9) | 2-(2,5-difluoro-phenyl)-ethyl |
| 253 (I-8) | 254 (I-9) | 2-(3-chloro-2-fluoro-phenyl)-ethyl |
| 255 (I-8) | 256 (I-9) | 2-(4-fluoro-phenyl)-ethyl |
| 257 (I-8) | 258 (I-9) | 2-(indol-3-yl)-ethyl |
| 259 (I-8) | 260 (I-9) | 2-(3-methoxy-phenyl)-ethyl |
| 261 (I-8) | 262 (I-9) | 2-(2-chloro-phenyl)-ethyl |
| 263 (I-8) | 264 (I-9) | 2-(2,5-dimethyl-phenyl)-ethyl |
| 265 (I-8) | 266 (I-9) | 2-(2,5-dichloro-phenyl)-ethyl |
| 267 (I-8) | 268 (I-9) | 2-(3,5-dimethyl-phenyl)-ethyl |
| 269 (I-8) | 270 (I-9) | 1-methyl-2-phenyl-ethyl |
| 271 (I-8) | 272 (I-9) | 4-methoxy-benzyl |
| 273 (I-8) | 274 (I-9) | 4-trifluoromethoxy-benzyl |
| 275 (I-8) | 276 (I-9) | 3-(4-methoxy-phenyl)-propyl |
| 277 (I-8) | 278 (I-9) | 2-phenylsulfanyl-ethyl |
| 279 (I-8) | 280 (I-9) | 3-chloro-benzyl |
| 281 (I-8) | 282 (I-9) | 2-(naphthalen-1-yl)-ethyl |
| 283 (I-8) | 284 (I-9) | (2,3-dihydro-benzo[1,4]dioxin-2-yl)-methyl |
| 285 (I-8) | 286 (I-9) | 3-phenyl-propyl |
| 287 (I-8) | 288 (I-9) | 3-fluoro-benzyl |
| 289 (I-8) | 290 (I-9) | cyclohexyl-methyl |
| 291 (I-8) | 292 (I-9) | 3-cyclopentyl-propyl |
| 293 (I-8) | 294 (I-9) | 2,5-dimethyl-benzyl |
| 295 (I-8) | 296 (I-9) | 2-(4-fluoro-phenylsulfanyl)-ethyl |
| 297 (I-8) | 298 (I-9) | 2-(6,6-dimethyl-bicyclo[3.1.1]hept-2-en-2-yl)-ethyl |

In analogy to example 92, the example compounds of the formula I-10 listed in table 10 were synthesized by reacting cis-1-amino-4-ethyl-cyclohexanecarboxylic acid methyl ester hydrochloride instead of 1-amino-cycloheptanecarboxylic acid methyl ester hydrochloride with 5-bromo-6- methoxy-nicotinic acid in analogy to step 2 of example 92, and reacting the obtained cis-1-[(5-bromo-6-methoxy-pyridine-3-carbonyl)-amino]-4-ethyl-cyclohexanecarboxylic acid methyl ester with the respective phenylboronic acid and hydrolyzing the obtained methyl ester in analogy to steps 3 and 4, respectively, of example 92. The compounds can be named as cis-4-ethyl-1-[(5-$R^{110}$-6-methoxy-pyridine-3-carbonyl)-amino]-cyclohexanecarboxylic acid, for example as cis-4-ethyl-1-{[6-methoxy-5-(3-trifluoromethoxy-phenyl)-pyridine-3-carbonyl]-amino}-cyclohexanecarboxylic acid in the case of example 299.

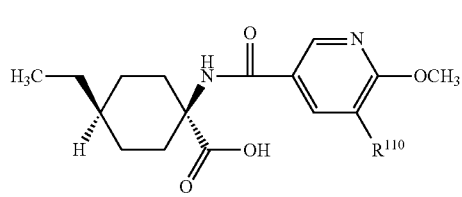

I-10

TABLE 10

Example compounds of the formula I-10

| Example | $R^{110}$ | LC/MS Method | m/z [MH+] | Retention time [min] |
|---|---|---|---|---|
| 299 | 3-trifluoromethoxy-phenyl | LC4 | 467.3 | 1.37 |
| 300 | 2,3-dichloro-phenyl | LC4 | 451.23 | 1.35 |
| 301 | 3,4,5-trifluoro-phenyl | LC4 | 437.28 | 1.36 |
| 302 | 3-chloro-5-trifluoromethyl-phenyl | LC4 | 485.3 | 1.40 |
| 303 | 3-trifluoromethyl-phenyl | LC6 | 451.31 | 4.89 |
| 304 | 2-fluoro-3-trifluoromethyl-phenyl | LC4 | 469.26 | 1.34 |

EXAMPLE 305 cis-1-{[5-(3-Chloro-4-methoxy-phenyl)-6-methoxy-pyridine-3-carbonyl]-amino}-4-ethyl-cyclohexanecarboxylic acid

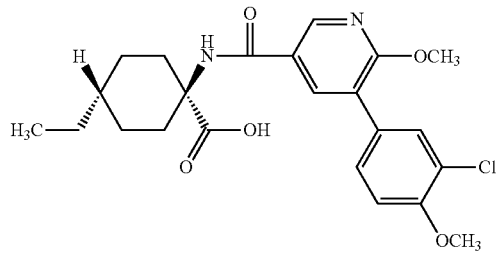 [SMILES: CC[C@H]1CC[C@@](NC(=O)c2cnc(OC)c(-c3ccc(OC)c(Cl)c3)c2)(C(=O)O)CC1]

The compound was prepared in analogy to example 92 using cis-1-amino-4-ethylcyclohexanecarboxylic acid methyl ester hydrochloride instead of 1-amino-cycloheptanecarboxylic acid methyl ester hydrochloride.

LC/MS (Method LC4): Rt=1.17 min; m/z=466.23 [MH+]

In analogy to example 92, the example compounds of the formulae I-11, I-12 and I-13 listed in table 11, in which $R^{111}$, $R^{112}$ and $R^{113}$ have the meanings given in table 11, were prepared.

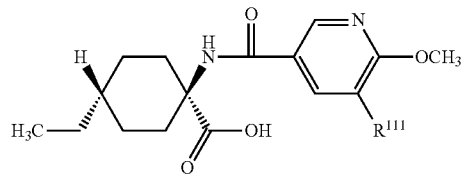

I-11

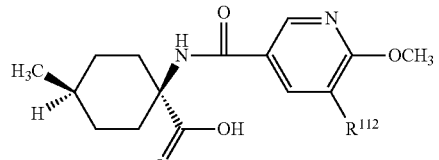

I-12

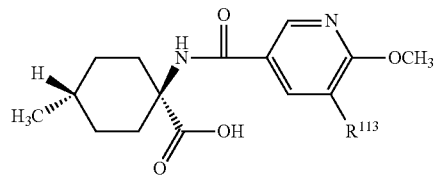

I-13

TABLE 11

Example compounds of the formulae I-11, I-12 and I-13

| Example | Formula | $R^{111}/R^{112}/R^{113}$ | LC/MS Method | m/z [MH+] | Retention time [min] |
|---|---|---|---|---|---|
| 306 | I-11 | 3-trifluoromethoxy-phenyl | LC4 | 467.28 | 1.39 |
| 307 | I-12 | 3-trifluoromethoxy-phenyl | LC4 | 453.25 | 1.36 |
| 308 | I-13 | 3-trifluoromethoxy-phenyl | LC4 | 453.25 | 1.35 |
| 309 | I-11 | 2,3-dichloro-phenyl | LC4 | 451.21 | 1.37 |
| 310 | I-12 | 2,3-dichloro-phenyl | LC4 | 437.19 | 1.34 |
| 311 | I-13 | 2,3-dichloro-phenyl | LC4 | 437.17 | 1.34 |
| 312 | I-11 | 3,4,5-trifluoro-phenyl | LC4 | 437.25 | 1.37 |
| 313 | I-12 | 3,4,5-trifluoro-phenyl | LC4 | 423.21 | 1.34 |
| 314 | I-13 | 3,4,5-trifluoro-phenyl | LC4 | 423.22 | 1.33 |
| 315 | I-13 | 3-chloro-5-trifluoromethyl-phenyl | LC4 | 471.22 | 1.39 |
| 316 | I-11 | 3-trifluoromethyl-phenyl | LC4 | 451.27 | 1.38 |
| 317 | I-12 | 3-trifluoromethyl-phenyl | LC4 | 437.24 | 1.35 |
| 318 | I-13 | 3-trifluoromethyl-phenyl | LC4 | 437.24 | 1.34 |
| 319 | I-12 | 3-chloro-4-methoxy-phenyl | LC4 | 433.21 | 1.32 |
| 320 | I-13 | 3-chloro-4-methoxy-phenyl | LC4 | 433.21 | 1.31 |

In analogy to example 92, the compounds of the formulae I-11, I-12 and I-13 listed in table 12, in which $R^{111}$, $R^{112}$ and $R^{113}$ have the meanings given in table 12, can be prepared.

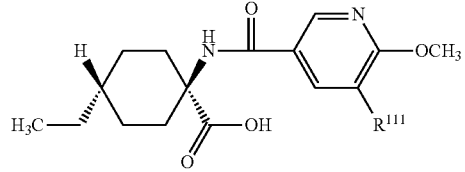

I-11

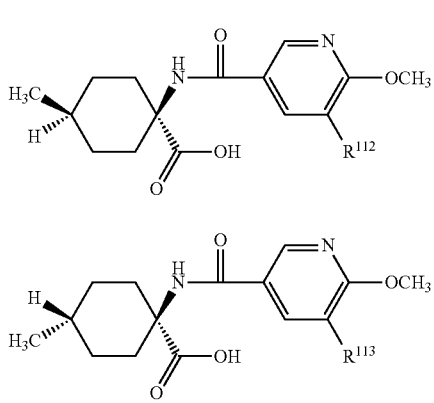

I-12

I-13

TABLE 12

Compounds of the formulae I-11, I-12 and I-13

| Example | Formula | $R^{111}/R^{112}/R^{113}$ | LC/MS Method | m/z [MH$^+$] | Retention time [min] |
|---|---|---|---|---|---|
| 321 | I-11 | 3-chloro-5-trifluoro-methyl-phenyl | | | |
| 322 | I-12 | 3-chloro-5-trifluoro-methyl-phenyl | | | |
| 323 | I-11 | 2-fluoro-3-trifluoro-methyl-phenyl | | | |
| 324 | I-12 | 2-fluoro-3-trifluoro-methyl-phenyl | | | |
| 325 | I-13 | 2-fluoro-3-trifluoro-methyl-phenyl | | | |
| 326 | I-11 | 3-chloro-4-methoxy-phenyl | LC4 | 447.17 | 1.34 |

In analogy to example 92, the example compounds of the formulae I-14, I-15, I-16 and I-17 listed in table 13, in which $R^{114}$, $R^{115}$, $R^{116}$ and $R^{117}$ have the meanings given in table 13, were prepared.

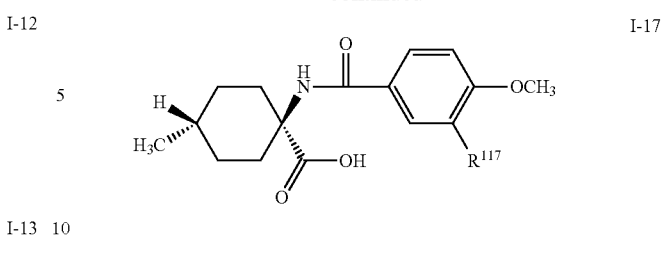

I-17

TABLE 13

Example compounds of the formulae I-14, I-15, I-16 and I-17

| Example | Formula | $R^{114}/R^{115}/R^{116}/R^{117}$ | LC/MS Method | m/z [MH$^+$] | Retention time [min] |
|---|---|---|---|---|---|
| 327 | I-14 | 3-trifluoromethoxy-phenyl | LC4 | 466.25 | 1.40 |
| 328 | I-15 | 3-trifluoromethoxy-phenyl | LC4 | 466.25 | 1.39 |
| 329 | I-16 | 3-trifluoromethoxy-phenyl | LC4 | 452.17 | 1.37 |
| 330 | I-17 | 3-trifluoromethoxy-pheny | LC4 | 452.22 | 1.36 |
| 331 | I-14 | 3-trifluoromethyl-phenyl | LC4 | 450.2 | 1.38 |
| 332 | I-15 | 3-trifluoromethyl-phenyl | LC4 | 450.2 | 1.38 |
| 333 | I-16 | 3-trifluoromethyl-phenyl | LC4 | 436.2 | 1.35 |
| 334 | I-17 | 3-trifluoromethyl-phenyl | LC4 | 436.17 | 1.35 |

In analogy to example 92, the compounds of the formulae I-14, I-15, I-16 and I-17 listed in table 14, in which $R^{114}$, $R^{115}$, $R^{116}$ and $R^{117}$ have the meanings given in table 14, can be prepared.

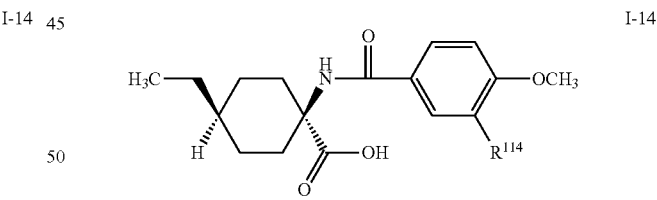

I-14

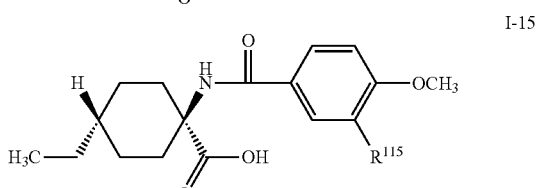

I-15

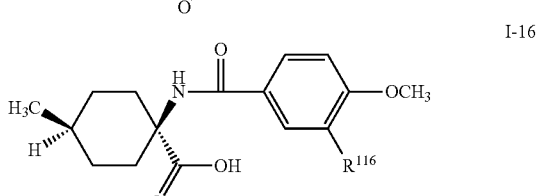

I-16

-continued

I-17

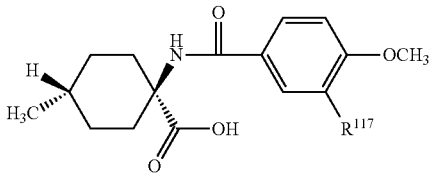

TABLE 14

Compounds of the formulae I-14, I-15, I-16 and I-17

| Example (formula) | Example (formula) | Example (formula) | Example (formula) | $R^{114}/R^{115}/R^{116}/R^{117}$ |
|---|---|---|---|---|
| 335 (I-14) | 336 (I-15) | 337 (I-16) | 338 (I-17) | 2,3-dichloro-phenyl |
| 339 (I-14) | 340 (I-15) | 341 (I-16) | 342 (I-17) | 3,4,5-trifluoro-phenyl |
| 343 (I-14) | 344 (I-15) | 345 (I-16) | 346 (I-17) | 3-chloro-5-trifluoro-methyl-phenyl |
| 347 (I-14) | 348 (I-15) | 349 (I-16) | 350 (I-17) | 2-fluoro-3-trifluoro-methyl-phenyl |
| 351 (I-14) | 352 (I-15) | 353 (I-16) | 354 (I-17) | 3-chloro-4-methoxy-phenyl |

| Example | Formula | $R^{114}/R^{115}/R^{116}/R^{117}$ | LC/MS Method | m/z [MH⁺] | Retention time [min] |
|---|---|---|---|---|---|
| 351 | I-14 | 3-chloro-4-methoxy-phenyl | LC4 | 446.21 | 1.35 |
| 352 | I-15 | 3-chloro-4-methoxy-phenyl | LC4 | 446.21 | 1.34 |

EXAMPLE 355 trans-4-Ethyl-1-[(6-methoxy-5-phenethyloxy-pyridine-3-carbonyl)-amino]-cyclohexanecarboxylic acid

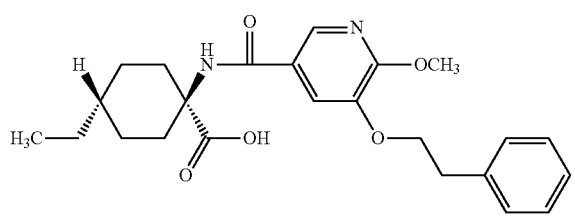 [SMILES: CC[C@H]1CC[C@@](NC(=O)c2cnc(OC)c(OCCc3ccccc3)c2)(C(=O)O)CC1]

Step 1:
trans-1-Amino-4-ethyl-cyclohexanecarboxylic acid methyl ester hydrochloride 4-Ethyl-cyclohexanone was reacted in a Strecker aminonitrile synthesis in analogy to the procedure described in I. L. Munday, J. Chem. Soc. (1961), 4372-4379 to yield trans-1-amino-4-ethyl-cyclohexanecarbonitrile. This intermediate (10 g, 65.8 mmol) was stirred in 150 ml of 8 N hydrochloric acid under reflux for 72 h. The volatiles were evaporated, the residue was twice evaporated with water, resuspended in water and adjusted to pH=6 with sodium hydroxide. After cooling in an ice bath, the precipitate was filtered off, washed with water and acetone and dried in vacuo. The obtained amino acid was suspended in methanol, cooled to −30° C. and thionyl chloride (3 equivalents) was added. The mixture was warmed to room temperature and stirred overnight. The volatiles were evaporated to yield the title compound.

Step 2: trans-4-Ethyl-1-[(6-methoxy-5-phenethyloxy-pyridine-3-carbonyl)-amino]-cyclohexanecarboxylic acid The title compound was synthesized in analogy to example 77 using 2-phenylethanol in the etherification step and using the compound of step 1 as amino acid methyl ester hydrochloride intermediate.

LC/MS (Method LC4): Rt=1.33 min; m/z=427.29 [MH⁺]

EXAMPLE 356 cis-1-({5-[2-(3-Chloro-phenyl)-ethoxy]-6-methoxy-pyridine-3-carbonyl}-amino)-4-methyl-cyclohexanecarboxylic acid

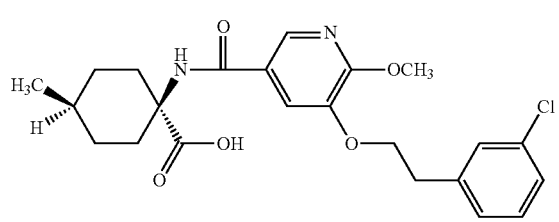 [SMILES: COc1ncc(C(=O)N[C@]2(C(=O)O)CC[C@H](C)CC2)cc1OCCc1cccc(Cl)c1]

The title compound was synthesized in analogy to example 79 using 2-(3-chlorophenyl)ethanol in the etherification step.

LC/MS (Method LC4): Rt=1.29 min; m/z=447.28 [MH⁺]

EXAMPLE 357 cis-1-({5-[2-(3-Chloro-phenyl)-ethoxy]-6-methoxy-pyridine-3-carbonyl}-amino)-4-ethyl-cyclohexanecarboxylic acid

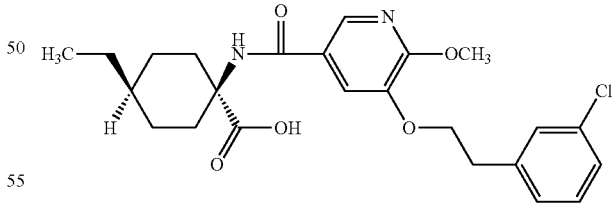

The title compound was synthesized in analogy to example 77 using 2-(3-chlorophenyl)ethanol in the etherification step and cis-1-amino-4-ethyl-cyclohexanecarboxylic acid methyl ester hydrochloride (synthesized from 4-ethylcyclohexanone via the Bucherer-Bergs hydantoin route in analogy to the procedure described in J. W. Tsang et al., J. Med. Chem. 27 (1984), 1663-1668) instead of 1-amino-cycloheptanecarboxylic acid methyl ester hydrochloride.

LC/MS (Method LC4): Rt=1.38 min; m/z=461.25 [MH⁺]

EXAMPLE 358 cis-4-Ethyl-1-[(6-methoxy-5-phenethyloxy-pyridine-3-carbonyl)-amino]-cyclohexanecarboxylic acid

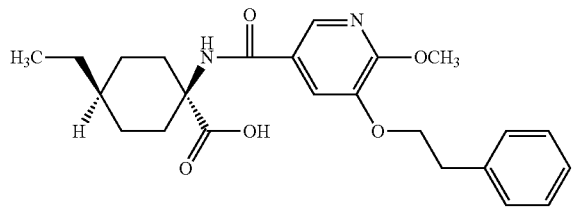 [SMILES: CC[C@H]1CC[C@](NC(=O)c2cnc(OC)c(OCCc3ccccc3)c2)(C(=O)O)CC1]

The title compound was synthesized in analogy to example 77 using 2-phenylethanol in the etherification step and cis-1-amino-4-ethyl-cyclohexanecarboxylic acid methyl ester hydrochloride instead of 1-amino-cycloheptanecarboxylic acid methyl ester hydrochloride.

LC/MS (Method LC4): Rt=1.34 min; m/z=427.3 [MH+]

EXAMPLE 359 cis-1-{[5-(3,4-Difluoro-phenyl)-6-methoxy-pyridine-3-carbonyl]-amino}-4-ethyl-cyclohexanecarboxylic acid

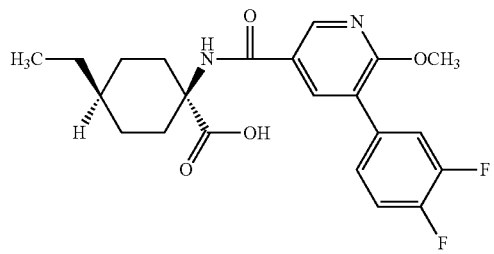 [SMILES: CC[C@H]1CC[C@](NC(=O)c2cnc(OC)c(-c3ccc(F)c(F)c3)c2)(C(=O)O)CC1]

The title compound was synthesized in analogy to example 92 using 3,4-difluoro-phenylboronic acid in the Suzuki coupling step and cis-1-amino-4-ethyl-cyclohexanecarboxylic acid methyl ester hydrochloride instead of 1-amino-cycloheptanecarboxylic acid methyl ester hydrochloride.

LC/MS (Method LC4): Rt=1.36 min; m/z=419.26 [MH+]

EXAMPLE 360 cis-1-{[5-(3,5-Difluoro-phenyl)-6-methoxy-pyridine-3-carbonyl]-amino}-4-ethyl-cyclohexanecarboxylic acid

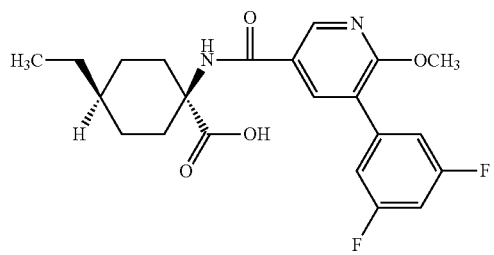 [SMILES: CC[C@H]1CC[C@](NC(=O)c2cnc(OC)c(-c3cc(F)cc(F)c3)c2)(C(=O)O)CC1]

The title compound was synthesized in analogy to example 92 using 3,5-difluoro-phenylboronic acid in the Suzuki coupling step and cis-1-amino-4-ethyl-cyclohexanecarboxylic acid methyl ester hydrochloride instead of 1-amino-cycloheptanecarboxylic acid methyl ester hydrochloride.

LC/MS (Method LC4): Rt=1.36 min; m/z=419.21 [MH+]

EXAMPLE 361

(1R,2R)-1-({5-[2-(3-Chloro-phenyl)-ethoxy]-6-methoxy-pyridine-3-carbonyl}-amino)-2-ethyl-cyclopropanecarboxylic acid

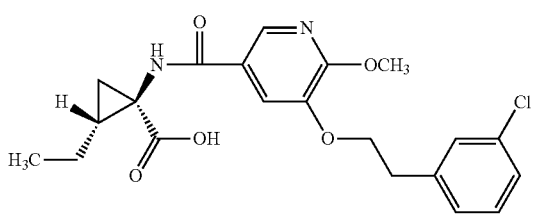 [SMILES: CC[C@@H]1C[C@]1(NC(=O)c1cnc(OC)c(OCCc2cccc(Cl)c2)c1)C(=O)O]

Step 1:
(1R,2R)-1-Amino-2-ethyl-cyclopropanecarboxylic acid ethyl ester (1R,2S)-1-tert-Butoxycarbonylamino-2-vinyl-cyclopropanecarboxylic acid ethyl ester (400 mg, 1.57 mmol) was dissolved in methanol (5 ml) and added to a suspension of azodicarboxylic acid dipotassium salt (1.46 g, 7.5 mmol; cf. D. J. Pasto et al., Organic Reactions 40 (1991), 91-155) in methanol (10 ml). Acetic acid (1.12 g, 18.8 mmol) was added in the course of 10 min and the mixture was stirred for 1 h at room temperature. Azodicarboxylic acid dipotassium salt (1.46 g) and acetic acid (1.12 g) were added once again and the mixture stirred for 1 h. LC/MS analysis then indicated complete conversion. The volatiles were evaporated, the residue was partitioned between EA and a saturated sodium hydrogencarbonate solution, and the combined organic extracts were dried over sodium chloride, decanted over a small plug of silica gel and evaporated to dryness. The obtained intermediate was dissolved in a mixture of DCM (5 ml) and TFA (1 ml) and stirred for 1 h at room temperature. The volatiles were evaporated, and the residue was partitioned between diethyl ether and saturated sodium hydrogencarbonate solution. The combined organic extracts were dried over sodium chloride, decanted and evaporated to dryness to yield the title compound.

Step 2: (1R,2R)-1-({5-[2-(3-Chloro-phenyl)-ethoxy]-6-methoxy-pyridine-3-carbonyl}-amino)-2-ethyl-cyclopropanecarboxylic acid The title compound was synthesized in analogy to example 77 using 2-(3-chlorophenyl)ethanol in the etherification step and using the compound of step 1 instead of 1-amino-cycloheptanecarboxylic acid methyl ester hydrochloride.

LC/MS (Method LC4): Rt=1.27 min; m/z=419.14 [MH+]

EXAMPLE 362 trans-4-Ethyl-1-{[5-fluoro-6-(2-hydroxy-ethoxy)-3'-trifluoromethyl-biphenyl-3-carbonyl]-amino}-cyclohexanecarboxylic acid

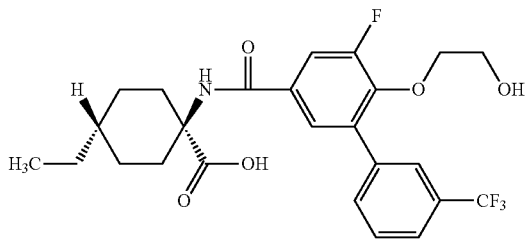 [SMILES: CC[C@H]1CC[C@@](NC(=O)c2cc(F)c(OCCO)c(-c3cccc(C(F)(F)F)c3)c2)(C(=O)O)CC1]

Step 1: 4-(2-Acetoxy-ethoxy)-3-bromo-5-fluoro-benzoic acid methyl ester

3-Bromo-5-fluoro-4-hydroxybenzoic acid methyl ester (500 mg, 2.01 mmol; T. Kline et al., J. Med. Chem. 45 (2002), 3112-3129), potassium carbonate (971 mg, 7.03 mmol) and 2-bromoethyl acetate (503 mg, 3.01 mmol) were reacted in DMF (5 ml) at room temperature for 72 h. Then the mixture was partitioned between EA and 2 N hydrochloric acid, and the combined organic extracts were dried over sodium chloride, decanted and evaporated to dryness. The raw material was purified by silica gel chromatography (EA/HEP gradient 0:1 to 4:6) to yield the title compound.

$^1$H-NMR: δ=7.97 (d, 1H); 7.81 (dd, 1H); 4.45-4.40 (m, 2H); 4.33-4.29 (m, 2H); 3.85 (s, 3H); 2.01 (s, 3H)

Step 2: trans-4-Ethyl-1-{[5-fluoro-6-(2-hydroxy-ethoxy)-3'-trifluoromethyl-biphenyl-3-carbonyl]-amino}-cyclohexanecarboxylic acid The compound of step 1 was coupled to 3-trifluoromethyl-phenylboronic acid in analogy to step 3 of example 92, and the obtained ester intermediate was hydrolyzed in analogy to step 4 of example 1 to yield 5-fluoro-6-(2-hydroxy-ethoxy)-3'-trifluoromethyl-biphenyl-3-carboxylic acid. This intermediate was coupled to the compound of step 1 of example 355 in analogy to step 1 of example 3, and the obtained ester intermediate hydrolyzed in analogy to step 4 of example 1 to yield the title compound.

LC/MS (Method LC4): Rt=1.32 min; m/z=498.23 [MH$^+$]

In analogy to example 3, the example compounds of the formula I-1 listed in table 15 were prepared.

I-1

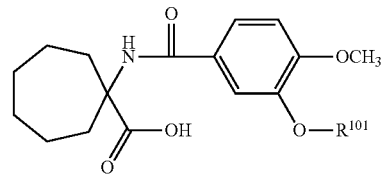

TABLE 15

Example compounds of the formula I-1

| Example | R$^{101}$ | LC/MS Method | m/z | Retention time [min] |
|---|---|---|---|---|
| 363 | 2-(3-trifluoromethyl-phenyl)-ethyl | LC8 | 480.20 [MH$^+$] | 2.54 |
| 364 | 2-(2-chlorophenyl)-ethyl | LC8 | 446.18 [MH$^+$] | 2.50 |
| 365 | 2-(3-fluorophenyl)-ethyl | LC6 | 428.08 [M − H$^+$] | 2.57 |

By coupling 4-methoxy-3-(2-m-tolyl-ethoxy)-benzoic acid to the respective amino acid methyl ester via the carboxylic acid chloride route as described in step 3 of example 1 or the TOTU coupling route as described in step 1 of example 3, the example compounds of the formula I-2 listed in table 16 were prepared. The amino acid methyl esters or the amino acids were commercially available or were prepared from the respective ketone in analogy to example 25. In the formulae of the groups R$^{102}$ in table 2 the line crossed with the symbol ~~ represents the free bond via which the group R$^{102}$ is bonded to the nitrogen atom of the amide group depicted in formula I-2. I.e., in the formula of the complete molecule the terminal endpoint of the line crossed with the said symbol ends on the nitrogen atom of the amide group.

I-2

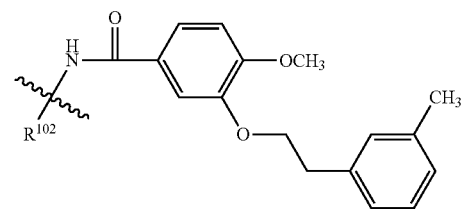

TABLE 16

Example compounds of the formula I-2

| Example | R$^{102}$ | Starting material | LC/MS Method | m/z [MH$^+$] | Retention time [min] |
|---|---|---|---|---|---|
| 366 | ![structure with H3C groups on cyclohexane-OH] | (a) | LC10 | 468.37 | 4.10 |

TABLE 16-continued

Example compounds of the formula I-2

| Example | R¹⁰² — (structure) | Starting material | LC/MS Method | m/z [MH⁺] | Retention time [min] |
|---|---|---|---|---|---|
| 367 | 3-methylcyclohexyl with COOH | (a) | LC6 | 426.36 | 4.78 |
| 368 | cyclopropyl with COOH | (b) | LC4 | 370.15 | 1.18 |

(a) The amino acid ester was prepared from the respective ketone.
(b) The amino acid ester or amino acid was commercially available.

In analogy to example 43, by employing the respective ketone instead of 4-methyl-cyclohexanone in the initial Strecker aminonitrile step, the example compounds of the formula I-3 listed in table 17 were prepared. In the formulae of the groups $R^{103}$ in table 17 the line crossed with the symbol ∿ represents the free bond via which the group $R^{103}$ is bonded to the nitrogen atom of the amide group depicted in formula I-3. I.e., in the formula of the complete molecule the terminal endpoint of the line crossed with the said symbol ends on the nitrogen atom of the amide group.

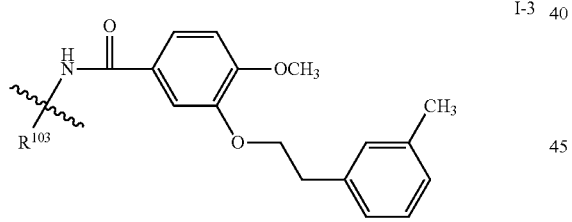

I-3

TABLE 17

Example compounds of the formula I-3

| Example | R¹⁰³ — (structure) | LC/MS Method | m/z [MH⁺] | Retention time [min] |
|---|---|---|---|---|
| 369 | F₃C-cyclohexyl-COOH (a) | LC1 | 480.22 | 1.81 |

TABLE 17-continued

Example compounds of the formula I-3

| Example | R¹⁰³ — (structure) | LC/MS Method | m/z [MH⁺] | Retention time [min] |
|---|---|---|---|---|
| 370 | (H₃C)₂CH-cyclohexyl-COOH (a) | LC10 | 454.35 | 3.97 |
| 371 | (H₃C)₃C-cyclohexyl-COOH (a) | LC4 | 468.34 | 1.35 |
| 372 | H₃C-cyclohexyl-COOH (a) | LC4 | 426.46 | 1.3 |

TABLE 17-continued

Example compounds of the formula I-3

| Example | R<sup>103</sup> | LC/MS Method | m/z [MH⁺] | Retention time [min] |
|---|---|---|---|---|
| 373 | (a) | LC4 | 412.28 | 1.28 |
| 374 | | LC4 | 442.13 | 1.15 |

(a) Other diastereomer than in example 28, example 29, example 366, example 367, example 33, respectively.

In analogy to example 92, the example compounds of the formula I-23 listed in table 18, in which $R^{123}$ has the meaning given in table 18, were prepared. The respective cis-1-amino-4-trifluoromethylcyclohexanecarboxylic acid methyl ester hydrochloride was prepared as for example 28

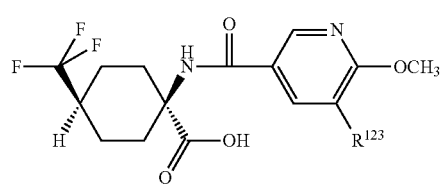

I-23

TABLE 18

Example compounds of the formulae I-23

| Example | R<sup>123</sup> | LC/MS Method | m/z [MH⁺] | Retention time [min] |
|---|---|---|---|---|
| 375 | 3,4,5-trifluorophenyl | LC4 | 477.28 | 1.32 |
| 376 | 3-trifluoromethylphenyl | LC4 | 491.33 | 1.35 |
| 377 | 2-fluoro-3-trifluoromethylphenyl | LC4 | 509.34 | 1.34 |
| 378 | 2,3-dichlorophenyl | LC4 | 491.21 | 1.32 |
| 379 | 3-trifluoromethoxyphenyl | LC4 | 507.2 | 1.32 |
| 380 | 3-chloro-5-trifluoromethylphenyl | LC4 | 525.16 | 1.36 |

In analogy to example 362, the example compounds of the formula I-18 listed in table 19, in which $R^{118}$ has the meaning given in table 19, were prepared.

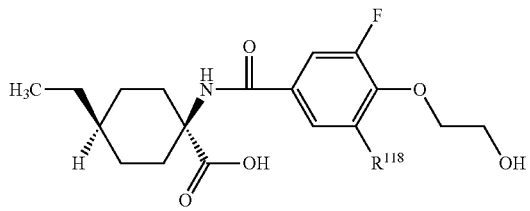

I-18

TABLE 19

Example compounds of the formula I-18

| Example | R<sup>118</sup> | LC/MS Method | m/z [MH⁺] | Retention time [min] |
|---|---|---|---|---|
| 381 | 3-chloro-4-methoxyphenyl | LC4 | 494.20 | 1.30 |
| 382 | 3-trifluoromethoxyphenyl | LC4 | 514.23 | 1.34 |
| 383 | 3-trifluoromethyl-phenyl | LC4 | 498.31 | 1.20 |
| 384 | 3,4-difluorophenyl | LC4 | 466.24 | 1.17 |
| 385 | 3,5-difluorophenyl | LC4 | 466.23 | 1.17 |

EXAMPLE 386 trans-4-Ethyl-1-{[6-(2-hydroxy-ethoxy)-3'-trifluoromethyl-biphenyl-3-carbonyl]-amino}-cyclohexanecarboxylic acid

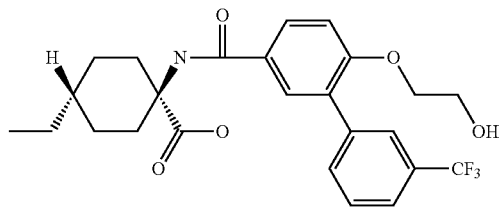 [SMILES: CC[C@H]1CC[C@@](NC(=O)c2ccc(OCCO)c(-c3cccc(C(F)(F)F)c3)c2)(C(=O)O)CC1]

Step 1: 4-(2-Acetoxy-ethoxy)-3-bromo-benzoic acid 2-acetoxy-ethyl ester

3-Bromo-4-hydroxy-benzoic acid (3.00 g, 13.8 mmol), caesium carbonate (9.01 g, 27.6 mmol) and 2-bromoethyl acetate (4.62 g, 27.6 mmol) were stirred in DMF for 3 days at room temperature. Volatiles were evaporated in vacuo, the remainder was partitioned between ethyl acetate and water, the combined organic extracts were dried over sodium chloride and evaporated to dryness. The raw material was titurated in ether, filtered and dried in vacuo to yield the title compound (4.66 g).

LC/MS (Method LC4): Rt=1.25 min; m/z=389.04 [MH⁺]

Step 2: trans-4-Ethyl-1-{[6-(2-hydroxy-ethoxy)-3'-trifluoromethyl-biphenyl-3-carbonyl]-amino}-cyclohexanecarboxylic acid The compound of step 1 was coupled to 3-trifluoromethylphenylboronic acid in analogy to step 3 of example 92, the obtained ester intermediate was hydrolyzed in analogy to step 4 of example 1 to yield 6-(2-Hydroxy-ethoxy)-3'-trifluoromethyl-biphenyl-3-carboxylic acid. This intermediate was coupled to trans-1-amino-4-ethylcyclohexanecarboxylic acid methylester hydrochloride in analogy to step 1 of example 3, and the obtained ester intermediate was hydrolyzed in analogy to step 4 of example 1 to yield the title compound.

LC/MS (Method LC4): Rt=1.30 min; m/z=480.19 [MH$^+$]

In analogy to example 386, the example compounds of the formula I-19 listed in table 20, in which R$^{119}$ has the meaning given in table 20, were prepared.

I-19

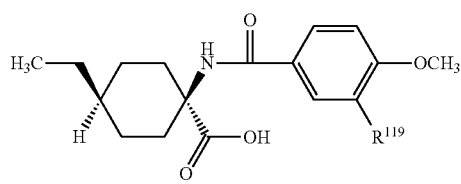

TABLE 20

Example compounds of the formula I-19

| Example | R$^{119}$ | LC/MS Method | m/z [MH$^+$] | Retention time [min] |
|---|---|---|---|---|
| 387 | 3-trifluoromethyl-phenyl | LC4 | 480.21 | 1.31 |
| 388 | 3,4-difluoro-phenyl | LC4 | 448.19 | 1.28 |
| 389 | 3,5-difluoro-phenyl | LC6 | 448.19 | 4.52 |
| 390 | 3-trifluoromethoxy-phenyl | LC6 | 496.16 | 4.69 |
| 391 | 3-chloro-4-methoxy-phenyl | LC4 | 476.22 | 1.27 |

EXAMPLE 392 trans-1-(3-Fluoro-5-{2-[3-(2-hydroxy-ethyl)-phenyl]-ethoxy}-4-methoxy-benzoylamino)-4-methyl-cyclohexanecarboxylic acid

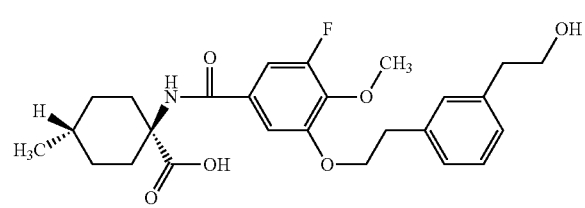 [SMILES: COc1c(F)cc(C(=O)N[C@]2(C(=O)O)CC[C@@H](C)CC2)cc1OCCc1cccc(CCO)c1]

3-Fluoro-5-hydroxy-4-methoxybenzoic acid methyl ester (see example 69) was etherified with 2-[3-(2-hydroxy-ethyl)-phenyl]-ethanol in analogy to step 1 of example 1. Hydrolysis of the ester group in analogy to step 2 of example 1, coupling of the obtained carboxylic acid to trans-1-amino-4-methyl-cyclohexanecarboxylic acid methyl ester hydrochloride in analogy to step 1 of example 3 and hydrolysis of the methyl ester in analogy to step 4 of example 1 yielded the title compound.

LC/MS (Method LC4): Rt=1.25 min; m/z=474.32 [MH$^+$]

EXAMPLE 393

1-(3-Fluoro-5-{2-[3-(2-hydroxy-ethyl)-phenyl]-ethoxy}-4-methoxy-benzoylamino)-cycloheptanecarboxylic acid

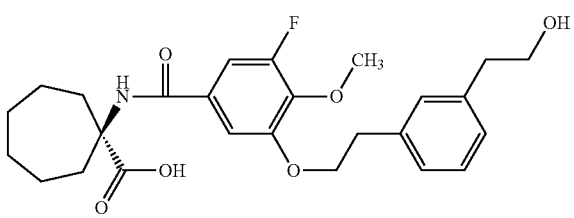

The title compound was synthesized in analogy to example 392 using 1-amino-cycloheptanecarboxylic acid methyl ester hydrochloride instead of trans-1-amino-4-methyl-cyclohexanecarboxylic acid methyl ester hydrochloride.

LC/MS (Method LC4): Rt=1.24 min; m/z=474.29 [MH$^+$]

EXAMPLE 394 trans-4-Ethyl-1-(3-fluoro-5-{2-[3-(2-hydroxy-ethyl)-phenyl]-ethoxy}-4-methoxy-benzoylamino)-cyclohexanecarboxylic acid

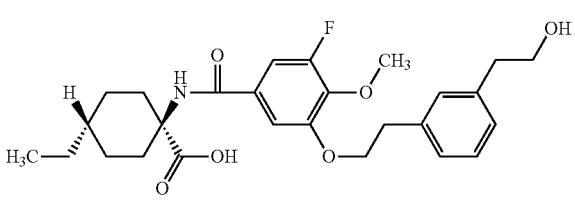 [SMILES: CC[C@H]1CC[C@@](NC(=O)c2cc(F)c(OC)c(OCCc3cccc(CCO)c3)c2)(C(=O)O)CC1]

The title compound was synthesized in analogy to example 392 using trans-1-amino-4-ethyl-cyclohexanecarboxylic acid methyl ester hydrochloride instead of trans-1-amino-4-methyl-cyclohexanecarboxylic acid methyl ester hydrochloride.

LC/MS (Method LC4): Rt=1.29 min; m/z=488.32 [MH$^+$]

EXAMPLE 395 trans-4-Ethyl-1-{[6-methoxy-5-(2-m-tolyl-ethoxy)-pyridine-3-carbonyl]-amino}-cyclohexanecarboxylic acid

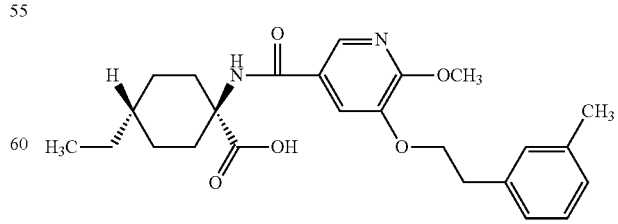

The title compound was synthesized in analogy to example 355 using 2-m-tolyl-ethanol in the etherification step.

LC/MS (Method LC3): Rt=4.67 min; m/z=441.31 [MH$^+$]

EXAMPLE 396 cis-4-Ethyl-1-{[6-methoxy-5-(2-m-tolyl-ethoxy)-pyridine-3-carbonyl]-amino}-cyclohexanecarboxylic acid

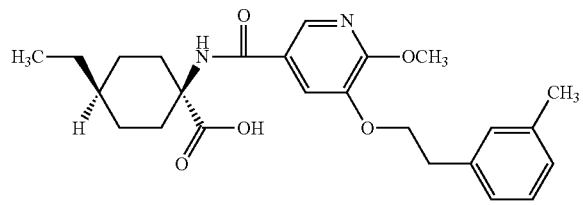 [SMILES: CC[C@H]1CC[C@](NC(=O)c2cnc(OC)c(OCCc3cccc(C)c3)c2)(C(=O)O)CC1]

The title compound was synthesized in analogy to example 357 using 2-m-tolyl-ethanol in the etherification step.

LC/MS (Method LC4): Rt=1.37 min; m/z=441.36 [MH$^+$]

EXAMPLE 397 trans-1-({5-[2-(3-Chloro-phenyl)-ethoxy]-6-methoxy-pyridine-3-carbonyl}-amino)-4-ethyl-cyclohexanecarboxylic acid

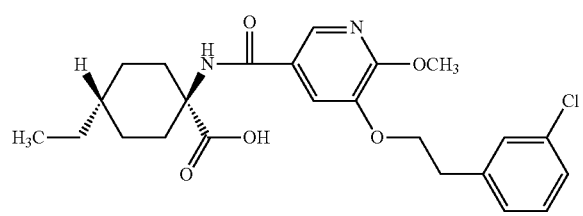 [SMILES: CC[C@H]1CC[C@@](NC(=O)c2cnc(OC)c(OCCc3cccc(Cl)c3)c2)(C(=O)O)CC1]

The title compound was synthesized in analogy to example 355 using 2-(3-chlorophenyl)-ethanol in the etherification step.

LC/MS (Method LC4): Rt=1.36 min; m/z=461.27 [MH$^+$]

EXAMPLE 398 trans-4-Ethyl-1-({6-methoxy-5-[2-(3-trifluoromethoxy-phenyl)-ethoxy]-pyridine-3-carbonyl}-amino)-cyclohexanecarboxylic acid

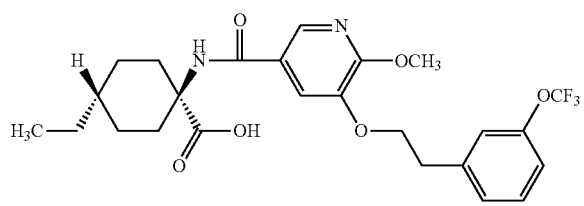 [SMILES: CC[C@H]1CC[C@@](NC(=O)c2cnc(OC)c(OCCc3cccc(OC(F)(F)F)c3)c2)(C(=O)O)CC1]

The title compound was synthesized in analogy to example 355 using 2-(3-trifluoromethoxyphenyl)-ethanol in the etherification step.

LC/MS (Method LC4): Rt=1.38 min; m/z=511.29 [MH$^+$]

EXAMPLE 399 cis-4-Ethyl-1-({6-methoxy-5-[2-(3-trifluoromethoxy-phenyl)-ethoxy]-pyridine-3-carbonyl}-amino)-cyclohexanecarboxylic acid

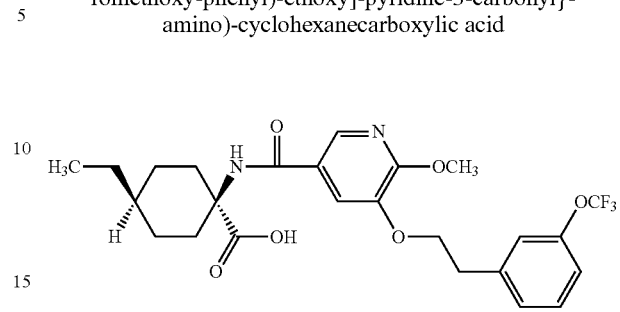

The title compound was synthesized in analogy to example 357 using 2-(3-trifluoromethoxyphenyl)-ethanol in the etherification step.

LC/MS (Method LC4): Rt=1.39 min; m/z=511.29 [MH$^+$]

EXAMPLE 400 cis-1-{[6-Methoxy-5-(2-phenyl-ethoxy)-pyridine-3-carbonyl]-amino}-4-methyl-cyclohexanecarboxylic acid

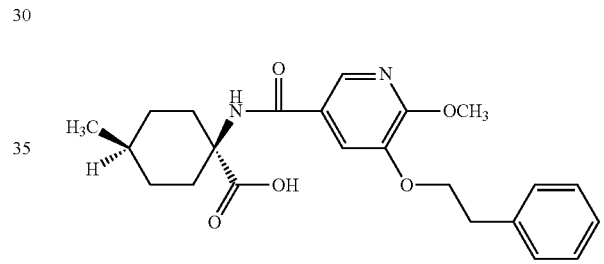

The title compound was synthesized in analogy to example 79 using 2-phenylethanol instead of 2-m-tolylethanol.

LC/MS (Method LC4): Rt=1.25 min; m/z=413.37 [MH$^+$]

EXAMPLE 401

1-({5-[2-(3-Chloro-phenyl)-ethoxy]-6-methoxy-pyridine-3-carbonyl}-amino)-cycloheptanecarboxylic acid

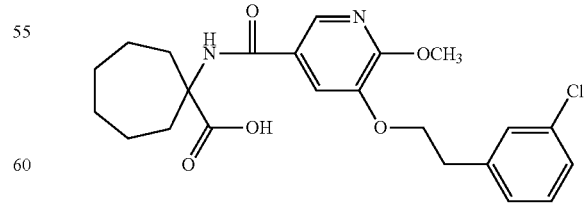

The title compound was synthesized in analogy to example 77 using 2-(3-chlorophenyl)ethanol instead of 2-m-tolylethanol.

LC/MS (Method LC4): Rt=1.31 min; m/z=447.15 [MH$^+$]

EXAMPLE 402 cis-1-{[6-Methoxy-5-(2-m-tolyl-ethoxy)-pyridine-3-carbonyl]-amino}-4-trifluoromethyl-cyclohexanecarboxylic acid

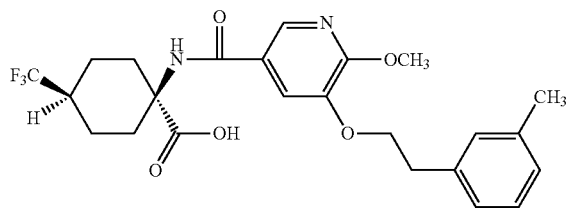

The title compound was synthesized in analogy to example 77 using cis-1-amino-4-trifluoromethylcyclohexanecarboxylic acid methyl ester hydrochloride instead of 1-aminocycloheptanecarboxylic acid methyl ester hydrochloride in the amide coupling step.
LC/MS (Method LC4): Rt=1.28 min; m/z=481.36 [MH$^+$]

EXAMPLE 403 cis-4-Ethyl-1-{4-methoxy-3-[2-(3-trifluoromethoxy-phenyl)-ethoxy]-benzoylamino}-cyclohexanecarboxylic acid

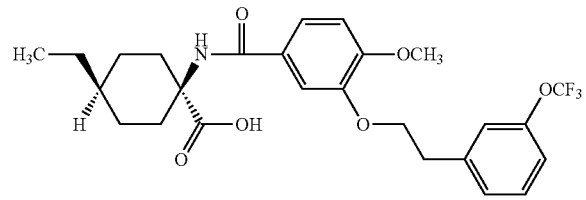 [SMILES: CC[C@H]1CC[C@](NC(=O)c2cnc(OC)c(OCCc3cccc(OC(F)(F)F)c3)c2)(C(=O)O)CC1]

The title compound was synthesized in analogy to example 3 using 2-(3-trifluoromethoxyphenyl)-ethanol in the etherification step and cis-1-amino-4-ethylcyclohexanecarboxylicacid methylester hydrochloride in the amide coupling step.
LC/MS (Method LC4): Rt=1.39 min; m/z=510.30 [MH$^+$]

EXAMPLE 404 cis-1-{3-[2-(5-Chloro-2-fluoro-phenyl)-ethoxy]-4-methoxy-benzoylamino}-4-methyl-cyclohexanecarboxylic acid

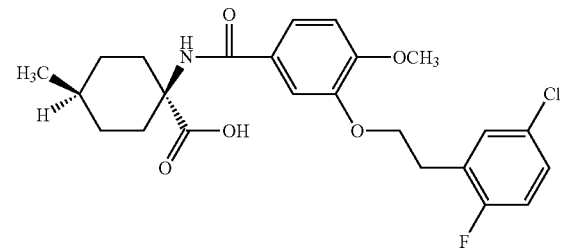 [SMILES: COc1ccc(C(=O)N[C@]2(C(=O)O)CC[C@H](C)CC2)cc1OCCc1cc(Cl)ccc1F]

The title compound was synthesized in analogy to example 3 using cis-1-amino-4-methylcyclohexanecarboxylic acid methyl ester hydrochloride instead of 1-amino-cycloheptanecarboxylic acid methyl ester hydrochloride in the amide coupling step.
LC/MS (Method LC3): Rt=4.57 min; m/z=464.21 [MH$^+$]

EXAMPLE 405 cis-1-{3-[2-(2-Fluoro-5-trifluoromethoxy-phenyl)-ethoxy]-4-methoxy-benzoylamino}-4-methyl-cyclohexanecarboxylic acid

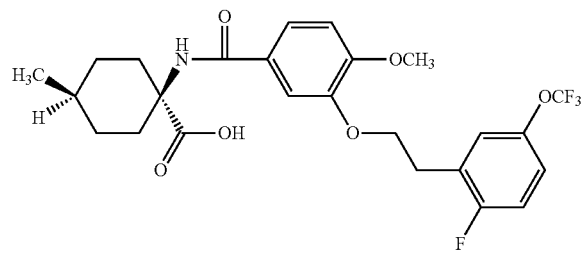 [SMILES: COc1ccc(C(=O)N[C@]2(C(=O)O)CC[C@H](C)CC2)cc1OCCc1cc(OC(F)(F)F)ccc1F]

The title compound was synthesized in analogy to example 404 using 2-(2-fluoro-5-trifluoromethoxyphenyl)ethanol instead of 2-(5-chloro-2-fluorophenyl)ethanol in the etherification step.
LC/MS (Method LC4): Rt=1.34 min; m/z=514.27 [MH$^+$]

EXAMPLE 406 cis-1-(4-Methoxy-3-phenethyloxy-benzoylamino)-4-methyl-cyclohexanecarboxylic acid

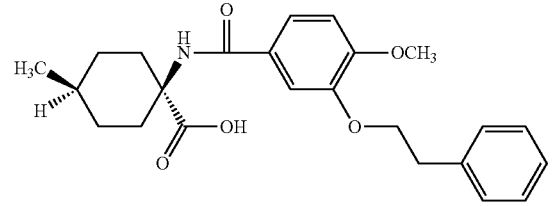

The title compound was synthesized in analogy to example 404 using 2-phenylethanol instead of 2-(5-chloro-2-fluorophenyl)ethanol in the etherification step.
LC/MS (Method LC4): Rt=1.30 min; m/z=412.29 [MH$^+$]
In analogy to example 92, the example compounds of the formulae I-10, I-11 and I-12 listed in table 21, in which R$^{110}$, R$^{111}$ and R$^{112}$ have the meanings given in table 21, were prepared.

I-10

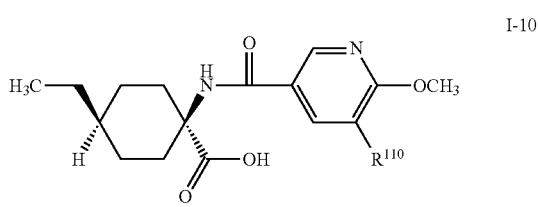

-continued

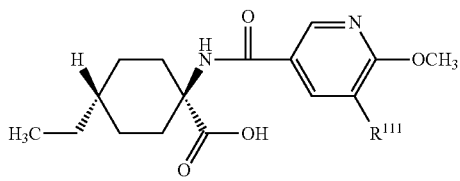

I-11

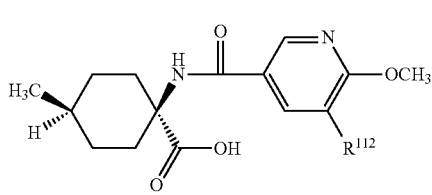

I-12

TABLE 21

Example compounds of the formulae I-10, I-11 and I-12

| Example | Formula | $R^{110}/R^{111}$ | LC/MS Method | m/z [MH⁺] | Retention time [min] |
|---|---|---|---|---|---|
| 407 | I-10 | 4-fluoro-phenyl | LC4 | 401.23 | 1.34 |
| 408 | I-11 | 4-chloro-3-trifluoro-methyl-phenyl | LC4 | 485.23 | 1.41 |
| 409 | I-10 | 3-fluoro-phenyl | LC4 | 401.19 | 1.34 |
| 410 | I-12 | 3,5-difluoro-phenyl | LC4 | 405.14 | 1.32 |
| 411 | I-10 | 3-fluoro-4-methoxy-phenyl | LC4 | 431.20 | 1.32 |
| 412 | I-11 | 3-fluoro-4-methoxy-phenyl | LC4 | 431.23 | 1.31 |

EXAMPLE 413

4-Ethyl-1-{[6-(2-hydroxy-ethoxy)-5-(3-trifluoromethyl-phenyl)-pyridine-3-carbonyl]-amino}-cyclohexanecarboxylic acid

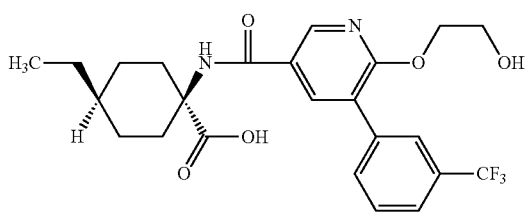 [SMILES: CC[C@H]1CC[C@](NC(=O)c2cnc(OCCO)c(-c3cccc(C(F)(F)F)c3)c2)(C(=O)O)CC1]

Step 1: 5-Bromo-6-chloro-nicotinic acid 2-hydroxy-ethyl ester

5-Bromo-6-chloro-nicotinoyl chloride (W. J. Thompson et al., J. Org. Chem. 49 (1984), 5237-5243, raw material; 7.00 g, apx 50% purity) was diluted with dichloromethane (50 ml), ethylenglycol (17 g) was added slowly and the mixture was stirred at room temperature over night. The mixture was partitioned between ether and water and the aqueous phase was extracted three times with ether. Each ether extract was washed with new water. The combined organic layers were dried over sodium chloride and evaporated to dryness in vacuo to yield the title compound (6.0 g) as raw material.

Step 2: 6-(2-Acetoxy-ethoxy)-5-bromo-nicotinic acid 2-acetoxy-ethyl ester

Sodium hydride (1.29 g, 60% purity in mineral oil) was dissolved in ethylene glycol (25 ml) and the raw material of step 1 was added. This mixture was stirred at 60° C. for 1 h. Volatiles were evaporated at 95° C., 1 mbar. The remainder was suspended in pyridine (25 ml), acetic anhydride (25 g) was added slowly during 30 minutes with stirring and stirring continued for 1 h. The mixture was partitioned between ethyl acetate and water, the organic phase was washed with 2N HCl and saturated sodium bicarbonate solution, dried over sodium chloride and evaporated to dryness in vacuo. The remainder was titurated in diethyl ether, cooled in an ice bath and filtered to yield 2.5 g of the title compound.

¹H-NMR: δ=8.70 (d, 1H); 8.40 (d, 1H); 4.65-4.62 (m, 2H); 4.47-4.45 (m, 2H); 4.40-4.37 (m, 2H); 4.36-4.32 (m, 2H); 2.02 (s, 3H); 2.01 (s, 3H)

Step 3: 4-Ethyl-1-{[6-(2-hydroxy-ethoxy)-5-(3-trifluoromethyl-phenyl)-pyridine-3-carbonyl]-amino}-cyclohexanecarboxylic acid The compound of step 2 was coupled to 3-trifluorophenyl-benzene boronic acid in analogy to step 3 of example 92, and the obtained ester intermediate was hydrolyzed in analogy to step 4 of example 1 to yield 6-(2-Hydroxy-ethoxy)-5-(3-trifluoro methyl-phenyl)-nicotinic acid. This intermediate was coupled to cis-1-amino-4-ethyl-cyclohexanecarboxylic acid methyl ester hydrochloride in analogy to step 1 of example 3, and the obtained ester intermediate was hydrolyzed in analogy to step 4 of example 1 to yield the title compound.

LC/MS (Method LC4): Rt=1.30 min; m/z=481.16 [MH⁺]

¹H-NMR: δ=12.2 (s, 1H); 8.64 (d, 1H); 8.24-8.18 (m, 2H); 8.06 (s, 1H); 8.01 (d, 1H); 7.78-7.70 (m, 2H); 4.78 (t, 1H); 4.44 (t, 2H); 3.71 (dt, 2H); 2.33-2.27 (m, 2H); 1.72-1.52 (m, 4H); 1.30-1.15 (m, 5H); 0.85 (t, 3H)

In analogy to example 413, the example compounds of the formula I-20 listed in table 22, in which $R^{120}$ has the meaning given in table 22, were prepared.

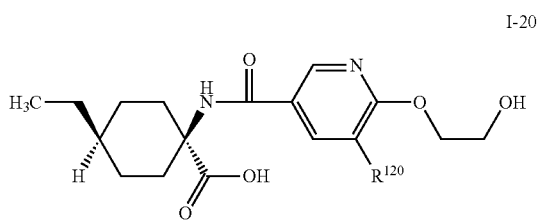

I-20

TABLE 22

Example compounds of the formula I-20

| Example | $R^{120}$ | LC/MS Method | m/z [MH⁺] | Retention time [min] |
|---|---|---|---|---|
| 414 | 3,4-difluoro-phenyl | LC4 | 449.20 | 1.27 |
| 415 | 3,5-difluoro-phenyl | LC4 | 449.21 | 1.27 |
| 416 | 3-trifluoromethoxy-phenyl | LC4 | 497.25 | 1.32 |
| 417 | 3-chloro-4-methoxy-phenyl | LC4 | 477.24 | 1.27 |

In analogy to example 119, the compounds of examples 418 and 419 were synthesized using the respective amino acid methyl ester hydrochloride in the amide coupling step.

EXAMPLE 418 trans-1-[3-[2-(3-Chloro-phenyl)-ethoxy]-4-(2-hydroxy-ethoxy)-benzoylamino]-4-ethyl-cyclohexanecarboxylic acid

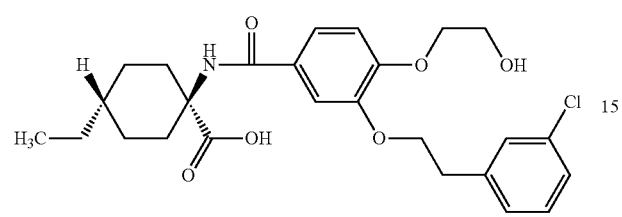

$^1$H-NMR: δ=12.0 (s, 1H); 8.0& (s, 1H); 7.48-7.44 (m, 2H); 7.42-7.38 (m, 1H); 7.37-7.25 (m, 3H); 7.03 (d, 1H); 4.82 (t, 1H); 4.22 (t, 2H); 4.02 (t, 2H); 3.78-3.70 (m, 2H); 3.06 (t, 2H); 2.31-2.22 (m, 2H); 1.68-1.52 (m, 4H); 1.32-1.12 (m, 5H); 0.85 (t, 3H)

EXAMPLE 419 cis-1-[3-[2-(3-Chloro-phenyl)-ethoxy]-4-(2-hydroxy-ethoxy)-benzoylamino]-4-ethyl-cyclohexanecarboxylic acid

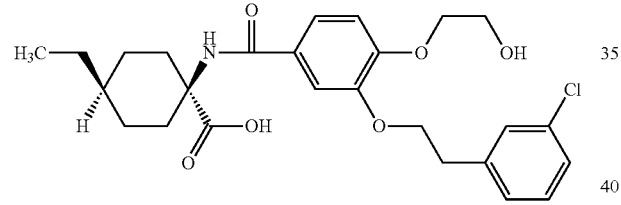

$^1$H-NMR: δ=12.1 (s, 1H); 7.97 (s, 1H); 7.49-7.43 (m, 2H); 7.41-7.38 (m, 1H); 7.37-7.26 (m, 3H); 7.03 (d, 1H); 4.82 (t, 1H); 4.23 (t, 2H); 4.02 (t, 2H); 3.78-3.70 (m, 2H); 3.08 (t, 2H); 2.34-2.24 (m, 2H); 1.68-1.50 (m, 4H); 1.27-1.11 (m, 5H); 0.83 (t, 3H)

In analogy to example 119, the compounds of examples 420, 421 and 422 were synthesized using 2-phenylethanol in the etherification step and the respective amino acid methyl ester hydrochloride in the amide coupling step.

EXAMPLE 420 trans-1-[4-(2-Hydroxy-ethoxy)-3-phenethyloxy-benzoylamino]-4-methyl-cyclohexanecarboxylic acid

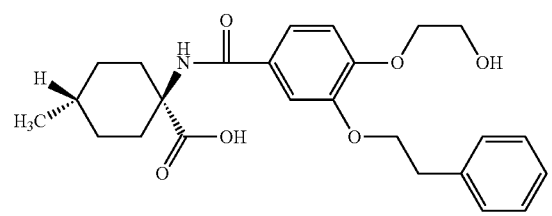 [SMILES: C[C@H]1CC[C@@](NC(=O)c2ccc(OCCO)c(OCCc3ccccc3)c2)(C(=O)O)CC1]

LC/MS (Method LC4): Rt=1.22 min; m/z=442.30 [MH$^+$]

EXAMPLE 421 cis-1-[4-(2-Hydroxy-ethoxy)-3-phenethyloxy-benzoylamino]-4-methyl-cyclohexanecarboxylic acid

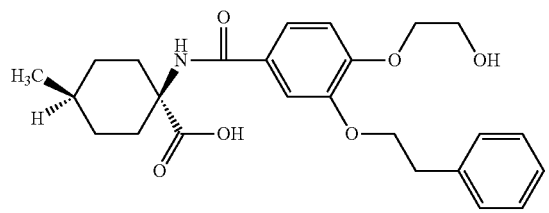 [SMILES: C[C@H]1CC[C@](NC(=O)c2ccc(OCCO)c(OCCc3ccccc3)c2)(C(=O)O)CC1]

LC/MS (Method LC4): Rt=1.21 min; m/z=442.29 [MH$^+$]

EXAMPLE 422

1-[4-(2-Hydroxy-ethoxy)-3-phenethyloxy-benzoylamino]cycloheptanecarboxylic acid

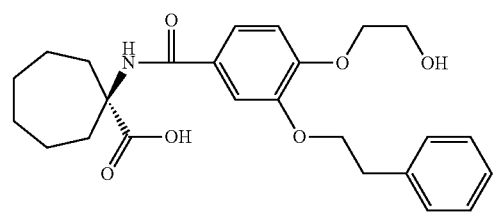

LC/MS (Method LC4): Rt=1.20 min; m/z=442.27 [MH$^+$]

EXAMPLE 423 cis-4-Ethyl-1-[(5-{2-[3-(2-hydroxy-ethyl)-phenyl]-ethoxy}-6-methoxy-pyridine-3-carbonyl)-amino]-cyclohexanecarboxylic acid

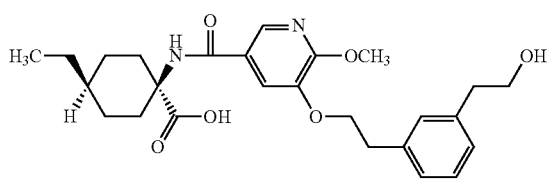 [SMILES: CC[C@H]1CC[C@](NC(=O)c2cnc(OC)c(OCCc3cccc(CCO)c3)c2)(C(=O)O)CC1]

The title compound was synthesized in analogy to example 90 using cis-1-amino-4-ethyl-cyclohexanecarboxylic acid methyl ester hydrochloride instead of trans-1-amino-4-methyl-cyclohexanecarboxylic acid methyl ester hydrochloride.

LC/MS (Method LC4): Rt=1.13 min; m/z=471.32 [MH$^+$]

EXAMPLE 424 trans-4-Ethyl-1-[(5-{2-[3-(2-hydroxy-ethyl)-phenyl]-ethoxy}-6-methoxy-pyridine-3-carbonyl)-amino]-cyclohexanecarboxylic acid

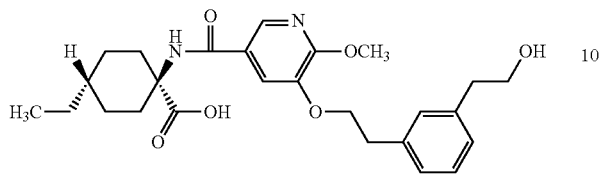

The title compound was synthesized in analogy to example 90 using trans-1-amino-4-ethyl-cyclohexanecarboxylic acid methyl ester hydrochloride instead of trans-1-amino-4-methyl-cyclohexanecarboxylic acid methyl ester hydrochloride.
LC/MS (Method LC4): Rt=1.12 min; m/z=471.33 [MH$^+$]

EXAMPLE 425 cis-4-Ethyl-1-[(3'-fluoro-6,4'-dimethoxy-biphenyl-3-carbonyl)-amino]-cyclohexanecarboxylic acid

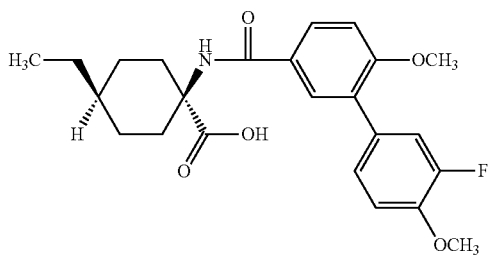 [SMILES: CC[C@H]1CC[C@](NC(=O)c2ccc(OC)c(-c3ccc(OC)c(F)c3)c2)(C(=O)O)CC1]

Step 1: 3'-Fluoro-6,4'-dimethoxy-biphenyl-3-carboxylic acid methyl ester

3-Bromo-4-methoxybenzoic acid methyl ester (500 mg, 2.04 mmol), 3-fluoro-4-methoxyphenylboronic acid (381 mg, 2.24 mmol), Tetrakis(triphenylphosphine)-palladium(0) (117 mmol, 0.10 mmol), and sodium bicarbonate (514 mg, 6.12 mmol) were partitioned between toluene (5 ml) and water (5 ml) and stirred in reflux for 36 hours. The mixture was partitioned between ethyl acetate and water, the combined organic extracts were dried over sodium sulfate and evaporated to dryness. The raw material was purified by silica gel chromatography with a heptane/ethyl acetate gradient. to yield the title compound (500 mg).
$^1$H-NMR: δ=7.95 (dd, 1H); 7.82 (d, 1H), 7.38 (dd, 1H); 7.30-7.19 (m, 3H); 3.88 (s, 3H); 3.87 (s, 3H), 3.83 (s, 3H).

Step 2: cis-4-Ethyl-1-[(3'-fluoro-6,4'-dimethoxy-biphenyl-3-carbonyl)-amino]-cyclohexanecarboxylic acid Hydrolysis of the ester group in analogy to step 2 of example 1, coupling of the obtained carboxylic acid to cis-1-amino-4-ethyl-cyclohexanecarboxylic acid methyl ester hydrochloride in analogy to step 1 of example 3 and hydrolysis of the methyl ester in analogy to step 4 of example 1 yielded the title compound.

$^1$H-NMR: δ=12.1 (br s, 1H); 8.06 (s, 1H); 7.84 (dd, 1H); 7.80 (d, 1H); 7.40 (dd, 1H); 7.32 (dd, 1H); 7.23 (dd, 1H), 7.18 (d, 1H); 3.88 (s, 3H); 3.83 (s, 3H); 2.85-2.77 (m, 2H); 1.70-1.50 (m, 4H); 1.25-1.10 (m, 5H); 0.85 (t, 3H).

EXAMPLE 426 cis-4-Ethyl-1-{[6-hydroxy-5-(3-trifluoromethyl-phenyl)-pyridine-3-carbonyl]-amino}-cyclohexanecarboxylic acid

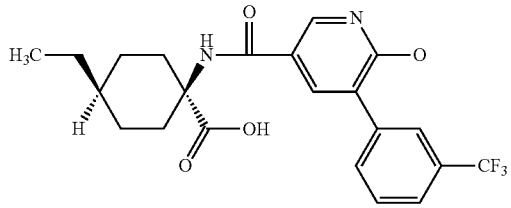 [SMILES: CC[C@H]1CC[C@](NC(=O)c2cnc(O)c(-c3cccc(C(F)(F)F)c3)c2)(C(=O)O)CC1]

Step 1:
6-Methoxy-5-(3-trifluoromethyl-phenyl)-nicotinic acid methyl ester

5-Bromo-6-methoxy-nicotinic acid methyl ester (1.03 g, 4.18 mmol), 3-trifluoromethylbenzeneboronic acid (0.795 g, 4.19 mmol), tetrakis(triphenylphosphine)palladium(0) (24 mg, 0.021 mmol) and sodium bicarbonate (1.05 g, 12.5 mmol) were partitioned between toluene (10 ml) and water (10 ml) under argon and stirred in reflux for 1 h. The material was partitioned between ethyl acetate and water, the combined organic extracts were dried over sodium chloride, filtered over a small plug of silica and evaporated to dryness. The solid material was titured with methanol, filtered and dried in vacuo to yield the title compound (1.4 g) sufficiently pure for further synthesis.

$^1$H-NMR: δ=8.80 (d, 1H); 8.20 (d, 1H); 7.93 (s, 1H); 7.90 (d, 1H); 7.78 (d, 1H); 7.71 (t, 1H); 3.97 (s, 3H); 3.88 (s, 3H).

Step 2:
6-Methoxy-5-(3-trifluoromethyl-phenyl)-nicotinic acid FFC.GFN2.004.4

The compound of step 1 was hydrolysed in analogy to step 2 of example 1 to yield the title compound.
$^1$H-NMR: δ=13.2 (br s, 1H); 8.78 (d, 1H); 8.19 (d, 1H); 7.93 (s, 1H); 7.90 (d, 1H); 7.78 (d, 1H); 7.70 (t, 1H); 3.97 (s, 3H).

Step 3: cis-4-Ethyl-1-{[6-hydroxy-5-(3-trifluoromethyl-phenyl)-pyridine-3-carbonyl]-amino}-cyclohexanecarboxylic acid methyl ester as mixture with cis-4-ethyl-1-{[6-methoxy-5-(3-trifluoromethyl-phenyl)-pyridine-3-carbonyl]-amino}-cyclohexanecarboxylic acid methyl ester The compound of step 3 (1.09 g, 3.67 mmol) was dissolved in thionyl chloride (5 ml) and stirred for 30 minutes at 60° C. Volatiles were evaporated, the remainder was dissolved in dichloromethane and added to a stirred mixture of cis-1-amino-4-ethylcyclohexanecarboxylic acid methyl ester hydrochloride (0.813 g, 3.67 mmol) and sodium bicarbonate (1.5 g, 18.3 mmol) in ethyl acetate (25 ml)/water (25 ml). Stirring continued over night, phases were separated, the aqueous phase was extracted twice with ethyl acetate, the combined organic extracts were dried over sodium chloride, decanted and evaporated to dryness in vacuo to yield the title compounds as mixture.

Step 4: cis-4-Ethyl-1-{[6-hydroxy-5-(3-trifluoromethyl-phenyl)-pyridine-3-carbonyl]-amino}-cyclohexanecarboxylic acid The compound of step 3 (1.71 g, 3.6 mmol)) was dissolved in dioxane (14 ml). 1 M aqueous lithium hydroxide (7 ml) was added, the mixture was stirred at 60° C. for 1 h, cooled, and partitioned between 2 N hydrochloric acid and EA. The aqueous phase was extracted with EA, the combined organic phases were dried over sodium chloride, filtered and evaporated to dryness. The residue was stirred in ethyl acetate (5 ml) and filtered, again to yield the title compound (0.28 g)

$^1$H-NMR: δ=12.7 (br s, 1H); 8.16 (s, 1H); 8.14-8.05 (m, 2H); 8.01 (d, 1H); 7.80-7.55 (m, 3H); 2.4-2.25 (m, 2H); 1.65-1.45 (m, 4H); 1.23-1.00 (m, 5H); 0.82 (t, 3H).

EXAMPLE 427

(1R,2R)-2-Ethyl-1-[(6-methoxy-3'-trifluoromethyl-biphenyl-3-carbonyl)-amino]-cyclopropanecarboxylic acid

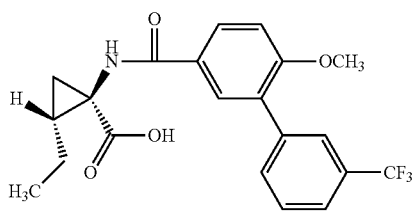 [SMILES: CC[C@@H]1C[C@]1(NC(=O)c1ccc(OC)c(-c2cccc(C(F)(F)F)c2)c1)C(=O)O]

3-bromo-4-methoxybenzoic acid methyl ester was coupled to 3-trifluoromethyl-phenylboronic acid in analogy to step 3 of example 92, and the obtained ester intermediate was hydrolyzed in analogy to step 4 of example 1 to yield 6-methoxy-3'-trifluoromethyl-biphenyl-3-carboxylic acid. This intermediate was coupled to the compound of step 1 of example 361 in analogy to step 1 of example 3, and the obtained ester intermediate was hydrolyzed in analogy to step 4 of example 1 to yield the title compound.

LC/MS (Method LC4): Rt=1.30 min; m/z=408.14 [MH$^+$]

EXAMPLE 428 cis-4-Ethyl-1-[(6-formyl-3'-trifluoromethyl-biphenyl-3-carbonyl)-amino]-cyclohexanecarboxylic acid

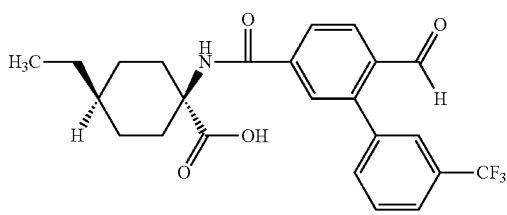 [SMILES: CC[C@H]1CC[C@](NC(=O)c2ccc(C=O)c(-c3cccc(C(F)(F)F)c3)c2)(C(=O)O)CC1]

Step 1: 6-Methyl-3'-trifluoromethyl-biphenyl-3-carboxylic acid methyl ester 3-trifluoromethylphenylboronic acid (278 mg, 1.46 mmol), tris(dibenzylideneacetone)-dipalladium(0) (61 mg, 0.066 mmol), potassium fluoride (255 mg, 4.38 mmol) and tri-tert-butylphosphonium tetrafluoroborate (46 mg, 0.159 mmol) in a flask were thoroughly flushed with argon. 3-bromo-4-methylbenzoic acid methyl ester (304 mg, 1.32 mmol) was added as solution in dioxane (5 ml). the mixture was stirred at 70° C. for 3 h, filtered over silica and evaporated to dryness. The raw material was purified by silica gel chromatography with a hetane/ethyl acetate gradient to yield the title compound (323 mg).

$^1$H-NMR: δ=7.91 (d, 1H); 7.82-7.77 (m, 2H); 7.75-7.70 (m, 3H); 7.51 (d, 1H); 3.85 (s, 3H); 2.30 (s, 3H)

Step 2: 6-Dibromomethyl-3'-trifluoromethyl-biphenyl-3-carboxylic acid methyl ester The compound of step 1 (1.48 g, 5.03 mmol), N-bromosuccinimide (2.27 g, 12.8 mmol) and dibenzoylperoxide (60 mg, 0.25 mmol) were suspended in tetrachloromethane and stirred for 3 h in reflux. The material was filtered over silica, eluted with diethyl ether and evaporated to dryness to yield the title compound as raw material.

Step 3: 6-Formyl-3'-trifluoromethyl-biphenyl-3-carboxylic acid methyl ester

The compound of step 2 (2.1 g, 4.65 mmol) was dissolved in acetonitrile (25 ml). Silver nitrate (1.97 g, 11.6 mmol) was dissolved in water (3 ml) and this solution was added to the acetonitrile solution. This mixture was stirred for 1 h in reflux. Acetonitrile was evaporated in vacuo, the remainder was partitioned between ethyl acetate and water, the combined organic extracts were dried over sodium chloride, filtered over a small plug of silica and evaporated to dryness. A crystalline crop was yielded on addition of methanol and filtration. The mother liquor was evaporated to dryness and purified by silica gel chromatography with a heptane/ethyl acetate gradient to yield a second crop. Both were combined to yield the title compound (1.0 g).

$^1$H-NMR: δ=9.9 (s, 1H); 8.18 (d, 1H); 8.10 (d, 1H); 8.02 (s, 1H); 7.90 (s, 1H); 7.88 (d, 1H); 7.83 (d, 1H); 7.76 (t, 1H); 3.91 (s, 3H)

Step 4: cis-4-Ethyl-1-[(6-formyl-3'-trifluoromethyl-biphenyl-3-carbonyl)-amino]-cyclohexanecarboxylic acid The title compound of step 3 was hydrolysed in analogy to step 4 of example 1. This intermediate was coupled to cis-1-amino-4-ethylcyclohexanecarboxylic acid methyl ester hydrochloride in analogy to step 1 of example 3, and the obtained ester intermediate was hydrolyzed in analogy to step 4 of example 1 to yield the title compound.

LC/MS (Method LC4): Rt=1.36 min; m/z=448.18 [MH$^+$]

EXAMPLE 429 trans-4-Ethyl-1-[(6-formyl-3'-trifluoromethyl-biphenyl-3-carbonyl)-amino]-cyclohexanecarboxylic acid

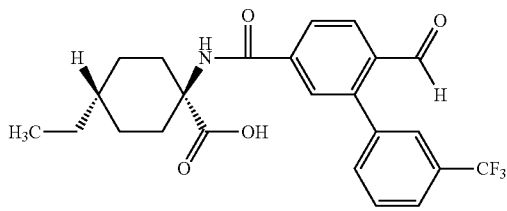 [SMILES: CC[C@H]1CC[C@@](NC(=O)c2ccc(C=O)c(-c3cccc(C(F)(F)F)c3)c2)(C(=O)O)CC1]

This compound was synthesized in analogy to example 428 using trans-1-amino-4-ethylcyclohexanecarboxylic acid methyl ester hydrochloride in the amide coupling step.
LC/MS (Method LC4): Rt=1.35 min; m/z=448.15 [MH$^+$]

EXAMPLE 430 cis-4-Ethyl-1-[(6-hydroxymethyl-3'-trifluoromethyl-biphenyl-3-carbonyl)-amino]-cyclohexanecarboxylic acid

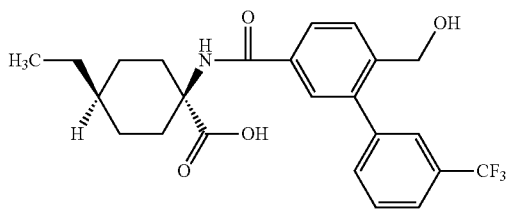 [SMILES: CC[C@H]1CC[C@](NC(=O)c2ccc(CO)c(-c3cccc(C(F)(F)F)c3)c2)(C(=O)O)CC1]

The compound of example 429 (21 mg, 0.047 mmol) was dissolved in tetrahydrofurane (1 ml), cooled in an ice bath, sodium borohydride (2 mg, 0.047 mmol) was added and thereafter methanol (0.2 ml) was added slowly with stirring. After 45 minutes, the mixture was partitioned between ethyl acetate and 2N hydrochloric acid, the combined organic layers were dried over sodium chloride and evaporated to dryness. The remainder was titured with heptane/diethylether and filtered to yield the title compound as white solid.
LC/MS (Method LC4): Rt=1.30 min; m/z=450.22 [MH$^+$]

EXAMPLE 431 trans-4-Ethyl-1-[(6-hydroxymethyl-3'-trifluoromethyl-biphenyl-3-carbonyl)-amino]-cyclohexanecarboxylic acid

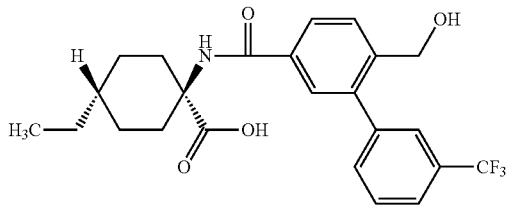 [SMILES: CC[C@H]1CC[C@@](NC(=O)c2ccc(CO)c(-c3cccc(C(F)(F)F)c3)c2)(C(=O)O)CC1]

This compound was synthesized in analogy to example 430 using the title compound of example 429 instead of example 428.
LC/MS (Method LC4): Rt=1.30 min; m/z=450.20 [MH$^+$]

EXAMPLE 432 trans-4-Ethyl-1-{[6-(3-hydroxy-propyl)-3'-trifluoromethyl-biphenyl-3-carbonyl]-amino}-cyclohexanecarboxylic acid

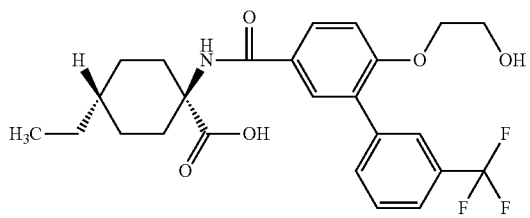 [SMILES: CC[C@H]1CC[C@@](NC(=O)c2ccc(OCCO)c(-c3cccc(C(F)(F)F)c3)c2)(C(=O)O)CC1]

Step 1 6-(2-Carboxy-vinyl)-3'-trifluoromethyl-biphenyl-3-carboxylic acid methyl ester The compound of step 3 of example 428 (400 mg, 1.30 mmol), malonic acid (262 mg, 2.52 mmol) and piperidine (16 mg, 0.19 mmol) were dissolved in pyridine (0.7 ml) and stirred in reflux for 1 h. The material was partitioned between 2N hydrochloric acid and ethyl acetate (product is only sparingly soluble). The combined organic extracts were dried over sodium chloride and evaporated to dryness to yield the title compound.
$^1$H-NMR: δ=12.55 (s, 1H); 8.09 (d, 1H); 8.03 (d, 1H); 7.92 (s, 1H); 7.87 (d, 1H); 7.76 (t, 1H); 7.74-7.68 (m, 2H); 7.40 (d, 1H); 7.61 (d, 1H); 3.88 (s, 3H)
LC/MS (Method LC4): Rt=1.30 min; m/z=349.16 [M–H$^+$]

Step 2: 6-(2-Carboxy-ethyl)-3'-trifluoromethyl-biphenyl-3-carboxylic acid methyl ester The compound of step 1 (400 mg, 1.14 mmol) and Palladium (10%) on charcoal (23 mg) were suspended in methanol (30 ml). The mixture was hydrogenated for 3 h at 4 bar hydrogen pressure, subsequently filtered over Celite and evaporated to dryness to yield the title compound (372 mg).
$^1$H-NMR: δ=12.2 (br s, 1H); 7.95 (d, 1H); 7.81 (d, 1H); 7.78-7.63 (m, 4H); 7.57 (d, 1H); 3.84 (s, 1H); 2.80 (t, 2H); 2.45 (t, 2H)
LC/MS (Method LC4): Rt=1.29 min; m/z=351.18 [M–H$^+$]

Step 3: 6-(3-Hydroxy-propyl)-3'-trifluoromethyl-biphenyl-3-carboxylic acid methyl ester The compound of step 2 (150 mg, 0.428 mmol) was dissolved in THF. N-methylmorpholine (56 mg, 0.556 mmol) and isobutylchloroformate (70 mg, 0.514 mmol) were added at room temperature. After stirring for 2 minutes, the mixture was filtered and rinsed with THF. Sodium borohydride (65 mg, 1.71 mmol) was added to the filtrate and thereafter slowly methanol until intensive foaming indicated the start of the reaction. After 5 minutes the reaction was complete as indicated by LC-MS analytics. Volatiles were evaporated in vacuo, the remainder was partitioned between ethyl acetate and saturated aqueous sodium bicarbonate solution, the combined organic extracts were dried over sodium chloride and evaporated to dryness. This raw material was purified by silica gel chromatography with a heptane/ethyl acetate gradient to yield the title compound (106 mg)

¹H-NMR: δ=7.95 (dd, 1H); 7.80 (d, 1H); 7.75-7.66 (m, 4H); 7.52 (d, 1H); 4.40 (t, 1H); 3.85 (s, 3H); 3.30-3.25 (m, 2H); 2.64-2.58 (m, 2H); 1.62-1.55 (m, 2H);

Step 4: 4-Ethyl-1-{[6-(3-hydroxy-propyl)-3'-trifluoromethyl-biphenyl-3-carbonyl]-amino}-cyclohexanecarboxylic acid The title compound of step 3 was hydrolysed in analogy to step 4 of example 1. This intermediate was coupled to trans-1-amino-4-ethylcyclohexanecarboxylic acid methyl ester hydrochloride in analogy to step 1 of example 3, and the obtained ester intermediate was hydrolyzed in analogy to step 4 of example 1 to yield the title compound.

LC/MS (Method LC4): Rt=1.32 min; m/z=478.22 [MH⁺]

EXAMPLE 433 cis-4-Ethyl-1-{[6-(3-hydroxy-propyl)-3'-trifluoromethyl-biphenyl-3-carbonyl]-amino}-cyclohexanecarboxylic acid

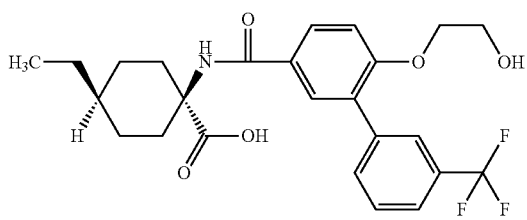 [SMILES: CC[C@H]1CC[C@](NC(=O)c2ccc(OCCO)c(-c3cccc(C(F)(F)F)c3)c2)(C(=O)O)CC1]

The title compound was synthesized in analogy to example 432 using cis-1-amino-4-ethyl-cyclohexanecarboxylic acid methyl ester hydrochloride instead of trans-1-amino-4-ethyl-cyclohexanecarboxylic acid methyl ester hydrochloride.

LC/MS (Method LC4): Rt=1.32 min; m/z=478.20 [MH⁺]

EXAMPLE 434 cis-1-{[6-(3-Hydroxy-propyl)-3'-trifluoromethyl-biphenyl-3-carbonyl]-amino}-4-methyl-cyclohexanecarboxylic acid

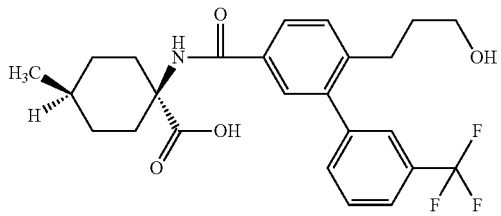 [SMILES: C[C@H]1CC[C@](NC(=O)c2ccc(CCCO)c(-c3cccc(C(F)(F)F)c3)c2)(C(=O)O)CC1]

The title compound was synthesized in analogy to example 432 using cis-1-amino-4-methyl-cyclohexanecarboxylic acid methyl ester hydrochloride instead of trans-1-amino-4-ethyl-cyclohexanecarboxylic acid methyl ester hydrochloride.

LC/MS (Method LC4): Rt=1.29 min; m/z=464.24 [MH⁺]

EXAMPLE 435 cis-1-({5-[2-(3-Chloro-phenyl)-ethoxy]-6-ethyl-pyridine-3-carbonyl}-amino)-4-methyl-cyclohexanecarboxylic acid

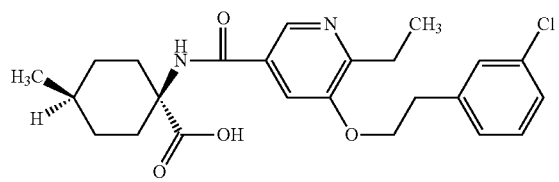 [SMILES: CCc1ncc(C(=O)N[C@]2(C(=O)O)CC[C@H](C)CC2)cc1OCCc1cccc(Cl)c1]

Step 1: 5-[2-(3-Chloro-phenyl)-ethoxy]-nicotinic acid ethyl ester

5-Hydroxy-nicotinic acid ethyl ester and 2-(3-chlorophenyl)ethanol were etherified in a Mitsunobu reaction in analogy to step 3 of example 3 to yield the title compound.

LC/MS (Method LC4): Rt=1.36 min; m/z=306.12 [MH⁺]

Step 2: 5-[2-(3-Chloro-phenyl)-ethoxy]-4-ethyl-4H-pyridine-1,3-dicarboxylic acid 3-ethyl ester 1-phenyl ester The compound of step 1 (100 mg, 0.327 mmol) was dissolved in THF (1.5 ml) and the mixture was cooled to −30° C. Phenyl chloroformate (77.6 mg, 0.49 mmol) was added and the mixture was stirred for 10 minutes. Ethyl magnesiumbromide (0.589 ml, 1M in THF) was added at −30° C. and the mixture was stirred for 30 minutes, partitioned between diethylether and aqueous ammonium chloride solution, the combined organic extracts were dried over sodium chloride and evaporated to dryness in vacuo. The raw material was purified by silica gel chromatography with a heptane/ethyl acetate gradient to yield the title compound (84 mg).

LC/MS (Method LC4): Rt=1.51 min; m/z=456.19 [MH⁺]

Step 3: 5-[2-(3-Chloro-phenyl)-ethoxy]-4-ethyl-nicotinic acid ethyl ester

The title compound of step 2 (80 mg, 0.175 mmol)) was dissolved in dichloromethane. 2,3-dichloro-5,6-dicyano-1,4-benzoquinone (80 mg, 0.35 mmol) was added and the mixture was stirred over night at room temperature. The mixture was partitioned between ethyl acetate and saturated sodium hydrogencarbonate solution with addition of some sodium sulfit. The combined organic extracts were dried over sodium chloride and evaporated to dryness in vacuo. The material was titured with diethyl ether, the solid material was separated by suction filtration, the filtrate was evaporated to dryness, again, to yield the title compound.

LC/MS (Method LC6): Rt=5.01 min; m/z=334.11 [MH⁺]

Step 4: cis-1-({5-[2-(3-Chloro-phenyl)-ethoxy]-6-ethyl-pyridine-3-carbonyl}-amino)-4-methyl-cyclohexanecarboxylic acid The title compound of step 3 was hydrolysed in analogy to step 2 of example 1, for extraction purpose, the aqueous phase was neutralised but not acidified. The crude acid was titured with ether and filtered but was reacted further as raw material with cis-1-amino-4-methylcyclohexanecarboxylic acid methyl ester hydrochloride in analogy to step 1 of example 3, and the obtained ester intermediate was hydrolyzed in analogy to step 4 of example 1 to yield the title compound.

LC/MS (Method LC4): Rt=1.34 min; m/z=445.18 [MH$^+$]

EXAMPLE 436 trans-1-({5-[2-(3-Chloro-phenyl)-ethoxy]-6-ethyl-pyridine-3-carbonyl}-amino)-4-methyl-cyclohexanecarboxylic acid

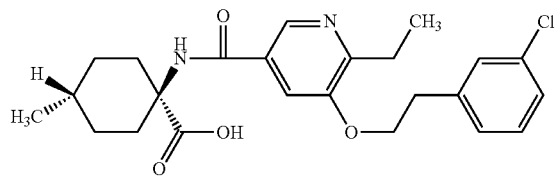 [SMILES: CCc1ncc(C(=O)N[C@]2(C(=O)O)CC[C@@H](C)CC2)cc1OCCc1cccc(Cl)c1]

The title compound was synthesized in analogy to example 435 using trans-1-amino-4-methyl-cyclohexanecarboxylic acid methyl ester hydrochloride instead of cis-1-amino-4-methyl-cyclohexanecarboxylic acid methyl ester hydrochloride.

LC/MS (Method LC4): Rt=1.33 min; m/z=445.17 [MH$^+$]

EXAMPLE 437 cis-1-({5-[2-(3-Chloro-phenyl)-ethoxy]-6-ethyl-pyridine-3-carbonyl}-amino)-4-ethyl-cyclohexanecarboxylic acid

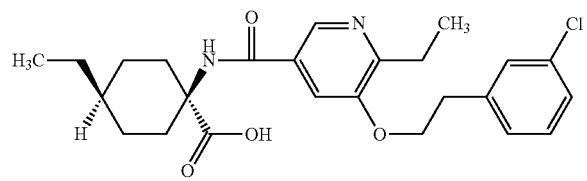 [SMILES: CCc1ncc(C(=O)N[C@]2(C(=O)O)CC[C@H](CC)CC2)cc1OCCc1cccc(Cl)c1]

The title compound was synthesized in analogy to example 435 using cis-1-amino-4-ethyl-cyclohexanecarboxylic acid methyl ester hydrochloride instead of cis-1-amino-4-methyl-cyclohexanecarboxylic acid methyl ester hydrochloride.

LC/MS (Method LC4): Rt=1.38 min; m/z=459.20 [MH$^+$]

EXAMPLE 438 trans-1-({5-[2-(3-Chloro-phenyl)-ethoxy]-6-ethyl-pyridine-3-carbonyl}-amino)-4-ethyl-cyclohexanecarboxylic acid

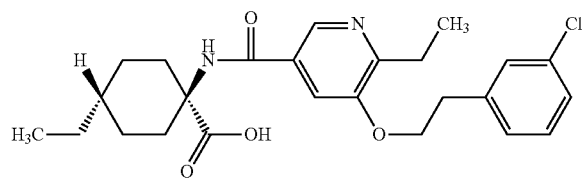 [SMILES: CCc1ncc(C(=O)N[C@]2(C(=O)O)CC[C@@H](CC)CC2)cc1OCCc1cccc(Cl)c1]

The title compound was synthesized in analogy to example 435 using trans-1-amino-4-ethyl-cyclohexanecarboxylic acid methyl ester hydrochloride instead of cis-1-amino-4-methyl-cyclohexanecarboxylic acid methyl ester hydrochloride.

LC/MS (Method LC4): Rt=1.23 min; m/z=459.26 [MH$^+$]

EXAMPLE 439 trans-1-({5-Acetyl-4-[2-(3-chloro-phenyl)-ethoxy]-thiophene-2-carbonyl}-amino)-4-ethyl-cyclohexanecarboxylic acid

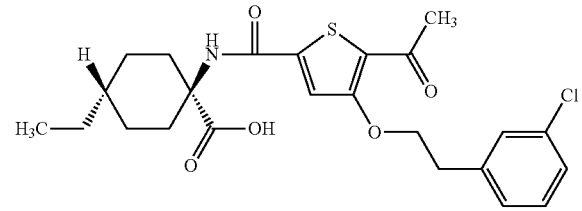 [SMILES: CC[C@H]1CC[C@@](NC(=O)c2cc(OCCc3cccc(Cl)c3)c(C(C)=O)s2)(C(=O)O)CC1]

5-Acetyl-4-hydroxythiophene-2-carboxylic acid methyl ester and 2-(3-chlorophenyl)ethanol were etherified in a Mitsunobu reaction in analogy to step 3 of example 3. This intermediate was hydrolysed in analogy to step 2 of example 1, coupled with trans-1-amino-4-ethylcyclohexanecarboxylic acid methyl ester hydrochloride in analogy to step 1 of example 3, and the obtained ester intermediate was hydrolyzed in analogy to step 4 of example 1 to yield the title compound.

LC/MS (Method LC4): Rt=1.37 min; m/z=478.15 [MH$^+$]

EXAMPLE 440 trans-1-({4-[2-(3-Chloro-phenyl)-ethoxy]-5-ethyl-thiophene-2-carbonyl}-amino)-4-ethyl-cyclohexanecarboxylic acid

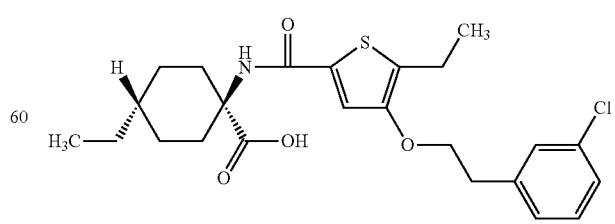

5-Acetyl-4-[2-(3-chloro-phenyl)-ethoxy]-thiophene-2-carboxylic acid methyl ester (78 mg, 0.23 mmol) was dissolved in 0.5 M methanolic hydrogen chloride and hydrogenated with 15 mg Palladium 10% on charcoal at room temperature with 3 bar hydrogen pressure for 14 days. The mixture was filtered over Celite, evaporated to dryness in vacuo and purified by silica gel chromatography with a heptane/ethyl acetate gradient. This intermediate was hydrolysed in analogy to step 2 of example 1, coupled with trans-1-amino-4-ethylcyclohexanecarboxylic acid methyl ester hydrochloride in analogy to step 1 of example 3, and the obtained ester intermediate was hydrolyzed in analogy to step 4 of example 1 to yield the title compound.

LC/MS (Method LC4): Rt=1.31 min; m/z=464.22 [MH$^+$]

EXAMPLE 441 trans-4-Ethyl-1-{[4-methoxy-3-(2-m-tolyl-ethoxy)-benzoyl]-methyl-amino}-cyclohexanecarboxylic acid

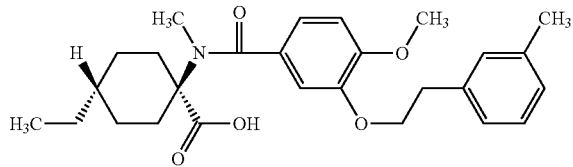 [SMILES: CC[C@H]1CC[C@](C(=O)O)(N(C)C(=O)c2ccc(OC)c(OCCc3cccc(C)c3)c2)CC1]

Trans-4-ethyl-1-methylaminocyclohexanecarboxylic acid methyl ester hydrochloride was synthesized in via a Strecker aminonitrile synthesis using N-methylamine hydrochloride instead of ammonium chloride, subsequent acidic hydrolysis of the nitrile to the carboxylic acid and acidic esterification in in methanol. This intermediate was coupled to 4-methoxy-3-(2-m-tolyl-ethoxy)-benzoic acid chloride in analogy to step 3 of example 1, and the obtained ester intermediate was hydrolyzed in analogy to step 4 of example 1 to yield the title compound.

LC/MS (Method LC4): Rt=1.39 min; m/z=454.33 [MH$^+$]

EXAMPLE 442

(R,S)-trans-4-Methyl-1-[4-(2-m-tolyl-ethoxy)-3-(2,2,2-trifluoro-1-hydroxy-ethyl)-benzoylamino]-cyclohexanecarboxylic acid

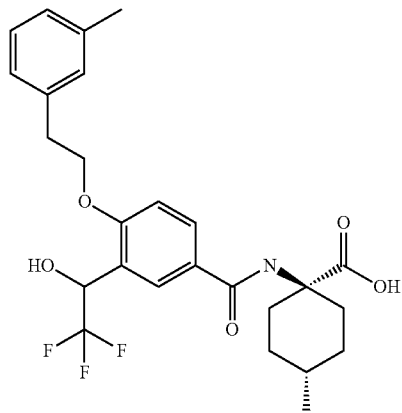 [SMILES: Cc1cccc(CCOc2ccc(C(=O)N[C@]3(C(=O)O)CC[C@@H](C)CC3)cc2C(O)C(F)(F)F)c1]

Step 1: 3-Formyl-4-(2-m-tolyl-ethoxy)-benzoic acid 2-m-tolyl-ethyl ester 4.0 g 3-Formyl-4-hydroxybenzoic acid, 9.6 g 1-(2-Bromoethyl)-3-methyl-benzene, and 13.3 g K$_2$CO$_3$ were added to 100 ml of anhydrous DMF and stirred at 90° C. for 14 h. Then 300 ml of water were added, and extracted three times with 200 ml EA each. The organic layer was then washed with 200 ml of water, dried using MgSO$_4$, and evaporated yielding 8.0 g of the title compound that was used without further purification.

Step 2: 3-Formyl-4-(2-m-tolyl-ethoxy)-benzoic acid 8.0 g of 3-Formyl-4-(2-m-tolyl-ethoxy)-benzoic acid 2-m-tolyl-ethyl ester and 1.7 g of LiOH (Monohydrate) were stirred in 30 ml of THF and 2 ml of water at room temperature for 16 h. Then, an additional 1 g of LiOH (monohydrate) was added and the mixture stirred at room temperature for 4 h. Then, 100 ml of water were added, the THF evaporated and the aqueous layer was washed twice with diisopropylether, 100 ml each. The aqueous layer was then acidified to pH=3 using aqueous HCl-solution and the crude product collected by filtration. Chromatography on silica gel using a gradient EA/HEP to EA yielded 1.2 g of the title compound that was used without further purification.

Step 3: (R,S)4-(2-m-Tolyl-ethoxy)-3-(2,2,2-trifluoro-1-hydroxy-ethyl)-benzoic acid 0.75 g of 3-Formyl-4-(2-m-tolyl-ethoxy)-benzoic acid, 8.9 mg of 1,3-Bis(1-adamantyl)imidazol-2-ylidene, and 1.9 g of (Trifluormethyl)trimethylsilane were dissolved in 10 ml of anhydrous DMF and stirred at room temperature for 24 h. Then, another 5 mg of 1,3-Bis(1-adamantyl)imidazol-2-ylidene and 1.0 g of (Trifluormethyl)trimethylsilane were added and stirring was continued at room temperature for 24 h. Then, 10 ml of a 2n aqueous solution of HCl were added and the mixture was stirred at room temperature for 4 h. Then, 50 ml of water were added and the mixture extracted tree times using 30 ml EA each. The organic layer was dried using MgSO$_4$ and the solvent evaporated to yield 0.7 g of the title compound that was used without further purification.

Step 4: 4-Methyl-1-[4-(2-m-tolyl-ethoxy)-3-(2,2,2-trifluoro-1-hydroxy-ethyl)-benzoylamino]-cyclohexanecarboxylic acid methyl ester The title compound was synthesized form (R,S)4-(2-m-Tolyl-ethoxy)-3-(2,2,2-trifluoro-1-hydroxy-ethyl)-benzoic acid and trans-1-Amino-4-methyl-cyclohexanecarboxylic acid methyl ester in analogy to example 126, step 4.

R$_f$(EA/HEP 1:2)=0.28

Step 5: 4-Methyl-1-[4-(2-m-tolyl-ethoxy)-3-(2,2,2-trifluoro-1-hydroxy-ethyl)-benzoylamino]-cyclohexanecarboxylic acid 170 mg of 4-Methyl-1-[4-(2-m-tolyl-ethoxy)-3-(2,2,2-trifluoro-1-hydroxy-ethyl)-benzoylamino]-cyclohexanecarboxylic acid methyl ester and 28 mg of lithium hydroxide were stirred in 50 ml of methanol and 1 ml of water for 5 h at 40° C. The reaction mixture was then diluted using 10 ml of water, the methanol evaporated and acidified to pH=2 using aqueous NaHSO$_4$-solution. The mixture was then stirred for 30 minutes at room temperature, the product isolated by filtration and dried in vacuo to yield 138 mg of the title compound.

LC/MS (Method LC4): Rt=1.32 min. m/z=494.29 [MH+]

EXAMPLE 443

Trans-1-{[3'-Chloro-6-(3,3-difluoro-cyclobutoxy)-4'-methoxy-biphenyl-3-carbonyl]-amino}-4-methyl-cyclohexanecarboxylic acid

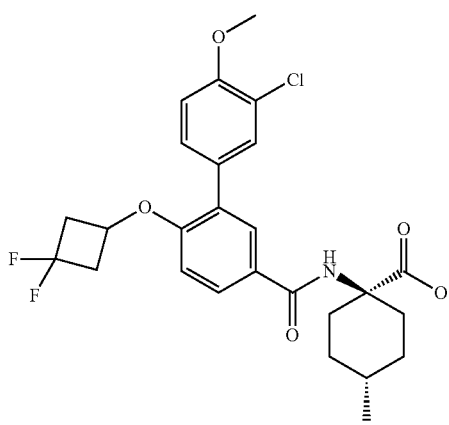 [SMILES: COc1ccc(-c2cc(C(=O)N[C@]3(C(=O)O)CC[C@@H](C)CC3)ccc2OC2CC(F)(F)C2)cc1Cl]

Step 1: 4-(3,3-Difluoro-cyclobutoxy)-3-nitro-benzoic acid methyl ester 1.0 g of Methyl 4-fluoro-3-nitrobenzoate, 1.6 g of 3,3-Difluoro-cyclobutanol, and 3.3 g of $Cs_2CO_3$ were stirred in 10 ml of anhydrous DMF for 7 h at 60° C. The reaction mixture was then poured into 100 ml of water and extracted three times using 30 ml of EA each. The organic layer was dried using $MgSO_4$ and volatiles were evaporated to yield 1.4 g of the title compound that was used without further purification.

Step 2: 3-Amino-4-(3,3-difluoro-cyclobutoxy)-benzoic acid methyl ester 1.4 g of 4-(3,3-Difluoro-cyclobutoxy)-3-nitro-benzoic acid methyl ester were dissolved using 50 ml of EA and 10 ml of acetic acid, 200 mg of Pd/C 10% (50% water) added and hydrogenated under an atmosphere of hydrogen at normal pressure for 16 h at room temperature. The reaction mixture was filtrated, 100 ml of EA added and washed twice using 30 ml of a saturated aqueous $Na_2CO_3$-solution. The organic layer was dried using $MgSO_4$ and volatiles were evaporated to yield 1.0 g of the title compound that was used without further purification.

Step 3: 3-Bromo-4-(3,3-difluoro-cyclobutoxy)-benzoic acid methyl ester 1.0 g of 3-Amino-4-(3,3-difluoro-cyclobutoxy)-benzoic acid methyl ester was dissolved in 100 ml of half-concentrated aqueous HBr-solution. Then, a solution of 295 mg NaNO₂ in 5 ml of water was added dropwise at 0° C. Stirring was continued at 0° C. for 15 minutes. Then, a solution of 558 mg CuBr in 10 ml of half-concentrated aqueous HBr-solution was added dropwise and the reaction mixture was stirred for 2 h at room temperature. Then, the reaction mixture was extracted three times using 100 ml of EA each. The organic layer was then washed three times using 100 ml of a saturated aqueous $NaHCO_3$-solution, dried using $MgSO_4$ and volatiles were evaporated to yield 150 mg of the title compound that was used without further purification.

Step 4: 3'-Chloro-6-(3,3-difluoro-cyclobutoxy)-4'-methoxy-biphenyl-3-carboxylic acid methyl ester 150 mg of 3-Bromo-4-(3,3-difluoro-cyclobutoxy)-benzoic acid methyl ester, 113 mg of 3-chloro-4-methoxyphenylboronic acid, 129 mg $K_2CO_3$, 10 mg of palladium(II)acetate, and 25 mg of triphenylphosphine were dissolved using 10 ml of DMF and 0.5 ml of water. The reaction mixture was stirred at 120° C. for 2 h, then cooled to room temperature, 50 ml of water added and extracted three times using 30 ml of EA each. The organic layer was dried using $MgSO_4$ and volatiles were evaporated. Chromatography on silica gel using EA/HEP 1:5 yielded 90 mg of the title compound, viscous oil.

$R_f$(EA/HEP 1:5)=0.37

Step 5: 3'-Chloro-6-(3,3-difluoro-cyclobutoxy)-4'-methoxy-biphenyl-3-carboxylic acid 85 mg of 3'-Chloro-6-(3,3-difluoro-cyclobutoxy)-4'-methoxy-biphenyl-3-carboxylic acid methyl ester and 14 mg of LiOH (monohydrate) were dissolved using 5 ml of methanol and 0.5 ml of water. The mixture was stirred for 15 h at room temperature. Then, 14 mg of LiOH (monohydrate) were added and the reaction mixture stirred for 24 h at room temperature. Then, 10 ml of water were added and the methanol evaporated. The mixture was then acidified to pH=2 using aqueous $NaHSO_4$-solution. The mixture was stirred for 30 minutes at room temperature. The product was then collected by filtration and dried in vacuo to yield 65 mg of the title compound that was used without further purification.

Step 6: 1-{[3'-Chloro-6-(3,3-difluoro-cyclobutoxy)-4'-methoxy-biphenyl-3-carbonyl]-amino}-4-methyl-cyclohexanecarboxylic acid methyl ester The title compound was synthesized form 3'-Chloro-6-(3,3-difluoro-cyclobutoxy)-4'-methoxy-biphenyl-3-carboxylic acid and trans-1-Amino-4-methyl-cyclohexanecarboxylic acid methyl ester in analogy to example 126, step 4.

$R_f$(EA/HEP 1:1)=0.40

Step 7: Trans-1-{[3'-Chloro-6-(3,3-difluoro-cyclobutoxy)-4'-methoxy-biphenyl-3-carbonyl]-amino}-4-methyl-cyclohexanecarboxylic acid The title compound was synthesized in analogy to example 442, step 5.

LC/MS (Method LC4): Rt=1.35 min. m/z=508.18 [MH+]

EXAMPLE 444

1-[(2',6'-Difluoro-4'-methoxy-6-trifluoromethyl-biphenyl-3-carbonyl)-amino]-4-methyl-cyclohexanecarboxylic acid

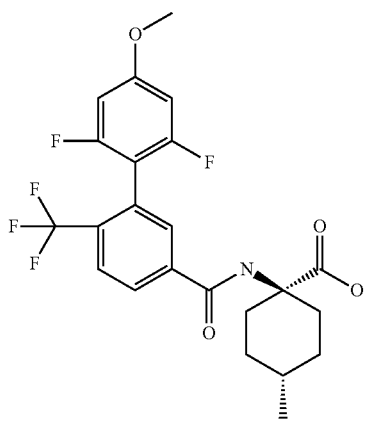 [SMILES: COc1cc(F)c(-c2cc(C(=O)N[C@]3(C(=O)O)CC[C@@H](C)CC3)ccc2C(F)(F)F)c(F)c1]

Step 1: 3-Bromo-4-trifluoromethyl-benzoic acid 5.0 g of 3-amino-4-trifluoromethyl-benzoic acid were dissolved using 50 ml of acetic acid. Then, 50 g of ice and 50 ml of a saturated aqueous HBr-solution were added and a solution of 2.0 g NaNO$_2$ in 10 ml of water was added dropwise at 0° C. The reaction mixture was then stirred at room temperature for 10 minutes. Then, the reaction mixture was added dropwise to a suspension of 7.0 g CuBr and 10.9 g CuBr2 in 100 ml of a half-concentrated aqueous solution of HBr. The resulting mixture was then stirred for 2 h at room temperature, then diluted using 2l of water, stirred for 1 h and finally the precipitate was isolated by filtration. The precipitate was dried in vacuo to yield 5.2 g of the title compound that was used without further purification.

Step 2: 1-(3-Bromo-4-trifluoromethyl-benzoylamino)-4-methyl-cyclohexanecarboxylic acid methyl ester The title compound was synthesized form 3-Bromo-4-trifluoromethyl-benzoic acid and trans-1-Amino-4-methyl-cyclohexanecarboxylic acid methyl ester in analogy to example 126, step 4.
R$_f$(EA/HEP 1:2)=0.31

Step 3: 1-[(2',6'-Difluoro-4'-methoxy-6-trifluoromethyl-biphenyl-3-carbonyl)-amino]-4-methyl-cyclohexanecarboxylic acid methyl ester 300 mg of 1-(3-Bromo-4-trifluoromethyl-benzoylamino)-4-methyl-cyclohexanecarboxylic acid methyl ester, 267 mg of 2,6-difluoro-4-methoxyphenylboronic acid, 65 mg of tris(dibenzylideneacetone)di-palladium(0), 96 mg of bis(2-dicyclohexylphosphinophenyl)ether, 453 mg of K$_3$PO$_4$, and 1 g of molecular sieve 4 Å were added to 10 ml of toluene. The mixture was made oxygen-free by passing argon through it. Then, the mixture was kept at 160° C. under microwave irradiation for 2 h. Then, 267 mg of 2,6-difluoro-4-methoxyphenylboronic acid, 65 mg of tris(dibenzylideneacetone)di-palladium(0), 96 mg of bis(2-dicyclohexylphosphinophenyl) ether were added and the mixture was kept at 160° C. under microwave irradiation for 2 h. The mixture was cooled to room temperature and 100 ml of EA added. The mixture was then washed twice using 20 ml of a saturated aqueous Na$_2$CO$_3$-solution each. The organic layer was dried using MgSO$_4$ and the solvent evaporated. Chromatography on silica gel using EA/HEP 1:5 yielded 16 mg of the title compound, viscous oil.

Step 4: 1-[(2',6'-Difluoro-4'-methoxy-6-trifluoromethyl-biphenyl-3-carbonyl)-amino]-4-methyl-cyclohexanecarboxylic acid The title compound was synthesized in analogy to example 442, step 5.
LC/MS (Method LC4): Rt=1.34 min. m/z=472.14 [MH$^+$]

EXAMPLE 445

1-[(3'-Chloro-2',6'-difluoro-6,4'-dimethoxy-biphenyl-3-carbonyl)-amino]-4-methyl-cyclohexanecarboxylic acid

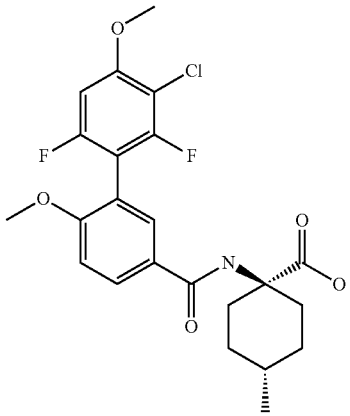 [SMILES: COc1ccc(C(=O)N[C@]2(C(=O)O)CC[C@@H](C)CC2)cc1-c1c(F)cc(OC)c(Cl)c1F]

Step 1:
3-Chloro-2,6-difluoro-4-methoxyphenylboronic acid 5.1 g of 2,2,6,6-tetramethylpiperidine were dissolved using 200 ml of anhydrous THF. 12.4 ml of a 2.7M solution of n-butyllithium in heptane were added at −10° C. and the mixture was stirred for 10 minutes at −10° C. The mixture was then cooled to −70° C. and a solution of 5.0 g 2-chloro-3,5-difluoroanisole in 40 ml of anhydrous THF added dropwise at −70° C. Stirring was continued for 1 h at −75° C. Then, 7.9 g of triisopropyl borat were added and the mixture was allowed to warm to room temperature. Stirring was continued for 1 h at room temperature. Then, the reaction mixture was poured into 200 ml of a saturated aqueous NaHSO$_4$-solution and extracted twice using 100 ml EA each. The organic layer was washed using 100 ml of a saturated aqueous NaHSO$_4$-solution, dried using MgSO$_4$ and evaporated to yield 5.6 g of the title compound that was used without further purification.

Step 2: 1-(3-Bromo-4-methoxy-benzoylamino)-4-methyl-cyclohexanecarboxylic acid methyl ester The title compound was synthesized form 3-bromo-4-methoxy-benzoic acid and trans-1-amino-4-methyl-cyclohexanecarboxylic acid methyl ester in analogy to example 126, step 4.
R$_f$(EA/HEP 1:2)=0.12

Step 3: 1-[(3'-Chloro-2',6'-difluoro-6,4'-dimethoxy-biphenyl-3-carbonyl)-amino]-4-methyl-cyclohexanecarboxylic acid methyl ester 300 mg of 1-(3-Bromo-4-methoxy-benzoylamino)-4-methyl-cyclohexanecarboxylic acid methyl ester, 36 mg of tris(dibenzylideneacetone)di-palladium(0), 150 mg of KF, 27 mg of tri-tert-butylphosphonium tetrafluoroborate, and 347 mg of 3-Chloro-2,6-difluoro-4-methoxyphenylboronic acid were suspended using 5 ml of anhydrous dioxane and oxygen was removed by passing argon through. Then, 12 mg of N,N-diisopropylethylamine were added and again argon passed through the suspension. Stirring was continued for 24 h at room temperature. The reaction mixture was then filtered and evaporated. The residue was purified by preparative RP HPLC (water/ACN gradient) to yield 150 mg of the title compound, viscous oil.

Step 4: 1-[(3'-Chloro-2',6'-difluoro-6,4'-dimethoxy-biphenyl-3-carbonyl)-amino]-4-methyl-cyclohexanecarboxylic acid 150 mg of 1-[(3'-Chloro-2',6'-difluoro-6,4'-dimethoxy-biphenyl-3-carbonyl)-amino]-4-methyl-cyclohexanecarboxylic acid methyl ester and 25 mg NaOH were dissolved using 5 ml of dioxane and 0.5 ml of water. The mixture was stirred at 80° C. for 6 h. Then, 15 ml of water were added, the dioxane evaporated and acidified to pH=3 using aqueous NaHSO$_4$-solution. The mixture was stirred for 30 minutes at room temperature. The product was then isolated by filtration and dried in vacuo to yield 110 mg of the title compound.

LC/MS (Method LC4): Rt=1.32 min. m/z=468.16 [MH$^+$]

EXAMPLE 446

Trans-1-[(3'-Chloro-5-fluoro-6,4'-dimethoxy-biphenyl-3-carbonyl)-amino]-4-methyl-cyclohexanecarboxylic acid

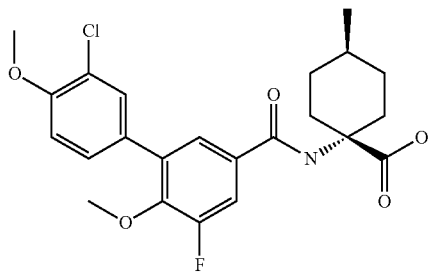 [SMILES: COc1ccc(-c2cc(C(=O)N[C@]3(C(=O)O)CC[C@@H](C)CC3)cc(F)c2OC)cc1Cl]

Step 1: 3-Bromo-5-fluoro-4-hydroxy-benzoic acid methyl ester 3.9 g of 3-fluoro-4-hydroxy-benzoic acid methyl ester were dissolved using 25 ml of acetic acid and 25 ml of DCM. The mixture was cooled to 0° C. and 1.4 ml bromine added slowly (30 minutes) at 0° C. Stirring was continued at room temperature for 18 h. Then, 200 ml of EA and a solution of 7.6 g Na$_2$SO$_3$ in 50 ml of water were added and the resulting mixture was stirred for 10 minutes at room temperature. The layers were separated, and the organic layer was washed using first 50 ml of water and second 50 ml of a saturated aqueous NaCl-solution. The organic layer was dried using MgSO$_4$ and evaporated to yield 5.0 g of the title compound that was used without further purification.

Step 2: 3-Bromo-5-fluoro-4-methoxy-benzoic acid methyl ester 5.0 g of 3-Bromo-5-fluoro-4-hydroxy-benzoic acid methyl ester were dissolved using 50 ml of acetone. Then, 8.3 g of K$_2$CO$_3$ and 2.5 ml of CH$_3$I were added and the reaction mixture stirred at room temperature for 48 h. The reaction mixture was then filtrated and evaporated. Chromatography on silica gel using EA/HEP 1:2 yielded 2.0 g of the title compound, oil.

Step 3: 3'-Chloro-5-fluoro-6,4'-dimethoxy-biphenyl-3-carboxylic acid methyl ester 500 mg of 3-Bromo-5-fluoro-4-methoxy-benzoic acid methyl ester, 532 mg of 3-chloro-4-methoxyphenylboronic acid, 110 mg of tetrakis(triphenylphosphine) palladium(0), and 2.5 g Cs$_2$CO$_3$ were dissolved using 16.5 ml of DMF and 3.5 ml of water. The reaction mixture was stirred at 45° C. for 2 h and then poured into 75 ml of water. The reaction mixture was then extracted three times using 50 ml of EA each. The organic layer was washed twice using 25 ml of a half-saturated aqueous NaCl-solution, dried using MgSO$_4$ and evaporated. Chromatography on silica gel using EA/HEP 1:3 yielded 500 mg of the title compound, viscous oil.

Step 4: 3'-Chloro-5-fluoro-6,4'-dimethoxy-biphenyl-3-carboxylic acid 500 mg of 3'-Chloro-5-fluoro-6,4'-dimethoxy-biphenyl-3-carboxylic acid methyl ester were dissolved using 10 ml of methanol and 1.8 ml of a 1M aqueous NaOH-solution added. The reaction mixture was stirred at 60° C. for 5 h and was then allowed to cool to room temperature. The reaction mixture was then poured into 25 ml of water and acidified to pH=4 using aqueous NaHSO$_4$-solution. The mixture was extracted three times using 20 ml of EA each. The organic layer was dried using MgSO$_4$ and evaporated to yield 430 mg of the title compound that was used without further purification.

Step 5: 1-[(3'-Chloro-5-fluoro-6,4'-dimethoxy-biphenyl-3-carbonyl)-amino]-4-methyl-cyclohexanecarboxylic acid methyl ester The title compound was synthesized form 3'-Chloro-5-fluoro-6,4'-dimethoxy-biphenyl-3-carboxylic acid and trans-1-amino-4-methyl-cyclohexanecarboxylic acid methyl ester in analogy to example 126, step 4.

Step 6: 1-[(3'-Chloro-5-fluoro-6,4'-dimethoxy-biphenyl-3-carbonyl)-amino]-4-methyl-cyclohexanecarboxylic acid The title compound was synthesized form 1-[(3'-Chloro-5-fluoro-6,4'-dimethoxy-biphenyl-3-carbonyl)-amino]-4-methyl-cyclohexanecarboxylic acid methyl ester in analogy to example 126, step 5.

LC/MS (Method LC4): Rt=1.34 min. m/z=450.11 [MH$^+$]

EXAMPLE 447

Cis-1-[(3'-chloro-5-fluoro-6,4'-dimethoxy-biphenyl-3-carbonyl)-amino]-4-ethyl-cyclohexanecarboxylic acid

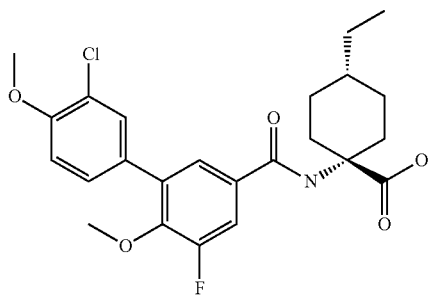 [SMILES: CC[C@H]1CC[C@](NC(=O)c2cc(F)c(OC)c(-c3ccc(OC)c(Cl)c3)c2)(C(=O)O)CC1]

The title compound synthesized in analogy to example XX+4 using cis-1-amino-4-ethyl-cyclohexanecarboxylic acid methyl ester instead of trans-1-amino-4-methyl-cyclohexanecarboxylic acid methyl ester.
LC/MS (Method LC4): Rt=1.38 min. m/z=464.14 [MH$^+$]

EXAMPLE 448

Cis-1-[(3'-Chloro-5-fluoro-6,4'-dimethoxy-biphenyl-3-carbonyl)-amino]-4-trifluoromethyl-cyclohexanecarboxylic acid

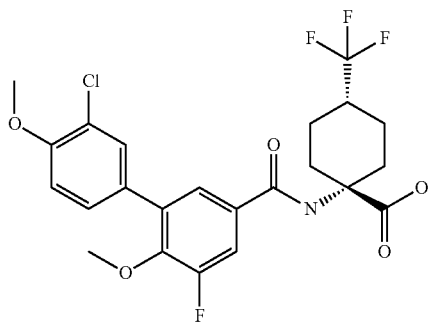 [SMILES: COc1ccc(-c2cc(C(=O)N[C@]3(C(=O)O)CC[C@H](C(F)(F)F)CC3)cc(F)c2OC)cc1Cl]

The title compound synthesized in analogy to example 446 using cis-1-Amino-4-trifluoromethyl-cyclohexanecarboxylic acid methyl ester hydrochloride instead of trans-1-amino-4-methyl-cyclohexanecarboxylic acid methyl ester.
LC/MS (Method LC4): Rt=1.34 min. m/z=504.1 [MH$^+$]

EXAMPLE 449

1-[3-(5-Chloro-6-methoxy-pyridin-3-yl)-5-fluoro-4-methoxy-benzoylamino]-4-methyl-cyclohexanecarboxylic acid

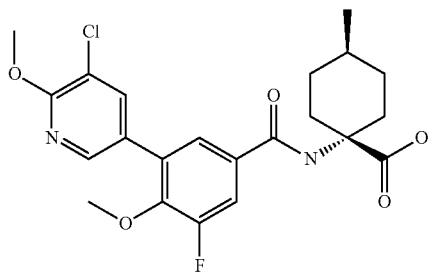 [SMILES: COc1ncc(-c2cc(C(=O)N[C@]3(C(=O)O)CC[C@@H](C)CC3)cc(F)c2OC)cc1Cl]

The title compound was synthesized in analogy to example 446, but using 5-Chloro-6-methoxy-pyridine-3-boronic acid instead of 3-chloro-4-methoxyphenylboronic acid in step 3
LC/MS (Method LC4): Rt=1.34 min. m/z=451.12 [MH$^+$]

EXAMPLE 450

1-[3-(5-Chloro-6-methoxy-pyridin-3-yl)-5-fluoro-4-methoxy-benzoylamino]-4-ethyl-cyclohexanecarboxylic acid

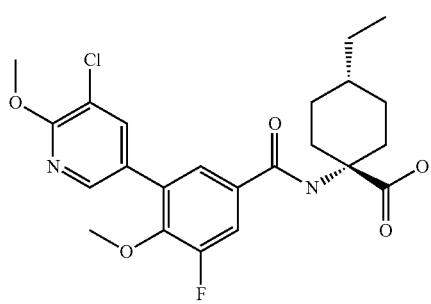 [SMILES: CC[C@H]1CC[C@](NC(=O)c2cc(F)c(OC)c(-c3cnc(OC)c(Cl)c3)c2)(C(=O)O)CC1]

The title compound was synthesized in analogy to example 449, but using cis-1-amino-4-ethyl-cyclohexanecarboxylic acid methyl ester instead of trans-1-amino-4-methyl-cyclohexanecarboxylic acid methyl ester.
LC/MS (Method LC4): Rt=1.38 min. m/z=465.14 [MH$^+$]

EXAMPLE 451

1-{[5-(3-Chloro-4-methoxy-phenyl)-pyridine-3-carbonyl]-amino}-4-trifluoromethyl-cyclohexanecarboxylic acid

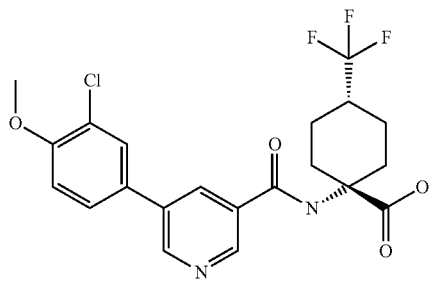

The title compound was synthesized in analogy to examples 446 and 448, but using 5-Bromo-nicotinic acid methyl ester instead of 3-Bromo-5-fluoro-4-methoxy-benzoic acid methyl ester.
LC/MS (Method LC4): Rt=1.24 min. m/z=457.11 [MH$^+$]

EXAMPLE 452

1-(3-Indol-1-yl-4-trifluoromethyl-benzoylamino)-4-methyl-cyclohexanecarboxylic acid

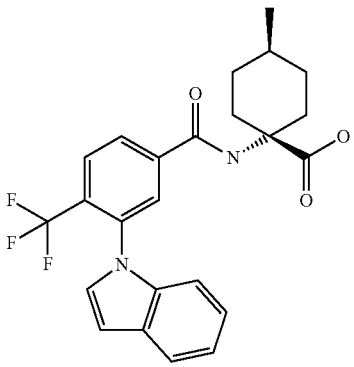

Step 1: 3-Amino-4-trifluoromethyl-benzoic acid methyl ester 2.5 g of 3-Amino-4-trifluoromethyl-benzoic acid were dissolved using 50 ml of diethyl ether and 25 ml of methanol. Then, 6.1 ml of a 2M solution of trimethylsilyldiazomethane in hexane were added at 10-20° C. The reaction mixture was stirred at room temperature for 1 h. Then, 6.1 ml of a 2M solution of trimethylsilyldiazomethane in hexane were added at 10-20° C. The reaction mixture was stirred at room temperature for 1 h. The reaction mixture was then evaporated. Chromatography on silica gel using EA/HEP 1:2 yielded 2.3 g of the title compound, viscous oil.

Step 2: 3-Indol-1-yl-4-trifluoromethyl-benzoic acid methyl ester 690 mg of 3-Amino-4-trifluoromethyl-benzoic acid methyl ester, 650 mg of $K_2CO_3$, 30 mg of CuI, and 28 mg of N,N'-dimethylethylendiamine were suspended using 4.1 ml of anhydrous toluene. 410 mg of o-bromo-(2-bromo)vinyl-benzene were added and the reaction mixture stirred at 110° C. for 14 h. The reaction mixture was allowed to cool to room temperature, 50 ml of EA added, filtrated, and evaporated. Chromatography on silica gel using EA/HEP (gradient) yielded 220 mg of the title compound, viscous oil.

Step 3: 1-(3-Indol-1-yl-4-trifluoromethyl-benzoylamino)-4-methyl-cyclohexanecarboxylic acid methyl ester The title compound synthesized in analogy to example 126, step 4.

Step 4: 1-(3-Indol-1-yl-4-trifluoromethyl-benzoylamino)-4-methyl-cyclohexanecarboxylic acid The title compound synthesized in analogy to example 126, step 5.

LC/MS (Method LC4): Rt=1.23 min. m/z=445.22 [MH$^+$]

EXAMPLE 453

1-{[5-(3-Chloro-4-methoxy-phenyl)-pyridine-3-carbonyl]-amino}-4-ethyl-cyclohexanecarboxylic acid

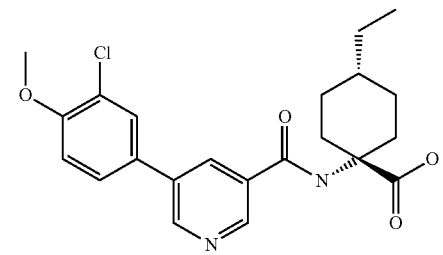

The title compound was synthesized in analogy to example 451.

LC/MS (Method LC4): Rt=1.17 min. m/z=417.09 [MH$^+$]

EXAMPLE 454

Cis-1-{[2,2-Difluoro-7-(2-m-tolyl-ethoxy)-benzo[1,3]dioxole-5-carbonyl]-amino}-4-trifluoromethyl-cyclohexanecarboxylic acid

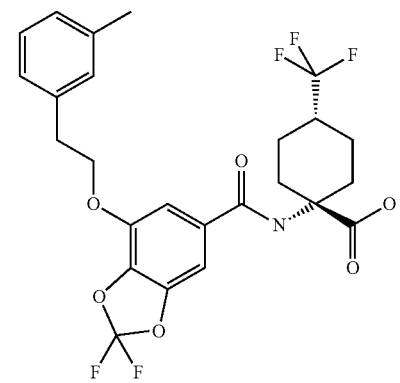

Step 1: 2,2-Difluoro-7-triethylsilanyl-benzo[1,3]dioxole-5-carboxylic acid 200 ml of anhydrous diethyl ether were poured to 1.9 g of Mg turnings and 2.0 g of (6-bromo-2,2-difluoro-benzo[1,3]dioxol-4-yl)-triethyl-silane (Eur. J. Org. Chem. 2004, 1, 64) added. The mixture was then stirred at 35° C. for 30 minutes. Then, the heating was shut down and 23.4 g of (6-bromo-2,2-difluoro-benzo[1,3]dioxol-4-yl)-triethyl-silane was added dropwise to the stirred mixture at a rate that ensured gentle boiling. Stirring was continued at 35° C. for 2 h. Then, the mixture was intensely stirred at room temperature under an excess of anhydrous $CO_2$ for 2 h. The reaction mixture was then poured into 300 ml of a saturated aqueous $NH_4Cl$-solution, acidified to pH=3 using aqueous HCl-solution and the organic layer separated. The aqueous layer was then extracted using 200 ml of diethyl ether. The combined organic layer was dried using $MgSO_4$ and evaporated to yield 22.0 g of the title compound that was used without further purification.

Step 2: 2,2-Difluoro-7-triethylsilanyl-benzo[1,3] dioxole-5-carboxylic acid methyl ester 22.0 g of 2,2-difluoro-7-triethylsilanyl-benzo[1,3]dioxole-5-carboxylic acid were dissolved using 200 ml of diethyl ether and 100 ml of methanol. Then, 35.0 ml of a 2M solution of trimethylsilyldiazomethane was added at 10° C.-20° C. Stirring was continued for 1 h at room temperature and the mixture then evaporated. Chromatography on silica gel using EA/HEP 1:10 yielded 17.0 g of the title compound, colorless oil. $R_f$(EA/HEP 1:20)=0.39

Step 3: 2,2-Difluoro-7-iodo-benzo[1,3]dioxole-5-carboxylic acid methyl ester 17.0 g of 2,2-difluoro-7-triethylsilanyl-benzo[1,3]dioxole-5-carboxylic acid methyl ester were dissolved using 100 ml of $CCl_4$ and 2.9 ml of ICl added. The mixture was then stirred for 3 h at 77° C., 1.5 ml of ICl added and stirred for 2 h at 77° C. The mixture was then allowed to cool to room temperature, 200 ml of $CH_2Cl_2$ added, and washed three times using 300 ml of a saturated aqueous $Na_2SO_3$-solution each. The organic layer was then dried using $MgSO_4$ and evaporated. Chromatography on silica gel using EA/HEP 1:20 yielded 10.2 g of the title compound, colorless oil. $R_f$(EA/HEP 1:20)=0.30

Step 4: 7-(5,5-Dimethyl-[1,3,2]dioxaborinan-2-yl)-2,2-difluoro-benzo[1,3]dioxole-5-carboxylic acid methyl ester 8.5 g of 2,2-difluoro-7-iodo-benzo[1,3]dioxole-5-carboxylic acid methyl ester, 11.2 g of bis(neopentyl glycolato) diboron, 9.8 g of $K_2CO_3$, and 1.8 g of 1,1'-bis(diphenylphosphino)ferrocene-palladium(II)dichloride were added to 100 ml of anhydrous DMSO and the mixture stirred at 80° C. for 5 h. The mixture was then allowed to cool to room temperature, 500 ml of EA added, and washed three times using 300 ml of water each. The organic layer was dried using $MgSO_4$ and evaporated to yield 8.2 g of the title compound that was used without further purification.

Step 5: 2,2-Difluoro-7-hydroxy-benzo[1,3]dioxole-5-carboxylic acid methyl ester 6.0 g of 7-(5,5-dimethyl-[1,3,2]dioxaborinan-2-yl)-2,2-difluoro-benzo[1,3]dioxole-5-carboxylic acid methyl ester were dissolved using 200 ml of methanol and 30 ml of a 33% aqueous solution of $H_2O_2$ added. Stirring was continued for 30 minutes at room temperature. The reaction mixture was then concentrated to 20 ml and 100 ml of water and 100 ml of a saturated aqueous NaCl-solution added. The reaction mixture was then extracted three times using 100 ml of $CH_2Cl_2$ each, dried using $MgSO_4$, and evaporated. Chromatography on silica gel using EA/HEP 1:4 yielded 1.8 g of the title compound, colorless oil.

Step 6: 2,2-Difluoro-7-(2-m-tolyl-ethoxy)-benzo[1,3]dioxole-5-carboxylic acid methyl ester 1.8 g of 2,2-difluoro-7-hydroxy-benzo[1,3]dioxole-5-carboxylic acid methyl ester, 4.6 g of 1-(bromo-ethyl)-3-methyl-benzene, and 3.2 g of $K_2CO_3$ were added to 70 ml of anhydrous DMF and the reaction mixture stirred at 80° C. for 3 h. The reaction mixture was then allowed to cool to room temperature, 300 ml of water added and extracted three times using 100 ml of EA each. The organic layer was then dried using $MgSO_4$ and evaporated. Chromatography on silica gel using EA/HEP 1:4 yielded 2.4 g of the title compound, colorless oil. $R_f$(EA/HEP 1:4)=0.32

Step 7: 2,2-Difluoro-7-(2-m-tolyl-ethoxy)-benzo[1,3]dioxole-5-carboxylic acid The title compound was synthesized from 2,2-difluoro-7-(2-m-tolyl-ethoxy)-benzo[1,3]dioxole-5-carboxylic acid methyl ester in analogy to example 443, step 5.

Step 8: Cis-1-{[2,2-Difluoro-7-(2-m-tolyl-ethoxy)-benzo[1,3]dioxole-5-carbonyl]-amino}-4-trifluoromethyl-cyclohexanecarboxylic acid methyl ester The title compound was synthesized from 2,2-difluoro-7-(2-m-tolyl-ethoxy)-benzo[1,3]dioxole-5-carboxylic acid and cis-1-amino-4-trifluoromethyl-cyclohexanecarboxylic acid methyl ester in analogy to example 126, step 4.
$R_f$(EA/HEP 1:2)=0.22

Step 9: Cis-1-{[2,2-Difluoro-7-(2-m-tolyl-ethoxy)-benzo[1,3]dioxole-5-carbonyl]-amino}-4-trifluoromethyl-cyclohexanecarboxylic acid 100 mg of cis-1-{[2,2-difluoro-7-(2-m-tolyl-ethoxy)-benzo[1,3]dioxole-5-carbonyl]-amino}-4-trifluoromethyl-cyclohexanecarboxylic acid methyl ester were dissolved using 10 ml of methanol, 10 ml of THF, and 2 ml of water. 15.4 mg of lithium hydroxide monohydrate were then added and the reaction mixture was stirred at room temperature for 14 h. Stirring was continued for 5 h at 40° C. Then, the mixture was evaporated, 10 ml of water added and acidified to pH=2 using aqueous $NaHSO_4$-solution. The resulting mixture was then stirred for 1 h at room temperature, and extracted three times using 10 ml of $CH_2Cl_2$. The organic layer was then dried using $MgSO_4$ and evaporated to yield 55 mg of the title compound, amorphous solid.
LC/MS (Method LC4): Rt=1.38 min. m/z=530.33 [MH$^+$]

EXAMPLE 455

1-{[2,2-Difluoro-7-(2-m-tolyl-ethoxy)-benzo[1,3]dioxole-5-carbonyl]-amino}-cycloheptanecarboxylic acid

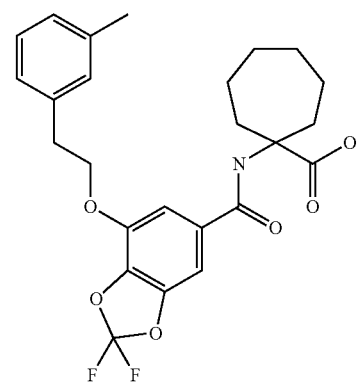 [SMILES: Cc1cccc(CCOc2cc(C(=O)NC3(C(=O)O)CCCCCC3)cc3c2OC(F)(F)O3)c1]

The title compound was synthesized in analogy to example 454.
LC/MS (Method LC4): Rt=1.38 min. m/z=476.36 [MH$^+$]

EXAMPLE 456

Cis-1-{[2,2-Difluoro-7-(2-m-tolyl-ethoxy)-benzo[1,3]dioxole-5-carbonyl]-amino}-4-ethyl-cyclohexanecarboxylic acid

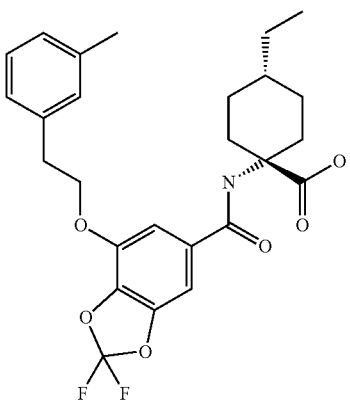

The title compound was synthesized in analogy to example 454.

LC/MS (Method LC4): Rt=1.42 min. m/z=490.38 [MH$^+$]

EXAMPLE 457

1-[(6-Methoxy-3'-oxetan-3-yl-biphenyl-3-carbonyl)-amino]-cycloheptanecarboxylic acid

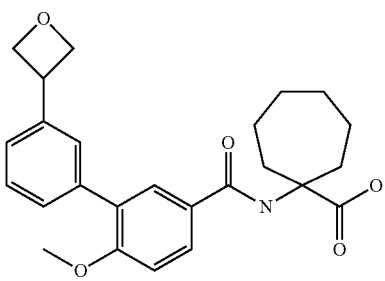 [SMILES: COc1ccc(C(=O)NC2(C(=O)O)CCCCCC2)cc1-c1cccc(C2COC2)c1]

Step 1: 3-(3-Bromo-phenyl)-oxetane 4.7 g of 3-bromophenylboronic acid, 219 mg of NiI$_2$, 4.3 g of sodium bis(trimethylsilyl)amide, and 106 mg of trans-2-aminocyclohexanol hydrochloride were added to 14 ml of anhydrous 2-propanol and oxygen removed by passing argon through the mixture for 10 minutes. Then, a solution of 2.2 g of 3-iodo-oxetane in 1 ml of anhydrous 2-propanol was added and the mixture kept at 80° C. under microwave irradiation for 50 minutes. The mixture was then evaporated, distributed between 100 ml of water and 100 ml of EA, and the aqueous layer extracted twice using 20 ml of EA each. The organic layer was then dried using MgSO$_4$ and evaporated. Chromatography on silica gel using EA/HEP 1:4 yielded 1.4 g of the title compound, colorless oil. R$_f$(EA/HEP 1:4)=0.27

Step 2: 6-Methoxy-3'-oxetan-3-yl-biphenyl-3-carboxylic acid methyl ester 1.3 g of 3-(3-bromo-phenyl)-oxetane, 1.3 g of 2-methoxy-5-methoxycarbonylphenylboronic acid, 1.3 g of Na$_2$CO$_3$, 69 mg of palladium(II)acetate, and 160 mg of triphenylphosphine were combined and 15 ml of DMF and 1 ml of water added. The mixture was stirred at 100° C. for 1 h and then allowed to cool to room temperature. 100 ml of EA were then added and washed three times using 30 ml of water each. The organic layer was then dried using MgSO$_4$ and evaporated. Chromatography on silica gel using EA/HEP 1:3 yielded 1.3 g of the title compound, colorless oil.

Step 3: 6-Methoxy-3'-oxetan-3-yl-biphenyl-3-carboxylic acid

The title compound was synthesized from 6-methoxy-3'-oxetan-3-yl-biphenyl-3-carboxylic acid methyl ester in analogy to example 443, step 5.

Step 4: 1-[(6-Methoxy-3'-oxetan-3-yl-biphenyl-3-carbonyl)-amino]-cycloheptanecarboxylic acid methyl ester The title compound was synthesized from 6-Methoxy-3'-oxetan-3-yl-biphenyl-3-carboxylic acid and 1-amino-cycloheptanecarboxylic acid methyl ester in analogy to example 126, step 4.

R$_f$(EA/HEP 1:1)=0.13

Step 5: 1-[(6-Methoxy-3'-oxetan-3-yl-biphenyl-3-carbonyl)-amino]-cycloheptanecarboxylic acid The title compound has been synthesized from 1-[(6-Methoxy-3'-oxetan-3-yl-biphenyl-3-carbonyl)-amino]-cycloheptanecarboxylic acid methyl ester in analogy to example 442, step 5.

LC/MS (Method LC4): Rt=1.21 min. m/z=424.35 [MH$^+$]

EXAMPLE 458

Cis-4-Ethyl-1-[(6-methoxy-3'-oxetan-3-yl-biphenyl-3-carbonyl)-amino]-cyclohexanecarboxylic acid

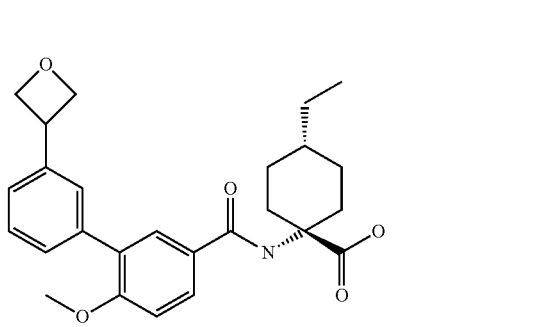

The title compound has been synthesized in analogy to example 457.

LC/MS (Method LC4): Rt=1.26 min. m/z=438.36 [MH$^+$]

EXAMPLE 459

1-[(6-Methoxy-3'-oxetan-3-yl-biphenyl-3-carbonyl)-amino]-4-trifluoromethyl-cyclohexanecarboxylic acid

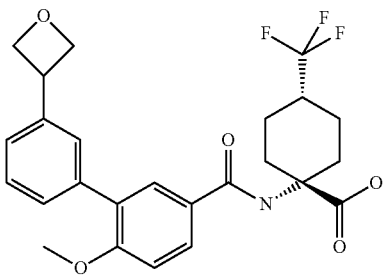

The title compound has been synthesized in analogy to example 457.

LC/MS (Method LC4): Rt=1.22 min. m/z=478.34 [MH$^+$]

EXAMPLE 460

1-{4-Methoxy-3-[2-(3-oxetan-3-yl-phenyl)-ethoxy]-benzoylamino}-4-trifluoromethyl-cyclohexanecarboxylic acid

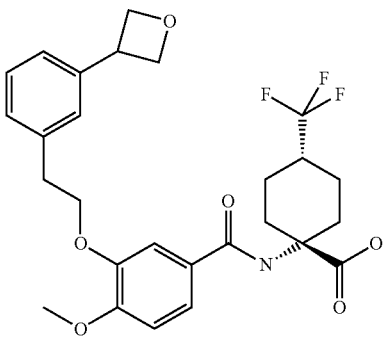

Step 1: 3-[2-(tert-Butyl-dimethyl-silanyloxy)-ethyl]-benzeneboronic acid 50.0 g of [2-(3-Bromo-phenyl)-ethoxy]-tert-butyl-dimethyl-silane was dissolved using 500 ml of anhydrous THF and 64.6 ml of a 2.7M solution of n-butyllithium in n-heptane added dropwise at −70° C. The reaction mixture was then stirred at −70° C. for 1 h. 40.2 ml of triisopropylborate was then added dropwise at −70° C. and stirring was continued for 30 minutes at −70° C. The mixture was then allowed to warm to −20° C. and 500 ml of water added. The reaction mixture was then allowed to warm to room temperature and extracted three times using 300 ml of CH$_2$Cl$_2$ each. The organic layer was then dried using MgSO$_4$ and evaporated to yield 43.6 g of the title compound, used without further purification.

Step 2: tert-Butyl-dimethyl-[2-(3-oxetan-3-yl-phenyl)-ethoxy]-silane 18.3 g of 3-[2-(tert-Butyl-dimethyl-silanyloxy)-ethyl]-benzeneboronic acid, 510 mg of NiI$_2$, 19.9 g of sodium bis(trimethylsilyl)amide, and 250 mg of trans-2-aminocyclohexanol hydrochloride were added to 14.0 ml of 2-propanol and the mixture was stirred for 10 minutes at room temperature. Then, a solution of 10.0 g of 3-Iodo-oxetane in 6.0 ml of 2-propanol was added and the reaction mixture kept at 80° C. under microwave irradiation for 30 minutes. The reaction mixture was then poured into 100 ml of a saturated aqueous NaHCO$_3$-solution and extracted three times using 100 ml of EA each. The organic layer was then dried using MgSO$_4$ and evaporated. Chromatography on silica gel using EA/HEP (gradient) yielded 22.0 g of the title compound, colorless oil.

Step 3: 2-(3-Oxetan-3-yl-phenyl)-ethanol 9.0 g of tert-Butyl-dimethyl-[2-(3-oxetan-3-yl-phenyl)-ethoxy]-silane were dissolved using 200 ml of anhydrous THF and 92 ml of a 1M solution of tetra-n-butylammonium fluoride in THF added at room temperature. The reaction mixture was stirred at room temperature for 3 h and then poured into 500 ml of a saturated aqueous NaHCO$_3$-solution and extracted three times using 300 ml of EA each. The organic layer was then dried using MgSO$_4$ and evaporated. Chromatography on silica gel using EA/HEP (gradient) yielded 4.9 g of the title compound, colorless oil.

Step 4: Toluene-4-sulfonic acid 2-(3-oxetan-3-yl-phenyl)-ethyl ester 4.9 g of 2-(3-Oxetan-3-yl-phenyl)-ethanol were dissolved using 30 ml of CH$_2$Cl$_2$ and 9.5 ml of pyridine added. Then, 6.3 g of p-toluenesulfonyl chloride was added at 0° C. and the reaction mixture stirred for 6 h at room temperature. The reaction mixture was then evaporated, re-dissolved using 100 ml of EA and washed using 100 ml of a saturated aqueous NaHCO$_3$-solution. The aqueous layer was then extracted twice using 100 ml of EA each. The combined organic layer was then dried using MgSO$_4$ and evaporated. Chromatography on silica gel using EA/HEP 1:1 yielded 2.0 g of the title compound, colorless oil.

Step 5: 3-Acetoxy-4-methoxy-benzoic acid 17.0 g of 3-Hydroxy-4-methoxy-benzoic acid were added to 51.6 g of acetic ahydride and the mixture stirred at 140° C. for 3 h. The mixture was then allowed to cool to 100° C., 50 ml of water added dropwise and the temperature kept at 100° C. Then, 200 ml of water were added and the mixture was stirred at 100° C. for 30 minutes. The mixture was then cooled and stirred at 0° C. for 1 h. The product was then isolated by filtration, washed with 50 ml of water and dried under reduced pressure to yield 18.8 g of the title compound that was used without further purification.

Step 6: 1-(3-Acetoxy-4-methoxy-benzoylamino)-4-trifluoromethyl-cyclohexanecarboxylic acid methyl ester 80.3 mg of 3-Acetoxy-4-methoxy-benzoic acid were combined with 1 ml of CH$_2$Cl$_2$, 3 μl of DMF added and 0.57 ml of a 2M solution of oxalyl chloride in CH$_2$Cl$_2$ added dropwise under stirring at room temperature. Stirring was continued until the evolution of gas ceased. Then, the reaction mixture was evaporated, 5 ml of CH$_2$Cl$_2$ added and again evaporated. The residue (crude acid chloride) was then dissolved using 2 ml of CH$_2$Cl$_2$ and added dropwise to an intensely stirred mixture of 100 mg of 1-Amino-4-trifluoromethyl-cyclohexanecarboxylic acid methyl ester, 5 ml of EA, and 10 ml of a saturated aqueous NaHCO$_3$-solution at 0° C. Stirring was continued for 1 h at room temperature. Then, the organic layer was separated and the aqueous layer was extracted twice using 15 ml of EA each. The organic layer was then dried using MgSO$_4$ and evaporated to yield 105 mg of the title compound that was used without further purification.

Step 7: 1-(3-Hydroxy-4-methoxy-benzoylamino)-4-trifluoromethyl-cyclohexanecarboxylic acid methyl ester 105 mg of 1-(3-Acetoxy-4-methoxy-benzoylamino)-4-trifluoromethyl-cyclohexanecarboxylic acid methyl ester and 7.0 mg of K$_2$CO$_3$ were stirred in 4 ml of anhydrous methanol for 1 h at room temperature. Then, 10.4 mg of K$_2$CO$_3$ were added and stirring was continued for 2 h at room temperature. 10 ml of EA and 10 ml of a 1N aqueous HCl-solution were then added. The layers were separated and the aqueous layer was extracted twice using 10 ml of EA each. The combined organic layers were washed twice using 10 ml of a saturated aqueous NaHCO$_3$-solution, once using 10 ml of a 1N aqueous HCl-solution, and once using a 10 ml of a saturated aqueous NaCl-solution. The organic layer was then dried using MgSO$_4$ and evaporated to yield 60 mg of the title compound that was used without further purification.

Step 8: 1-{4-Methoxy-3-[2-(3-oxetan-3-yl-phenyl)-ethoxy]-benzoylamino}-4-trifluoromethyl-cyclohexanecarboxylic acid methyl ester 60 mg of 1-(3-Hydroxy-4-methoxy-benzoylamino)-4-trifluoromethyl-cyclohexanecarboxylic acid methyl ester, 53 mg of toluene-4-sulfonic acid 2-(3-oxetan-3-yl-phenyl)-ethyl ester, and 66 mg of K$_2$CO$_3$ were added to 3 ml of DMF and the mixture was stirred for 8 h at 40° C. Then, 27 mg of toluene-4-sulfonic acid 2-(3-oxetan-3-yl-phenyl)-ethyl ester were added and stirring was continued for 8 h at 40° C. Then, 10 ml of EA and 15 ml of a half-saturated aqueous NaCl-solution were added. The layers were separated and the aqueous layer was extracted twice using 10 ml of EA each. The combined organic layer was then dried using MgSO$_4$ and evaporated. Chromatography on silica gel using EA/HEP 1:1 yielded 77 mg of the title compound, amorphous solid.

Step 9: 1-{4-Methoxy-3-[2-(3-oxetan-3-yl-phenyl)-ethoxy]-benzoylamino}-4-trifluoromethyl-cyclohexanecarboxylic acid 77 mg of 1-{4-Methoxy-3-[2-(3-oxetan-3-yl-phenyl)-ethoxy]-benzoylamino}-4-trifluoromethyl-cyclohexanecarboxylic acid methyl ester were dissolved using 3.5 ml of methanol and 173 µl of a 1M aqueous solution of NaOH added. The mixture was stirred at 60° C. for 8 h. The mixture was then poured into 10 ml of water and acidified to pH=5 using 5% aqueous NaHSO$_4$-solution. The mixture was then extracted three times using 15 ml of EA each. The organic layer was then dried using MgSO$_4$ and evaporated.

LC/MS (Method LC4): Rt=1.23 min. m/z=522.29 [MH$^+$]

EXAMPLE 461

Cis-1-{[5-(3-Chloro-4-methoxy-phenyl)-pyridine-3-carbonyl]-amino}-4-ethyl-cyclohexanecarboxylic acid

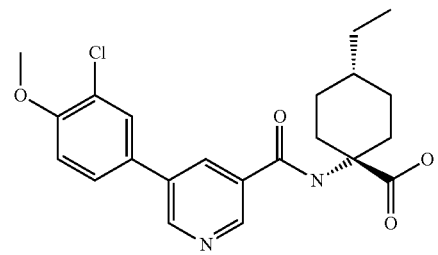

Step 1: 5-(3-Chloro-4-methoxy-phenyl)-nicotinic acid methyl ester 6.5 g of 3-chloro-4-methoxyphenylboronic acid, 5.0 g of methyl 5-bromonicotinate, 1.3 g of tetrakis(triphenylphosphine)palladium(0), and 22.6 g of Cs$_2$CO$_3$ were stirred in 325 ml of DMF and 65 ml of water for 3 h at 45° C. The reaction mixture was then poured into 750 ml of water and extracted three times using 300 ml of EA each. The combined organic layers were then washed twice using 150 ml of water each. The organic layer was then dried using MgSO$_4$ and evaporated. Chromatography on silica gel using EA/HEP (gradient) yielded 2.4 g of the title compound, colorless oil.

Step 2: 5-(3-Chloro-4-methoxy-phenyl)-nicotinic acid 5-(3-Chloro-4-methoxy-phenyl)-nicotinic acid methyl ester was saponified in analogy to example 460, step 9.

Step 3: 1-{[5-(3-Chloro-4-methoxy-phenyl)-pyridine-3-carbonyl]-amino}-4-ethyl-cyclohexanecarboxylic acid methyl ester The title compound was synthesized from 5-(3-Chloro-4-methoxy-phenyl)-nicotinic acid and 1-Amino-4-ethyl-cyclohexanecarboxylic acid methyl ester in analogy to example 126, step 4.

Step 4: Cis-1-{[5-(3-Chloro-4-methoxy-phenyl)-pyridine-3-carbonyl]-amino}-4-ethyl-cyclohexanecarboxylic acid The title compound has been synthesized in analogy to example 460, step 9.

LC/MS (Method LC4): Rt=1.17 min. m/z=417.09 [MH$^+$]

EXAMPLE 462

Cis-4-Ethyl-1-[4-(2-methanesulfonyl-ethyl)-3-(2-m-tolyl-ethoxy)-benzoylamino]-cyclohexanecarboxylic acid

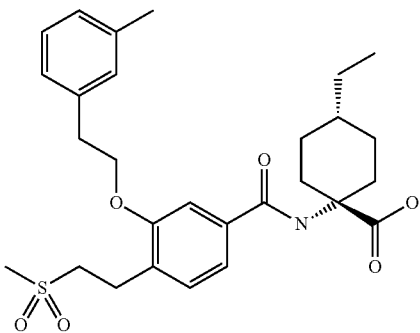

Step 1: 3-Hydroxy-4-iodo-benzoic acid methyl ester 37.0 g of methyl 4-amino-3-hydroxybenzoate were stirred in 200 ml of water and 200 g of ice and 300 ml of a saturated aqueous HCl-solution added. Stirring was continued for 5 minutes. A solution of 16.8 g NaNO$_2$ was then added dropwise at 0° C. and the mixture was stirred at 0° C. for 10 minutes. The resulting solution was then added portion-wise to a solution 73.5 g KI in 300 ml of water at 25° C. Stirring was continued for 1 h at 25° C.-30° C. The reaction mixture was the extracted three times using 200 ml of EA each. The organic layer was then washed successively once using 100 ml of a 1M aqueous HCl-solution, once using 100 ml of a saturated aqueous Na$_2$SO$_3$-solution, and three times using 100 ml of a saturated aqueous NaHCO$_3$-solution each. The organic layer was then dried using MgSO$_4$ and evaporated. Chromatography on silica gel using EA/HEP 1:2 yielded 37.0 g of the title compound, colorless oil.
R$_f$(EA/HEP 1:2)=0.34

Step 2: 4-Iodo-3-(2-m-tolyl-ethoxy)-benzoic acid methyl ester 10.0 g of 3-Hydroxy-4-iodo-benzoic acid methyl ester, 14.3 g of 1-(2-bromo-ethyl)-3-methyl-benzene, and 10.0 g of K$_2$CO$_3$ were stirred in anhydrous DMF at 80° C. for 10 h. Then, 14.3 g of 1-(2-bromo-ethyl)-3-methyl-benzene, and 10.0 g of K$_2$CO$_3$ were added and stirring was continued at 80° C. for 10 h. 400 ml of EA were then added and the mixture was washed twice using 200 ml of water each. The organic layer was then dried using MgSO$_4$ and evaporated. Chromatography on silica gel using EA/HEP (gradient) yielded 11.5 g of the title compound, colorless oil.

Step 3: 4-((E)-2-Methanesulfonyl-vinyl)-3-(2-m-tolyl-ethoxy)-benzoic acid methyl ester 500 mg of 4-Iodo-3-(2-m-tolyl-ethoxy)-benzoic acid methyl ester, 200 mg of methyl vinyl sulfone, 115 mg of tri-o-tolylphosphine, and 43 mg of palladium(II) acetate were stirred in 4 ml of acetonitrile and 1.5 ml of diisopropylethylamin for 2 h at 82° C. The reaction mixture was allowed to cool to room temperature. 10 ml of EA were then added and the mixture was washed successively twice using 5 ml of water each and twice using 5 ml of a saturated aqueous Na$_2$CO$_3$-solution. The organic layer was then dried using MgSO$_4$ and evaporated. Chromatography on silica gel using EA/HEP 1:2 yielded 270 mg of the title compound. R$_f$(EA/HEP 1:2)=0.17

Step 4: 4-(2-Methanesulfonyl-ethyl)-3-(2-m-tolyl-ethoxy)-benzoic acid methyl ester 250 mg of 4-((E)-2-Methanesulfonyl-vinyl)-3-(2-m-tolyl-ethoxy)-benzoic acid methyl ester were dissolved using 10 ml of methanol and hydrogenated under an 1.5 bar atmosphere of hydrogen using 50 mg of Pd/C (10%, 50% water) for 30 minutes. The catalyst was then removed by filtration and the solution evaporated to yield 250 mg of the title compound that was used without further purification.

Step 5: 4-(2-Methanesulfonyl-ethyl)-3-(2-m-tolyl-ethoxy)-benzoic acid

The title compound was synthesized in analogy to example 443, step 5.

Step 6: cis-4-Ethyl-1-[4-(2-methanesulfonyl-ethyl)-3-(2-m-tolyl-ethoxy)-benzoylamino]-cyclohexanecarboxylic acid methyl ester The title compound was synthesized from 4-(2-Methanesulfonyl-ethyl)-3-(2-m-tolyl-ethoxy)-benzoic acid and 1-Amino-4-ethyl-cyclohexanecarboxylic acid methyl ester in analogy to example 126, step 4.

Step 7: cis-4-Ethyl-1-[4-(2-methanesulfonyl-ethyl)-3-(2-m-tolyl-ethoxy)-benzoylamino]-cyclohexanecarboxylic acid The title compound was synthesized in analogy to example 443, step 5.
LC/MS (Method LC4): Rt=1.32 min. m/z=516.39 [MH$^+$]

EXAMPLE 463

Cis-1-{[7-(3-Chloro-4-methoxy-phenyl)-2,2-difluoro-benzo[1,3]dioxole-5-carbonyl]-amino}-4-ethyl-cyclohexanecarboxylic acid

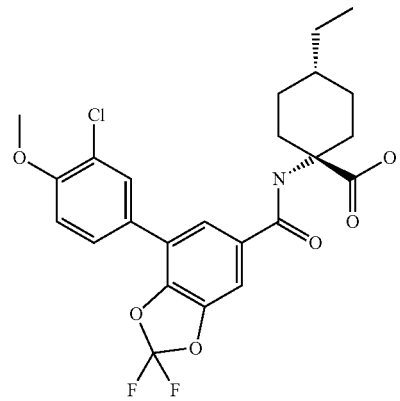

Step 1: 7-(3-Chloro-4-methoxy-phenyl)-2,2-difluoro-benzo[1,3]dioxole-5-carboxylic acid methyl ester 1.9 g of 7-(5,5-Dimethyl-[1,3,2]dioxaborinan-2-yl)-2,2-difluoro-benzo[1,3]dioxole-5-carboxylic acid methyl ester (example YY, step 4), 1.5 g of 4-bromo-2-chloro-1-methoxy-benzene, 152 mg of triphenylphosphine, 65 mg of palladium (II) acetate, and 2.4 g of $K_2CO_3$ were stirred in 30 ml of DMF and 3 ml of water under an argon atmosphere at 100° C. for 4 h. 200 ml of water were then added and the mixture was extracted three times using 100 ml of EA each. The organic layer was then dried using $MgSO_4$ and evaporated. Chromatography on silica gel using EA/HEP 1:5 yielded 330 mg of the title compound, colorless oil. $R_f$ (EA/HEP 1:5)=0.29

Step 2: 7-(3-Chloro-4-methoxy-phenyl)-2,2-difluoro-benzo[1,3]dioxole-5-carboxylic acid The title compound was synthesized in analogy to example 442, step 5.

Step 3: cis-1-{[7-(3-Chloro-4-methoxy-phenyl)-2,2-difluoro-benzo[1,3]dioxole-5-carbonyl]-amino}-4-ethyl-cyclohexanecarboxylic acid methyl ester The title compound was synthesized form 7-(3-Chloro-4-methoxy-phenyl)-2,2-difluoro-benzo[1,3]dioxole-5-carboxylic acid and cis-1-amino-4-ethyl-cyclohexanecarboxylic acid methyl ester in analogy to example 126, step 4.

Step 4: Cis-1-{[7-(3-Chloro-4-methoxy-phenyl)-2,2-difluoro-benzo[1,3]dioxole-5-carbonyl]-amino}-4-ethyl-cyclohexanecarboxylic acid The title compound was synthesized in analogy to example 442, step 5.
LC/MS (Method LC4): Rt=1.42 min. m/z=496.28 [MH$^+$]
Pharmacological Tests
A) Determination of Edg-2 Receptor Inhibition by Fluorescence Imaging Plate Reader (FLIPR) Measurements The inhibition of the Edg-2 receptor ($LPA_1$ receptor) by the compounds of the invention was quantified by the inhibitory effect on the LPA-mediated calcium liberation in a cell-based calcium fluorescence assay by use of Chinese hamster ovarian (CHO) cells in which the human Edg-2 receptor was stably overexpressed (Flp-In system, Invitrogen). In order to enforce G-Protein coupling and to direct signaling towards $Ca^{2+}$ liberation, the overexpressed receptor additionally had a C-terminal sequence of a modified G-protein ($G_{\alpha i4qi4}$) (WO 02/04665). Changes in intracellular calcium were determined by fluorescence measurement with the calcium-sensitive dye fluo-4 (Invitrogen) in a fluorescence imaging plate reader (FLIPR, Molecular Dynamics).

CHO cells stably overexpressing the human Edg-2 receptor were seeded (40.000 per well) in black clear-bottomed poly-D-lysine-coated 96 well plates (Becton Dickinson, Biocoat cellware) approximately 18-24 h prior to the experiments. Cells were grown in an incubator at 37° C., 5% carbon dioxide and 95% humidity in cell culture media based on F-12 glutamax media (Gibco, #31765) supplemented with 1% (vol/vol) penicilline/streptomycine (PAN, #P06-07100), 10% (vol/vol) fetal calf serum (FCS, PAA, #A15-151) and hygromycin B (Invitrogen, #10687-010) 300 mg/l (final concentrations).

Prior to the FLIPR experiment, cells were loaded with fluo-4 acetoxymethyl ester (fluo-4 AM, Invitrogen, #F14202) for 60 min in an incubator at 37° C., 5% carbon dioxide and 95% humidity in dye-loading buffer consisting of Hanks' Balanced Salt Solution (HBSS, Invitrogen, #14065049) supplemented with fluo-4 AM at 2 µM (all data given for final concentration), Pluronic® F-127 0.05% (vol/vol) (Invitrogen, #P-3000 MP), HEPES 20 mM (Gibco, #15630), probenecid 2.5 mM (Sigma, #P-8761) and bovine serum albumin 0.05% (BSA, Sigma, #A-6003), adjusted to pH 7.5 with sodium hydroxide. During cell loading, fluo-4 AM is cleaved by intracellular esterase resulting in trapping of the dye fluo-4 within the cells. Loading was terminated by washing of the cells in a cell washer (Tecan Power washer) three times with the buffer specified afore but without fluo-4 AM and BSA. This latter buffer was also used as the buffer in the subsequent cell fluorescence measurements.

The dye-loaded and washed cells were pre-incubated for approximately 5 min with various concentrations of the test compound added as a solution in DMSO (0.3% vol/vol maximum final concentration of DMSO), or with DMSO in the respective concentration only (positive control). Subsequent addition of LPA (18:1, 1-oleoyl-sn-glycerol 3-phosphate; 100 nM final concentration) leads to liberation of intracellular calcium from internal stores resulting in a large transient increase of the fluo-4 fluorescence signal which was monitored over approximately 3 min. The percent inhibition caused by the test compound was determined from the maximum fluorescence response after LPA addition to cells pre-incubated with the compound as compared to the maximum fluorescence response after LPA addition to cells pre-incubated with DMSO only. All fluorescence values were corrected for the baseline fluorescence values obtained with cells which were pre-incubated with DMSO only and were not treated with LPA (baseline control). All measurements were performed in triplicate. From the percent inhibitions the inhibitory concentration $IC_{50}$ was determined.

Inhibitory concentrations $IC_{50}$ of various example compounds are given in table 23, wherein "a" denotes an $IC_{50}$ of less than 0.1 µM, "b" denotes an $IC_{50}$ between 0.1 µM and 1 µM, and "c" denotes an $IC_{50}$ between 1 µM and 30 µM.

TABLE 23

Inhibitory concentrations $IC_{50}$ for inhibition of the Edg-2 receptor

| Example | $IC_{50}$ |
|---------|-----------|
| 1 | b |
| 2 | a |
| 3 | a |
| 4 | b |
| 5 | a |
| 6 | b |
| 7 | a |
| 8 | a |
| 9 | a |
| 10 | a |
| 11 | b |
| 12 | b |
| 13 | a |
| 14 | b |
| 15 | c |
| 16 | a |
| 17 | a |
| 18 | b |
| 19 | b |
| 20 | a |
| 21 | b |
| 22 | a |
| 23 | b |
| 24 | b |
| 25 | c |
| 26 | a |
| 27 | a |
| 28 | a |
| 29 | a |
| 30 | a |
| 31 | a |
| 32 | c |
| 33 | a |

TABLE 23-continued

Inhibitory concentrations $IC_{50}$ for inhibition of the Edg-2 receptor

| Example | $IC_{50}$ |
|---|---|
| 34 | c |
| 35 | c |
| 36 | b |
| 37 | c |
| 38 | b |
| 39 | c |
| 40 | b |
| 41 | a |
| 43 | a |
| 44 | b |
| 45 | b |
| 46 | a |
| 47 | a |
| 48 | c |
| 49 | c |
| 50 | a |
| 51 | a |
| 52 | c |
| 53 | b |
| 54 | a |
| 55 | b |
| 56 | a |
| 57 | a |
| 58 | c |
| 59 | a |
| 60 | b |
| 61 | b |
| 62 | a |
| 63 | a |
| 64 | b |
| 65 | a |
| 66 | b |
| 66 | b |
| 67 | b |
| 67 | c |
| 68 | a |
| 69 | b |
| 70 | a |
| 71 | a |
| 72 | a |
| 73 | c |
| 74 | a |
| 75 | a |
| 76 | a |
| 77 | a |
| 78 | b |
| 79 | a |
| 80 | a |
| 81 | a |
| 82 | a |
| 83 | a |
| 84 | c |
| 85 | a |
| 86 | c |
| 87 | c |
| 88 | a |
| 89 | c |
| 90 | a |
| 91 | a |
| 92 | c |
| 93 | c |
| 94 | b |
| 95 | b |
| 96 | a |
| 97 | a |
| 98 | a |
| 99 | a |
| 100 | a |
| 103 | b |
| 104 | b |
| 105 | b |
| 106 | c |
| 107 | a |
| 108 | a |
| 109 | a |
| 110 | a |

TABLE 23-continued

Inhibitory concentrations $IC_{50}$ for inhibition of the Edg-2 receptor

| Example | $IC_{50}$ |
|---|---|
| 111 | a |
| 112 | a |
| 113 | b |
| 114 | b |
| 115 | c |
| 116 | c |
| 117 | c |
| 118 | c |
| 119 | a |
| 121 | b |
| 122 | a |
| 123 | a |
| 124 | b |
| 125 | a |
| 126 | a |
| 127 | a |
| 128 | b |
| 129 | b |
| 130 | a |
| 131 | a |
| 132 | a |
| 133 | a |
| 134 | a |
| 205 | a |
| 206 | a |
| 207 | a |
| 208 | a |
| 299 | a |
| 300 | a |
| 301 | a |
| 302 | a |
| 303 | a |
| 304 | a |
| 305 | a |
| 306 | a |
| 307 | a |
| 308 | a |
| 309 | a |
| 310 | a |
| 311 | a |
| 312 | b |
| 313 | a |
| 314 | a |
| 315 | a |
| 316 | a |
| 317 | a |
| 318 | a |
| 319 | a |
| 320 | a |
| 326 | a |
| 327 | a |
| 328 | b |
| 329 | a |
| 330 | c |
| 331 | a |
| 332 | a |
| 333 | a |
| 334 | b |
| 351 | a |
| 352 | a |
| 355 | a |
| 356 | a |
| 357 | a |
| 358 | a |
| 359 | a |
| 360 | a |
| 361 | a |
| 362 | a |
| 363 | b |
| 364 | a |
| 365 | b |
| 366 | b |
| 367 | b |
| 368 | b |
| 369 | b |
| 370 | a |

TABLE 23-continued

Inhibitory concentrations IC$_{50}$ for inhibition of the Edg-2 receptor

| Example | IC$_{50}$ |
|---|---|
| 371 | b |
| 372 | b |
| 373 | b |
| 374 | a |
| 375 | a |
| 376 | a |
| 377 | a |
| 378 | a |
| 379 | a |
| 380 | a |
| 381 | a |
| 382 | a |
| 383 | a |
| 384 | a |
| 385 | a |
| 386 | a |
| 387 | a |
| 388 | a |
| 389 | a |
| 390 | a |
| 391 | a |
| 392 | a |
| 393 | a |
| 394 | a |
| 395 | a |
| 396 | a |
| 397 | a |
| 398 | a |
| 399 | a |
| 400 | a |
| 401 | a |
| 402 | a |
| 403 | a |
| 404 | a |
| 405 | a |
| 406 | b |
| 407 | a |
| 408 | b |
| 409 | a |
| 410 | a |
| 411 | a |
| 412 | a |
| 413 | a |
| 414 | a |
| 415 | a |
| 416 | a |
| 417 | a |
| 418 | a |
| 419 | a |
| 420 | b |
| 421 | b |
| 422 | b |
| 423 | a |
| 424 | a |
| 425 | b |
| 426 | b |
| 427 | b |
| 428 | a |
| 429 | b |
| 430 | b |
| 431 | b |
| 432 | b |
| 433 | a |
| 434 | b |
| 435 | b |
| 436 | b |
| 437 | a |
| 438 | a |
| 439 | b |
| 440 | b |
| 441 | c |
| 442 | b |
| 443 | b |
| 444 | b |
| 445 | a |
| 446 | a |
| 447 | a |
| 448 | a |
| 449 | b |
| 450 | a |
| 451 | a |
| 452 | b |
| 453 | a |
| 454 | a |
| 455 | a |
| 456 | a |
| 457 | b |
| 458 | a |
| 459 | a |
| 460 | b |
| 461 | a |
| 462 | b |
| 463 | a |

B) In Vivo Antihypertrophic and Renoprotective Activity

The in vivo pharmacological activity of the compounds of the invention can be investigated, for example, in the model of DOCA-salt sensitive rats with unilateral nephrectomy. Briefly, in this model unilateral nephrectomy of the left kidney (UNX) is performed on Sprague Dawley rats of 150 g to 200 g of body weight. After the operation as well as at the beginning of each of the following weeks 30 mg/kg of body weight of DOCA (desoxycorticosterone acetate) are administered to the rats by subcutaneous injection. The nephrectomized rats treated with DOCA are supplied with drinking water containing 1% of sodium chloride (UNX/DOCA rats). The UNX/DOCA rats develop high blood pressure, endothelial dysfunction, myocardial hypertrophy and fibrosis as well as renal dysfunction. In the test group (UNX/DOCA Test) and the placebo group (UNX/DOCA Placebo), which consist of randomized UNX/DOCA rats, the rats are treated orally by gavage in two part administrations at 6 a.m. and 6 p.m. with the daily dose of the test compound (for example 10 mg/kg of body weight dissolved in vehicle) or with vehicle only, respectively. In a control group (control), which consists of animals which have not been subjected to UNX and DOCA administration, the animals receive normal drinking water and are treated with vehicle only. After five weeks of treatment, systolic blood pressure (SBP) and heart rate (HR) are measured non-invasively via the tail cuff method. For determination of albuminuria and creatinine, 24 h urine is collected on metabolic cages. Endothelial function is assessed in excised rings of the thoracic aorta as described previously (W. Linz et al., JRAAS (Journal of the renin-angiotensin-aldosterone system) 7 (2006), 155-161). As a measure of myocardial hypertrophy and fibrosis, heart weight, left ventricular weight and the relation of hydroxyproline and proline are determined in excised hearts.

We claim:
1. A compound of formula I,

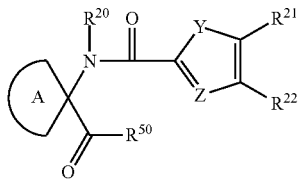

wherein
ring A is a 6- or 7-membered carbocyclic ring, wherein ring A is optionally substituted on ring carbon atoms by one or more identical or different substituents chosen from the series consisting of halogen, $R^1$, $R^2$, $(C_2-C_6)$-alkenyl, HO—, $R^1$—O—, phenyl-$(C_1-C_4)$-alkyl-O—, $R^1$—C(O)—O—, $R^1$—S(O)$_2$—O—, $R^1$—S(O)$_m$—, $H_2N$—, $R^1$—NH—, $R^1$—N($R^1$)—, $R^1$—C(O)—NH—, $R^1$—C(O)—N($R^1$)—, $R^1$—S(O)$_2$—NH—, $R^1$—S(O)$_2$—N($R^1$)—, $R^1$—C(O)—, HO—C(O)—, $R^1$—O—C(O)—, $H_2N$—C(O)—, $R^1$—NH—C(O)—, $R^1$—N($R^1$)—C(O)—, $H_2N$—S(O)$_2$—, $R^1$—NH—S(O)$_2$—, $R^1$—N($R^1$)—S(O)$_2$—, $F_5S$—, NC—, oxo and methylene;
Y is $C(R^{12})=C(R^{13})$;
Z is chosen from the series consisting of N and $C(R^{16})$;
$R^0$ is chosen from the series consisting of hydrogen and $R^1$;
$R^1$ is chosen from the series consisting of $(C_1-C_6)$-alkyl, $(C_3-C_7)$-cycloalkyl and $(C_3-C_7)$-cycloalkyl-$(C_1-C_4)$-alkyl-;
$R^2$ is $(C_1-C_4)$-alkyl which is substituted by one or more identical or different substituents chosen from the series consisting of HO— and $(C_1-C_4)$-alkyl-O—;
$R^{10}$ is chosen from the series consisting of hydrogen and $R^{11}$;
$R^{11}$, $R^{30}$, $R^{33}$, $R^{35}$, $R^{54}$, $R^{55}$, $R^{57}$ and $R^{58}$ are, independently of each other group $R^{11}$, $R^{30}$, $R^{33}$, $R^{35}$, $R^{54}$, $R^{55}$, $R^{57}$ and $R^{58}$, chosen from the series consisting of $(C_1-C_6)$-alkyl, $(C_2-C_6)$-alkenyl, $(C_2-C_6)$-alkynyl, $(C_3-C_7)$-cycloalkyl and $(C_3-C_7)$-cycloalkyl-$(C_1-C_4)$-alkyl- which are all optionally substituted by one or more identical or different substituents $R^{70}$;
$R^{12}$, $R^{13}$, $R^{14}$, $R^{15}$ and $R^{16}$ are independently of each other chosen from the series consisting of hydrogen, halogen, $(C_1-C_4)$-alkyl, HO—$(C_1-C_4)$-alkyl-, $(C_1-C_4)$-alkyl-O—, $(C_1-C_4)$-alkyl-S(O)$_m$—, $H_2N$—, $(C_1-C_4)$-alkyl-NH—, $(C_1-C_4)$-alkyl-N($(C_1-C_4)$-alkyl)-, $(C_1-C_4)$-alkyl-C(O)— and NC—, or $R^{13}$ or $R^{14}$, together with the one of the groups $R^{21}$ and $R^{22}$ which is not the group of the formula II, forms a chain consisting of 3 to 5 chain members of which 0, 1 or 2 chain members are identical or different hetero chain members chosen from the series consisting of N($R^{17}$), O and S, but two hetero chain members cannot be present in adjacent positions, and the other chain members are identical or different groups $C(R^{18})(R^{18})$;
$R^{17}$ and $R^{25}$ are independently of each other chosen from the series consisting of hydrogen and $(C_1-C_4)$-alkyl;
$R^{18}$, independently of each other group $R^{18}$, is chosen from the series consisting of hydrogen, fluorine and $(C_1-C_4)$-alkyl, or two of the groups $R^{18}$ bonded to the same carbon atom, together with the carbon atom carrying them, form a 3-membered to 6-membered cycloalkane ring which is optionally substituted by one more identical or different substituents chosen from the series consisting of fluorine and $(C_1-C_4)$-alkyl;
$R^{20}$ is chosen from the series consisting of hydrogen and $(C_1-C_4)$-alkyl;
one of the groups $R^{21}$ and $R^{22}$ is a group of the formula II $$R^{24}-R^{23}-\quad\quad\quad\quad\text{II}$$

and the other of the groups $R^{21}$ and $R^{22}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, $H_2N$—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, $H_2N$—C(O)—, $R^{30}$—NH—C(O)—, $R^{30}$—N($R^{30}$)—C(O)—, $H_2N$—S(O)$_2$—, $R^{30}$—NH—S(O)$_2$—, $R^{30}$—N($R^{30}$)—S(O)$_2$—, NC—, $O_2N$— and Het$^1$, or together with $R^{13}$ or $R^{14}$ forms a chain as specified in the definition of $R^{13}$ and $R^{14}$;
$R^{23}$ is a direct bond or a chain consisting of 1 to 5 chain members of which 0, 1 or 2 chain members are identical or different hetero chain members chosen from the series consisting of N($R^{25}$), O, S, S(O) and S(O)$_2$, but two hetero chain members can be present in adjacent positions only if one of them is chosen from the series consisting of S(O) and S(O)$_2$ and the other is chosen from the series consisting of N($R^{25}$), O and S, and the other chain members are identical or different groups $C(R^{26})(R^{26})$;
$R^{24}$ is a 3-membered to 10-membered, monocyclic or bicyclic ring, which is saturated and contains 0 or 1 hetero ring members, or is unsaturated and contains 0, 1 or 2 identical or different hetero ring members, wherein the hetero ring members are chosen from the series consisting of N, N($R^{32}$), O, S, S(O) and S(O)$_2$, and wherein the ring is optionally substituted on ring carbon atoms by one or more identical or different substituents chosen from the series consisting of halogen, $R^{33}$, oxetanyl, HO—, $R^{33}$—O—, $R^{33}$—C(O)—O—, $R^{33}$—S(O)$_2$—O—, $R^{33}$—S(O)$_m$—, $H_2N$—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, $H_2N$—S(O)$_2$—NH—, $R^{33}$—NH—S(O)$_2$—NH—, $R^{33}$—N($R^{33}$)—S(O)$_2$—NH—, $H_2N$—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, $R^{33}$—C(O)—, HO—C(O)—, $R^{33}$—O—C(O)—, $H_2N$—C(O)—, $R^{33}$—NH—C(O)—, $R^{33}$—N($R^{33}$)—C(O)—, $H_2N$—S(O)$_2$—, $R^{33}$—NH—S(O)$_2$—, $R^{33}$—N($R^{33}$)—S(O)$_2$—, NC—, $O_2N$— and oxo;
$R^{26}$, independently of each other group $R^{26}$, is chosen from the series consisting of hydrogen, fluorine, $(C_1-C_4)$-alkyl and HO—, or two groups $R^{26}$ bonded to the same carbon atom together are oxo, or two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, N($R^{34}$), O, S, S(O) and S(O)$_2$, which ring is optionally substituted on ring carbon atoms by one more identical or different substituents chosen from the series consisting of fluorine and $(C_1-C_4)$-alkyl;
$R^{32}$ and $R^{34}$ are independently of each other chosen from the series consisting of hydrogen, $R^{35}$, $R^{35}$—S(O)$_2$—, $R^{35}$—C(O)—, $R^{35}$—O—C(O)— and phenyl;
$R^{50}$ is chosen from the series consisting of $R^{51}$—O— and $R^{52}$—N($R^{53}$)—;

$R^{51}$ is chosen from the series consisting of hydrogen and $R^{54}$;

$R^{52}$ is chosen from the series consisting of $R^{55}$, NC— and $R^{56}$—S(O)$_2$—;

$R^{53}$ is chosen from the series consisting of hydrogen and $R^{57}$;

$R^{56}$ is chosen from the series consisting of $R^{58}$ and phenyl;

$R^{60}$, independently of each other group $R^{60}$, is chosen from the series consisting of hydrogen and (C$_1$-C$_4$)-alkyl;

$R^{70}$ is chosen from the series consisting of HO—, $R^{71}$—O—, $R^{71}$—C(O)—O—, $R^{71}$—S(O)$_m$—, H$_2$N—, $R^{71}$—NH—, $R^{71}$—N(R$^{71}$)—, $R^{71}$—C(O)—NH—, $R^{71}$—C(O)—N(R$^{71}$)—, $R^{71}$—S(O)$_2$—NH—, $R^{71}$—S(O)$_2$—N(R$^{71}$)—, HO—C(O)—, $R^{71}$—O—C(O)—, H$_2$N—C(O)—, $R^{71}$—NH—C(O)—, $R^{71}$—N(R$^{71}$)—C(O)—, H$_2$N—S(O)$_2$—, $R^{71}$—NH—S(O)$_2$—, $R^{71}$—N(R$^{71}$)—S(O)$_2$— and oxo;

$R^{71}$, independently of each other group $R^{71}$, is chosen from (C$_1$-C$_4$)-alkyl, (C$_3$-C$_4$)-cycloalkyl and (C$_3$-C$_4$)-cycloalkyl-(C$_1$-C$_2$)-alkyl-;

Het$^1$ is a monocyclic 4-membered to 7-membered heterocyclic ring which comprises 1 or 2 identical or different hetero ring members chosen from the series consisting of N, N(R$^{60}$), O, S, S(O) and S(O)$_2$, which ring is saturated and is optionally substituted by one or more identical or different substituents chosen from the series consisting of fluorine and (C$_1$-C$_4$)-alkyl;

m, independently of each other number m, is an integer chosen from the series consisting of 0, 1 and 2;

phenyl, independently of each other group phenyl, is optionally substituted by one or more identical or different substituents chosen from the series consisting of halogen, (C$_1$-C$_4$)-alkyl, (C$_1$-C$_4$)-alkyl-O— and NC—, unless specified otherwise;

cycloalkyl, independently of each other group cycloalkyl, and independently of any other substituents on cycloalkyl, is optionally substituted by one or more identical or different substituents chosen from fluorine and (C$_1$-C$_4$)-alkyl; and alkyl, alkenyl and alkynyl, independently of each other group alkyl, alkenyl and alkynyl, and independently of any other substituents on alkyl, alkenyl and alkynyl, is optionally substituted by one or more fluorine substituents;

provided that the compound of the formula I is not 1-[(biphenyl-4-carbonyl)-amino]-cyclohexanecarboxylic acid, 1-[4-(2-pyrrolidin-1-yl-ethoxy)-benzoylamino]-cyclohexanecarboxylic acid, 1-[4-(2-piperidin-1-yl-ethoxy)-benzoylamino]-cyclohexanecarboxylic acid, 1-[4-(2-oxo-pyrrolidin-1-yl)-benzoylamino]-cyclohexanecarboxylic acid, 1-[(2',3-dichloro-biphenyl-4-carbonyl)-amino]-cycloheptanecarboxylic acid, 1-[4-(4,6-dimethyl-pyrimidin-2-ylsulfanyl)-benzoylamino]-cyclopentanecarboxylic acid ethyl ester, 1-[4-(4-oxo-piperidin-1-yl)-benzoylamino]-cyclopropanecarboxylic acid methyl ester or 1-[2-chloro-4-(3-hydroxy-benzylcarbamoyl)-benzoylamino]-cyclopropanecarboxylic acid;

or a stereoisomeric form thereof or a mixture of stereoisomeric forms in any ratio, or a physiologically acceptable salt thereof.

2. The compound according to claim 1, wherein ring A is a cyclohexane ring or cycloheptane ring, each of which is optionally substituted by one or more identical or different substituents chosen from the series consisting of halogen, $R^1$, $R^2$, (C$_2$-C$_6$)-alkenyl, HO—, $R^1$—O—, phenyl-(C$_1$-C$_4$)-alkyl-O—, $R^1$—C(O)—O—, $R^1$—S(O)$_2$—O—, HO—C(O)—, $R^1$—O—C(O)—, H$_2$N—C(O)—, $R^1$—NH—C(O)—, $R^1$—N(R$^1$)—C(O)— and oxo;

or a stereoisomeric form thereof or a mixture of stereoisomeric forms in any ratio, or a physiologically acceptable salt thereof.

3. The compound according to claim 1, wherein Z is C(R$^{16}$);

or a stereoisomeric form thereof or a mixture of stereoisomeric forms in any ratio, or a physiologically acceptable salt thereof.

4. The compound according to claim 1, wherein $R^{21}$ is chosen from the series consisting of hydrogen, halogen, (C$_1$-C$_4$)-alkyl, HO—(C$_1$-C$_4$)-alkyl-, (C$_1$-C$_4$)-alkyl-O—(C$_1$-C$_4$)-alkyl-, (C$_1$-C$_4$)-alkyl-O—, HO—(C$_1$-C$_4$)-alkyl-O—, (C$_1$-C$_4$)-alkyl-O—(C$_1$-C$_4$)-alkyl-O—, (C$_1$-C$_4$)-alkyl-S(O)$_m$—, (C$_1$-C$_4$)-alkyl-C(O)—, NC— and Het$^1$, or together with $R^{13}$ or $R^{14}$ forms a chain as specified in the definition of $R^{13}$ and $R^{14}$; and $R^{22}$ is a group of the formula II $$R^{24}-R^{23}-\qquad\qquad II$$

$R^{23}$ is a direct bond or a chain consisting of 2, 3 or 4 chain members of which 0 or 1 chain members are hetero chain members chosen from the series consisting of N(R$^{25}$), O, S, S(O) and S(O)$_2$, and the other chain members are identical or different groups C(R$^{26}$)(R$^{26}$); or a stereoisomeric form thereof or a mixture of stereoisomeric forms in any ratio, or a physiologically acceptable salt thereof.

5. The compound according to claim 1, wherein $R^{24}$ is a 3-membered to 7-membered monocyclic ring or a 7-membered to 10-membered bicyclic ring, which rings are saturated and contain 0 or 1 hetero ring members, or are unsaturated and contain 0, 1 or 2 identical or different hetero ring members chosen from the series consisting of N, N(R$^{32}$), O, S, S(O) and S(O)$_2$, and which rings are optionally substituted on ring carbon atoms by one or more identical or different substituents chosen from the series consisting of halogen, $R^{33}$, oxetanyl, HO—, $R^{33}$—O—, $R^{33}$—S(O)$_m$—, H$_2$N—, $R^{33}$—NH—, $R^{33}$—N(R$^{33}$)—, $R^{33}$—C(O)—NH—, $R^{33}$—C(O)—N(R$^{71}$)—, $R^{33}$—S(O)$_2$—NH—, $R^{33}$—S(O)$_2$—N(R$^{71}$)—, H$_2$N—S(O)$_2$—NH—, $R^{33}$—NH—S(O)$_2$—NH—, $R^{33}$—N(R$^{33}$)—S(O)$_2$—NH—, H$_2$N—S(O)$_2$—N(R$^{71}$)—, $R^{33}$—NH—S(O)$_2$—N(R$^{71}$)—, $R^{33}$—N(R$^{33}$)—S(O)$_2$—N(R$^{71}$)—, HO—C(O)—, $R^{33}$—O—C(O)—, H$_2$N—C(O)—, $R^{33}$—NH—C(O)—, $R^{33}$—N(R$^{33}$)—C(O)—, NC— and oxo; and $R^{32}$ is chosen from the series consisting of hydrogen, $R^{35}$, $R^{35}$—C(O)—, $R^{35}$—O—C(O)— and phenyl;

or a stereoisomeric form thereof or a mixture of stereoisomeric forms in any ratio, or a physiologically acceptable salt thereof.

6. The compound according to claim 1, wherein ring A is a cyclohexane ring or a cycloheptane ring which is optionally substituted by one or two identical or different substituents chosen from the series consisting of halogen, (C$_1$-C$_4$)-alkyl and (C$_1$-C$_4$)-alkyl-O—;

Z is C(R$^{16}$);

$R^{12}$, $R^{13}$, $R^{15}$ and $R^{16}$ are independently of each other chosen from the series consisting of hydrogen, halogen, (C$_1$-C$_4$)-alkyl; or $R^{13}$ forms together with $R^{21}$ a chain which is chosen from the series consisting of —O—C(R$^{18}$)(R$^{18}$)—O—, —CH$_2$—CH$_2$—CH$_2$—, —CH$_2$—O—CH$_2$—, —CH$_2$—CH$_2$—CH$_2$—CH$_2$— and —O—C(R$^{18}$)(R$^{18}$)—C(R$^{18}$)(R$^{18}$)—O—;

$R^{18}$ is chosen from the series consisting of hydrogen or fluorine;

$R^{21}$ is chosen from the series consisting of hydrogen, halogen, $(C_1-C_4)$-alkyl, HO—$(C_1-C_4)$-alkyl-, $(C_1-C_4)$-alkyl-O—, $(C_1-C_4)$-alkyl-C(O)—, $(C_1-C_4)$-alkyl-O—$(C_1-C_4)$alkyl-, HO—$(C_1-C_4)$-alkyl-O—, $(C_1-C_4)$-alkyl-O—$(C_1-C_4)$-alkyl-O—, NC— and oxetanyl, or together with $R^{13}$ forms a chain as specified in the definition of $R^{13}$;

$R^{22}$ is a group of the formula II $$R^{24}—R^{23}— \qquad \text{II}$$

$R^{23}$ is a direct bond or a chain consisting of 2, 3 or 4 chain members of which 0 or 1 chain members are hetero chain members chosen from the series consisting of O and S, and the other chain members are identical or different groups $C(R^{26})(R^{26})$;

$R^{24}$ is a benzene ring which is optionally substituted by one or more identical or different substituents chosen from the series consisting of halogen, $R^{33}$, oxetanyl, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—S(O)$_2$—NH—, HO—C(O)—, $R^{33}$—O—C(O)—, $H_2N$—C(O)—, $R^{33}$—NH—C(O)—, $R^{33}$—N($R^{33}$)—C(O)— and NC—;

$R^{26}$, independently of each other group $R^{26}$, is chosen from the series consisting of hydrogen, fluorine, $(C_1-C_4)$-alkyl, or two of the groups $R^{26}$ which are bonded to the same carbon atom in the chain, together with the carbon atom carrying them, form a cyclopropane ring or an oxetane ring;

$R^{33}$, independently of each other group $R^{33}$, is chosen from the series consisting of $(C_1-C_4)$-alkyl, $(C_3-C_7)$-cycloalkyl and $(C_3-C_7)$-cycloalkyl-$(C_1-C_2)$-alkyl-, which are all optionally substituted by one or more identical or different substituents $R^{70}$;

$R^{50}$ is chosen from the series consisting of $R^{51}$O— and $R^{52}(R^{53})N$—;

$R^{51}$, $R^{52}$ and $R^{53}$ are independently of each other chosen from the series consisting of hydrogen and $(C_1-C_4)$-alkyl;

$R^{70}$ is chosen from the series consisting of HO— and $R^{71}$—O—;

$R^{71}$ is $(C_1-C_4)$-alkyl;

m, independently of each other number m, is an integer chosen from the series consisting of 0 and 2;

cycloalkyl, independently of each other group cycloalkyl, and independently of any other substituents on cycloalkyl, is optionally substituted by one or more identical or different substituents chosen from fluorine and $(C_1-C_4)$-alkyl; and alkyl, independently of each other group alkyl, and independently of any other substituents on alkyl, is optionally substituted by one or more fluorine substituents;

or a stereoisomeric form thereof or a mixture of stereoisomeric forms in any ratio, or a physiologically acceptable salt thereof.

7. A compound according to claim 1, which is:
cis-1-[(3'-Chloro-6,4'-dimethoxy-biphenyl-3-carbonyl)-amino]-4-ethyl-cyclohexanecarboxylic acid,
trans-1-[(3'-Chloro-6,4'-dimethoxy-biphenyl-3-carbonyl)-amino]-4-ethyl-cyclohexanecarboxylic acid,
trans-4-Ethyl-1-{[6-(2-hydroxy-ethoxy)-3'-trifluoromethyl-biphenyl-3-carbonyl]-amino}-cyclohexanecarboxylic acid,
trans-1-[3-[2-(3-Chloro-phenyl)-ethoxy]-4-(2-hydroxy-ethoxy)-benzoylamino]-4-ethyl-cyclohexanecarboxylic acid,
cis-1-[3-[2-(3-Chloro-phenyl)-ethoxy]-4-(2-hydroxy-ethoxy)-benzoylamino]-4-ethyl-cyclohexanecarboxylic acid,
Trans-1-[(3'-Chloro-5-fluoro-6,4'-dimethoxy-biphenyl-3-carbonyl)-amino]-4-methyl-cyclohexanecarboxylic acid,
Cis-1-[(3'-chloro-5-fluoro-6,4'-dimethoxy-biphenyl-3-carbonyl)-amino]-4-ethyl-cyclohexanecarboxylic acid,
Cis-1-[(3'-Chloro-5-fluoro-6,4'-dimethoxy-biphenyl-3-carbonyl)-amino]-4-trifluoromethyl-cyclohexanecarboxylic acid, or
or a stereoisomeric form thereof or a mixture of stereoisomeric forms in any ratio, or a physiologically acceptable salt thereof.

8. A process for preparing the compound according to claim 1, comprising reacting a compound of formula III with a compound of formula IV,

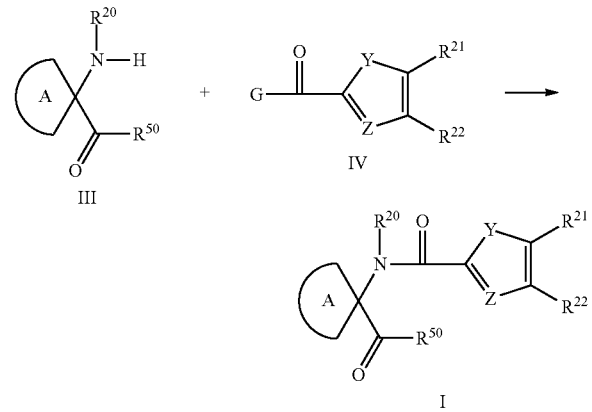

wherein the ring A and the groups Y, Z, $R^{20}$ to $R^{22}$ and $R^{50}$ in the compounds of the formulae III and IV are defined as in claim 1 and additionally functional groups can be present in protected form or in the form of a precursor group, and the group G in the compound of formula IV is HO—, $(C_1-C_4)$-alkyl-O— or halogen.

9. A pharmaceutical composition comprising the compound according to claim 1 or a physiologically acceptable salt thereof and a pharmaceutically acceptable carrier.

* * * * *